US006610844B2

United States Patent
Ng et al.

(10) Patent No.: US 6,610,844 B2
(45) Date of Patent: Aug. 26, 2003

(54) PROCESSES FOR PREPARATION OF 9,11-EPOXY STEROIDS AND INTERMEDIATES USEFUL THEREIN

(75) Inventors: John S. Ng, Chicago, IL (US); Chin Liu, Vernon Hills, IL (US); Dennis K. Anderson, St. Charles, MO (US); Jon P. Lawson, Glencoe, MO (US); Joseph Wieczorek, Cary, IL (US); Sastry A. Kunda, Chesterfield, MO (US); Leo J. Letendre, Manchester, MO (US); Mark J. Pozzo, Chesterfield, MO (US); Yuen-Lung L. Sing, St. Louis, MO (US); Ping T. Wang, Ballwin, MO (US); Edward E. Yonan, Carol Stream, IL (US); Richard M. Weier, Lake Bluff, IL (US); Thomas R. Kowar, Mt. Prospect, IL (US); Julio A. Baez, San Diego, CA (US); Bernhard Erb, Gipf-Oberfrick (CH)

(73) Assignee: G.D. Searle & Company, Skokie, IL (US)

(*) Notice: Subject to any disclaimer, the term of this patent is extended or adjusted under 35 U.S.C. 154(b) by 0 days.

(21) Appl. No.: 10/112,355

(22) Filed: Mar. 29, 2002

(65) Prior Publication Data

US 2003/0055274 A1 Mar. 20, 2003

Related U.S. Application Data

(63) Continuation of application No. 09/319,673, filed as application No. PCT/US97/23090 on Dec. 11, 1997, now abandoned.
(60) Provisional application No. 60/033,315, filed on Dec. 11, 1996, and provisional application No. 60/049,388, filed on Jun. 11, 1997.

(51) Int. Cl.[7] .................. C07J 21/00; C07J 1/00
(52) U.S. Cl. .......................... 540/41; 552/638
(58) Field of Search .................... 540/41; 552/638

(56) References Cited

U.S. PATENT DOCUMENTS

| | | |
|---|---|---|
| 3,053,856 A | 9/1962 | Payne et al. |
| 3,200,113 A | 8/1965 | Christiansen et al. |
| 3,300,489 A | 1/1967 | Holden et al. |
| 3,413,288 A | 11/1968 | Creger et al. |
| 3,759,791 A | 9/1973 | Marsheck et al. |
| 3,897,417 A | 7/1975 | Wamant et al. |
| 3,972,878 A | 8/1976 | Schirmann et al. |
| 4,118,488 A | 10/1978 | Philippson et al. |
| 4,270,994 A | 6/1981 | Behling |
| 4,559,332 A | 12/1985 | Grob et al. |
| 5,565,588 A | 10/1996 | Batist et al. |
| 5,616,742 A | 4/1997 | Fu et al. |

FOREIGN PATENT DOCUMENTS

| | | |
|---|---|---|
| DE | 2404947 | 8/1974 |
| DE | 2443746 A1 | 10/1976 |
| DE | 2349022 A1 | 5/1977 |
| DE | 2932925 A1 | 5/1981 |
| EP | 123 734 A1 | 11/1984 |
| EP | 122 232 A1 | 12/1985 |
| EP | 165 902 A1 | 2/1987 |
| WO | WO 97/21720 A2 | 6/1997 |

OTHER PUBLICATIONS

Grob et al., "Steroidal, Aldosterone Antagonists, Increased Selectivity of 9α, 11-Epoxy Derivatives", *Helvetica Chimica Acta*, vol. 80, No. 2, pp. 566–585, Mar. 24, 1997.

(List continued on next page.)

*Primary Examiner*—Barbara P. Badio
(74) *Attorney, Agent, or Firm*—Senniger, Powers, Leavitt & Roedel

(57) ABSTRACT

Multiple novel reaction schemes, novel process steps and novel intermediates are provided for the synthesis of epoxymexrenone and other compounds of Formula I

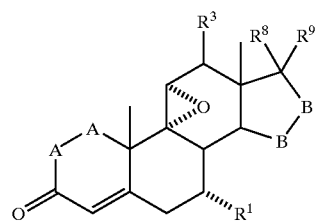

(I)

wherein
—A—A— represents the group —CHR$^4$—CHR$^5$— or —CR$^4$=CR$^5$—;
R$^3$, R$^4$ and R$^5$ are independently selected from the group consisting of hydrogen, halo, hydroxy, lower alkyl, lower alkoxy, hydroxyalkyl, alkoxyalkyl, hydroxycarbonyl, cyano and aryloxy;
R$^1$ represents an alpha-oriented lower alkoxycarbonyl or hydroxyalkyl radical;
—B—B— represents the group —CHR$^6$—CHR$^7$— or an alpha- or beta-oriented group:

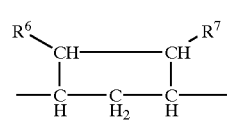

(III)

where R$^6$ and R$^7$ are independently selected from the group consisting of hydrogen, halo, lower alkoxy, acyl, hydroxyalkyl, alkoxyalkyl, hydroxycarbonyl, alkyl, alkoxycarbonyl, acyloxyalkyl, cyano and aryloxy; and
R$^8$ and R$^9$ are independently selected from the group consisting of hydrogen, hydroxy, halo, lower alkoxy, acyl, hydroxyalkyl, alkoxyalkyl, hydroxycarbonylalkyl, alkoxycarbonylalkyl, alkoxycarbonyl, acyloxyalkyl, cyano and aryloxy, or R$^8$ and R$^9$ together comprise a carbocyclic or heterocyclic ring structure, or R$^8$ or R$^9$ together with R$^6$ or comprise a carbocyclic or heterocyclic ring structure fused to the pentacyclic D ring.

18 Claims, 5 Drawing Sheets

OTHER PUBLICATIONS

Brown et al., "Steroidal Aldosterone Blockers VII", *J. Med. Chem.*, vol. 6, pp. 732–735, 1963.

Brown et al., "Steroidal Aldosterone Blockers III", *J. Org. Chem.*, vol. 25, No. 1, pp. 96–99, 1960.

Peterson et al., "Microbiological Transformations of Steroids. VI. Preparation of 11α–Hydroxy–6–dehydroproges–terone", Journal Of The American Chemical Society, vol. 75, No. 2, pp. 419–421, Jan. 29, 1953.

Christiansen et al., "The Reaction Of Steroidal 4,6–dien–3–ones With Cyanide", Steroids, vol. 1, No. 6, pp. 620–627, Jun. 1963.

Weir et al., "7α–Carboalkoxy Steroidal Spirolactones As Aldosterone Antagonists", Journal of Medicinal Chemistry, vol. 18, No. 8, pp. 817–821, Aug. 1975.

C.M.P. Deshayes, "Utilisation De Modéles Mathématiques Pour l'optimisation En Fermentation. Applicatoins Aux Transfor–mations Par Les Micro–organismes", Bulletine De La Societe Chimque De France 2 Partie—Chimie Organique, Biochimie, No. 1–2, pp. 24–34, May 18, 1979 (translation).

Database WPI, Section Ch, Week 8145, Derwent Publications, Ltd., London, GB; Class B01, AN 81–82258D and JP 56 120 697 A (Mitsubishi Chem. Ind. Ltd.), Sep. 22, 1981.

Abstract 084228, "Hydroxylated Androstane Production From Sterols", Chemical Abstracts, vol. 100, No. 11, p. 430, Mar. 12, 1984 and JP 58 179 498 A (Danippon Ink and Chemicals, Inc.); Japan, Oct. 20, 1983.

Van Leusen et al., "Chemistry of Sulfonylmethyl Isocya-–nides. 33. Synthesis of 17–(isocyanotosylmethylene) Steroids: Precursors To Pregnane Derivatives" Recueil Des Travaux Chimiques Des Pays–Bas, vol. 110, No. 10, pp. 393–401, Oct. 1991.

Hellberg et al., "5α–Hydroxy–3α–Cholestanecarboxylic Lactone", *OPPI Briefs*, vol. 15, No. 3, pp. 154–156, 1983.

Nickisch et al., "Aldosterone Antagonists.3.Synthesis and Activities of Steroidal 7α–(Alkoxycarbonyl)–15,16–Methylene Methylene Spirolactones", *Journal of Medicinal Chemistry*, vol. 33, No. 2, pp. 509–513, Feb. 1990.

Arias et al., "Epoxidation of Alkenes With Trichloroacetonitrile/Hydrogen Peroxide In A Neutral Biphasic Solvent System", *J. Org. Chem.*, vol. 48, pp. 888–890, 1983.

Carruthers et al., "Synthesis Of Corticoids From 9α–Hydroxyandrost–4–ene–8,17–dione", *J. Org. Chem.*, vol. 57, pp. 961–965, 1992.

Degasparo et al., "Antialdosterones: Incidence And Prevention Of Sexual Side Effects", *J. Steroid Biochem*, vol. 32, No 13, pp. 223–227, 1989.

Gabriel, S., "Condensationsproducte aus Phtalsaureanhydrid", *Ber.*, pp. 1389–1396, 1884.

Nagata et al., "Angular–Substituted Polycyclic Compounds. I. Cyanation of Δ–Cholesten–3–one", *Journal Of Organic Chemistry*, vol. 26, pp. 2413–2420, 1961.

Nagata et al., "Hydrocyanation, VI. Application Of The New Hydrocyanation Methods To Conjugate Hydrocyanation Of α,β–Unsaturated Ketones, Conjugated Dienones, And Conjugated Enamines And To Preparation Of α–Cyanohydrins", *J. Amer. Chem. Soc.*, vol. 94:13, pp. 4654–4672, 1972.

Ogata et al., "The Alkali Phosphate–Catalyzed Epoxidation And Oxidation By A Mixture Of Nitrile And Hydrogen Peroxide", Tetrahedron, vol. 20, pp. 2065–2068, 1964.

Payne et al., "Reactions of Hydrogen Peroxide. VII. Alkali–Catalyzed Epoxidation and Oxidation Using A Nitrile As Co–reactant", *J. Org. Chem.*, vol. 26, pp. 659–663, 1961.

Turner et al., "Applications Of High–potential Quinones. Part I. The Mechanism Of Dehydrogenation Of Steroidal Ketones By 2,3 Dichloro–5,6–dicyanobenzoquinone", *J. Chem. Soc.*, pp. 1720–1730, 1967.

de Gasparo et al., "Three New Epoxy–Spirolactone Derivatives: Characterization in Vivo and in Vitro", The Journal Of Pharmacology And Experimental Therapeutics, vol. 240, No. 2, pp. 650–656, 1987.

Ogata, "The Kinetics Of The Phosphate/Catalyzed Epoxidation Of Styrenes With A Mixture Of Nitrile & Hydrogen Peroxide", Bull. Chem. Soc. Of Japan, vol. 38, No. 2, pp. 194–1999, 1965.

PROCESSES FOR PREPARATION OF 9,11-EPOXY STEROIDS AND INTERMEDIATES USEFUL THEREIN

This application is a continuation of U.S. application Ser. No. 09/319,673 filed Dec. 13, 1999, now abandoned, which is a 371 of PCT/US97/23090 filed Dec. 11, 1999, which claims priority to U.S. provisional Application Ser. No. 60/049,388 filed Jun. 11, 1997 and U.S. provisional Application Ser. No. 60/033,315 filed Dec. 11, 1996.

BACKGROUND OF THE INVENTION

This invention relates to the novel processes for the preparation of 9,11-epoxy steroid compounds, especially those of the 20-spiroxane series and their analogs, novel intermediates useful in the preparation of steroid compounds, and processes for the preparation of such novel intermediates. Most particularly, the invention is directed to novel and advantageous methods for the preparation of methyl hydrogen 9,11α-epoxy-17α-hydroxy-3-oxopregn-4-ene-7α,21-dicarboxylate, γ-lactone (also referred to as eplerenone or epoxymexrenone).

Methods for the preparation of 20-spiroxane series compounds are described in U.S. Pat. No. 4,559,332. The compounds produced in accordance with the process of the '332 patent have an open oxygen containing ring E of the general formula:

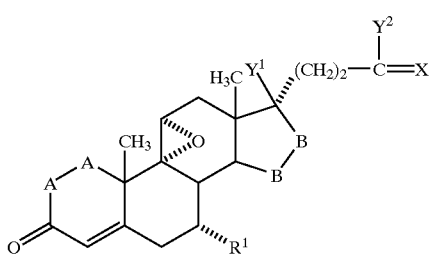

in which
—A—A— represents the group —CH$_2$—CH$_2$— or —CH=CH—;
R$^1$ represents an α-oriented lower alkoxycarbonyl or hydroxycarbonyl radical;
—B—B— represents the group —CH$_2$—CH$_2$— or an α- or β-oriented group;

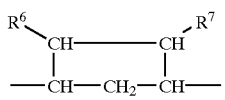

R$^6$ and R$^7$ being hydrogen;
X represents two hydrogen atoms or oxo;
Y$^1$ and Y$^2$ together represent the oxygen bridge —O—, or
Y$^1$ represents hydroxy, and
Y$^2$ represents hydroxy, lower alkoxy or, if X represents H$_2$, also lower alkanoyloxy;
and salts of such compounds in which X represents oxo and Y$^2$ represents hydroxy, that is to say of corresponding 17β-hydroxy-21-carboxylic acids.

U.S. Pat. No. 4,559,332 describes a number of methods for the preparation of epoxymexrenone and related compounds of Formula IA. The advent of new and expanded clinical uses for epoxymexrenone create a need for improved processes for the manufacture of this and other related steroids.

SUMMARY OF THE INVENTION

The primary object of the present invention is the provision of improved processes for the preparation of epoxymexrenone, other 20-spiroxanes and other steroids having common structural features. Among the particular objects of the invention are: to provide an improved process that produces products of Formula IA and other related compounds in high yield; the provision of such a process which involves a minimum of isolation steps; and the provision of such a process which may be implemented with reasonable capital expense and operated at reasonable conversion cost.

Accordingly, the present invention is directed to a series of synthesis schemes for epoxymexrenone; intermediates useful in the manufacture of epoxymexrenone; and syntheses for such novel intermediates.

The novel synthesis schemes are described in detail in the Description of Preferred Embodiments. Among the novel intermediates of this invention are those described immediately below.

A compound of Formula IV corresponds to the structure:

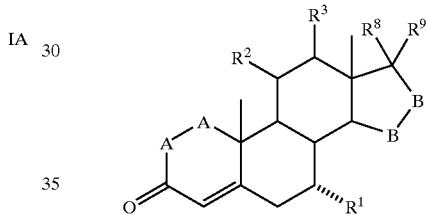

wherein:
—A—A— represents the group —CHR$^4$—CHR$^5$— or —CR$^4$=CR$^5$—;
R$^3$, R$^4$ and R$^5$ are independently selected from the group consisting of hydrogen, halo, hydroxy, lower alkyl, lower alkoxy, hydroxyalkyl, alkoxyalkyl, hydroxy carbonyl, cyano and aryloxy;
R$^1$ represents an alpha-oriented lower alkoxycarbonyl or hydroxycarbonyl radical;
R$^2$ is an 11α-leaving group the abstraction of which is effective for generating a double bond between the 9- and 11-carbon atoms;
—B—B— represents the group —CHR$^6$—CHR$^7$— or an alpha- or beta-oriented group:

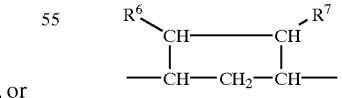

where
R$^6$ and R$^7$ are independently selected from the group consisting of hydrogen, halo, lower alkoxy, acyl, hydroxyalkyl, alkoxyalkyl, hydroxycarbonyl, alkyl, alkoxycarbonyl, acyloxyalkyl, cyano and aryloxy; and
R$^8$ and R$^9$ are independently selected from the group consisting of hydrogen, hydroxy, halo, lower alkoxy, acyl, hydroxyalkyl, alkoxyalkyl, hydroxycarbonyl, alkyl, alkoxycarbonyl, acyloxyalkyl, cyano and aryloxy, or $R^8$ and $R^9$ together comprise a carbocyclic or heterocyclic ring structure, or $R^8$ or $R^9$ together with $R^6$ or $R^7$ comprise a carbocyclic or heterocyclic ring structure fused to the pentacyclic D ring.

A compound of Formula IVA corresponds to Formula IV wherein $R^8$ and $R^9$ together with the ring carbon to which they are attached form the structure:

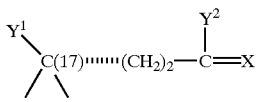

XXXIV where X, $Y^1$, $Y^2$ and C(17) are as defined above.

A compound of Formula IVB corresponds to Formula IV wherein $R^8$ and $R^9$ together form the structure of Formula XXXIII:

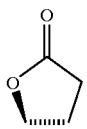

XXXIII

Compounds of Formulae IVC, IVD and IVE, respectively, correspond to any of Formula IV, IVA, or IVB wherein each of —A—A— and —B—B— is —CH$_2$—CH$_2$—, $R^3$ is hydrogen, and $R^1$ is alkoxycarbonyl, preferably methoxycarbonyl. Compounds within the scope of Formula IV may be prepared by reacting a lower alkylsulfonylating or acylating reagent, or a halide generating agent, with a corresponding compound within the scope of Formula V.

A compound of Formula V corresponds to the structure:

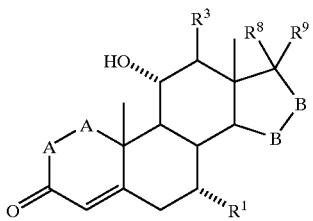

V wherein —A—A—, —B—B—, $R^1$, $R^3$, $R^8$ and $R^9$ are as defined in Formula IV.

A compound of Formula VA corresponds to Formula V wherein $R^8$ and $R^9$ with the ring carbon to which they are attached together form the structure:

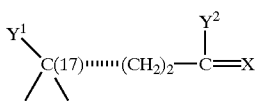

XXXIV where X, $Y^1$, $Y^2$ and C(17) are as defined above.

A compound of Formula VB corresponds to Formula V wherein $R^8$ and $R^9$ together form the structure of Formula XXXIII:

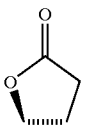

XXXIII

Compounds of Formulae VC, VD and VE, respectively, correspond to any of Formula V, VA, or VB wherein each of —A—A— and —B—B— is —CH$_2$—CH$_2$—, $R^3$ is hydrogen, and $R^1$ is alkoxycarbonyl, preferably methoxycarbonyl. Compounds within the scope of Formula V may be prepared by reacting an alkali metal alkoxide with a corresponding compound of Formula VI.

A compound of Formula VI corresponds to the structure:

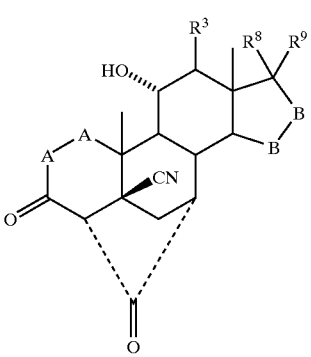

VI wherein —A—A—, —B—B—, $R^3$, $R^8$ and $R^9$ are as defined in Formula IV.

A compound of Formula VIA corresponds to Formula VI wherein $R^8$ and $R^9$ together with the ring carbon to which they are attached form the structure:

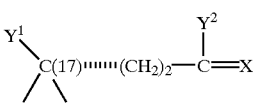

XXXIV where X, $Y^1$, $Y^2$ and C(17) are as defined above.

A compound of Formula VIB corresponds to Formula VI wherein $R^8$ and $R^9$ together form the structure of Formula XXXIII:

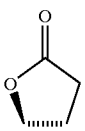

XXXIII

Compounds of Formulae VIC, VID and VIE, respectively, correspond to any of Formula VI, VIA, or VIB wherein each of —A—A— and —B—B— is —CH$_2$—CH$_2$—, and $R^3$ is hydrogen. Compounds of Formula VI, VIA, VIB and VIC are prepared by hydrolyzing a compound corresponding to Formula VII, VIIA, VIIB or VIIC, respectively.

A compound of Formula VII corresponds to the structure:

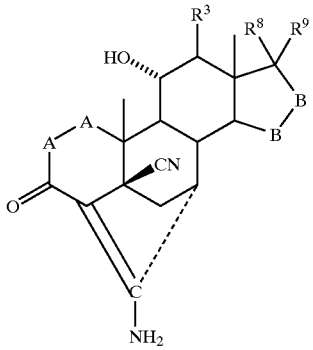

VII wherein —A—A—, —B—B—, $R^3$, $R^8$ and $R^9$ are as defined in Formula IV.

A compound of Formula VIIA corresponds to Formula VII wherein $R^8$ and $R^9$ together with the ring carbon to which they are attached form the structure:

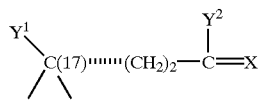

XXXIV where X, $Y^1$, $Y^2$ and C(17) are as defined above.

A compound of Formula VIIB corresponds to Formula VII wherein $R^8$ and $R^9$ together form the structure of Formula XXXIII:

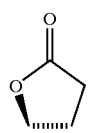

XXXIII

Compounds of Formulae VIIC, VIID and VIIE, respectively, correspond to any of Formula VII, VIIA, or VIIB wherein each of —A—A— and —B—B— is —CH$_2$—CH$_2$—, and $R^3$ is hydrogen. A compound within the scope of Formula VII may be prepared by cyanidation of a compound within the scope of Formula VIII.

A compound of Formula VIII corresponds to the structure:

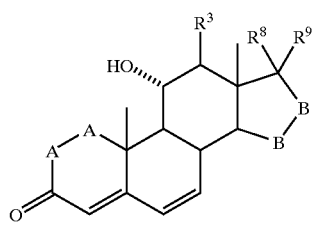

VIII wherein —A—A—, —B—B—, $R^3$, $R^8$ and $R^9$ are as defined in Formula IV.

A compound of Formula VIIIA corresponds to Formula VIII wherein $R^8$ and $R^9$ together with the ring carbon to which they are attached form the structure:

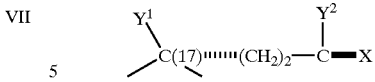

XXXIV where X, $Y^1$, $Y^2$ and C(17) are as defined above.

A compound of Formula VIIIB corresponds to Formula VIII wherein $R^8$ and $R^9$ together form the structure of Formula XXXIII:

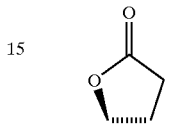

XXXIII

Compounds of Formulae VIIIC, VIIID and VIIIE, respectively, correspond to any of Formula VIII, VIIIA, or VIIIB wherein each of —A—A— and —B—B— is —CH$_2$—CH$_2$—, and $R^3$ is hydrogen. Compounds within the scope of Formula VIII are prepared by oxidizing a substrate comprising a compound of Formula XXX as described hereinbelow by fermentation effective for introducing an 11-hydroxy group into the substrate in α-orientation.

A compound of Formula IX corresponds to the structure:

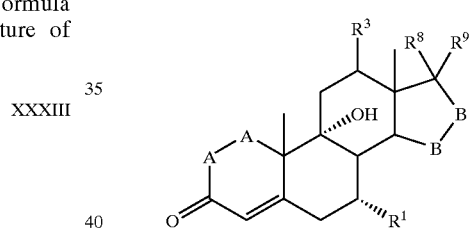

IX where —A—A—, —B—B—, $R^3$, $R^8$ and $R^9$ are as defined in Formula IV, and $R^1$ is as defined in Formula V.

A compound of Formula IXA corresponds to Formula IX wherein $R^8$ and $R^9$ together with the ring carbon to which they are attached form the structure:

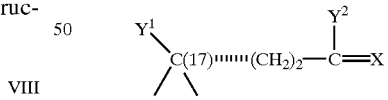

XXXIV where X, $Y^1$, $Y^2$ and C(17) are as defined above.

A compound of Formula IXB corresponds to Formula IX wherein $R^8$ and $R^9$ together with the ring carbon to which they are attached form the structure of Formula XXXIII:

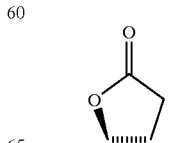

XXXIII

Compounds of Formulae IXC, IXD and IXE, respectively, correspond to any of Formula IX, IXA, or IXB wherein each of —A—A— and —B—B— is —CH$_2$—CH$_2$—, and R$^3$ is hydrogen. Compounds within the scope of Formula IX can be prepared by bioconversion of a corresponding compound within the scope of Formula X.

A compound of Formula XIV corresponds to the structure:

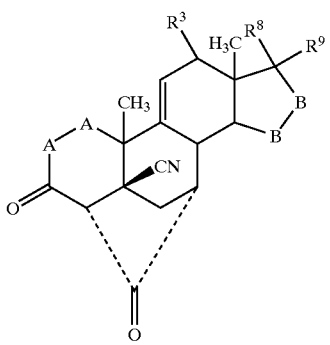

XIV wherein —A—A—, —B—B—, R$^3$, R$^8$ and R$^9$ are as defined in Formula IV.

A compound of Formula XIVA corresponds to Formula XIV wherein R$^8$ and R$^9$ together with the ring carbon to which they are attached form the structure:

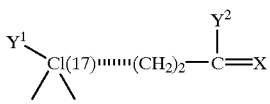

XXXIV where X, Y$^1$, Y$^2$ and C(17) are as defined above.

A compound of Formula XIVB corresponds to Formula XIV wherein R$^8$ and R$^9$ together with the ring carbon to which they are attached form the structure of Formula XXXIII:

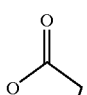

XXXIII

Compounds of Formulae XIVC, XIVD and XIVE, respectively, correspond to any of Formula XIV, XIVA, or XIVB wherein each of —A—A— and —B—B— is —CH$_2$—CH$_2$—, and R$^3$ is hydrogen. Compounds within the scope of Formula XIV can be prepared by hydrolysis of a corresponding compound within the scope of Formula XV.

A compound of Formula XV corresponds to the structure:

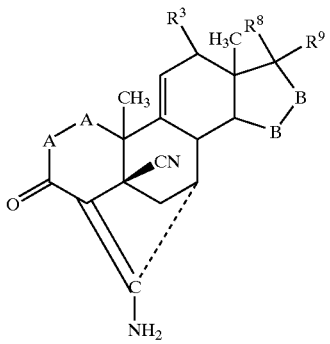

XV wherein —A—A—, —B—B—, R$^3$, R$^8$ and R$^9$ are as defined in Formula IV.

A compound of Formula XVA corresponds to Formula XV wherein R$^8$ and R$^9$ together with the ring carbon to which they are attached form the structure:

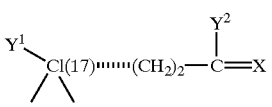

XXXIV where X, Y$^1$, Y$^2$ and C(17) are as defined above.

A compound of Formula XVB corresponds to Formula XV wherein R$^8$ and R$^9$ together with the ring carbon to which they are attached form the structure of Formula XXXIII:

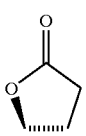

XXXIII

Compounds of Formulae XVC, XVD and XVE, respectively, correspond to any of Formula XV, XVA, or XVB wherein each of —A—A— and —B—B— is —CH$_2$—CH$_2$—, and R$^3$ is hydrogen. Compounds within the scope of Formula XV can be prepared by cyanidation of a corresponding compound within the scope of Formula XVI.

A compound of Formula XXI corresponds to the structure:

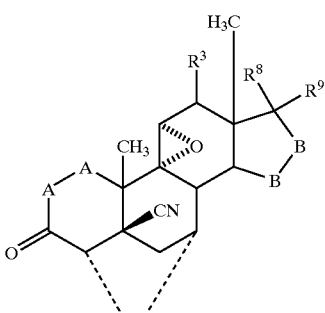

XXI wherein —A—A—, —B—B—, R$^3$, R$^8$ and R$^9$ are as defined in Formula IV.

A compound of Formula XXIA corresponds to Formula XXI wherein R$^8$ and R$^9$ together with the ring carbon to which they are attached form the structure:

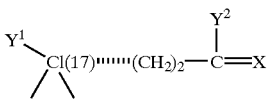

XXXIV where X, Y$^1$, Y$^2$ and C(17) are as defined above.

A compound of Formula XXIB corresponds to Formula XXI wherein $R^8$ and $R^9$ together form the structure of Formula XXXIII:

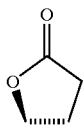

XXXIII

Compounds of Formulae XXIC, XXID and XXIE, respectively, correspond to any of Formula XXI, XXIA, or XXIB wherein each of —A—A— and —B—B— is —$CH_2$—$CH_2$—, and $R^3$ is hydrogen. Compounds within the scope of Formula XXI may be prepared by hydrolyzing a corresponding compound within the scope of Formula XXII.

A compound of Formula XXII corresponds to the structure:

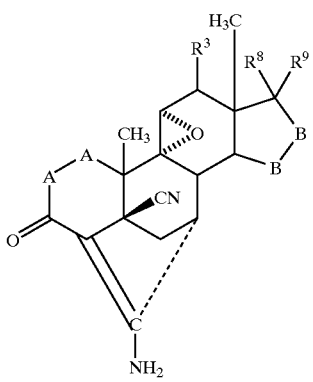

XXII wherein —A—A—, —B—B—, $R^3$, $R^8$ and $R^9$ are as defined in Formula IV.

A compound of Formula XXIIA corresponds to Formula XXII wherein $R^8$ and $R^9$ together with the ring carbon to which they are attached form the structure:

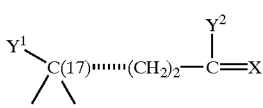

XXXIV where X, $Y^1$, $Y^2$ and C(17) are as defined above.

A compound of Formula XXIIB corresponds to Formula XXII wherein $R^8$ and $R^9$ together form the structure of Formula XXXIII:

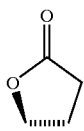

XXXIII

Compounds of Formulae XXIIC, XXIID and XXIIE, respectively, correspond to any of Formula XXII, XXIIA, or XXIIB wherein each of —A—A— and —B—B— is —$CH_2$—$CH_2$—, and $R^3$ is hydrogen. Compounds within the scope of Formula XXII may be prepared by cyanidation of a compound within the scope of Formula XXIII.

A compound of Formula XXIII corresponds to the structure:

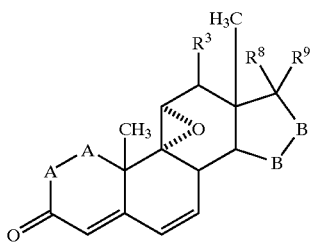

XXIII wherein —A—A—, —B—B—, $R^3$, $R^8$ and $R^9$ are as defined in Formula IV.

A compound of Formula XXIIIA corresponds to Formula XXIII wherein $R^8$ and $R^9$ together with the ring carbon to which they are attached form the structure:

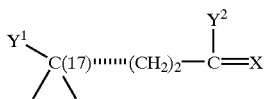

XXXIV where X, $Y^1$, $Y^2$ and C(17) are as defined above.

A compound of Formula XXIIIB corresponds to Formula XXIII wherein $R^8$ and $R^9$ together form the structure of Formula XXXIII:

XXXIII

Compounds of Formulae XXIIIC, XXIIID and XXIIIE, respectively, correspond to any of Formula XXIII, XXIIIA, or XXIIIB wherein each of —A—A— and —B—B— is —$CH_2$—$CH_2$—, and $R^3$ is hydrogen. Compounds within the scope of Formula XXIII can be prepared by oxidation of a compound of Formula XXIV, as described hereinbelow.

A compound of Formula XXVI corresponds to the structure:

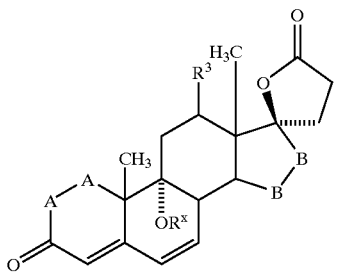

XXVI wherein —A—A—, —B—B—, $R^3$, $R^8$ and $R^9$ are as defined in Formula IV.

A compound of Formula XXVIA corresponds to Formula XXVI wherein each of —A—A— and —B—B— is —$CH_2$—$CH_2$—, and $R^3$ is hydrogen. Compounds within the scope of Formula XXVI can be prepared by oxidation of a compound of Formula XXVII.

A compound of Formula XXV corresponding to the structure:

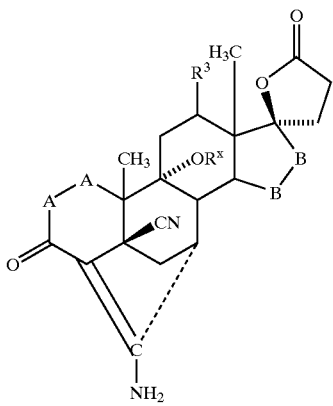

wherein —A—A—, —B—B—, $R^3$, $R^8$ and $R^9$ are as defined in Formula IV.

A compound of Formula XXVA corresponds to Formula XXV wherein each of —A—A— and —B—B— is —CH$_2$—CH$_2$—, and $R^3$ is hydrogen. Compounds within the scope of Formula XXV can be prepared by cyanidation of a compound of Formula XXVI.

A compound of Formula 104 corresponds to the structure:

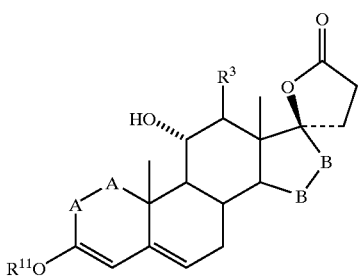

wherein —A—A—, —B—B— and $R^3$ are as defined in Formula IV, and $R^{11}$ is $C_1$ to $C_4$ alkyl.

A compound of Formula 104A corresponds to Formula 104 wherein each of —A—A— and —B—B— is —CH$_2$—CH$_2$—, and $R^3$ is hydrogen. Compounds within the scope of Formula 104 may be prepared by thermal decomposition of a compound of Formula 103.

A compound of Formula 103 corresponds to the structure:

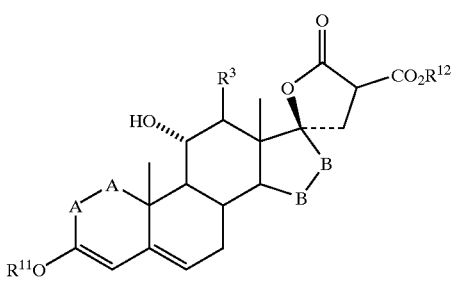

wherein —A—A—, —B—B—, $R^3$ and $R^{11}$ are as defined in Formula 104, and $R_{12}$ is a $C_1$ to $C_4$ alkyl.

A compound of Formula 103A corresponds to Formula 103 wherein each of —A—A— and —B—B— is —CH$_2$—CH$_2$—, and $R^3$ is hydrogen. Compounds within the scope of Formula 103 may be prepared by reaction of a corresponding compound of Formula 102 with a dialkyl malonate in the presence of a base such as an alkali metal alkoxide.

A compound of Formula 102 corresponds to the structure:

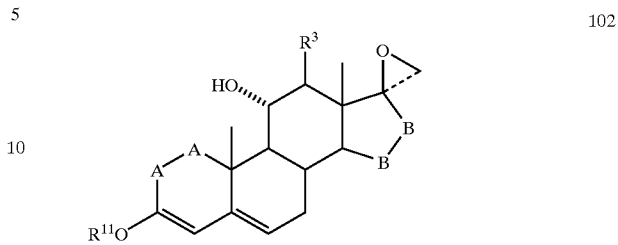

wherein —A—A—, —B—B—, $R^3$ and $R^{11}$ are as defined in Formula 104.

A compound of Formula 102A corresponds to Formula 102 wherein each of —A—A— and —B—B— is —CH$_2$—CH$_2$—, and $R^3$ is hydrogen. Compounds within the scope of Formula 102 may be prepared by reaction of a corresponding compound of Formula 101 with a trialkyl sulfonium compound in the presence of a base.

A compound of Formula 101 corresponds to the structure:

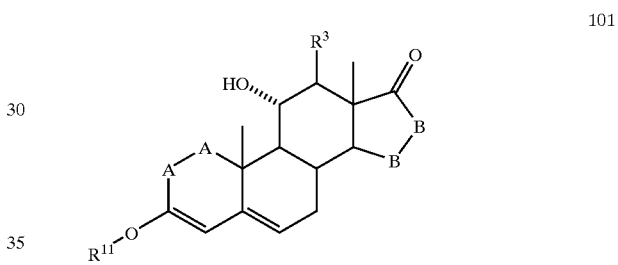

wherein —A—A—, —B—B—, $R^3$ and $R^{11}$ are as defined in Formula 104.

A compound of Formula 101A corresponds to Formula 101 wherein each of —A—A— and —B—B— is —CH$_2$—CH$_2$—, and $R^3$ is hydrogen. Compounds within the scope of Formula 101 may be prepared by reaction of 11α-hydroxyandrostene-3,17-dione or other compound of Formula XXXVI with a trialkyl orthoformate in the presence of an acid.

A compound of Formula XL corresponds to the Formula:

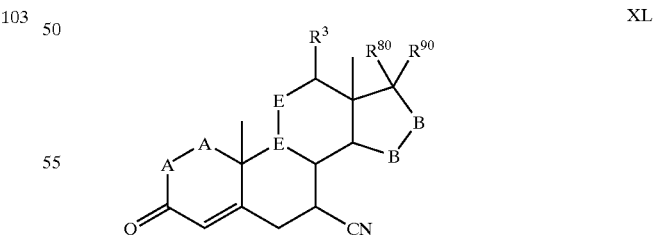

wherein —E—E— is selected from among:

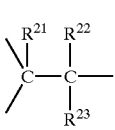

-continued

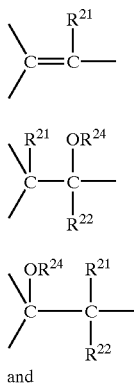

XLIV

XLV

XLVI and

XLVII $R^{21}$, $R^{22}$ and $R^{23}$ are independently selected from among hydrogen, alkyl, halo, nitro, and cyano; $R^{24}$ is selected from among hydrogen and lower alkyl; $R^{80}$ and $R^{90}$ are independently selected from keto and the substituents that may constitute $R^8$ and $R^9$ (as defined hereinabove with reference to Formula IV); and —A—A—, —B—B— and $R^3$ are as defined in Formula IV.

A compound of Formula XLA corresponds to Formula XL wherein $R^{21}$, $R^{22}$ and $R^{23}$ are independently selected from among hydrogen, halogen and lower alkyl.

A compound of Formula XLB corresponds to Formula XLA wherein —E—E— corresponds to Formula XLIII, XLIV, XLV or XLVII. A compound of Formula XLC corresponds to Formula XLB wherein —E—E— corresponds to Formula XLV. A compound of XLD corresponds to Formula XLB wherein —E—E— corresponds to Formula XLVII.

A compound of Formula XLE corresponds to Formula XL wherein $R^{80}$ and $R^{90}$ together with the ring carbon atom to which they are attached comprise keto or:

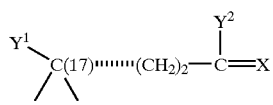

XXXIV where X, $Y^1$, $Y^2$ and C(17) are as defined above, or

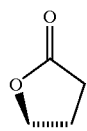

XXXIII

Compounds of Formula XLIE correspond to Formula XL in which $R^{80}$ and $R^{90}$ together form keto.

Compounds of Formulae XLF, XLG, XLH, XLJ, XLM, and XLN correspond to Formula XL, XLA, XLB, XLC, XLD and XLE, respectively, in which —A—A—, —B—B— and $R^3$ are as defined above.

A compound of Formula XLI corresponds to the Formula:

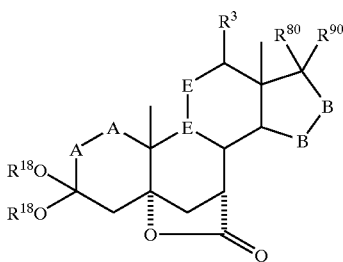

XLI (see scheme 9)
XLI wherein —E—E— is selected from among:

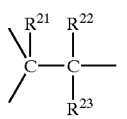

XLIII

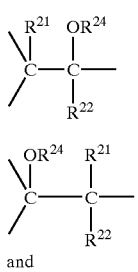

XLV

XLVI and

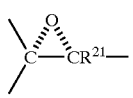

XLVII $R^{18}$ is $C_1$ to $C_4$ alkyl or the $R^{18}O$-groups together form an O,O-oxyalkylene bridge; $R^{21}$, $R^{22}$ and $R^{23}$ are independently selected from among hydrogen, alkyl, halo, nitro, and cyano; $R^{24}$ is selected from among hydrogen and lower alkyl; $R^{80}$ and $R^{90}$ are independently selected from keto and the substituents that may constitute $R^8$ and $R^9$; and —A—A—, —B—B— and $R^3$ are as defined in Formula IV.

A compound of Formula XLIA corresponds to Formula XLI wherein $R^{21}$, $R^{22}$ and $R^{23}$ are independently selected from among hydrogen, halogen, and lower alkyl.

A compound of Formula XLIB corresponds to Formula XLIA wherein —E—E— corresponds to Formula XLIII, XLIV, XLV or XLVII.

A compound of Formula XLIC corresponds to Formula XLI wherein $R^{80}$ and $R^{90}$ together with the ring carbon atom to which they are attached comprise keto or:

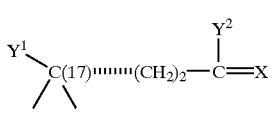

XXXIV where X, $Y^1$, $Y^2$ and C(17) are as defined above.

Compounds of Formulae XLID correspond to Formula XLI in which the substituent XXXIV corresponds to the structure XXXIII

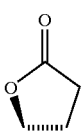

XXXIII

Compounds of Formula XLIE correspond to Formula XL in which $R^{80}$ and $R^{90}$ together form keto.

Compounds of Formulae XLIF, XLIG, XLIH, XLIJ, XLIM, and XLIN correspond to Formula XLI, XLIA, XLIB, XLIC, XLID and XLIE, respectively, in which —A—A—, —B—B— and $R^3$ are as defined above. Compounds within the scope of Formula XLI are prepared by hydrolysis of corresponding compounds of Formula XL as defined hereinbelow.

A compound of Formula XLII corresponds to the Formula:

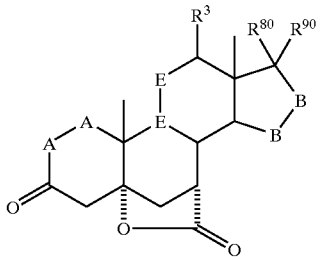

XLII wherein —E—E— is selected from among:

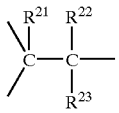

XLIII

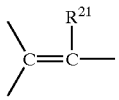

XLIV

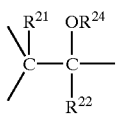

XLV

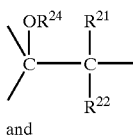

XLVI and

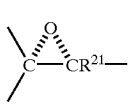

XLVII $R^{21}$, $R^{22}$ and $R^{23}$ are independently selected from among hydrogen, alkyl, halo, nitro, and cyano; $R^{24}$ is selected from among hydrogen and lower alkyl; $R^{80}$ and $R^{90}$ are independently selected from keto and the substituents that may constitute $R^8$ and $R^9$; and —A—A—, —B—B— and $R^3$ are as defined in Formula IV.

A compound of Formula XLIIA corresponds to Formula XLII wherein $R^{21}$, $R^{22}$ and $R^{23}$ are independently selected from among hydrogen, halogen and lower alkyl.

A compound of Formula XLIIB corresponds to Formula XLIIA wherein —E—E— corresponds to Formula XLIII, XLIV, XLV or XLVII.

A compound of Formula XLIIC corresponds to Formula XLII wherein $R^{80}$ and $R^{90}$ together with the ring carbon to which they are attached comprise keto or:

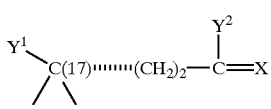

XXXIV where X, $Y^1$, $Y^2$ and C(17) are as defined above.

Compounds of Formulae XLIID correspond to Formula XLII in which the substituent XXXIV corresponds to the structure XXXIII

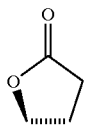

XXXIII

Compounds of Formula XLIIE correspond to Formula XLII in which $R^{80}$ and $R^{90}$ together form keto. Compounds of Formulae XLIIF, XLIIG, XLIIH, XLIIJ, XLIIM and XLIIN correspond to Formulae XLII, XLIIA, XLIIB, XLIIC, XLIID and XLIIE, respectively, in which —A—A— and —B—B— are —CH$_2$—CH$_2$ and $R^3$ is hydrogen. Compounds within the scope of Formula XLII are prepared by deprotecting a corresponding compound of Formula XLI.

A compound of the Formula XLIX corresponds to the structure:

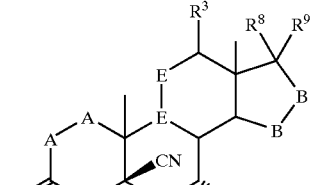

XLIX wherein —E—E— is as defined in Formula XL, and —A—A—, —B—B—, $R^1$, $R^3$, $R^8$ and $R^9$ are as defined in Formula IV.

A compound of Formula XLIXA corresponds to Formula XLIX wherein $R^8$ and $R^9$ with the ring carbon to which they are attached together form the structure:

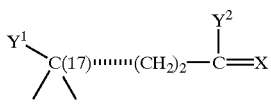

XXXIV where X, $Y^1$, $Y^2$ and C(17) are as defined above.

A compound of Formula XLIXB corresponds to Formula XLIX wherein $R^8$ and $R^9$ together form the structure of Formula XXXIII:

XXXIII

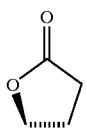

Compounds of Formulae XLIXC, XLIXD, XLIXE, respectively, correspond to any of Formula XLIX, XLIXA or XLIXB wherein each of —A—A— and —B—B— is —CH$_2$—CH$_2$—, R$^3$ is hydrogen and R$^1$ is alkoxycarbonyl, preferably methoxycarbonyl. Compounds within the scope of Formula XLIX may be prepared by reacting an alcoholic or aqueous solvent with a corresponding compound Formula VI in the presence of a suitable base.

A compound of Formula A203 corresponds to the structure:

[A203]

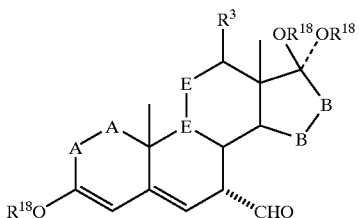

wherein —E—E— is selected from among:

XLIII

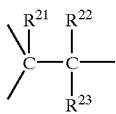

XLV

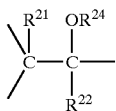

XLVI

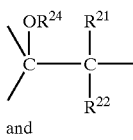

and

XLVII

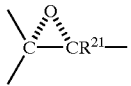

R$^{18}$ is selected from among C$_1$ to C$_4$ alkyl; R$^{21}$, R$^{22}$ and R$^{23}$ are independently selected from among hydrogen, alkyl, halo, nitro, and cyano; R$^{24}$ is selected from among hydrogen and lower alkyl; and —A—A—, —B—B— and R$^3$ are as defined in Formula IV.

A compound of Formula A203A corresponds to Formula A203 wherein R$^{21}$, R$^{22}$ and R$^{23}$ are independently selected from among hydrogen, halogen, and lower alkyl.

A compound of Formula A203B corresponds to Formula A203A wherein —E—E— corresponds to Formula XLIII, XLIV, XLV or XLVII.

Compounds of Formulae A203C, A203D, and A203E respectively correspond to Formula A203, A203A and A203B wherein each of —A—A— and —B—B— is —CH$_2$—CH$_2$—, and R$^3$ is hydrogen. Compounds within the scope of Formula A203 are prepared by reducing a compound of Formula A202 as defined hereinbelow.

A compound of Formula A204 corresponds to the structure:

[A204]

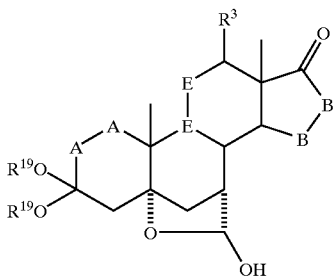

wherein R$^{19}$ is C$_1$ to C$_4$ alkyl, and —E—E—, —A—A—, —B—B— and R$^3$ are as defined in Formula 203.

A compound of Formula A204A corresponds to Formula A204 wherein R$^{21}$, R$^{22}$ and R$^{23}$ are independently selected from among hydrogen, halogen, and lower alkyl.

A compound of Formula A204B corresponds to Formula A204A wherein —E—E— corresponds to Formula XLIII, XLIV, XLV or XLVII.

Compounds of Formulae A204C, A204D, and A204E respectively correspond to Formulae A204, A204A, and A204B wherein each of —A—A— and —B—B— is —CH$_2$—CH$_2$—, and R$^3$ is hydrogen. Compounds within the scope of Formula A204 are prepared by hydrolysis of corresponding compounds of Formula A203.

A compound of Formula A205 corresponds to the structure:

[A205]

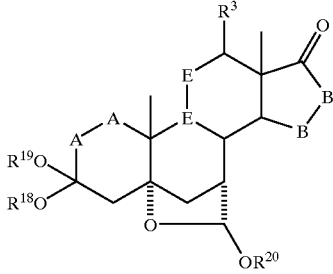

wherein R$^{20}$ is C$_1$ to C$_4$ alkyl, and —E—E—, R$^{19}$, —A—A—, —B—B— and R$^3$ are as defined in Formula 204.

A compound of Formula A205A corresponds to Formula A205 wherein R$^{21}$, R$^{22}$ and R$^{23}$ are independently selected from among hydrogen, halogen, and lower alkyl.

A compound of Formula A205B corresponds to Formula A205A wherein —E—E— corresponds to Formula XLIII, XLIV, XLV or XLVII.

Compounds of Formulae A205C, A205D and A205E respectively correspond to Formula A205, A205A and A205B wherein each of —A—A— and —B—B— is —CH$_2$—CH$_2$—, and R$^3$ is hydrogen. Compounds within the scope of Formula A205 may be prepared by reacting a corresponding compound of Formula A204 with an alkanol and acid.

A compound of Formula A206 corresponds to the structure:

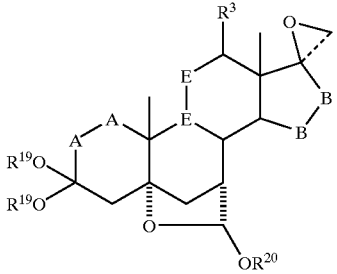

[A206]

wherein $R^{19}$, $R^{20}$, —E—E—, —A—A—, —B—B— and $R^3$ are as defined in Formula 205.

A compound of Formula A206A corresponds to Formula A206 wherein $R^{21}$, $R^{22}$ and $R^{23}$ are independently selected from among hydrogen, halogen, and lower alkyl.

A compound of Formula A206B corresponds to Formula A206A wherein —E—E— corresponds to Formula XLIII, XLIV, XLV or XLVII.

Compounds of Formulae A206C, A206D and A206E respectively correspond to Formula A206, A206A, and A206B wherein each of —A—A— and —B—B— is —CH$_2$—CH$_2$—, and $R^3$ is hydrogen. Compounds within the scope of Formula A206 may be prepared by reacting a corresponding compound within the scope of Formula A205 with a trialkyl sulfonium halide.

A compound of Formula A207 corresponds to the structure:

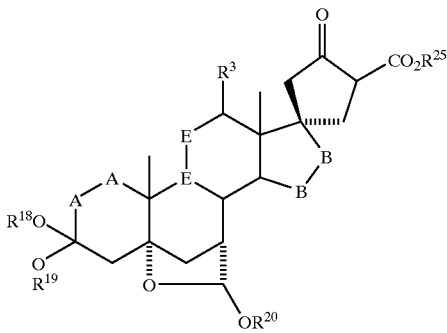

[A207]

wherein $R^{25}$ is $C_1$ to $C_4$ alkyl, and —E—E—, $R^{19}$, $R^{20}$, —A—A—, —B—B— and $R^3$ are as defined in Formula A205.

A compound of Formula A207A corresponds to Formula A207 wherein $R^{21}$, $R^{22}$ and $R^{23}$ are independently selected from among hydrogen, halogen, and lower alkyl.

A compound of Formula A207B corresponds to Formula A207A wherein —E—E— corresponds to Formula XLIII, XLIV, XLV or XLVII.

Compounds of Formulae A207C, A207D and A207E respectively correspond to Formula A207, A207A and A207B wherein each of —A—A— and —B—B— is —CH$_2$—CH$_2$—, and $R^3$ is hydrogen. Compounds of Formula A207 can be prepared by reaction of compounds of Formula A206 with a dialkyl malonate.

A compound of Formula A208 corresponds to the structure:

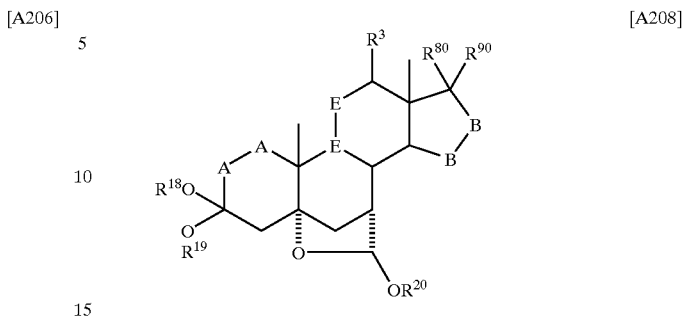

[A208]

wherein —E—E—, $R^{80}$ and $R^{90}$ are as defined in Formula XLII; —A—A—, —B—B— and $R^3$ are as defined in Formula 104; and $R^{19}$, $R^{20}$, —A—A—, —B—B—, and $R^3$ are as defined in Formula 205.

A compound of Formula A208A corresponds to Formula A208 wherein $R^{21}$ and $R^{22}$ are independently selected from among hydrogen, halogen, and lower alkyl.

A compound of Formula A208B corresponds to Formula A208A wherein —E—E— corresponds to Formula XLIII, XLIV, XLV or XLVII.

A compound of Formula A208C corresponds to Formula A208 wherein $R^{80}$ and $R^{90}$ together with the ring carbon to which they are attached comprise keto or:

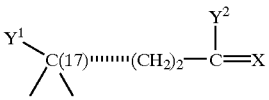

XXXIV where X, $Y^1$, $Y^2$ and C(17) are as defined above.

Compounds of Formulae 208D correspond to Formula 208C in which the substituent XXXIV corresponds to the structure XXXIII

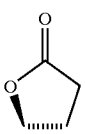

XXXIII

Compounds of Formulae A208E, A208F, A208G, A208H and A208J respectively correspond to Formula A208, A208A, A208B, A208C and A208D wherein each of —A—A— and —B—B— is —CH$_2$—CH$_2$—, and $R^3$ is hydrogen. Compounds within the scope of Formula A208 can be prepared by thermal decomposition of corresponding compounds of Formula A207.

A compound of Formula A209 corresponds to the structure:

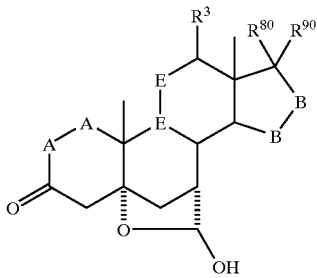

[A209]

wherein $R^{80}$ and $R^{90}$ are as defined in Formula XLI, and —E—E— and —A—A—, —B—B—, and $R^3$ are as defined in Formula 205.

A compound of Formula A209A corresponds to Formula A209 wherein $R^{21}$ and $R^{22}$ are independently selected from among hydrogen, halogen, and lower alkyl.

A compound of Formula A209B corresponds to Formula A209A wherein —E—E— corresponds to Formula XLIII, XLIV, XLV or XLVII.

A compound of Formula A209C corresponds to Formula A209B wherein —E—E— corresponds to Formula XLIV.

A compound of Formula A209D corresponds to Formula A208 wherein $R^{80}$ and $R^{90}$ together with the ring carbon to which they are attached comprise keto or:

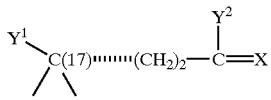

XXXIV where X, $Y^1$, $Y^2$ and C(17) are as defined above.

Compounds of Formulae 209E correspond to Formula A209D in which the substituent XXXIV corresponds to the structure XXXIII

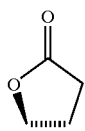

XXXIII

Compounds of Formulae A209F, A209G, A209H, A209J, A209L, and A209M respectively correspond to Formula A209, A209A, A209B, A209C, A209D and A209E wherein each of —A—A— and —B—B— is —CH$_2$—CH$_2$—, and $R^3$ is hydrogen. Compounds within the scope of Formula A209 may be prepared by hydrolysis of a corresponding compound of Formula A208.

A compound of Formula A210 corresponds to the structure:

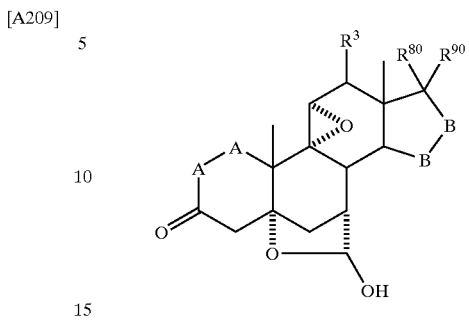

[A210]

wherein $R^{80}$ and $R^{90}$ are as defined in Formula XLI, and the substituents —A—A—, —B—B— and $R^3$ are as defined in Formula IV.

A compound of Formula A210A corresponds to Formula A210 wherein $R^{80}$ and $R^{90}$ together with the ring carbon to which they are attached comprise keto or:

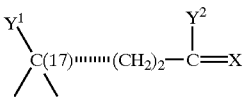

XXXIV wherein X, $Y^{1,}$ $^{Y2}$ and C(17) are as defined above.

Compounds of Formulae A210B correspond to Formula A210A in which the substituent XXXIV corresponds to the structure XXXIII

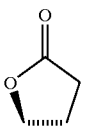

XXXIII

Compounds of Formula A210C correspond to Formula A210A in which $R^{80}$ and $R^{90}$ together form keto.

Compounds of Formulae A210D, A210E, A210F and A210G respectively correspond to Formula A210, A210A, A210B and A210C wherein each of —A—A— and —B—B— is —CH$_2$—CH$_2$— and and $R^3$ is hydrogen. Compounds within the scope of Formula 210 can be prepared by epoxidation of a compound of Formula 209 in which —E—E— is

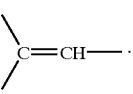

A compound of Formula A211 corresponds to the Formula

[A211]

where —A—A—, —B—B— and $R^3$ are as described above.

A compound of Formula A211A corresponds to Formula A211 wherein $R^{80}$ and $R^{90}$ together comprise keto or:

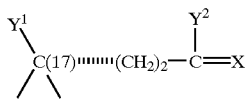

XXXIV wherein X, $Y^1$, $Y^2$ and C(17) are as defined above.

Compounds of Formulae A211B correspond to Formula A211A in which the substituent XXXIV corresponds to the structure XXXIII

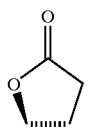

XXXIII

Compounds of Formula A211C correspond to Formula A210A in which $R^{80}$ and $R^{90}$ together form keto.

Compounds of Formulae A211D, A211E, A211F, and A211G, respectively correspond to Formula A211, A211A, A211B and A211C wherein each of —A—A— and —B—B— is —$CH_2$—$CH_2$—, and $R^3$ is hydrogen. Compounds within the scope of Formula A211 can be prepared by oxidation of a corresponding compound of Formula A210, or in the course of epoxidation of the corresponding compound of Formula A209 where —E—E— is

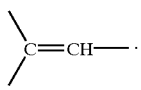

Compounds of Formula A211 may be converted to compounds of Formula I in the manner described hereinbelow.

A compound of Formula L corresponds to the structure:

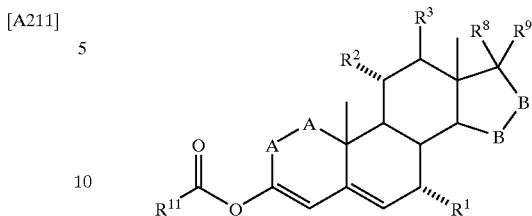

L wherein $R^{11}$ is $C_1$ to $C_4$ alkyl, and —A—A—, —B—B—, $R^1$, $R^2$, $R^3$, $R^8$ and $R^9$ are as defined above.

Compounds of Formula LA correspond to Formula L wherein $R^8$ and $R^9$ together with the carbon atom to which they are attached comprises

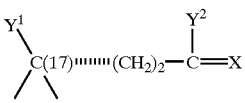

XXXIV wherein X, $Y^1$ and $Y^2$ are as defined above.

Compounds of Formula LB correspond to Formula L wherein $R^8$ and $R^9$ correspond to Formula XXXIII

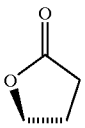

XXXIII

Compounds of Formulae LC, LD, LE correspond to Formulae L, LA and LB, respectively, where —A—A— and —B—B— are each —$CH_2$—$CH_2$— and $R^3$ is hydrogen.

Based on the disclosure of specific reaction schemes as set out hereinbelow, it will be apparent which of these compounds have the greatest utility relative to a particular reaction scheme. The compounds of this invention are useful as intermediates for epoxymexrenone and other steroids.

Other objects and features will be in part apparent and in part pointed out hereinafter.

BRIEF DESCRIPTION OF THE DRAWINGS

Corresponding reference characters indicate corresponding parts throughout the drawings.

DESCRIPTION OF THE PREFERRED EMBODIMENTS

Figure 1:
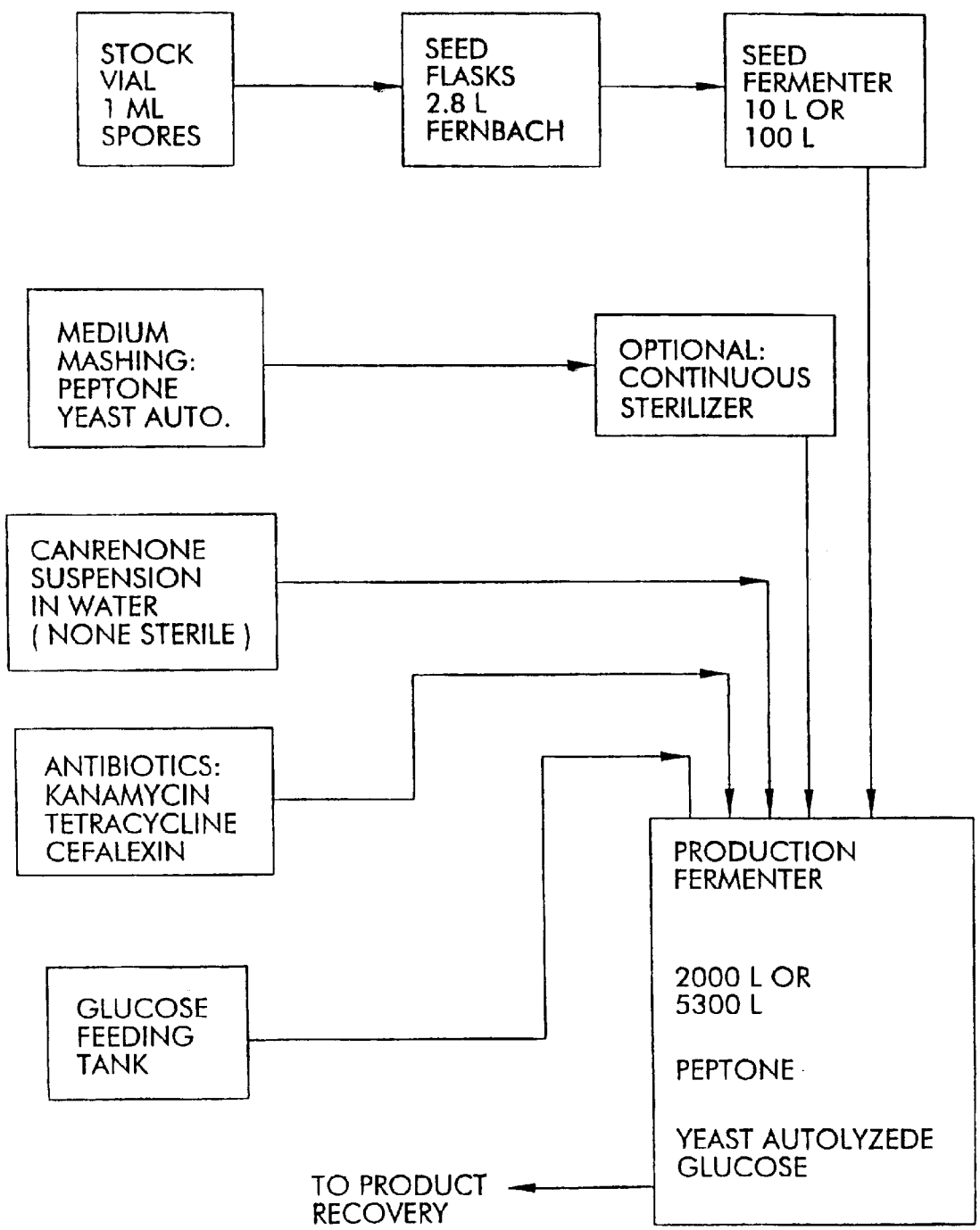
FIG. 1 is a schematic flow sheet of a process for the bioconversion of canrenone or a canrenone derivative to the corresponding 11α-hydroxy compound.

In accordance with the present invention, various novel process schemes have been devised for the preparation of epoxymexrenone and other compounds corresponding Formula I:

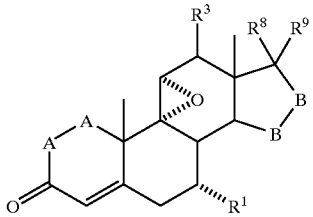

wherein:
—A—A— represents the group —CHR$^4$—CHR$^5$— or —CR$^4$=CR$^5$—;
R$^3$, R$^4$ and R$^5$ are independently selected from the group consisting of hydrogen, halo, hydroxy, lower alkyl, lower alkoxy, hydroxyalkyl, alkoxyalkyl, hydroxycarbonyl, cyano and aryloxy;
R$^1$ represents an alpha-oriented lower alkoxycarbonyl or hydroxyalkyl radical; and
—B—B— represents the group —CHR$^6$—CHR$^7$— or an alpha- or beta-oriented group:

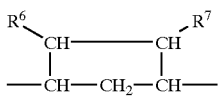

where
R$^6$ and R$^7$ are independently selected from the group consisting of hydrogen, halo, lower alkoxy, acyl, hydroxyalkyl, alkoxyalkyl, hydroxycarbonyl, alkyl, alkoxycarbonyl, acyloxyalkyl, cyano and aryloxy; and
R$^8$ and R$^9$ are independently selected from the group consisting of hydrogen, hydroxy, halo, lower alkoxy, acyl, hydroxyalkyl, alkoxyalkyl, hydroxycarbonyl, alkyl, alkoxycarbonyl, acyloxyalkyl, cyano and aryloxy, or R$^8$ and R$^9$ together comprise a carbocyclic or heterocyclic ring structure, or R$^8$ or R$^9$ together with R$^6$ or R$^7$ comprise a carbocyclic or heterocyclic ring structure fused to the pentacyclic D ring.

Unless stated otherwise, organic radicals referred to as "lower" in the present disclosure contain at most 7, and preferably from 1 to 4, carbon atoms.

A lower alkoxycarbonyl radical is preferably one derived from an alkyl radical having from 1 to 4 carbon atoms, such as methyl, ethyl, propyl, isopropyl, butyl, isobutyl, sec.-butyl and tert.-butyl; especially preferred are methoxycarbonyl, ethoxycarbonyl and isopropoxycarbonyl. A lower alkoxy radical is preferably one derived from one of the above-mentioned C$_1$–C$_4$ alkyl radicals, especially from a primary C$_1$–C$_4$ alkyl radical; especially preferred is methoxy. A lower alkanoyl radical is preferably one derived from a straight-chain alkyl having from 1 to 7 carbon atoms; especially preferred are formyl and acetyl.

A methylene bridge in the 15,16-position is preferably β-oriented.

A preferred class of compounds that may be produced in accordance with the methods of the invention are the 20-spiroxane compounds described in U.S. Pat. No. 4,559,332, i.e., those corresponding to Formula IA:

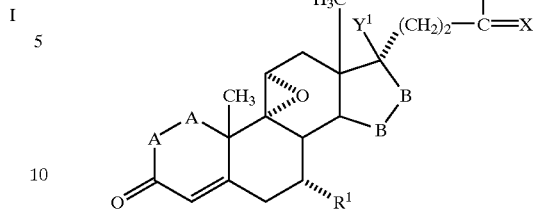

where:
—A—A— represents the group —CH$_2$—CH$_2$— or —CH=CH—;
—B—B— represents the group —CH$_2$—CH$_2$— or an alpha- or beta-oriented group of Formula IIIA:

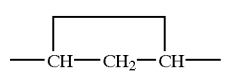

R$^1$ represents an alpha-oriented lower alkoxycarbonyl or hydroxycarbonyl radical;
X represents two hydrogen atoms, oxo or =S;
Y$^1$ and Y$^2$ together represent the oxygen bridge —O—, or
Y$^1$ represents hydroxy, and
Y$^2$ represents hydroxy, lower alkoxy or, if X represents H$_2$, also lower alkanoyloxy.

Preferably, 20-spiroxane compounds produced by the novel methods of the invention are those of Formula I in which Y$^1$ and Y$^2$ together represent the oxygen bridge —O—.

Especially preferred compounds of the formula I are those in which X represents oxo. Of compounds of the 20-spiroxane compounds of Formula IA in which X represents oxo, there are most especially preferred those in which Y$^1$ together with Y$^2$ represents the oxygen bridge —O—.

As already mentioned, 17β-hydroxy-21-carboxylic acid may also be in the form of their salts. There come into consideration especially metal and ammonium salts, such as alkali metal and alkaline earth metal salts, for example sodium, calcium, magnesium and, preferably, potassium salts, and ammonium salts derived from ammonia or a suitable, preferably physiologically tolerable, organic nitrogen-containing base. As bases there come into consideration not only amines, for example lower alkylamines (such as triethylamine), hydroxy-lower alkylamines (such as 2-hydroxyethylamine, di-(2-hydroxyethyl)-amine or tri-(2-hydroxyethyl)-amine), cycloalkylamines (such as dicyclohexylamine) or benzylamines (such as benzylamine and N,N'-dibenzylethylenediamine), but also nitrogen-containing heterocyclic compounds, for example those of aromatic character (such as pyridine or quinoline) or those having an at least partially saturated heterocyclic ring (such as N-ethylpiperidine, morpholine, piperazine or N,N'-dimethylpiperazine).

Also included amongst preferred compounds are alkali metal salts, especially potassium salts, of compounds of the formula IA in which R$^1$ represents alkoxycarbonyl, with X representing oxo and each of Y$^1$ and Y$^2$ representing hydroxy.

Especially preferred compounds of the formula I and IA are, for example, the following:
9α,11α-epoxy-7α-methoxycarbonyl-20-spirox-4-ene-3,21-dione, 9α,11α-epoxy-7α-ethoxycarbonyl-20-spirox-4-ene-3,21-dione,
9α,11α-epoxy-7α-isopropoxycarbonyl-20-spirox-4-ene-3,21-dione,
and the 1,2-dehydro analogue of each of the compounds;
9α,11α-epoxy-6α,7α-methylene-20-spirox-4-ene-3,21-dione,
9α,11α-epoxy-6β,7β-methylene-20-spirox-4-ene-3,21-dione,
9α,11α-epoxy-6β,7β;15β,16β-bismethylene-20-spirox-4-ene-3,21-dione,
and the 1,2-dehydro analogue of each of these compounds;
9α,11α-epoxy-7α-methoxycarbonyl-17β-hydroxy-3-oxo-pregn-4-ene-21-carboxylic acid,
9α,11α-epoxy-7α-ethoxycarbonyl-17β-hydroxy-3-oxo-pregn-4-ene-21-carboxylic acid,
9α,11α-epoxy-7α-isopropoxycarbonyl-17β-hydroxy-3-oxo-pregn-4-ene-21-carboxylic acid,
9α,11α-epoxy-17β-hydroxy-6α,7α-methylene-3-oxo-pregn-4-ene-21-carboxylic acid,
9α,11α-epoxy-17β-hydroxy-6β,7β-methylene-3-oxo-pregn-4-ene-21-carboxylic acid,
9α,11α-epoxy-17β-hydroxy-6β,7β;15β,16β-bismethylene-3-oxo-pregn-4-ene-21-carboxylic acid,
and alkali metal salts, especially the potassium salt or ammonium of each of these acids, and also a corresponding 1,2-dehydro analogue of each of the mentioned carboxylic acids or of a salt thereof;
9α,11α-epoxy-15β,16β-methylene-3,21-dioxo-20-spirox-4-ene-7α-carboxylic acid methyl ester, ethyl ester and isopropyl ester,
9α,11α-epoxy-1565β,16β-methylene-3,21-dioxo-20-spiroxa-1,4-diene-7α-carboxylic acid methyl ester, ethyl ester and isopropyl ester,
9α,11α-epoxy-3-oxo-20-spirox-4-ene-7α-carboxylic acid methyl ester, ethyl ester and isopropyl ester,
9α,11α-epoxy-6β,6β-methylene-20-spirox-4-en-3-one,
9α,11α-epoxy-6β,7β;15β,16β-bismethylene-20-spirox-4-en-3-one,
9α,11α-epoxy,17β-hydroxy-17α(3-hydroxy-propyl)-3-oxo-androst-4-ene-7α-carboxylic acid methyl ester, ethyl ester and isopropyl ester,
9α,11α-epoxy,17β-hydroxy-17α-(3-hydroxypropyl)-6α,7α-methylene-androst-4-en-3-one,
9α,11α-epoxy-17β-hydroxy-17α-(3-hydroxypropyl)-6β,7β-methylene-androst-4-en-3-one,
9α,11α-epoxy-17β-hydroxy-17α-(3-hydroxypropyl)-6β,7β;15β,16β-bismethylene-androst-4-en-3-one,
including 17α-(3-acetoxypropyl) and 17α-(3-fromyloxypropyl) analogues of the mentioned androstane compounds,
and also 1,2-dehydro analogues of all the mentioned compounds of the androst-4-en-3-one and 20-spirox-4-en-3-one series.

The chemical names of the compounds of the Formulae I and IA, and of analogue compounds having the same characteristic structural features, are derived according to current nomenclature in the following manner: for compounds in which $Y^1$ together with $Y^2$ represents —O—, from 20-spiroxane (for example a compound of the formula IA in which X represents oxo and $Y^1$ together with $Y^2$ represents —O— is derived from 20-spiroxan-21-one); for those in which each of $Y^1$ and $Y^2$ represents hydroxy and X represents oxo, from 17β-hydroxy-17α-pregnene-21-carboxylic acid; and for those in which each of $Y^1$ and $Y^2$ represents hydroxy and X represents two hydrogen atoms, from 17β-hydroxy-17α-(3-hydroxypropyl)-androstane.

Since the cyclic and open-chain forms, that is to say lactones and 17β-hydroxy-21-carboxylic acids and their salts, respectively, are so closely related to each other that the latter may be considered merely as a hydrated form of the former, there is to be understood hereinbefore and hereinafter, unless specifically stated otherwise, both in end products of the formula I and in starting materials and intermediates of analogous structure, in each case all the mentioned forms together.

In accordance with the invention, several separate process schemes have been devised for the preparation of compounds of Formula I in high yield and at reasonable cost. Each of the synthesis schemes proceeds through the preparation of a series of intermediates. A number of these intermediates are novel compounds, and the methods of preparation of these intermediates are novel processes.

Scheme 1 (Starting with Canrenone or Related Material)

One preferred process scheme for the preparation of compounds of Formula I advantageously begins with canrenone or a related starting material corresponding to Formula XIII (or, alternatively, the process can begin with androstendione or a related starting material)

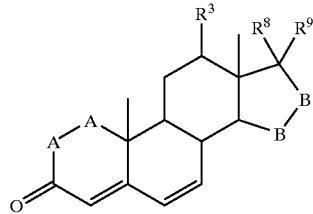

XIII wherein

—A—A— represents the group —CHR$^4$—CHR$^5$— or —CR$^4$=CR$^5$—;

$R^3$, $R^4$ and $R^5$ are independently selected from the group consisting of hydrogen, halo, hydroxy, lower alkyl, lower alkoxy, hydroxyalkyl, alkoxyalkyl, hydroxycarbonyl, cyano and aryloxy;

—B—B— represents the group —CHR$^6$—CHR$^7$— or an alpha- or beta-oriented group:

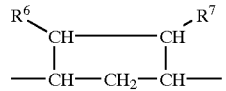

III where $R^6$ and $R^7$ are independently selected from the group consisting of hydrogen, halo, lower alkoxy, acyl, hydroxyalkyl, alkoxyalkyl, hydroxycarbonyl, alkyl, alkoxycarbonyl, acyloxyalkyl, cyano and aryloxy; and $R^8$ and $R^9$ are independently selected from the group consisting of hydrogen, hydroxy, halo, lower alkoxy, acyl, hydroxyalkyl, alkoxyalkyl, hydroxycarbonyl, alkyl, alkoxycarbonyl, acyloxyalkyl, cyano and aryloxy, or $R^8$ and $R^9$ together comprise a keto, carbocyclic or heterocyclic ring structure, or $R^8$ and $R^9$ together with $R^6$ or $R^7$ comprise a carbocyclic or heterocyclic ring structure fused to the pentacyclic D ring.

Figure 2:
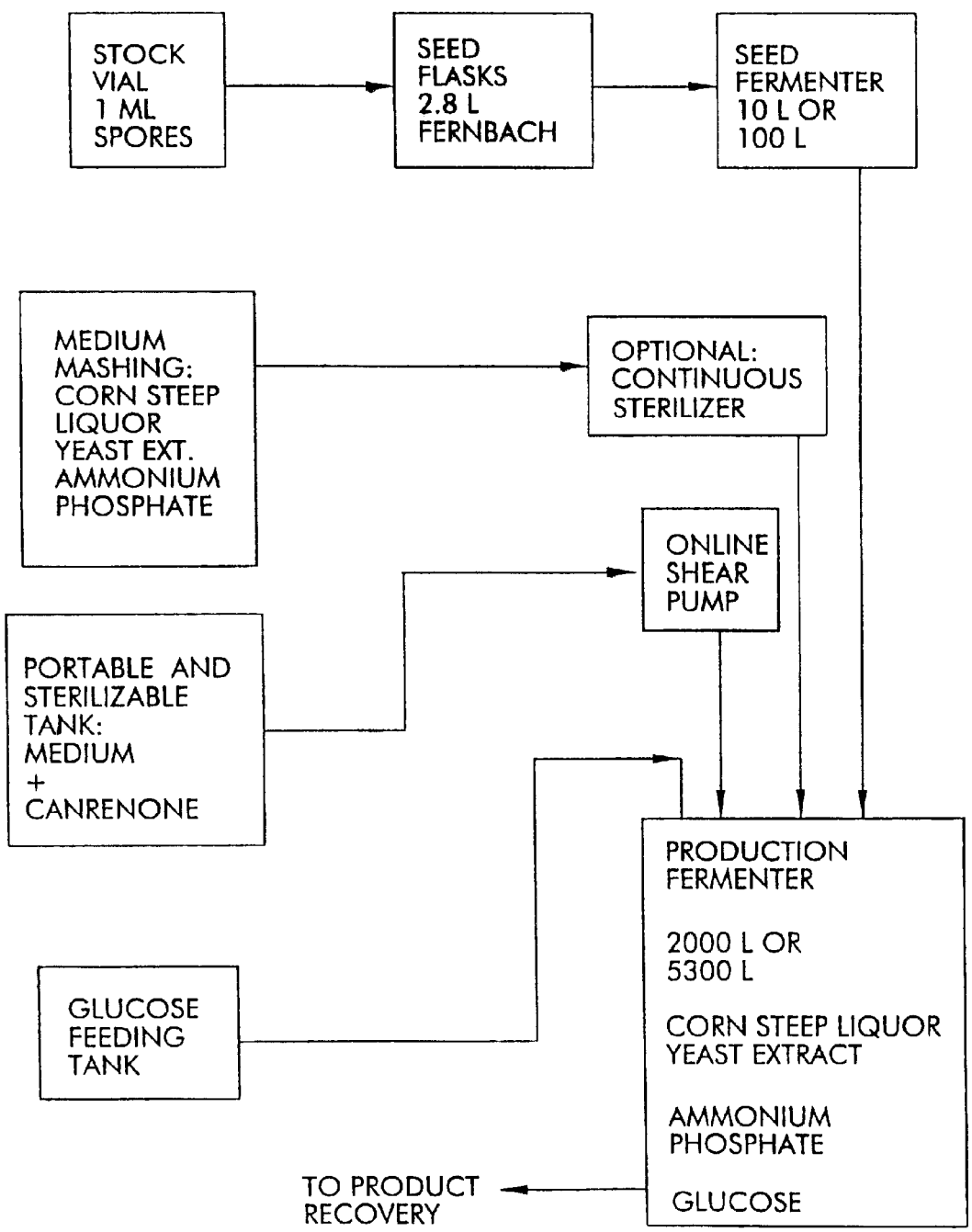
FIG. 2 is a schematic flow sheet of a preferred process for the bioconversion/11-α-hydroxylation of canrenone and canrenone derivatives.

Using a bioconversion process of the type illustrated in FIGS. 1 and 2, an 11-hydroxy group of α-orientation is introduced in the compound of Formula XIII, thereby producing a compound of Formula VIII:

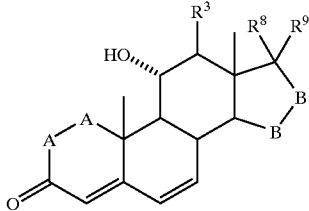

VIII where

—A—A—, —B—B—, $R^3$, $R^8$ and $R^9$ are as defined in Formula XIII. Preferably, the compound of Formula XIII has the structure

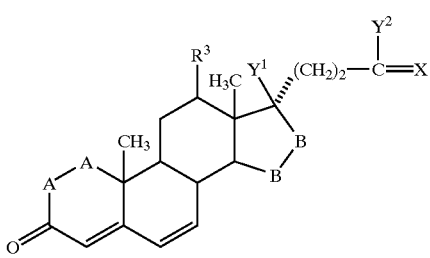

XIIIA and the 11α-hydroxy product has the structure

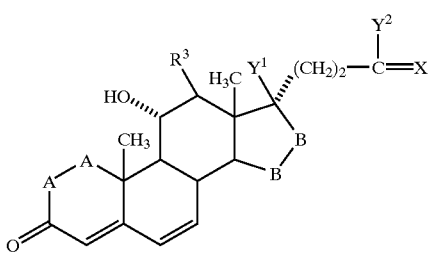

VIIIA in each of which

—A—A— represents the group —CH$_2$—CH$_2$— or —CH=CH—;

—B—B— represents the group —CH$_2$—CH$_2$— or an alpha- or beta-oriented group:

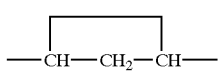

IIIA $R^3$ is hydrogen, lower alkyl or lower alkoxy;

X represents two hydrogen atoms, oxo or =S;

$Y^1$ and $Y^2$ together represent the oxygen bridge —O—, or $Y^1$ represents hydroxy, and $Y^2$ represents hydroxy, lower alkoxy or, if X represents H$_2$, also lower alkanoyloxy;

and salts of compounds in which X represents oxo and $Y^2$ represents hydroxy. More preferably, the compound of Formula VIIIA produced in the reaction corresponds to a compound of Formula VIIIA wherein —A—A— and —B—B— are each —CH$_2$—CH$_2$—; $R^3$ is hydrogen; $Y^1$, $Y^2$, and X are as defined in Formula XIIIA; and $R^8$ and $R^9$ together form the 20-spiroxane structure:

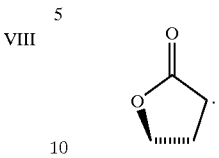

XXXIII

Among the preferred organisms that can be used in this hydroxylation step are *Aspergillus ochraceus* NRRL 405, *Aspergillus ochraceus* ATCC 18500, *Aspergillus niger* ATCC 16888 and ATCC 26693, *Aspergillus nidulans* ATCC 11267, *Rhizopus oryzae* ATCC 11145, *Rhizopus stolonifer* ATCC 6227b, *Streptomyces fradiae* ATCC 10745, *Bacillus megaterium* ATCC 14945, *Pseudomonas cruciviae* ATCC 13262, and *Trichothecium roseum* ATCC 12543. Other preferred organisms include *Fusarium oxysporum* f.sp.cepae ATCC 11171 and *Rhizopus arrhizus* ATCC 11145.

Other organisms that have exhibited activity for this reaction include *Absidia coerula* ATCC 6647, *Absidia glauca* ATCC 22752, *Actinomucor elegans* ATCC 6476, *Aspergillus flavipes* ATCC 1030, *Aspergillus fumigatus* ATCC 26934, *Beauveria bassiana* ATCC 7159 and ATCC 13144, *Botryosphaeria obtusa* IMI 038560, *Calonectria decora* ATCC 14767, *Chaetomium cochliodes* ATCC 10195, *Corynespora cassiicola* ATCC 16718, *Cunninghamella blakesleeana* ATCC 8688a, *Cunninghamella echinulata* ATCC 3655, *Cunninghamella elegans* ATCC 9245, *Curvularia clavata* ATCC 22921, *Curvularia lunata* ACTT 12017, *Cylindrocarpon radicicola* ATCC 1011, *Epicoccum humicola* ATCC 12722, *Gongronella butleri* ATCC 22822, *Hypomyces chrysospermus* ATCC IMI 109891, *Mortierella isabellina* ATCC 42613, *Mucor mucedo* ATCC 4605, *Mucor qriseo-cyanus* ATCC 1207A, *Myrothecium verrucaria* ATCC 9095, *Nocardia corallina* ATCC 19070, *Paecilomyces carneus* ATCC 46579, *Penicillum patulum* ATCC 24550, *Pithomyces atro-olivaceus* IFO 6651, *Pithomyces cynodontis* ATCC 26150, *Pycnosporium sp.* ATCC 12231, *Saccharopolyspora erythrae* ATCC 11635, *Sepedonium chrysospermum* ATCC 13378, *Stachylidium bicolor* ATCC 12672, *Streptomyces hygroscopicus* ATCC 27438, *Streptomyces purpurascens* ATCC 25489, *Syncephalastrum racemosum* ATCC 18192, *Thamnostylum piriforme* ATCC 8992, *Thielavia terricola* ATCC 13807, and *Verticillium theobromae* ATCC 12474.

Additional organisms that may be expected to show activity for the 11α-hydroxylation include *Cephalosporium aphidicola* (Phytochemistry (1996), 42(2), 411–415), *Cochliobolus lunatas* (J. Biotechnol. (1995), 42(2), 145–150), *Tieghemella orchidis* (Khim.-Farm.Zh. (1986), 20(7), 871–876), *Tieghemella hyalospora* (Khim.-Farm.Zh. (1986), 20(7), 871–876), *Monosporium olivaceum* (Acta Microbiol. Pol., Ser. B. (1973), 5(2), 103–110), *Aspergillus ustus* (Acta Microbiol. Pol., Ser. B. (1973), 5(2), 103–110), *Fusarium graminearum* (Acta Microbiol. Pol., Ser. B. (1973), 5(2), 103–110), *Verticillium glaucum* (Acta Microbiol. Pol., Ser. B. (1973), 5(2), 103–110), and *Rhizopus nigricans* (J. Steroid Biochem. (1987), 28(2), 197–201).

The 11β-hydroxy derivatives of androstendione and mexrenone can be prepared according to the bioconversion processes set forth in Examples 19A and 19B, respectively. The inventors hypothesize by analogy that the corresponding β-hydroxy isomer of the compound of Formula VIII having a C11 β-hydroxy substituent instead of a C11

α-hydroxy substituent can also be prepared using a similar bioconversion process employing suitable microorganisms capable of carrying out the 11β-hydroxylation, such as one or more of the microorganisms disclosed herein.

Preparatory to production scale fermentation for hydroxylation of canrenone or other substrates of Formula XIII, an inoculum of cells is prepared in a seed fermentation system comprising a seed fermenter, or a series of two or more seed fermenters. A working stock spore suspension is introduced into the first seed fermenter, together with a nutrient solution for growth of cells. If the volume of inoculum desired or needed for production exceeds that produced in the first seed fermenter, the inoculum volume may be progressively and geometrically amplified by progression through the remaining fermenters in the seed fermentation train. Preferably, the inoculum produced in the seed fermentation system is of sufficient volume and viable cells for achieving rapid initiation of reaction in the production fermenter, relatively short production batch cycles, and high production fermenter activity. Whatever the number of vessels in a train of seed fermenters, the second and subsequent seed fermenters are preferably sized so that the extent of dilution at each step in the train is essentially the same. The initial dilution of inoculum in each seed fermenter can be approximately the same as the dilution in the production fermenter. Canrenone or other Formula XIII substrate is charged to the production fermenter along with inoculum and nutrient solution, and the hydroxylation reaction conducted there.

The spore suspension charged to the seed fermentation system is from a vial of working stock spore suspension taken from a plurality of vials constituting a working stock cell bank that is stored under cryogenic conditions prior to use. The working stock cell bank is in turn derived from a master stock cell bank that has been prepared in the following manner. A spore specimen obtained from an appropriate source, e.g., ATCC, is initially suspended in an aqueous medium such as, for example, saline solution, nutrient solution or a surfactant solution, (e.g., a nonionic surfactant such as Tween 20 at a concentration of about 0.001% by weight), and the suspension distributed among culture plates, each plate bearing a solid nutrient mixture, typically based on a non-digestible polysaccharide such as agar, where the spores are propagated. The solid nutrient mixture preferably contains between about 0.5% and about 5% by weight glucose, between about 0.05% and about 5% by weight of a nitrogen source, e.g., peptone, between about 0.05% and about 0.5% by weight of a phosphorus source, e.g., an ammonium or alkali metal phosphate such as dipotassium hydrogen phosphate, between about 0.25% and about 2.5% by weight yeast lysate or extract (or other amino acid source such as meat extract or brain heart infusion), between about 1% and about 2% by weight agar or other non-digestible polysaccharide. Optionally, the solid nutrient mixture may further comprise and/or contain between about 0.1% and about 5% by weight malt extract. The pH of the solid nutrient mixture is preferably between about 5.0 and about 7.0, adjusted as required by alkali metal hydroxide or orthophosphoric acid. Among useful solid growth media are the following;

| | |
|---|---|
| 1. Solid Medium #1: | 1% glucose, 0.25% yeast extract, 0.3% $K_2HPO_4$, and 2% agar (Bacto); pH adjusted to 6.5 with 20% NaOH. |
| 2. Solid Medium #2: | 2% peptone (Bacto), 1% yeast extract (Bacto), 2% glucose, and 2% agar (Bacto); pH adjusted to 5 with 10% $H_3PO_4$. |
| 3. Solid Medium #3: | 0.1% peptone (Bacto), 2% malt extract (Bacto), 2% glucose, and 2% agar (Bacto); pH as is 5.3. |
| 4. Liquid Medium: | 5% blackstrap molasses, 0.5% cornsteep liquor, 0.25% glucose, 0.25% NaCl, and 0.5% $KH_2PO_4$, pH adjusted to 5.8. |
| 5. Difco Mycological agar (low pH). | |

The number of agar plates used in the development of a master stock cell bank can be selected with a view to future demands for master stock, but typically about 15 to about 30 plates are so prepared. After a suitable period of growth, e.g., 7 to 10 days, the plates are scraped in the presence of an aqueous vehicle, typically saline or buffer, for harvesting the spores, and the resulting master stock suspension is divided among small vials, e.g., one ml. in each of a plurality of 1.5 ml vials. To prepare a working stock spore suspension for use in research or production fermentation operations, the contents of one or more of these second generation master stock vials can be distributed among and incubated on agar plates in the manner described above for the preparation of master stock spore suspension. Where routine manufacturing operations are contemplated, as many as 100 to 400 plates may be used to generate second generation working stock. Each plate is scraped into a separate working stock vial, each vial typically containing one ml of the inoculum produced. For permanent preservation, both the master stock suspension and the second generation production inoculum are advantageously stored in the vapor space of a cryogenic storage vessel containing liquid $N_2$ or other cryogenic liquid.

In the process illustrated in FIG. 1, aqueous growth medium is prepared which includes a nitrogen source such as peptone, a yeast derivative or equivalent, glucose, and a source of phosphorus such as a phosphate salt. Spores of the microorganism are cultured in this medium in the seed fermentation system. The preferred microorganism is *Aspergillus ochraceus* NRRL 405 (ATCC 18500). The seed stock so produced is then introduced into the production fermenter together with the substrate of Formula XIII. The fermentation broth is agitated and aerated for a time sufficient for the reaction to proceed to the desired degree of completion.

The medium for the seed fermenter preferably comprises an aqueous mixture which contains: between about 0.5% and about 5% by weight glucose, between about 0.05% and about 5% by weight of a nitrogen source, e.g., peptone, between about 0.05% and about 0.5% by weight of a phosphorus source, e.g., an ammonium or alkali metal phosphate such as ammonium phosphate monobasic or dipotassium hydrogen phosphate, between about 0.25% and about 2.5% by weight yeast lysate or extract (or other amino acid source such as distiller's solubles), between about 1% and about 2% by weight agar or other non-digestable polysaccharide. A particularly preferred seed growth medium contains about 0.05% and about 5% by weight of a nitrogen source such as peptone, between about 0.25% and about 2.5% by weight of autolyzed yeast or yeast extract, between about 0.5% and about 5% by weight glucose, and between about 0.05% by weight and about 0.5% by weight of a phosphorus source such as ammonium phosphate monobasic. Especially economical process operations are afforded by the use of another preferred seed culture which contains between about 0.5% and about 5% by weight corn steep liquor, between about 0.25% and about 2.5% autolyzed yeast or yeast extract, between about 0.5% and about 5% by weight glucose and about 0.05% and about 0.5% by weight ammonium phosphate monobasic. Corn steep liquor is a particularly economical source of proteins, peptides, carbohydrates, organic acids, vitamins, metal ions, trace matters and phosphates. Mash liquors from other grains may be used in place of, or in addition to, corn steep liquor. The pH of the medium is preferably adjusted within the range of between about 5.0 and about 7.0, e.g., by addition of an alkali metal hydroxide or orthophosphoric acid. Where corn steep liquor serves as the source of nitrogen and carbon, the pH is preferably adjusted within the range of about 6.2 to about 6.8. The medium comprising peptone and glucose is preferably adjusted to a pH between about 5.4 and about 6.2. Among useful growth media for use in seed fermentation:

| | |
|---|---|
| 1. Medium #1: | 2% peptone, 2% yeast autolyzed (or yeast extract), and 2% glucose; pH adjusted to 5.8 with 20% NaOH. |
| 2. Medium #2: | 3% corn steep liquor, 1.5% yeast extract, 0.3% ammonium phosphate monobasic, and 3% glucose; pH adjusted to 6.5 with 20% NaOH. |

Spores of the microorganism are introduced into this medium from a vial typically containing in the neighborhood of $10^9$ spores per ml. of suspension. Optimal productivity of seed generation is realized where dilution with growth medium at the beginning of a seed culture does not reduce the spore population density below about $10^7$ per ml. Preferably, the spores are cultured in the seed fermentation system until the packed mycelial volume (PMV) in the seed fermenter is at least about 20%, preferably about 35% to about 45%. Since the cycle in the seed fermentation vessel (or any vessel of a plurality which comprise a seed fermentation train) depends on the initial concentration in that vessel, it may be desirable to provide two or three seed fermentation stages to accelerate the overall process. However, it is preferable to avoid the use of significantly more than three seed fermenters in series, since activity may be compromised if seed fermentation is carried through an excessive number of stages. The seed culture fermentation is conducted under agitation at a temperature in the range of about 23° to about 37° C., preferably in range of between about 24° and about 28° C.

Culture from the seed fermentation system is introduced into a production fermenter, together with a production growth medium. In one embodiment of the invention, non-sterile canrenone or other substrate of Formula XIII serves as the substrate for the reaction. Preferably, the substrate is added to the production fermenter in the form of a 10% to 30% by weight slurry in growth medium. To increase the surface area available for 11α-hydroxylation reaction, the particle size of the Formula XIII substrate is reduced by passing the substrate through an off line micronizer prior to introduction into the fermenter. A sterile nutrient feed stock containing glucose, and a second sterile nutrient solution containing a yeast derivative such as autolyzed yeast (or equivalent amino acid formulation based on alternative sources such as distiller's solubles), are also separately introduced. The medium comprises an aqueous mixture containing: between about 0.5% and about 5% by weight glucose, between about 0.05% and about 5% by weight of a nitrogen source, e.g., peptone, between about 0.05% and about 0.5% by weight of a phosphorus source, e.g., an ammonium or alkali metal phosphate such as dipotassium hydrogen phosphate, between about 0.25% and about 2.5% by weight yeast lysate or extract (or other amino acid source such as distiller's solubles), between about 1% and about 2% by weight agar or other non-digestible polysaccharide. A particularly preferred production growth medium contains about 0.05% and about 5% by weight of a nitrogen source such as peptone, between about 0.25% and about 2.5% by weight of autolyzed yeast or yeast extract, between about 0.5% and about 5% by weight glucose, and between about 0.05% and about 0.5% by weight of a phosphorus source such as ammonium phosphate monobasic. Another preferred production medium contains between about 0.5% and about 5% by weight corn steep liquor, between about 0.25% and about 2.5% autolyzed yeast or yeast extract, between about 0.5% and about 5% by weight glucose and about 0.05% and about 0.5% by weight ammonium phosphate monobasic. The pH of the production fermentation medium is preferably adjusted in the manner described above for the seed fermentation medium, with the same preferred ranges for the pH of peptone/glucose based media and corn steep liquor based media, respectively. Useful bioconversion growth media are set forth below:

| | |
|---|---|
| 1. Medium #1: | 2% peptone, 2% yeast autolyzed (or yeast extract), and 2% glucose; pH adjusted to 5.8 with 20% NaOH. |
| 2. Medium #2: | 1% peptone, 1% yeast autolyzed (or yeast extract), and 2% glucose; pH adjusted to 5.8 with 20% NaOH. |
| 3. Medium #3: | 0.5% peptone, 0.5% yeast autolyzed (or yeast extract), and 0.5% glucose; pH adjusted to 5.8 with 20% NaOH. |
| 4. Medium #4: | 3% corn steep liquor, 1.5% yeast extract, 0.3% ammonium phosphate monobasic, and 3% glucose; pH adjusted to 6.5 with 20% NaOH. |
| 5. Medium #5: | 2.55% corn steep liquor, 1.275% yeast extract, 0.255% ammonium phosphate monobasic, and 3% glucose; pH adjusted to 6.5 with 20% NaOH. |
| 6. Medium #6: | 2.1% corn steep liquor, 1.05% yeast extract, 0.21% ammonium phosphate monobasic, and 3% glucose; pH adjusted to 6.5 with 20% NaOH. |

Non-sterile canrenone and sterile nutrient solutions are chain fed to the production fermenter in about five to about twenty, preferably about ten to about fifteen, preferably substantially equal, portions each over the production batch cycle. Advantageously, the substrate is initially introduced in an amount sufficient to establish a concentration of between about 0.1% by weight and about 3% by weight, preferably between about 0.5% and about 2% by weight, before inoculation with seed fermentation broth, then added periodically, conveniently every 8 to 24 hours, to a cumulative proportion of between about 1% and about 8% by weight. Where additional substrate is added every 8 hour shift, total addition may be slightly lower, e.g., 0.25% to 2.5% by weight, than in the case where substrate is added only on a daily basis. In the latter instance cumulative canrenone addition may need to be in the range 2% to about 8% by weight. The supplemental nutrient mixture fed during the fermentation reaction is preferably a concentrate, for example, a mixture containing between about 40% and about 60% by weight sterile glucose, and between about 16% and about 32% by weight sterile yeast extract or other sterile source of yeast derivative (or other amino acid source). Since the substrate fed to the production fermenter of FIG. 1 is non-sterile, antibiotics are periodically added to the fermentation broth to control the growth of undesired organisms. Antibiotics such as kanamycin, tetracycline, and cefalexin can be added without disadvantageously affecting growth and bioconversion. Preferably, these are introduced into the fermentation broth in a concentration, e.g., of between about 0.0004% and about 0.002% based on the total amount of the broth, comprising, e.g., between about 0.0002% and about 0.0006% kanamycin sulfate, between about 0.0002% and about 0.006% tetracycline HCl and/or between about 0.001% and about 0.003% cefalexin, again based on the total amount of broth.

Typically, the production fermentation batch cycle is in the neighborhood of about 80–160 hours. Thus, portions of each of the Formula XIII substrates and nutrient solutions are typically added about every 2 to 10 hours, preferably about every 4 to 6 hours. Advantageously, an antifoam is also incorporated in the seed fermentation system, and in the production fermenter.

Preferably, in the process of FIG. 1, the inoculum charge to the production fermenter is about 0.5% to about 7%, more preferably about 1% to about 2%, by volume based on the total mixture in the fermenter, and the glucose concentration is maintained between about 0.01% and about 1.0%, preferably between about 0.025% and about 0.5%, more preferably between about 0.05% and about 0.25% by weight with periodic additions that are preferably in portions of about 0.05% to about 0.25% by weight, based on the total batch charge. The fermentation temperature is conveniently controlled within a range of about 20° to about 37° C., preferably about 24° C. to about 28° C., but it may be desirable to step down the temperature during the reaction, e.g., in 2° C. increments, to maintain the packed mycelium volume (PMV) below about 60%, more preferably below about 50%, and thereby prevent the viscosity of the fermentation broth from interfering with satisfactory mixing. If the biomass growth extends above the liquid surface, substrate retained within the biomass may be carried out of the reaction zone and become unavailable for the hydroxylation reaction. For productivity, it is desirable to reach a PMV in the range of 30 to 50%, preferably 35% to 45%, within the first 24 hours of the fermentation reaction, but thereafter conditions are preferably managed to control further growth within the limits stated above. During reaction, the pH of the fermentation medium is controlled at between about 5.0 and about 6.5, preferably between about 5.2 and about 5.8, and the fermenter is agitated at a rate of between about 400 and about 800 rpm. A dissolved oxygen level of at least about 10% of saturation is achieved by aerating the batch at between about 0.2 and about 1.0 vvm, and maintaining the pressure in the head space of the fermenter at between about atmospheric and about 1.0 bar gauge, most preferably in the neighborhood of about 0.7 bar gauge. Agitation rate may also be increased as necessary to maintain minimum dissolved oxygen levels. Advantageously, the dissolved oxygen is maintained at well above about 10%, in fact as high as about 50% to promote conversion of substrate. Maintaining the pH in the range of 5.5±0.2 is also optimal for bioconversion. Foaming is controlled as necessary by addition of a common antifoaming agent. After all substrate has been added, reaction is preferably continued until the molar ratio of Formula VIII product to remaining unreacted Formula XIII substrate is at least about 9 to 1. Such conversion may be achieve within the 80–160 hour batch cycle indicated above.

It has been found that high conversions are associated with depletion of initial nutrient levels below the initial charge level, and by controlling aeration rate and agitation rate to avoid splashing of substrate out of the liquid broth. In the process of FIG. 1, the nutrient level was depleted to and then maintained at no greater than about 60%, preferably about 50%, of the initial charge level; while in the processes of FIGS. 2 and 3, the nutrient level was reduced to and maintained at no greater than 80%, preferably about 70%, of the initial charge level. Aeration rate is preferably no greater than one vvm, more preferably in the range of about 0.5 vvm; while agitation rate is preferably not greater than 600 rpm.

A particularly preferred process for preparation of a compound of Formula VIII is illustrated in FIG. 2. A preferred microorganism for the 11α-hydroxylation of a compound of Formula XIII (for example, canrenone) is *Aspergillus ochraceus* NRRL 405 (ATCC 18500). In this process, growth medium preferably comprises between about 0.5% and about 5% by weight corn steep liquor, between about 0.5% and about 5% by weight glucose, between about 0.1% and about 3% by weight yeast extract, and between about 0.05% and about 0.5% by weight ammonium phosphate. However, other production growth media as described herein may also be used. The seed culture is prepared essentially in the manner described for the process of FIG. 1, using any of the seed fermentation media described herein. A suspension of non-micronized canrenone or other Formula XIII substrate in the growth medium is prepared aseptically in a blender, preferably at a relatively high concentration of between about 10% and about 30% by weight substrate. Preferably, aseptic preparation may comprise sterilization or pasteurization of the suspension after mixing. The entire amount of sterile substrate suspension required for a production batch is introduced into the production fermenter at the beginning of the batch, or by periodical chain feeding. The particle size of the substrate is reduced by wet milling in an on-line shear pump which transfers the slurry to the production fermenter, thus obviating the need for use of an off-line micronizer. Where aseptic conditions are achieved by pasteurization rather than sterilization, the extent of agglomeration may be insignificant, but the use of a shear pump may be desirable to provide positive control of particle size. Sterile growth medium and glucose solution are introduced into the production fermenter essentially in the same manner as described above. All feed components to the production fermenter are sterilized before introduction, so that no antibiotics are required.

Preferably, in operation of the process of FIG. 2, the inoculum is introduced into the production fermenter in a proportion of between about 0.5% and about 7%, the fermentation temperature is between about 20° and about 37° C., preferably between about 24° C. and about 28° C., and the pH is controlled between about 4.4 and about 6.5, preferably between about 5.3 and about 5.5, e.g., by introduction of gaseous ammonia, aqueous ammonium hydroxide, aqueous alkali metal hydroxide, or orthophosphoric acid. As in the process of FIG. 1, the temperature is preferably trimmed to control growth of the biomass so that PMV does not exceed 55–60%. The initial glucose charge is preferably between about 1% and about 4% by weight, most preferably 2.5% to 3.5% by weight, but is preferably allowed to drift below about 1.0% by weight during fermentation. Supplemental glucose is fed periodically in portions of between about 0.2% and about 1.0% by weight based on the total batch charge, so as to maintain the glucose concentration in the fermentation zone within a range of between about 0.1% and about 1.5% by weight, preferably between about 0.25% and about 0.5% by weight. Optionally, nitrogen and phosphorus sources may be supplemented along with glucose. However, because the entire canrenone charge is made at the beginning of the batch cycle, the requisite supply of nitrogen and phosphorus bearing nutrients can also be introduced at that time, allowing the use of only a glucose solution for supplementation during the reaction. The rate and nature of agitation is a significant variable. Moderately vigorous agitation promotes mass transfer between the solid substrate and the aqueous phase. However, a low shear impeller should be used to prevent degradation of the myelin of the microorganisms. Optimal agitation velocity varies within the range of 200 to 800 rpm, depending on culture broth viscosity, oxygen concentration, and mixing conditions as affected by vessel, baffle and impeller configuration. Ordinarily, a preferred agitation rate is in the range of 350–600 rpm. Preferably the agitation impeller provides a downward axially pumping function so as to assist in good mixing of the fermented biomass. The batch is preferably aerated at a rate of between about 0.3 and about 1.0 vvm, preferably 0.4 to 0.8 vvm, and the pressure in the head space of the fermenter is preferably between about 0.5 and about 1.0 bar gauge. Temperature, agitation, aeration and back pressure are preferably controlled to maintain dissolved oxygen in the range of at least about 10% by volume during the bioconversion. Total batch cycle is typically between about 100 and about 140 hours.

Although the principle of operation for the process of FIG. 2 is based on early introduction of substantially the entire canrenone charge, it will be understood that growth of the fermentation broth may be carried out before the bulk of the canrenone is charged. Optionally, some portion of the canrenone can also be added later in the batch. Generally, however, at least about 75% of the sterile canrenone charge should be introduced into the transformation fermenter within 48 hours after initiation of fermentation. Moreover, it is desirable to introduce at least about 25% by weight canrenone at the beginning of the fermentation, or at least within the first 24 hours in order to promote generation of the bioconversion enzyme(s).

Figure 3:
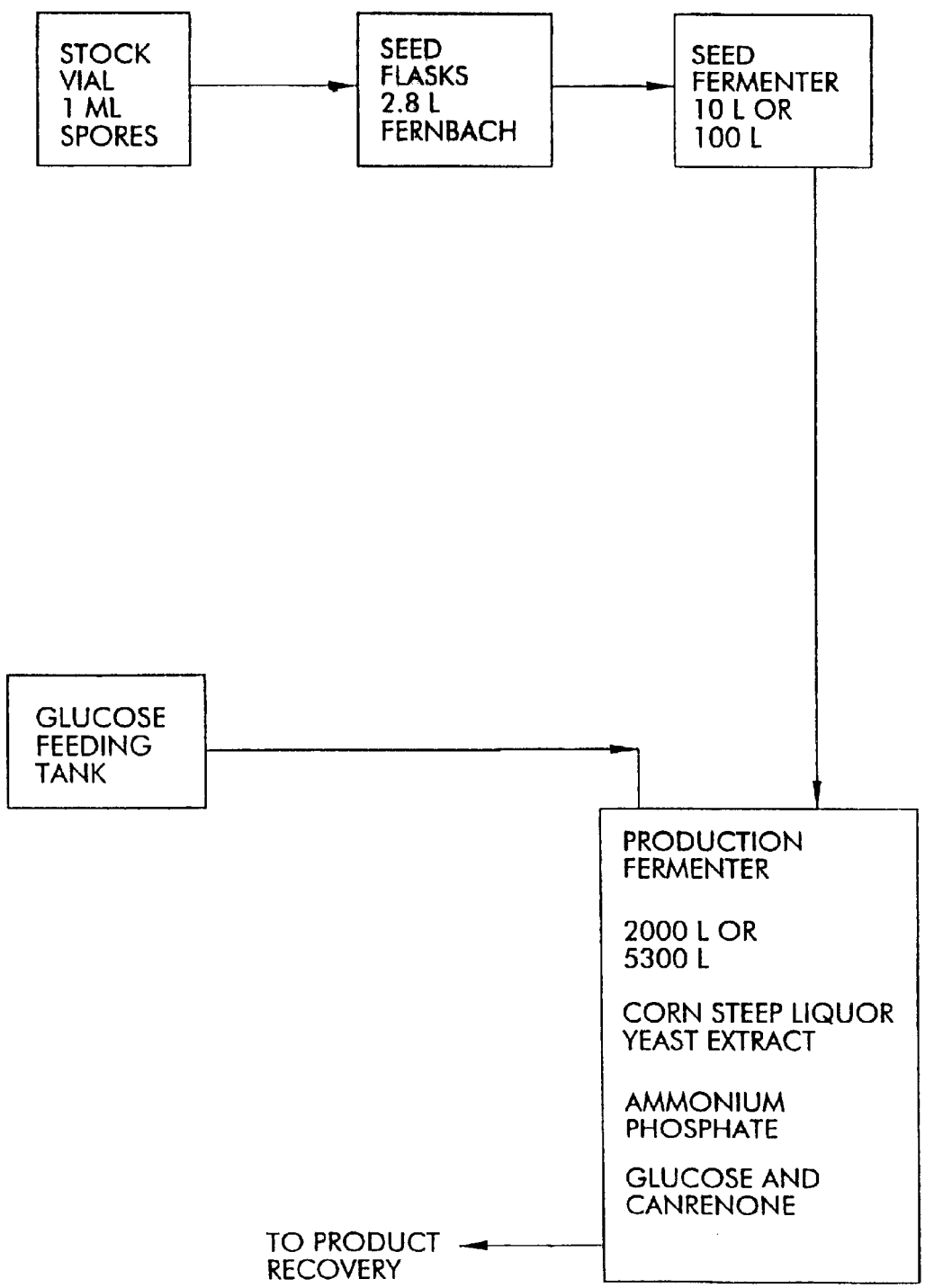
FIG. 3 is a schematic flow sheet of a particularly preferred process for the bioconversion/11-α-hydroxylation of canrenone and canrenone derivatives.

In a further preferred process as illustrated in FIG. 3, the entire batch charge and nutrient solution are sterilized in the production fermentation vessel prior to the introduction of inoculum. The nutrient solutions that may be used, as well as the preferences among them, are essentially the same as in the process of FIG. 2. In this embodiment of the invention, the shearing action of the agitator impeller breaks down the substrate agglomerates that otherwise tend to form upon sterilization. It has been found that the reaction proceeds satisfactorily if the mean particle size of the canrenone is less than about $300\mu$ and at least 75% by weight of the particles are smaller than $240\mu$. The use of a suitable impeller, e.g., a disk turbine impeller, at an adequate velocity in the range of 200 to 800 rpm, with a tip speed of at least about 400 cm/sec., has been found to provide a shear rate sufficient to maintain such particle size characteristics despite the agglomeration that tends to occur upon sterilization within the production fermenter. The remaining operation of the process of FIG. 3 is essentially the same as the process of FIG. 2. The processes of FIGS. 2 and 3 offer several distinct advantages over the process of FIG. 1. A particular advantage is the amenability to use of a low cost nutrient base such as corn steep liquor. But further advantages are realized in eliminating the need of antibiotics, simplifying feeding procedures, and allowing for batch sterilization of canrenone or other Formula XIII substrate. Another particular advantage is the ability to use a simple glucose solution rather than a complex nutrient solution for supplementation during the reaction cycle.

In processes depicted in FIGS. 1 to 3, the product of Formula VIII is a crystalline solid which, together with the biomass, may be separated from the reaction broth by filtration or low speed centrifugation. Alternatively, the product can be extracted from the entire reaction broth with organic solvents. Product of Formula VIII is recovered by solvent extraction. For maximum recovery, both the liquid phase filtrate and the biomass filter or centrifuge cake are treated with extraction solvent, but usually $\geq 95\%$ of the product is associated with the biomass. Typically, hydrocarbon, ester, chlorinated hydrocarbon, and ketone solvents may be used for extraction. A preferred solvent is ethyl acetate. Other typically suitable solvents include toluene and methyl isobutyl ketone. For extraction from the liquid phase, it may be convenient to use a volume of solvent approximately equal to the volume of reaction solution which it contacts. To recover product the from the biomass, the latter is suspended in the solvent, preferably in large excess relative to the initial charge of substrate, e.g., 50 to 100 ml. solvent per gram of initial canrenone charge, and the resulting suspension preferably refluxed for a period of about 20 minutes to several hours to assure transfer of product to the solvent phase from recesses and pores of the biomass. Thereafter, the biomass is removed by filtration or centrifugation, and the filter cake preferably washed with both fresh solvent and deionized water. Aqueous and solvent washes are then combined and the phases allowed to separate. Formula VIII product is recovered by crystallization from the solution. To maximize yield, the mycelium is contacted twice with fresh solvent. After settling to allow complete separation of the aqueous phase, product is recovered from the solvent phase. Most preferably, the solvent is removed under vacuum until crystallization begins, then the concentrated extract is cooled to a temperature of about 0° to about 20° C., preferably about 10° to about 15° C. for a time sufficient for crystal precipitation and growth, typically about 8 to about 12 hours.

The processes of FIG. 2, and especially that of FIG. 3, are particularly preferred. These processes operate at low viscosity, and are amenable to close control of process parameters such as pH, temperature and dissolved oxygen. Moreover, sterile conditions are readily preserved without resort to antibiotics.

The bioconversion process is exothermic, so that heat should be removed, using a jacketed fermenter or a cooling coil within the production fermenter. Alternatively, the reaction broth may be circulated through an external heat exchanger. Dissolved oxygen is preferably maintained at a level of at least about 5%, preferably at least about 10%, by volume, sufficient to provide energy for the reaction and assure conversion of the glucose to $CO_2$ and $H_2O$, by regulating the rate of air introduced into the reactor in response to measurement of oxygen potential in the broth. The pH is preferably controlled at between about 4.5 and about 6.5.

In each of the alternative processes for 11-hydroxylation of the substrate of Formula XIII, productivity is limited by mass transfer from the solid substrate to the aqueous phase, or the phase interface, where reaction is understood to occur. As indicated above, productivity is not significantly limited by mass transfer rates so long as the particle mean particle size of the substrate is reduced to less than about $300\mu$, and at least 75% by weight of the particles are smaller than $240\mu$. However, productivity of these processes may be further enhanced in certain alternative embodiments which provide a substantial charge of canrenone or other Formula XIII substrate to the production fermenter in an organic solvent. According to one option, the substrate is dissolved in a water-immiscible solvent and mixed with the aqueous growth medium inoculum and a surfactant. Useful water-immiscible solvents include, for example, DMF, DMSO, $C_6$–$C_{12}$ fatty acids, $C_6$–$C_{12}$ n-alkanes, vegetable oils, sorbitans, and aqueous surfactant solutions. Agitation of this charge generates an emulsion reaction system having an extended interfacial area for mass transfer of substrate from the organic liquid phase to the reaction sites.

A second option is to initially dissolve the substrate in a water miscible solvent such as acetone, methylethyl ketone, methanol, ethanol, or glycerol in a concentration substantially greater than its solubility in water. By preparing the initial substrate solution at elevated temperature, solubility is increased, thereby further increasing the amount of solution form substrate introduced into the reactor and ultimately enhancing the reactor payload. The warm substrate solution is charged to the production fermentation reactor along with the relatively cool aqueous charge comprising growth medium and inoculum. When the substrate solution is mixed with the aqueous medium, precipitation of the substrate occurs. However, under conditions of substantial supersaturation and moderately vigorous agitation, nucleation is favored over crystal growth, and very fine particles of high surface area are formed. The high surface area promotes mass transfer between the liquid phase and the solid substrate. Moreover, the equilibrium concentration of substrate in the aqueous liquid phase is also enhanced in the presence of a water-miscible solvent. Accordingly, productivity is promoted.

Although the microorganism may not necessarily tolerate a high concentration of organic solvent in the aqueous phase, a concentration of ethanol, e.g., in the range of about 3% to about 5% by weight, can be used to advantage.

A third option is to solubilize the substrate in an aqueous cyclodextrin solution. Illustrative cyclodextrins include hydroxypropyl-β-cyclodextrin and methyl-β-cyclodextrin. The molar ratio of substrate:cyclodextrin can be about 1:0.5 to about 1:1.5, more preferably about 1:0.8 to about 1:1. The substrate:cyclodextrin mixture can then be added aseptically to the bioconversion reactor.

11α-Hydroxycanrenone and other products of the 11α-hydroxylation process (Formulae VIII and VIIIA) are novel compounds which may be isolated by filtering the reaction medium and extracting the product from the biomass collected on the filtration medium. Conventional organic solvents, e.g., ethyl acetate, acetone, toluene, chlorinated hydrocarbons, and methyl isobutyl ketone may be used for the extraction. The product of Formula VIII may then be recrystallized from an organic solvent of the same type. The compounds of Formula VIII have substantial value as intermediates for the preparation of compounds of Formula I, and especially of Formula IA.

Preferably, the compounds of Formula VIII correspond to Formula VIIIA in which —A—A— and —B—B— are —CH₂—CH₂—, $R^3$ is hydrogen, lower alkyl or lower alkoxy, and $R^8$ and $R^9$ together constitute the 20-spiroxane ring:

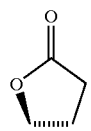

XXXIII

Further in accordance with the process of Scheme 1, the compound of Formula VIII is reacted under alkaline conditions with a source of cyanide ion to produce an enamine compound of Formula VII

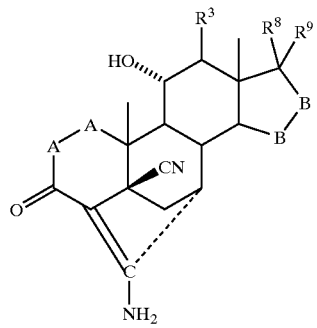

VII wherein —A—A—, —B—B—, $R^3$, $R^8$ and $R^9$ are as defined above. Where the substrate corresponds to Formula VIIIA, the product is of Formula VIIA

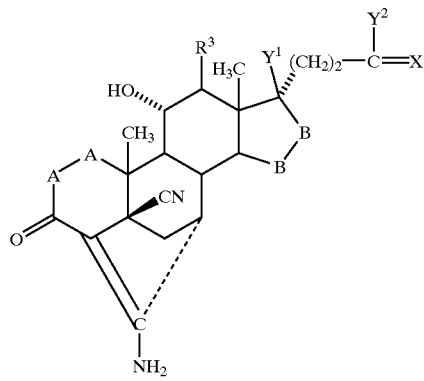

VIIA wherein —A—A—, —B—B—, $R^3$, $Y^1$, $Y^2$, and X are as defined in Formula XIIIA. Preferably, $R^3$ is hydrogen.

Cyanidation of the 11α-hydroxyl substrate of Formula VIII may be carried out by reacting it with a cyanide ion source such as a ketone cyanohydrin, most preferably acetone cyanohydrin, in the presence of a base and an alkali metal salt, most preferably LiCl. Alternatively, cyanidation can be effected without a cyanohydrin by using an alkali metal cyanide in the presence of an acid.

In the ketone cyanohydrin process, the reaction is conducted in solution, preferably using an aprotic polar solvent such as dimethylformamide or dimethyl sulfoxide. Formation of the enamine requires at least two moles of cyanide ion source per mole of substrate, and preferably a slight excess of the cyanide source is used. The base is preferably a nitrogenous base such as a dialkylamine, trialkylamine, alkanolamine, pyridine or the like. However, inorganic bases such as alkali metal carbonates or alkali metal hydroxides can also be used. Preferably, the substrate of Formula VIII is initially present in a proportion of between about 20 and about 50% by weight and the base is present in a proportion of between 0.5 to two equivalents per equivalent of substrate. The temperature of the reaction is not critical, but productivity is enhanced by operation at elevated temperature. Thus, for example, where triethylamine is used as the base, the reaction is advantageously conducted in the range of about 80° C. to about 90° C. At such temperatures, the reaction proceeds to completion in about 5 to about 20 hours. When diisopropylethyl amine is used as the base and the reaction is conducted at 105° C., the reaction is completed at 8 hours. At the end of the reaction period, the solvent is removed under vacuum and the residual oil dissolved in water and neutralized to pH 7 with dilute acid, preferably hydrochloric. The product precipitates from this solution, and is thereafter washed with distilled water and air dried. Liberated HCN may be stripped with an inert gas and quenched in an alkaline solution. The dried precipitate is taken up in chloroform or other suitable solvent, then extracted with concentrated acid, e.g., 6N HCl. The extract is neutralized to pH 7 by addition of an inorganic base, preferably an alkali metal hydroxide, and cooled to a temperature in the range of 0° C. The resulting precipitate is washed and dried, then recrystallized from a suitable solvent, e.g., acetone, to produce a product of Formula VII suitable for use in the next step of the process.

Alternatively, the reaction may be conducted in an aqueous solvent system comprising water-miscible organic solvent such as methanol or in a biphasic system comprising water and an organic solvent such as ethyl acetate. In this alternative, product may be recovered by diluting the reaction solution with water, and thereafter extracting the product using an organic solvent such as methylene chloride or chloroform, and then back extracting from the organic extract using concentrated mineral acid, e.g., 2N HCl. See U.S. Pat. No. 3,200,113.

According to a still further alternative, the reaction may be conducted in a water-miscible solvent such as dimethylformamide, dimethylacetamide, N-methyl, pyrolidone or dimethyl sulfoxide, after which the reaction product solution is diluted with water and rendered alkaline, e.g., by addition of an alkali metal carbonate, then cooled to 0° to 10° C., thereby causing the product to precipitate. Preferably, the system is quenched with an alkali metal hypohalite or other reagent effective to prevent evolution of cyanide. After filtration and washing with water, the precipitated product is suitable for use in the next step of the process.

According to a still further alternative, the enamine product of Formula VII may be produced by reaction of a substrate of Formula VIII in the presence of a proton source, with an excess of alkali metal cyanide, preferably NaCN, in an aqueous solvent comprising an aprotic water-miscible polar solvent such as dimethylformamide or dimethylacetamide. The proton source is preferably a mineral acid or $C_1$ to $C_5$ carboxylic acid, sulfuric acid being particularly preferred. Anomalously, no discrete proton source need be added where the cyanidation reagent is commercial LiCN in DMF.

A source of cyanide ion such as an alkali metal salt is preferably charged to the reactor in a proportion of between about 2.05 and about 5 molar equivalents per equivalent of substrate. The mineral acid or other proton source is believed to promote addition of HCN across the 4,5 and 6,7 double bonds, and is preferably present in a proportion of at least one mole equivalent per mole equivalent substrate; but the reaction system should remain basic by maintaining an excess of alkali metal cyanide over acid present. Reaction is preferably carried out at a temperature of at least about 75° C., typically 60° C. to 100° C., for a period of about 1 to about 8 hours, preferably about 1.5 to about 3 hours. At the end of the reaction period, the reaction mixture is cooled, preferably to about room temperature; and the product enamine is precipitated by acidifying the reaction mixture and mixing it with cold water, preferably at about ice bath temperature. Acidification is believed to close the 17-lactone, which tends to open under the basic conditions prevailing in the cyanidation. The reaction mixture is conveniently acidified using the same acid that is present during the reaction, preferably sulfuric acid. Water is preferably added in a proportion of between about 10 and about 50 mole equivalents per mole of product.

The compounds of Formula VII are novel compounds and have substantial value as intermediates for the preparation of compounds of Formula I, and especially of Formula IA. Preferably, the compounds of Formula VII correspond to Formula VIIA in which —A—A— and —B—B— are —CH$_2$—CH$_2$—, R$^3$ is hydrogen, lower alkyl or lower alkoxy, and R$^8$ and R$^9$ together constitute the 20-spiroxane ring:

XXXIII

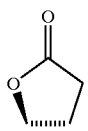

Most preferably the compound of Formula VII is 5'R(5'α), 7'β-20'-Aminohexadecahydro-11'β-hydroxy-10',13'α-dimethyl-3',5-dioxospiro[furan-2(3H),17'α(5'H)-[7,4] metheno[4H]cyclopenta[a]phenanthrene]-5'-carbonitrile.

In the conversion of the compound of Formula VIII to the enamine of Formula VII, the 7-cyano derivative of the compound of Formula VIII has been observed by chromatography in the crude product. It is hypothesized that the 7-cyano compound is an intermediate in the conversion process. It is further hypothesized that the 7-cyano intermediate itself reacts to form a second intermediate, the 5,7-dicyano derivative of the compound of Formula VIII, which in turn reacts to form the enester. See, e.g., R. Christiansen et al., The Reaction of Steroidal 4,6-Dien-3-Ones With Cyanide, *Steroids*, Vol. 1, June 1963, which is incorporated herein by reference. These novel compounds also have utility as chromatographic markers as well as being synthetic intermediates. In a preferred embodiment of this step of the overall Scheme 1 synthesis process, these intermediates are 7α-cyano-11α,17-dihydroxy-3-oxo-17α-pregn-4-ene-21-dicarboxylic acid, γ-lactone, and 5β,7α-dicyano-11α,17-dihydroxy-3-oxo-17α-pregnane-21-dicarboxylic acid, γ-lactone.

In the next step of the Scheme 1 synthesis, the enamine of Formula VII is hydrolyzed to produce a diketone compound of Formula VI

VI

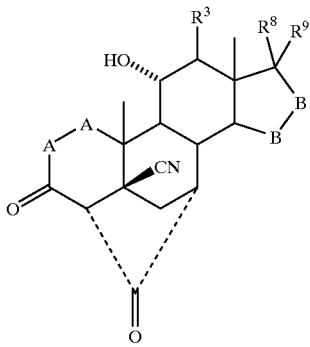

where —A—A—, —B—B—, $R^3$, $R^8$ and $R^9$ are as defined in Formula XIII. Any aqueous organic or mineral acid can be used for the hydrolysis. Hydrochloric acid is preferred. To enhance productivity, a water-miscible organic solvent, such as dimethylacetamnide or a lower alkanol, is preferably used as a cosolvent. More preferably, dimethylacetamide is the solvent. The acid should be present in proportion of at least one equivalent per equivalent of Formula VII substrate. In an aqueous system, the enamine substrate VII can be substantially converted to the diketone of Formula VI in a period of about 5 hours at about 80° C. Operation at elevated temperature increases productivity, but temperature is not critical. Suitable temperatures are selected based on the volatility of the solvent system and acid.

Preferably, the enamine substrate of Formula VII corresponds to Formula VIIA

VIIA

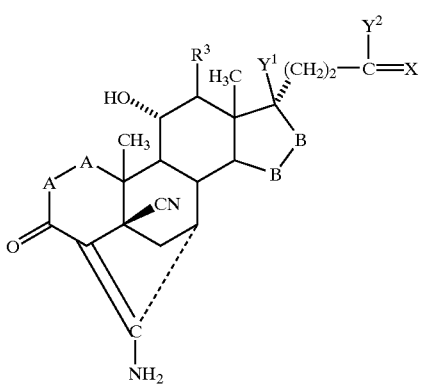

and the diketone product corresponds to Formula VIA

VIA

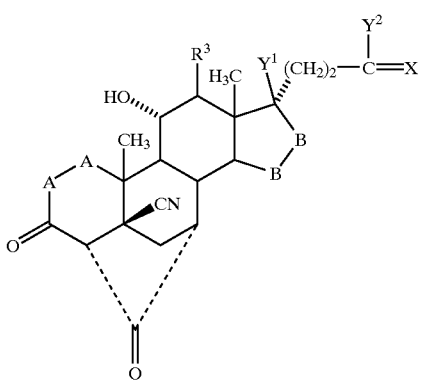

in each of which —A—A—, —B—B—, $R^3$, $Y^1$, $Y^2$, and X are as defined in Formula XIIIA. Preferably, $R^3$ is hydrogen.

At the end of the reaction period, the solution is cooled to between about 0° to 25° C. to crystallize the product. The product crystals may be recrystallized from a suitable solvent such as isopropanol or methanol to produce a product of Formula VI suitable for use in the next step of the process; but recrystallization is usually not necessary. The products of Formula VI are novel compounds which have substantial value as intermediates for the preparation of compounds of Formula I, and especially of Formula IA. Preferably, the compounds of Formula VI correspond to Formula VIA in which —A—A— and —B—B— are —$CH_2$—$CH_2$—, $R^3$ is hydrogen, lower alkyl or lower alkoxy, and $R^8$ and $R^9$ together constitute the 20-spiroxane ring:

XXXIII

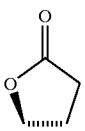

Most preferably, the compound of Formula VI is 4'S(4'α), 7'α-Hexadecahydro-11'α-hydroxy-10'β,13'β-dimethyl-3',5, 20'-trioxospiro[furan-2(3H),17'β-[4,7]methano[17H] cyclopenta[a]phenanthrene]-5'β(2'H)-carbonitrile.

In a particularly preferred embodiment of the invention, the product enamine of Formula VII is produced from the compound of Formula VIII in the manner described above, and converted in situ to the diketone of Formula VI. In this embodiment of the invention, a formula VIII substrate is reacted with an excess of alkali metal cyanide in an aqueous solvent containing a proton source, or optionally an excess of ketone cyanohydrin in the presence of a base and LiCl, as described hereinabove. However, instead of cooling the reaction mixture, acidifying, and adding water in proportions calculated to cause precipitation of the enamine, substantial cooling of the reaction mixture is preferably avoided. Water and an acid, preferably a mineral acid such as sulfuric, are instead added to the mixture at the end of the cyanidation reaction. The proportion of acid added is sufficient to neutralize excess alkali metal cyanide, which ordinarily requires introduction of at least one molar equivalent acid per mole of Formula VIII substrate, preferably between about 2 and about 5 mole equivalents per equivalent substrate. However, the temperature is maintained at high enough, and the dilution great enough, so that substantial precipitation is avoided and hydrolysis of the enamine to the diketone is allowed to proceed in the liquid phase. Thus, the process proceeds with minimum interruption and high productivity. Hydrolysis is preferably conducted at a temperature of at least 80° C., more preferably in the range of about 90° C. to about 100° C., for a period of typically about 1 to about 10 hours, more preferably about 2 to about 5 hours. Then the reaction mixture is cooled, preferably to a temperature of between about 0° C. and about 15° C., advantageously in an ice bath to about 5° C. to about 10° C., for precipitation of the product diketone of Formula VI. The solid product may be recovered, as by filtration, and impurities reduced by washing with water.

In the next step of the Scheme 1 synthesis, the diketone compound of Formula VI is reacted with a metal alkoxide to open up the ketone bridge between the 4 and 7 positions via cleavage of the bond between the carbonyl group and the 4-carbon, form an α-oriented alkoxycarbonyl substituent at the 7 position, and eliminate cyanide at the 5-carbon. The product of this reaction is a hydroxyester compound corresponding to Formula V

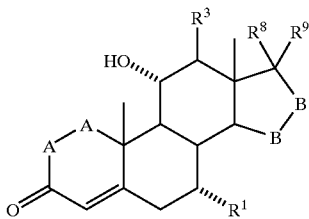

where —A—A—, —B—B—, $R^3$, $R^8$ and $R^9$ are as defined in Formula XIII, and $R^1$ is lower alkoxycarbonyl or hydroxycarbonyl. The metal alkoxide used in the reaction corresponds to the formula $R^{10}OM$ where M is alkali metal and $R^{10}O$— corresponds to the alkoxy substituent of $R^1$. Yields of this reaction are most satisfactory when the metal alkoxide is potassium methoxide or sodium methoxide, but other lower alkoxides can be used. A potassium alkoxide is particularly preferred. Phenoxides, other aryloxides may also be used, as well as arylsulfides. The reaction is conveniently carried out in the presence of an alcohol corresponding to the formula $R^{10}OH$ where $R^{10}$ is as defined above. Other conventional solvents may be used. Preferably, the Formula VI substrate is present in a proportion of between about 2% and about 12% by weight, more preferably at least about 6% by weight. Preferably, $R^{10}OM$ is present in a proportion of between about 0.5 and about 4 moles per mole of substrate, more preferably between about 1 and about 2 moles per mole of substrate, and still more preferably about 1.6 mole per mole of substrate. Temperature is not critical but elevated temperature enhances productivity. Reaction time is typically between about 4 and about 24 hours, preferably about 4 to 16 hours. Conveniently, the reaction is carried out at atmospheric reflux temperature depending on the solvent used.

The time required for the reaction to reach equilibrium is affected by the amount of alkoxide that is added to the reaction mixture and the manner in which the alkoxide is added. The alkoxide may be added in a single portion or in multiple portions or it may be added continuously. When alkoxide is added in multiple portions, it is preferable that about 1.6 equivalents of potassium methoxide be added in two steps. In this two-step addition, 1 equivalent of potassium methoxide is initially added to the reaction mixture followed by the addition of 0.6 equivalents of potassium methoxide about 90 minutes later. This two-step addition shortens the time to reach equilibrium relative to a single portion addition of 1.6 equivalents of potassium methoxide.

Because the equilibrium is more favorable for the production of the hydroxyester at low concentrations of the diketone, the reaction is preferably run at rather high dilution, e.g., as high as 40:1 for reaction with sodium methoxide. It has been found that significantly higher productivity can be realized by use of potassium methoxide rather than sodium methoxide, because a dilution in the range of about 20:1 is generally sufficient to minimize the extent of reverse cyanidation where potassium methoxide is the reagent.

In accordance with the invention, it has been further discovered that the reverse cyanidation reaction may be inhibited by taking appropriate chemical or physical measures to remove by-product cyanide ion from the reaction zone. Thus, in a further embodiment of the invention, the reaction of the diketone with alkali metal alkoxide may be carried out in the presence of a precipitating agent for cyanide ion such as, for example, a salt comprising a cation which forms an insoluble cyanide compound. Such salts may, for example, include zinc iodide, ferric sulfate, or essentially any halide, sulfate or other salt of an alkaline earth or transition metal that is more soluble than the corresponding cyanide. If zinc iodide is present in proportions in the range of about one equivalent per equivalent diketone substrate, it has been observed that the productivity of the reaction is increased substantially as compared to the process as conducted in the absence of an alkali metal halide.

Even where a precipitating agent is used for removal of cyanide ion, it remains preferable to run at fairly high dilution, but by use of a precipitating agent the solvent to diketone substrate molar ratio may be reduced significantly compared to reactions in the absence of such agent. Recovery of the hydroxyester of Formula V can be carried out according to either the extractive or non-extractive procedures described below.

The equilibrium of the reaction also can be controlled to favor the production of the hydroxyester of Formula V by removing this hydroxyester from the reaction mixture after it is synthesized. The removal of the hydroxyester can proceed either stepwise or continuously through means such as filtration. The removal of the hydroxyester can be used to control the equilibrium either alone or in combination with the chemical or physical removal of cyanide from the reaction mixture. Heating of the resulting filtrate then drives the reaction equilibrium to favor of the conversion of the remaining diketone of Formula VI to the hydroxyester of V.

In the conversion of the diketone of Formula VI to the hydroxyester of Formula V the 5-cyano hydroxyester has been observed in the crude product in small amounts, typically less than about 5% by weight. It is hypothesized that the 5-cyano hydroxyester is an equilibrium intermediate between the diketone of Formula VI and the hydroxyester of Formula V. It is further hypothesized that this equilibrium intermediate is formed from the diketone through methoxide attack on the 5,7-oxo group and protonation of the enolate, and from the hydroxyester through a Michael addition of by-product cyanide ion to the 3-keto-$\Delta^{4,5}$ function of the hydroxyester.

In addition, the 5-cyano-7-acid and the 17-alkoxide of the hydroxyester of Formula V have been observed by chromatography in the crude product. It is hypothesized that the 5-cyano hydroxyester intermediate reacts with by-product cyanide ion (present as a result of the decyanation which introduces the $\Delta^{4,5}$ double bond) to produce the 5-cyano-7-acid. It is hypothesized that the action of the cyanide ion dealkylates the 7-ester group of the 5-cyano hydroxyester to yield the 5-cyano-7-acid and the corresponding alkylnitrile.

It is further hypothesized that transient intermediate 17-alkoxide is formed from the attack of the methoxide on the 17-spirolactone of the hydroxyester (or a preceding intermediate which subsequently converts into the hydroxyester). The 17-alkoxide readily converts into the hydroxyester upon treatment with an acid. Therefore, it generally is not observed in the product matrix.

The 5-cyano hydroxyester, the 5-cyano-7-acid, and the 17-alkoxide are novel compounds which are useful as chromatographic markers and as intermediates in the preparation of the hydroxyester. They can be isolated from the crude product of this step of the Scheme 1 synthesis. Alternatively, they can be synthesized directly for use as markers or intermediates. The 5-cyano hydroxyester can be synthesized by reacting a solution of the isolated diketone of Formula VI with a base, such as an alkoxide or an amine, and isolating the resulting precipitate. The compound prepared preferably is 7-methyl hydrogen 5β-cyano-11α,17-dihydroxy-3-oxo-17α-pregnane-7α,21-dicarboxylate, γ-lactone.

The 5-cyano-7-carboxylic acid can be synthesized directly by reacting the diketone of Formula VI with a weak aqueous base, such as sodium acetate or sodium bicarbonate, and isolating the resulting precipitate. The compound prepared preferably is 5-β-cyano-11-α,17-dihydroxy-3-oxo-17α-pregnane-7α,21-dicarboxylic acid, γ-lactone.

The 17-alkoxide can be synthesized directly by reacting a solution of the hydroxyester of Formula V with an alkoxide to yield a mixture of the 17-alkoxide and the corresponding hydroxyester. The compound prepared preferably is dimethyl 11α,17-dihydroxy-3-oxo-17α-pregn-4-ene-7α,21-dicarboxylate, γ-lactone.

Preferably, the diketone substrate of Formula VI corresponds to Formula VIA

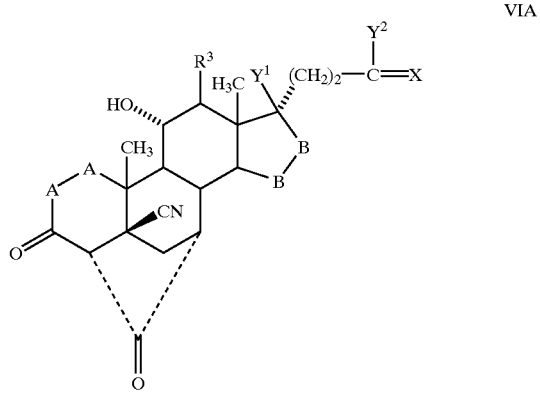

VIA and the hydroxyester product corresponds to Formula VA

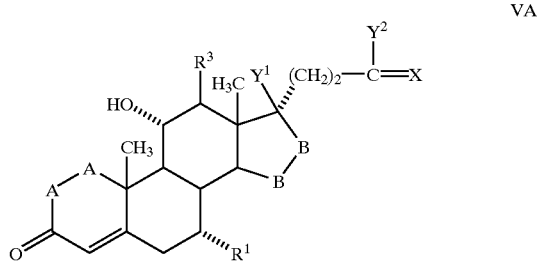

VA in each of which —A—A—, —B—B—, $R^3$, $Y^1$, $Y^2$, and X are as defined in Formula XIIIA and $R^1$ is as defined in Formula V. Preferably, $R^3$ is hydrogen.

The products of Formula V are novel compounds which have substantial value as intermediates for the preparation of compounds of Formula I, and especially of Formula IA. Preferably, the compounds of Formula V correspond to Formula VA in which —A—A— and —B—B— are —CH$_2$—CH$_2$—, $R^3$ is hydrogen, lower alkyl or lower alkoxy, and $R^8$ and $R^9$ together constitute the 20-spiroxane ring:

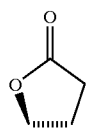

XXXIII

Most preferably, the compound of Formula V is Methyl Hydrogen 11α,17α-Dihydroxy-3-oxopregn-4-ene-7α,21-dicarboxylate, γ-Lactone.

The compound of Formula V may be isolated by filtration or by acidifying the reaction solution, e.g., with a mineral acid such as aqueous HCl or sulfuric acid, cooling to ambient temperature, and extracting the product with an organic solvent such as methylene chloride or ethyl acetate. The extract is washed with an aqueous alkaline wash solution, dried and filtered, after which the solvent is removed. Alternatively, the reaction solution containing the product of Formula V may be quenched with concentrated acid. The product solution is concentrated, cooled to between about 0° to 25° C. and the product solid is isolated by filtration.

In a preferred embodiment, methanol and HCN are removed by distillation after the conclusion of the reaction period, with mineral acid (such as hydrochloric acid or sulfuric acid) being added before the distillation and water being added after the distillation. The mineral acid can be added in a single step, in multiple steps or continuously. In a preferred embodiment, mineral acid is continuously added over a period of about 10 to about 40 minutes, more preferably about 15 to about 30 minutes. Likewise, water can be added to the still bottoms in a single step, in multiple steps or continuously. In a preferred embodiment, the concentrated reaction mixture is cooled from reflux temperature prior to addition of water. Preferably, the mixture is cooled to a temperature between about 50° C. to about 70° C., preferably between about 60° C. to about 70° C., and more preferably about 65° C., prior to addition of the water. Water is then added, preferably continuously over a period of about 15 minutes to about 3 hours, and more preferably over about 60 minutes to about 90 minutes, while maintaining the temperature approximately constant. Product of Formula V begins to crystallize from the still bottoms as the water addition proceeds. After the water has been added to the mixture, the diluted reaction mixture is maintained at about the same temperature for about 1 hour and then cooled to about 15° C. over an additional period of about 4 to about 5 hours. The mixture is maintained at about 15° C. for a period of about 1 to 2 hours. A longer holding period at 15° C. increases the yield of the cyanoester in the mixture. This mode of recovery provides a high quality crystalline product without extraction operations.

According to another preferred mode of recovery of the product of Formula V, methanol and HCN are removed by distillation after the conclusion of the reaction period, with water and acid being added before or during the distillation. Addition of water before the distillation simplifies operations, but progressive addition during the distillation allows the volume in the still to be maintained substantially constant. Product of Formula V crystallizes from the still bottoms as the distillation proceeds. This mode of recovery provides a high quality crystalline product without extraction operations.

In accordance with yet a further alternative, the reaction solution containing the product of Formula V may be quenched with mineral acid, e.g., 4N HCl, after which the solvent is removed by distillation. Removal of the solvent is also effective for removing residual HCN from the reaction product. It has been found that multiple solvent extractions for purification of the compound of Formula V are not necessary where the compound of Formula V serves as an intermediate in a process for the preparation of epoxymexrenone, as described herein. In fact, such extractions can often be entirely eliminated. Where solvent extraction is used for product purification, it is desirable to supplement the solvent washes with brine and caustic washes. But where the solvent extractions are eliminated, the brine and caustic washes are too. Eliminating the extractions and washes significantly enhances the productivity of the process, without sacrificing yield or product quality, and also eliminates the need for drying of the washed solution with a dessicant such as sodium sulfate.

The crude 11α-hydroxy-7α-alkoxycarbonyl product is taken up again in the solvent for the next reaction step of the process, which is the conversion of the 11-hydroxy group to a leaving group at the 11 position thereby producing a compound of Formula IV:

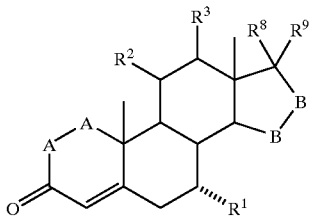

IV where —A—A—, $R^3$, —B—B—, $R^8$ and $R^9$ are as defined in Formula XIII, $R^1$ is as defined in Formula V, and $R^2$ is lower arylsulfonyloxy, alkylsulfonyloxy, acyloxy or halide. Preferably, the 11α-hydroxy is esterified by reaction with a lower alkylsulfonyl halide, an acyl halide or an acid anhydride which is added to the solution containing the intermediate product of Formula V. Lower acid anhydrides such as acetic anhydride and trihalogenated acid anhydrides such as trifluoroacetic anhydride can be used to prepare suitable acyloxy leaving groups. Lower alkylsulfonyl halides, and especially methanesulfonyl chloride, however, are preferred. Alternatively, the 11-α hydroxy group could be converted to a halide by reaction of a suitable reagent such as thionyl bromide, thionyl chloride, sulfuryl chloride or oxalyl chloride. Other reagents for forming 11α-sulfonic acid esters include tosyl chloride, benzenesulfonyl chloride and trifluoromethanesulfonic anhydride. The reaction is conducted in a solvent containing a hydrogen halide scavenger such as triethylamine or pyridine. Inorganic bases such as potassium carbonate or sodium carbonate can also be used. The initial concentration of the hydroxyester of Formula V is preferably between about 5% and about 50% by weight. The esterification reagent is preferably present in slight excess. Methylene chloride is a particularly suitable solvent for the reaction, but other solvents such as dichloroethane, pyridine, chloroform, methyl ethyl ketone, dimethoxyethane, methyl isobutyl ketone, acetone, other ketones, ethers, acetonitrile, toluene, and tetrahydrofuran can also be employed. The reaction temperature is governed primarily by the volatility of the solvent. In methylene chloride, the reaction temperature is preferably in the range of between about −10° C. and about 10° C.

Preferably, the hydroxyester substrate of Formula V corresponds to Formula VA

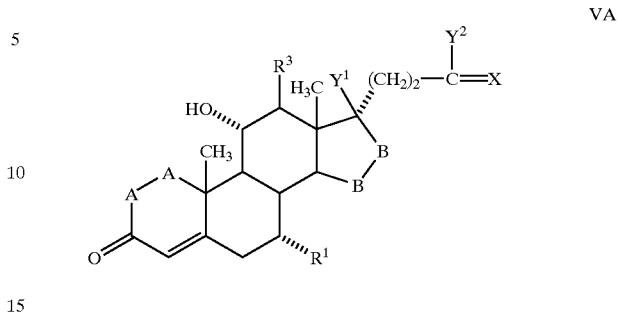

VA and the product corresponds to Formula IVA

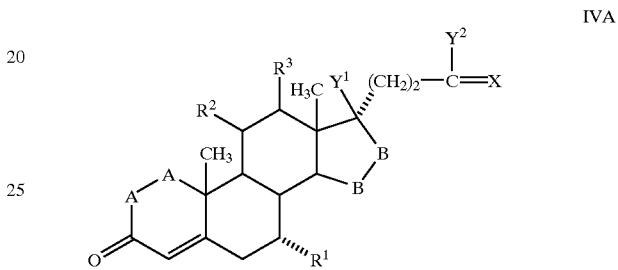

IVA in each of which —A—A—, —B—B—, $R^3$, $Y^1$, $Y^2$, and X are as defined in Formula XIIIA, $R^1$ is lower alkoxycarbonyl or hydroxycarbonyl, and $R^2$ is as defined in Formula IV. Preferably, $R^3$ is hydrogen.

The products of Formula IV are novel compounds which have substantial value as intermediates for the preparation of compounds of Formula I, and especially of Formula IA. Preferably, the compounds of Formula IVA correspond to Formula VA in which —A—A— and —B—B— are —$CH_2$—$CH_2$—, $R^3$ is hydrogen, lower alkyl or lower alkoxy, and $R^8$ and $R^9$ together constitute the 20-spiroxane ring:

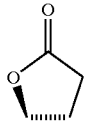

XXXIII

Most preferably, the compound of Formula IV is Methyl Hydrogen 17α-Hydroxy-11α-(methylsulfonyl)oxy-3-oxopregn-4-ene-7α,21-dicarboxylate, γ-Lactone. Where an acyloxy leaving group is desired, the compound of Formula IV is preferably 7-methyl hydrogen 17-hydroxy-3-oxo-11α-(2,2,2-trifluoro-1-oxoethoxy)-17α-pregn-4-ene-7α,21-dicarboxylate, γ-lactone; or 7-methyl 11α-(acetyloxy)-17-hydroxy-3-oxo-17α-pregn-4-ene-7α,21-dicarboxylate, γ-lactone.

If desired, the compound of Formula IV may be isolated by removal of the solvent. Preferably, the reaction solution is first washed with an aqueous alkaline wash solution, e.g., 0.5–2N NaOH, followed by an acid wash, e.g., 0.5–2N HCl.

After removal of the reaction solvent, the product is recrystallized, e.g., by taking the product up in methylene chloride and then adding another solvent such as ethyl ether which lowers the solubility of the product of Formula IV, causing it to precipitate in crystalline form.

In the recovery of the product of Formula IV, or in preparation of the reaction solution for conversion of the Formula IV intermediate to the intermediate of Formula II as is further described hereinbelow, all extractions and/or washing steps may be dispensed with if the solution is instead treated with ion exchange resins for removal of acidic and basic impurities. The solution is treated first with an anion exchange resin, then with a cation exchange resin. Alternatively, the reaction solution may first be treated with inorganic adsorbents such as basic alumina or basic silica, followed by a dilute acid wash. Basic silica or basic alumina may typically be mixed with the reaction solution in a proportion of between about 5 and about 50 g per kg of product, preferably between about 15 and about 20 g per kg product. Whether ion exchange resins or inorganic adsorbents are used, the treatment can be carried out by simply slurrying the resin or inorganic adsorbent with the reaction solution under agitation at ambient temperature, then removing the resin or inorganic adsorbent by filtration.

In an alternative and preferred embodiment of the invention, the product compound of Formula IV is recovered in crude form as a concentrated solution by removal of a portion of the solvent. This concentrated solution is used directly in the following step of the process, which is removal of the 11α-leaving group from the compound of Formula IV, thereby producing an enester of Formula II:

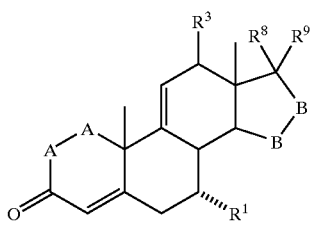

II where —A—A—, —B—B—, $R^3$, $R^8$ and $R^9$ are as defined in Formula XIII, and $R^1$ is as defined in Formula V. For purposes of this reaction, the $R^2$ substituent of the compound of Formula IV may be any leaving group the abstraction of which is effective for generating a double bond between the 9- and 11-carbons. Preferably, the leaving group is a lower alkylsulfonyloxy or acyloxy substituent which is removed by reaction with an acid and an alkali metal salt. Mineral acids can be used, but lower alkanoic acids are preferred. Advantageously, the reagent for the reaction further includes an alkali metal salt of the alkanoic acid utilized. It is particularly preferred that the leaving group comprise mesyloxy and the reagent for the reaction comprise formic acid or acetic acid and an alkali metal salt of one of these acids or another lower alkanoic acid. Where the leaving group is mesyloxy and the removal reagent is either acetic acid and sodium acetate or formic acid and potassium formate, a relatively high ratio of 9,11-olefin to 11,12-olefin is observed. If free water is present during removal of the leaving group, impurities tend to be formed, particularly a 7,9-lactone

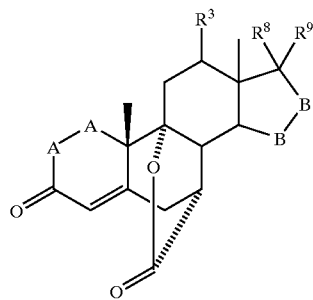

where —A—A—, $R^3$, —B—B—, $R^8$ and $R^9$ are as defined in Formula XIII, which is difficult to remove from the final product. Hence, acetic anhydride or other drying agent is used to remove the water present in formic acid. The free water content of the reaction mixture before reaction should be maintained at a level below about 0.5%, preferably below about 0.1% by weight, as measured by Karl Fischer analysis for water, based on total reaction solution. Although it is preferred that the reaction mixture be kept as dry as practicable, satisfactory results have been realized with 0.3% by weight water. Preferably, the reaction charge mixture contains between about 4% and about 50% by weight of the substrate of Formula IV in the alkanoic acid. Between about 4% and about 20% by weight of the alkali metal salt of the acid is preferably included. Where acetic anhydride is used as the drying agent, it is preferably present in a proportion of between about 0.05 moles and about 0.2 moles per mole of alkanoic acid.

It has been found that proportions of by-product 7,9-lactone and 11,12-olefin in the reaction mixture is relatively low where the elimination reagent comprises a combination of trifluoroacetic acid, trifluoroacetic anhydride and potassium acetate as the reagent for elimination of the leaving group and formation of the enester (9,11-olefin). Trifluoroacetic anhydride serves as the drying agent, and should be present in a proportion of at least about 3% by weight, more preferably at least about 15% by weight, most preferably about 20% by weight, based on the trifluoroacetic acid eliminating reagent.

In addition to the 7,9-lactone, other impurities and by-products which are useful as synthetic intermediates and chromatographic markers have been observed in this step of the Scheme 1 synthesis. The novel 4,9,13-triene of the enester of Formula II (for example, 7-methyl hydrogen 17-methyl-3-oxo-18-norpregna-4,9(11),13-triene-7α,21-dicarboxylate) has been isolated chromatographically from the product solution. The amount of this compound produced appears to increase with an increase in reaction time for this step of the synthesis. It is hypothesized that the compound is formed when the lactone is protonated and the resulting C17 carbonium ion facilitates the migration of the angular methyl group from the C13 position. Deprotonation of this intermediate yields the 4,9,13-triene.

The novel 5-cyano-$\Delta^{11,12}$ of the enester of Formula II (for example, 7-methyl hydrogen 5β-cyano-17-hydroxy-3-oxo-17α-pregn-11-ene-7α,21-dicarboxylate, γ-lactone) and the novel 5-cyano of the enester of Formula II (for example, 7-methyl hydrogen 5-cyano-17-hydroxy-3-oxo-17α-pregn-11-ene-7α,21-dicarboxylate, γ-lactone) also have been isolated chromatographically from the crude product. It is hypothesized that these compounds are formed via dehydration of the residual 5-cyano-7-acid and 5-cyano hydroxyester, respectively, which are present in the crude product solution as a result of the third step of the Scheme 1 synthesis.

The novel C17 epimer of the enester of Formula II (for example, 7-methyl hydrogen 17-hydroxy-3-oxo-17α-pregna-4,9(11)-diene-7,21-dicarboxylate, γ-lactone) also has been isolated chromatographically from the crude product. It is hypothesized that the acidic conditions of the elimination reaction can result in racemization of the C17 chiral center to yield the 17-epimer of the enester. The 17-epimer can be synthesized directly by reacting a compound of Formula IV with a solution of potassium formate, formic acid and acetic anhydride and isolating the 17-epimer.

Although not observed as an impurity in the crude product solution, the 11-ketone of the hydroxyester of formula V can be prepared by oxidizing the 11-hydroxy of the corresponding hydroxyester with a suitable oxidizing agent such as a Jones Reagent. The 11-ketone prepared preferably is 7-methyl hydrogen 17-hydroxy-3,11-dioxo-17α-pregna-4-ene-7α,21-dicarboxylate, γ-lactone.

Alternatively, the 11α-leaving groups from the compound of Formula IV, may be eliminated to produce an enester of Formula II by heating a solution of Formula IV in an organic solvent such as DMSO, DMF or DMA.

Further in accordance with the invention, the compound of Formula IV is reacted initially with an alkenyl alkanoate such as isopropenyl acetate in the presence of an acid such as toluene sulfonic acid or an anhydrous mineral acid such as sulfuric acid to form the 3-enol ester:

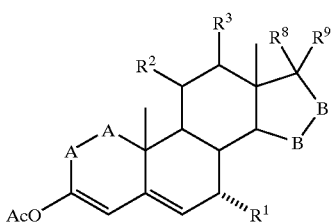

IV(Z)

of the compound of Formula IV. Alternatively, the 3-enol ester can be formed by treatment of the compound of Formula IV with an acid anhydride and base such as acetic acid and sodium acetate. Further alternatives include treatment of the compound of Formula IV with ketene in the presence of an acid to produce the compound of Formula IV(Z). The intermediate of Formula IV(Z) is thereafter reacted with an alkali metal formate or acetate in the presence of formic or acetic acid to produce the $\Delta^{9,11}$ enol acetate of Formula IV(Y)

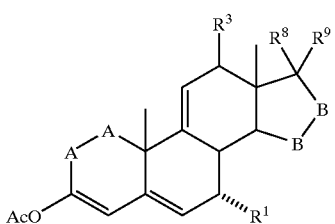

IV(Y)

which can then be converted to the enester of Formula II in an organic solvent, preferably an alcohol such as methanol, by either thermal decomposition of the enol acetate or reaction thereof with an alkali metal alkoxide. The elimination reaction is highly selective to the enester of Formula II in preference to the 11,12-olefin and 7,9-lactone, and this selectivity is preserved through conversion of the enol acetate to the enone.

Preferably, the substrate of Formula IV corresponds to Formula IVA

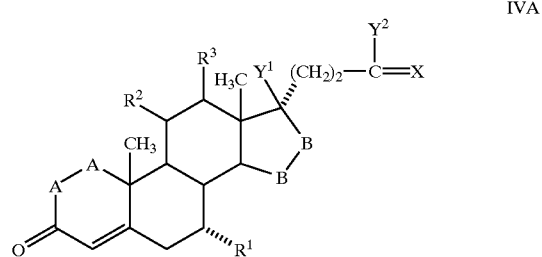

IVA and the enester product corresponds to Formula IIA

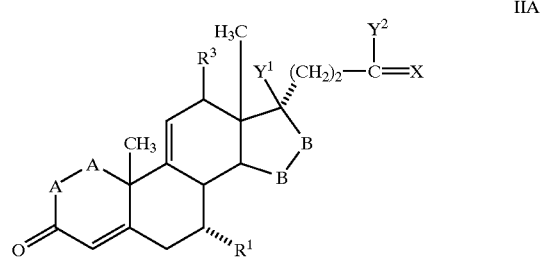

IIA in each of which —A—A—, —B—B—, $R_3$, $Y^1$, $Y^2$, and X are as defined in Formula XIIIA, and $R^1$ is as defined in Formula V. Preferably, $R_3$ is hydrogen.

If desired, the compound of Formula II may be isolated by removing the solvent, taking up the solid product in cold water, and extracting with an organic solvent, such as ethyl acetate. After appropriate washing and drying steps, the product is recovered by removing the extraction solvent. The enester is then dissolved in a solvent appropriate for the conversion to the product of Formula I. Alternatively, the enester can be isolated by adding water to the concentrated product solution and filtering the solid product, thereby preferentially removing the 7,9-lactone. Conversion of the substrate of Formula II to the product of Formula IA may be conducted in the manner described in U.S. Pat. No. 4,559,332 which is expressly incorporated herein by reference, or more preferably by the novel reaction using a haloacetamide promoter as described below.

In another embodiment of the invention, the hydroxyester of Formula V may be converted to the enester of Formula II without isolation of the intermediate compound of Formula IV. In this method, the hydroxyester is taken up in an organic solvent, such as methylene chloride; and either an acylating agent, e.g., methanesulfonyl chloride, or halogenating reagent, e.g., sulfuryl chloride, is added to the solution. The mixture is agitated and, where halogenation is involved, an HCl scavenger such as imidazole is added. This reaction is highly exothermic, and should therefore be conducted at a controlled rate with full cooling. After the base addition, the resulting mixture is warmed to moderate temperature, e.g., about 0° C. to room temperature or slightly above, and reacted for a period of typically about 1 to about 4 hours. After reaction is complete, the solvent is stripped, preferably under high vacuum (e.g., about 24" to about 28" Hg) conditions at about −10° to about +15° C., more preferably about 0° to about 5° C., to concentrate the solution and remove excess base The substrate is then redissolved in an organic solvent, preferably a halogenated solvent such as methylene chloride for conversion to the enester.

The leaving group elimination reagent is preferably prepared by mixing an organic acid, an organic acid salt and a drying agent, preferably formic acid, alkali metal formate and acetic anhydride, respectively, in a dry reactor. Addition of acetic anhydride is exothermic and results in release of CO, so the addition rate must be controlled accordingly. To promote the removal of water, the temperature of this reaction is preferably maintained in the range of about 60° to about 90° C., most preferably about 65° to about 75° C. This reagent is then added to the product solution of the compound of Formula IV to effect the elimination reaction. After about 4 to about 8 hours, the reaction mixture is preferably heated to a temperature of at least about 85° C., but preferably not above about 95° C. until all volatile distillate has been removed, and then for an additional period to complete the reaction, typically about 1 to about 4 hours. The reaction mixture is cooled, and after recovery by standard extraction techniques, the enester may be recovered as desired by evaporating the solvent.

It has further been found that the enester of Formula II may be recovered from the reaction solution by an alternative procedure which avoids the need for extraction steps following the elimination reaction, thereby providing savings in cost, improvement in yield and/or improvement in productivity. In this process, the enester product is precipitated by dilution of the reaction mixture with water after removal of formic acid. The product is then isolated by filtration. No extractions are required.

According to a further alternative for conversion of the hydroxyester of Formula V to the enester of Formula II without isolation of the compound of Formula IV, the 11α-hydroxy group of the Formula V hydroxyester is replaced by halogen, and the Formula II enester is then formed in situ by thermal dehydrohalogenation. Replacement of the hydroxy group by halogen is effected by reaction with sulfuryl halide, preferably sulfuryl chloride, in the cold in the presence of a hydrogen halide scavenger such as imidazole. The hydroxyester is dissolved in a solvent such as tetrahydrofuran and cooled to about 0° C. to about −70° C. The sulfuryl halide is added and the reaction mixture is warmed to moderate temperature, e.g., room temperature, for a time sufficient to complete the elimination reaction, typically about 1 to about 4 hours. The process of this embodiment not only combines two steps into one, but eliminates the use of: a halogenated reaction solvent; an acid (such as acetic acid); and a drying reagent (such as acetic anhydride or sodium sulfate). Moreover, the reaction does not require refluxing conditions, and avoids the generation of by-product CO which results when acetic acid is used as a drying reagent.

In accordance with a particularly preferred embodiment of the invention, the diketone compound of Formula VI can be converted to epoxymexrenone or other compound of Formula I without isolating any intermediate in purified form. In accordance with this preferred process, the reaction solution containing the hydroxyester is quenched with a strong acid solution, cooled to ambient temperature and then extracted with an appropriate extraction solvent. Advantageously, an aqueous solution of inorganic salt, e.g., about 10% by weight saline solution, is added to the reaction mixture prior to the extraction. The extract is washed and dried by azeotropic distillation for removal of the methanol solvent remaining from the ketone cleavage reaction.

The resulting concentrated solution containing between about 5% and about 50% by weight compound of Formula V is then contacted in the cold with an acylating or alkylsulfonylating reagent to form the sulfonic ester or dicarboxylic acid ester. After the alkylsulfonation or carboxylation reaction is complete, the reaction solution is passed over an acidic and then a basic exchange resin column for the removal of basic and acidic impurities. After each pass, the column is washed with an appropriate solvent, e.g., methylene chloride, for the recovery of residual sulfonic or dicarboxylic ester therefrom. The combined eluate and wash fractions are combined and reduced, preferably under vacuum, to produce a concentrated solution containing the sulfonic ester or dicarboxylic ester of Formula IV. This concentrated solution is then contacted with a dry reagent comprising an agent effect for removal of the 11α-ester leaving group and abstraction of hydrogen to form a 9,11 double bond. Preferably, the reagent for removal of the leaving group comprises the formic acid/alkali metal formate/acetic anhydride dry reagent solution described above. After reaction is complete, the reaction mixture is cooled and formic acid and/or other volatile components are removed under vacuum. The residue is cooled to ambient temperature, subjected to appropriate washing steps, and then dried to give a concentrated solution containing the enester of Formula II. This enester may then be converted to epoxymexrenone or other compound of Formula I using the method described herein, or in U.S. Pat. No. 4,559,332.

In an especially preferred embodiment of the invention, the solvent is removed from the reaction solution under vacuum, and the product of Formula IV is partitioned between water and an appropriate organic solvent, e.g., ethyl acetate. The aqueous layer is then back extracted with the organic solvent, and the back extract washed with an alkaline solution, preferably a solution of an alkali metal hydroxide containing an alkali metal halide. The organic phase is concentrated, preferably under vacuum, to yield the enester product of Formula II. The product of Formula II may then be taken up in an organic solvent, e.g., methylene chloride, and further reacted in the manner described in the '332 patent to produce the product of Formula I.

Where trihaloacetonitrile is used in the epoxidation reaction, it has been found that the selection of solvent is important, with halogenated solvents being highly preferred, and methylene chloride being especially preferred. Solvents such as dichloroethane and chlorobenzene give reasonably satisfactory yields, but yields are generally better in a methylene chloride reaction medium. Solvents such as acetonitrile and ethyl acetate generally give poor yields, while reaction in solvents such as methanol or water/tetrahydrofuran give little of the desired product.

Further in accordance with the present invention, it has been discovered that numerous improvements in the synthesis of epoxymexrenone can be realized by use of a trihaloacetamide rather than a trihaloacetonitrile as a peroxide activator for the epoxidation reaction. In accordance with a particularly preferred process, the epoxidation is carried out by reaction of the substrate of Formula IIA with hydrogen peroxide in the presence of trichloroacetamide and an appropriate buffer. Preferably, the reaction is conducted in a pH in the range of about 3 to about 7, most preferably between about 5 and about 7. However, despite these considerations, successful reaction has been realized outside the preferred pH ranges.

Especially favorable results are obtained with a buffer comprising dipotassium hydrogen phosphate, and/or with a buffer comprising a combination of dipotassium hydrogenphosphate and potassium dihydrogen phosphate in relative proportions of between about 1:4 and about 2:1, most preferably in the range of about 2:3. Borate buffers can also be used, but generally give slower conversions than dipotassium phosphate or $K_2HPO_4/KH_2PO_4$ mixtures. Whatever the makeup of the buffer, it should provide a pH in the range indicated above. Aside from the overall composition of the buffer or the precise pH it may impart, it has been observed that the reaction proceeds much more effectively if at least a portion of the buffer is comprised of dibasic hydrogenphosphate ion. It is believed that this ion may participate essentially as a homogeneous catalyst in the formation of an adduct or complex comprising the promoter and hydroperoxide ion, the generation of which may in turn be essential to the overall epoxidation reaction mechanism. Thus, the quantitative requirement for dibasic hydrogenphosphate (preferably from $K_2HPO_4$) may be only a small catalytic concentration. Generally, it is preferred that $K_2HPO_4$ be present in a proportion of at least about 0.1 equivalents, e.g., between about 0.1 and about 0.3 equivalents, per equivalent substrate.

The reaction is carried out in a suitable solvent, preferably methylene chloride, but alternatively other halogenated solvents such as chlorobenzene or dichloroethane can be used. Toluene and mixtures of toluene and acetonitrile have also been found satisfactory. Without committing to a particular theory, it is posited that the reaction proceeds most effectively in a two phase system in which a hydroperoxide intermediate is formed and distributes to the organic phase of low water content, and reacts with the substrate in the organic phase. Thus the preferred solvents are those in which water solubility is low. Effective recovery from toluene is promoted by inclusion of another solvent such as acetonitrile.

In the conversion of substrates of Formula II to products of Formula I, toluene provides a process advantage since the substrates are freely soluble in toluene and the products are not. Thus, the product precipitates during the reaction when conversions reach the 40–50% range, producing a three phase mixture from which the product can be conveniently separated by filtration. Methanol, ethyl acetate, acetonitrile alone, THF and THF/water have not proved to be as effective as the halogenated solvents or toluene in carrying out the conversion of this step of the process.

While trichloroacetamide is a highly preferred reagent, other trihaloacetamides such as trifluoroacetamide and chlorodifluoroacetamide can also be used. Trihalomethylbenzamide, and other compounds having an arylene, alkenyl or alkynyl moiety (or other group which allows the transfer of the electron withdrawing effect of the electron withdrawing group to the amide carbonyl) between the electron withdrawing trihalomethyl group and the carbonyl of the amide, may also be useful. Heptafluorobutyramides may also be used, but with less favorable results. Generically, the peroxide activator may correspond to the formula:

$R^oC(O)NH_2$ where $R^o$ is a group having an electron withdrawing strength (as measured by sigma constant) at least as high as that of the monochloromethyl group. The electron withdrawing group preferably is attached directly to the amide carbonyl for maximum effectiveness. More particularly, the peroxide activator may correspond to the formula:

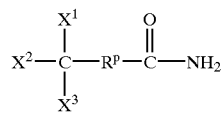

where $R^p$ is a group which allows the transfer of the electron withdrawing effect of an electron withdrawing group to the amide carbonyl, and preferably is selected from among arylene, alkenyl, alkynyl and $—(CX^4X^5)_n—$ moieties; $X^1$, $X^2$, $X^3$, $X^4$ and $X^5$ are independently selected from among halo, hydrogen, alkyl, haloalkyl and cyano and cyanoalkyl; and n is 0, 1 or 2; provided that when n is 0, then at least one of $X^1$, $X^2$ and $X^3$ is halo; and when $R^p$ is $—(CX^4X^5)_n—$ and n is 1 or 2, then at least one of $X^4$ and $X^5$ is halo. Where any of $X^1$, $X^2$, $X^3$, $X^4$ or $X^5$ is not halo, it is preferably haloalkyl, most preferably perhaloalkyl. Particularly preferred activators include those in which n is 0 and at least two of $X^1$, $X^2$ and $X^3$ are halo; or those in which $R^p$ is $—(CX^4X^5)_n—$, n is 1 or 2, at least one of $X^4$ and $X^5$ is halo, the other of $X^4$ and $X^5$ is halo or perhaloalkyl, and $X^1$, $X^2$ and $X^3$ are halo or perhaloalkyl. Each of $X^1$, $X^2$, $X^3$, $X^4$ and $X^5$ is preferably Cl or F, most preferably Cl, though mixed halides may also be suitable, as may perchloralkyl or perbromoalkyl and combinations thereof, provided that the carbon directly attached to the amide carbonyl is substituted with at least one halo group.

Preferably, the peroxide activator is present in a proportion of at least about 1 equivalent, more preferably between about 1.5 and about 2 equivalents, per equivalent of substrate initially present. Hydrogen peroxide should be charged to the reaction in at least modest excess, or added progressively as the epoxidation reaction proceeds. Although the reaction consumes only one to two equivalents of hydrogen peroxide per mole of substrate, hydrogen peroxide is preferably charged in substantial excess relative to substrate and activator initially present. Without limiting the invention to a particular theory, it is believed that the reaction mechanism involves formation of an adduct of the activator and the peroxide anion, that the formation of this reaction is reversible with the equilibrium favoring the reverse reaction, and that a substantial initial excess of hydrogen peroxide is therefore necessary in order to drive the reaction in the forward direction. Temperature of the reaction is not narrowly critical, and may be effectively carried out within the range of about 0° to about 100° C. The optimum temperature depends on the selection of solvent. Generally, the preferred temperature is between about 20° C. and about 30° C., but in certain solvents, e.g., toluene the reaction may be advantageously conducted in the range of about 60° to about 70° C. At about 25° C., reaction typically requires less than about 10 hours, typically about 3 to about 6 hours. If needed, additional activator and hydrogen peroxide may be added at the end of the reaction cycle to achieve complete conversion of the substrate.

At the end of the reaction cycle, the aqueous phase is removed, the organic reaction solution is preferably washed for removal of water soluble impurities, after which the product may be recovered by removal of the solvent. Before removal of solvent, the reaction solution should be washed with at least a mild to moderately alkaline wash, e.g., sodium carbonate. Preferably, the reaction mixture is washed successively with: a mild reducing solution such as a weak (e.g. about 3% by weight) solution of sodium sulfite in water; an alkaline solution, e.g., NaOH or KOH (preferably about 0.5N); an acid solution such as HCl (preferably about 1N); and a final neutral wash comprising water or brine, preferably saturated brine to minimize product losses. Prior to removal of the reaction solvent, another solvent such as an organic solvent, preferably ethanol may be advantageously added, so that the product may be recovered by crystallization after distillation for removal of the more volatile reaction solvent.

It should be understood that the novel epoxidation method utilizing trichloroacetamide or other novel peroxide activator has application well beyond the various schemes for the preparation of epoxymexrenone, and in fact may be used for the formation of epoxides across olefinic double bonds in a wide variety of substrates subject to reaction in the liquid phase. The reaction is particularly effective in unsaturated compounds in which the olefins are tetrasubstituted and trisubstituted, i.e., $R^aR^bC=CR^cR^d$ and $R^aR^bC=CR^cH$ where $R^a$ to $R^d$ represent substituents other than hydrogen. The reaction proceeds most rapidly and completely where the substrate is a cyclic compound with a trisubstituted double bond, or either a cyclic or acyclic compound with a tetrasubstituted double bond. Exemplary substrates for the epoxidation reaction include $\Delta^{9,11}$-canrenone, and the following substrates:

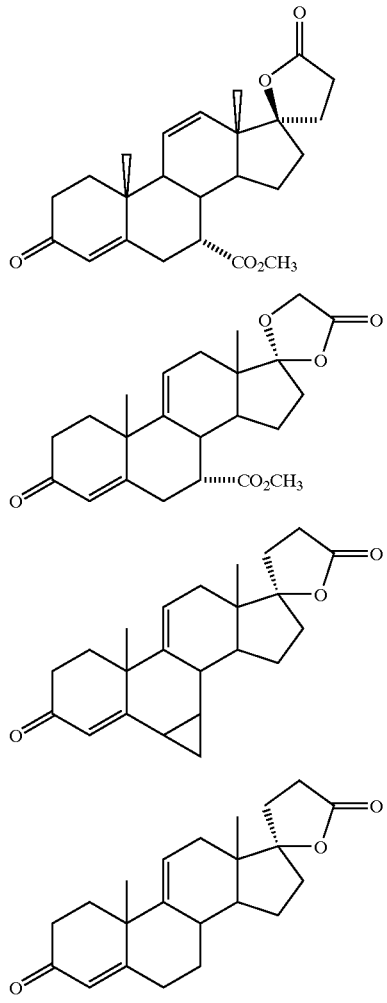

-continued

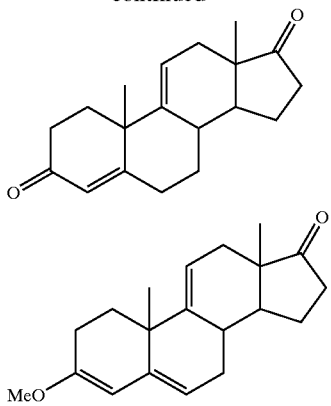

Because the reaction proceeds more rapidly and completely with trisubstituted and tetrasubstituted double bonds, it is especially effective for selective epoxidation across such double bonds in compounds that may include other double bonds where the olefinic carbons are monosubstituted, or even disubstituted.

Other non-limiting examples illustrating the generic epoxidation reaction include the following epoxidation reactions:

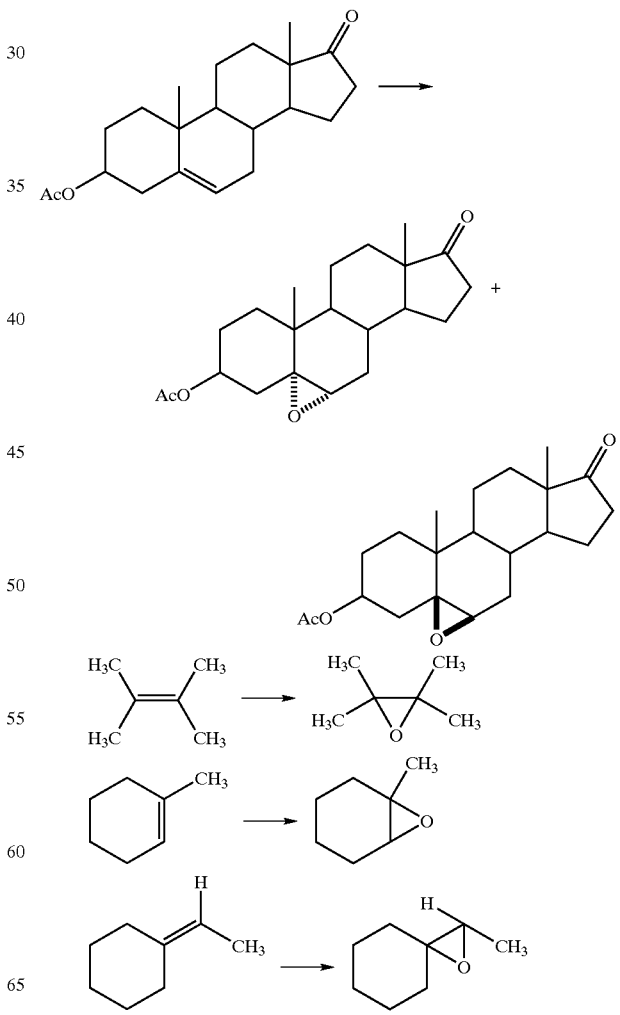

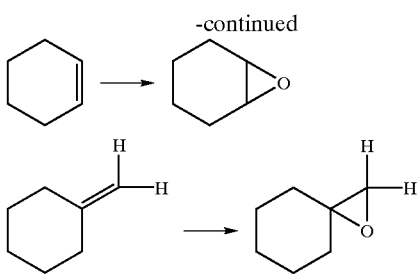

It should be further understood that the reaction may be used to advantage in the epoxidation of monosubstituted or even disubstituted double bonds, such as the 11,12-olefin in various steroid substrates. However, because it preferentially epoxidizes the more highly substituted double bonds, e.g., the 9,11-olefin, with high selectivity, the process of this invention is especially effective for achieving high yields and productivity in the epoxidation steps of the various reaction schemes described elsewhere herein.

The improved process has been shown to be a particularly advantageous application to the preparation of:

IB

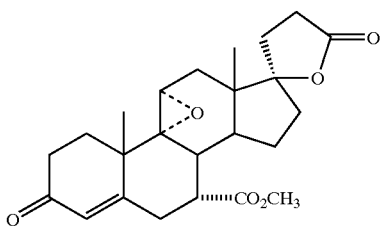

the epoxidation of:

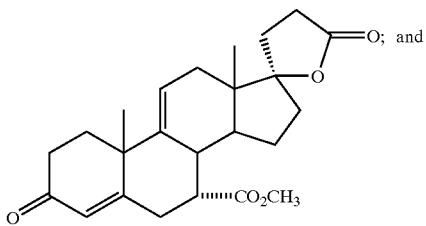

the preparation of:

IC

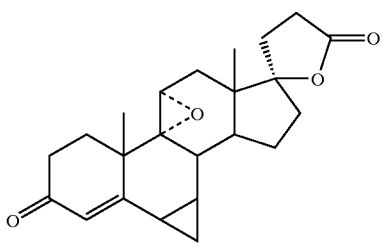

the epoxidation of:

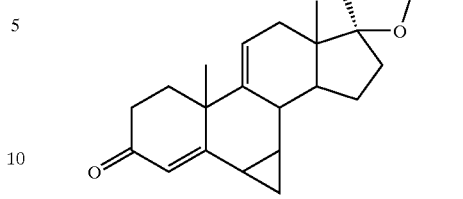

Multiple advantages have been demonstrated for the process of the invention in which trichloroacetamide is used in place of trichloroacetonitrile as the oxygen transfer reagent for the epoxidation reaction. The trichloroacetamide reagent system has a low affinity for electronically deficient olefins such as α,β-unsaturated ketones. This allows for selective epoxidation of a non-conjugated olefin in substrates containing both types of double bonds. Additionally, in complex substrates such as steroids, disubstituted and trisubstituted olefins can be differentiated by reaction. Thus, good selectivity is observed in the epoxidation of the isomeric Δ-9,11 and Δ-11,12 compounds. In this case, the 9,11 epoxide is formed with minimal reaction of the isomer containing the Δ-11,12 double bond. Accordingly, reaction yield, product profile and final purity are substantially enhanced in comparison to reactions in which a trihaloacetonitrile is used. It has further been discovered that the substantial excess oxygen generation observed with the use of trihaloacetonitrile is minimized with trichloroacetamide, imparting improved safety to the epoxidation process. Further in contrast to the trichloroacetonitrile promoted reaction, the trichloroacetamide reaction exhibits minimum exothermic effects, thus facilitating control of the thermal profile of the reaction. Agitation effects are observed to be minimal and reactor performance more consistent, a further advantage over the trichloroacetonitrile process. The reaction is more amenable to scaleup than the trichloroacetonitrile promoted reaction. Product isolation and purification is simple. There is no observable Bayer-Villager oxidation of carbonyl function (peroxide promoted conversion of ketone to ester) as experienced when using m-chloroperoxybenzoic acid or other peracids. The reagent is inexpensive, readily available, and easily handled.

In addition, the following compounds have been observed by chromatography in the crude product from the step of the Scheme 1 synthesis in which the enester of Formula II is converted to the compound of Formula I:

(1) the novel 11α,12α epoxide of the enester of formula II, for example, 7-methyl hydrogen 11α,12α-epoxy-17-hydroxy-3-oxo-17α-pregn-4-ene-7α,21-dicarboxylate, γ-lactone;

(2) the novel 4,5:9,11-diepoxide of the enester of formula II, for example 7-methyl hydrogen 4α,5α:9α,11α-diepoxy-17-hydroxy-3-oxo-17α-pregnane-7α,21-dicarboxylate, γ-lactone;

(3) the novel 12-ketone of the enester of formula II, for example 7-methyl hydrogen 17-hydroxy-3,12-dioxo-17α-pregna-4,9(11)-diene-7α,21-dicarboxylate, γ-lactone;

(4) the novel 9,11-dihydroxy of the enester of formula II, for example 7-methyl hydrogen 9α,11β,17-trihydroxy-3-oxo-17α-pregna-4-ene-7α,21-dicarboxylate, γ-lactone;

(5) the novel 12-hydroxy analog of the enester of formula II, for example 7-methyl hydrogen 12α,17-dihydroxy- 3-oxo-17α-pregna-4,9(11)-diene-7α,21-dicarboxylate, γ-lactone; and (6) the novel 7-acid of the compound of Formula I, for example 9,11α-epoxy-17-hydroxy-3-oxo-17α-pregn-4-ene-7α,21-dicarboxylic acid, γ-lactone.

These compounds have utility as synthetic intermediates and/or chromatographic markers in the preparation of the compound of Formula I, particularly epoxymexrenone.

The 11α,12α-epoxide of the enester of formula II is hypothesized to form via an impurity produced during the previous step in which a compound of formula IV is converted to the enester of formula II. This impurity was chromatographically isolated and is the $\Delta^{11,12}$ enester. It typically is produced with the $\Delta^{9,11}$ enester in a ratio of about 90:10 ($\Delta^{9,11}$ enester:$\Delta^{11,12}$ enester), although this ratio can vary. Oxidation of the $\Delta^{11,12}$ enester during the conversion of the enester of formula II to the compound of Formula I yields the 11α,12α-epoxide.

The 4,5:9,11-diepoxide of the enester of Formula I was chromatographically isolated. It is hypothesized to result from over-epoxidation of the enester. It typically is observed in the crude product at levels of about 5% by weight or less, although this amount can vary.

The 12-ketone of the enester of Formula II was chromatographically isolated. It is hypothesized to result from allylic oxidation of the enester. It typically is observed in the crude product at levels of about 5% by weight or less, although this amount can vary. The level of 12-ketone detected in the crude product when trichloroacetonitrile was used as the hydrogen peroxide activator was higher than the level detected when trichloroacetamide was used as the activator.

The 9,11-dihydroxy of the enester of Formula II was chromatographically isolated. It typically is observed in the crude product at levels of about 5% by weight or less, although this amount can vary. It is hypothesized to result from hydrolysis of the epoxide of Formula I.

The 12-hydroxy of the enester of formula II was chromatographically isolated. It typically is observed in the crude product at levels of about 5% by weight or less, although this amount can vary. It is hypothesized to result from hydrolysis of the 11,12 epoxide with subsequent elimination of the 11β-hydroxy.

In addition, the compounds of Formula I prepared in accordance with this disclosure can be further modified to provide a metabolite, derivative, prodrug or the like with improved properties (such as improved solubility and absorption) which facilitate the administration and/or efficacy of epoxymexrenone. The 6-hydroxy of the compound of Formula I (for example, 7-methyl hydrogen 6β,17-dihydroxy-9,11α-epoxy-3-oxo-17α-pregn-4-ene-7α,21-dicarboxylate, γ-lactone) is a novel compound which has been identified as a possible metabolite in the rat. The 6-hydroxy metabolite can be prepared from the corresponding ethyl enol ether (for example, 7-methyl hydrogen 9,11α-epoxy-3-ethoxy-17-hydroxy-17α-pregn-4-ene-7α,21-dicarboxylate, γ-lactone). The ethyl enol ether of of the compound of Formula I can be prepared in accordance with the procedure set forth in R. M. Weier and L. M. Hofmann (J. Med Chem 1977, 1304) which is incorporated by reference herein. The ethyl enol ether is then reacted with m-chloroperbenzoic acid to yield the corresponding 6-hydroxy of the compound of Formula I.

It is further hypothesized that the monocarboxylic salts of epoxymexrenone, particularly the potassium and sodium salts, are suitable alternatives to facilitate administration of a compound of Formula I to an individual for whom administration of an aldosterone antagonist is indicated. Under mild basic conditions it is possible to selectively open the spirolactone of the compounds of Formula I without hydrolyzing the C7 ester substituent to give the corresponding 17β-hydroxy-17α-(3-propionic acid) analog. These open chain analogs are more polar than their lactone counterparts and have shorter retention times when analyzed by reverse phase HPLC. Acidic conditions generally cause the regeneration of the lactone ring.

Under more forcing conditions, the spirolactone is opened and the C7 ester is hydrolyzed to give the corresponding by-products, 17β-hydroxy-17α-(3-propionic acid)-7-acid analogs of the compounds of Formula I. These dicarboxylic acids have shorter retention times than the monocarboxylic acids when analyzed by reverse phase HPLC. Acidic conditions (e.g., treatment with a dilute acid such as 0.1–4 M hydrochloric acid) generally cause the regeneration of the lactone ring of the dicarboxylic acid.

The novel epoxidation method of the invention is highly useful as the concluding step of the synthesis of Scheme 1. In a particularly preferred embodiment, the overall process of Scheme 1 proceeds as follows:

Scheme 2

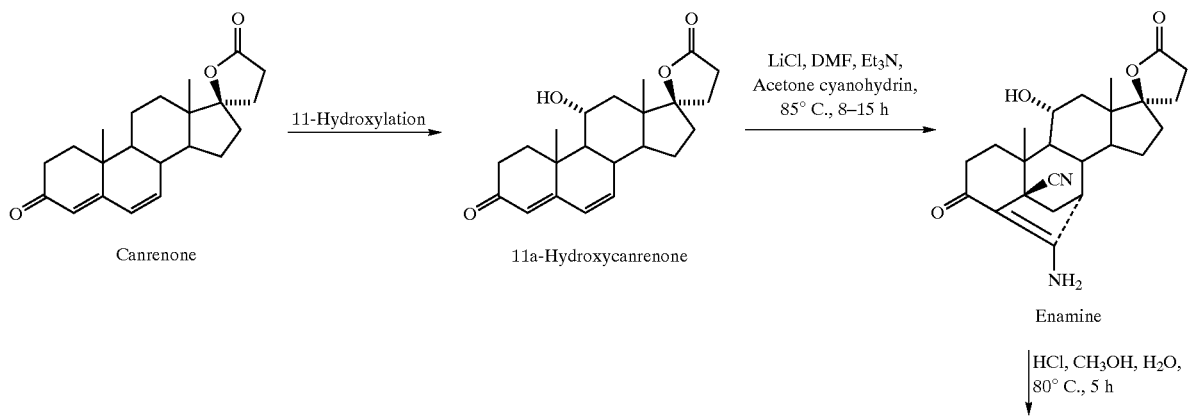

-continued

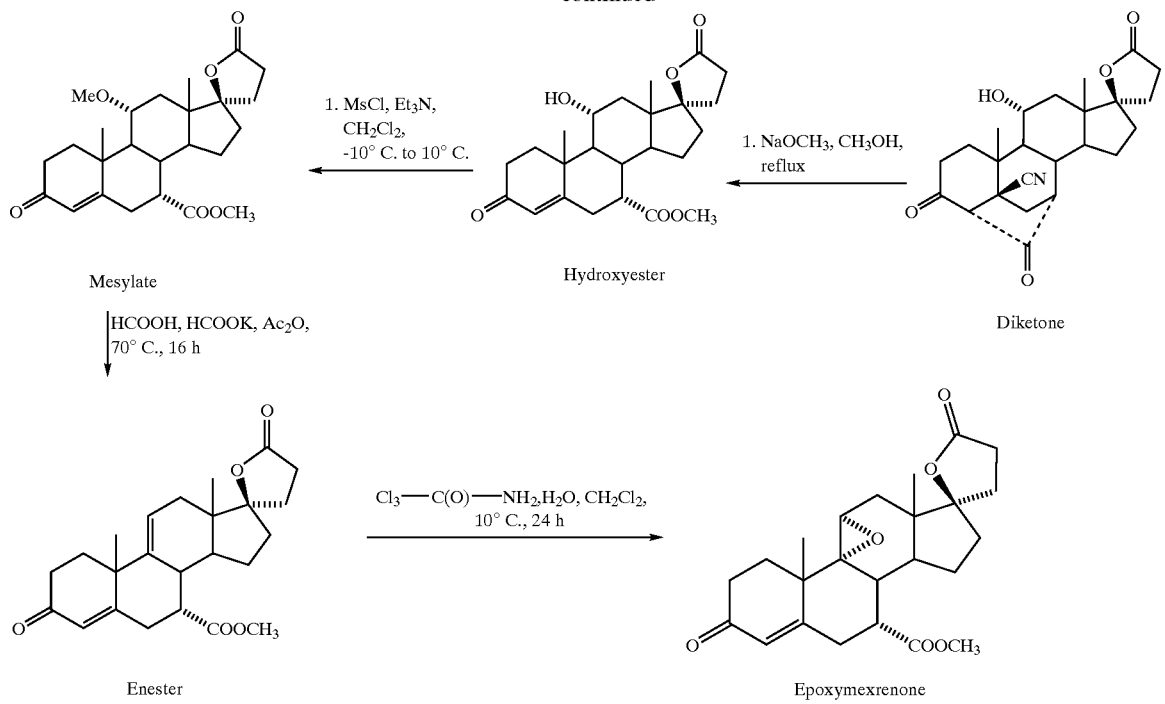

The second of the novel reaction schemes (Scheme 2) of this invention starts with canrenone or other substrate corresponding to Formula XIII

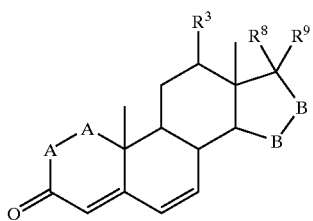

XIII where —A—A—, —B—B—, $R^3$, $R^8$ and $R^9$ are as defined in Formula XIII. In the first step of this process, the substrate of Formula XIII is converted to a product of Formula XII

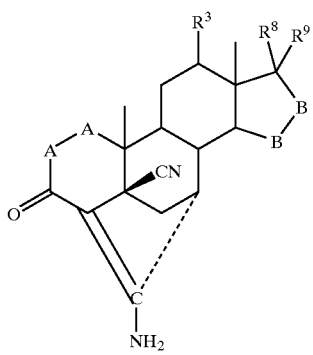

XII using a cyanidation reaction scheme substantially the same as that described above for conversion of the substrate of Formula VIII to the intermediate of Formula VII. Preferably, the substrate of Formula XIII corresponds to Formula XIIIA

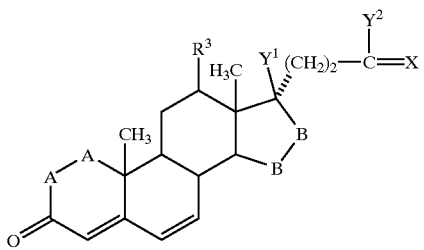

XIIIA and the enamine product corresponds to Formula XIIA

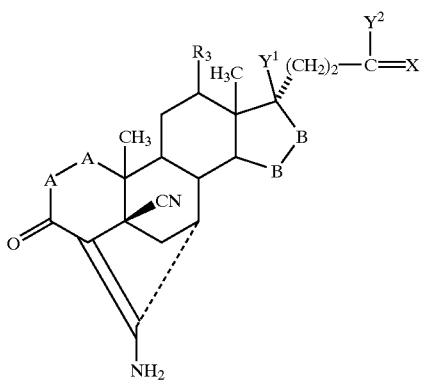

XIIA in each of which —A—A—, —B—B—, $R^3$, $^1$, $Y^2$, and X are as defined in Formula XIIIA. Preferably, $R^3$ is hydrogen.

In the second step of Scheme 2, the enamine of Formula XII is hydrolyzed to an intermediate diketone product of Formula XI

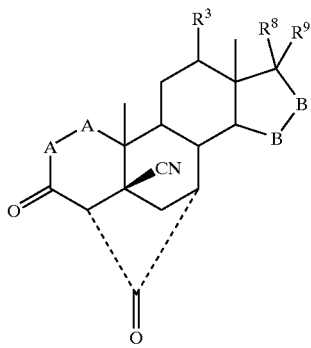

XI where —A—A—, —B—B—, $R^3$, $R^8$ and $R^9$ are as defined in Formula XIII, using a reaction scheme substantially the same as that described above for conversion of the substrate of Formula VIII to the intermediate of Formula VII. Preferably, the substrate of Formula XII corresponds to Formula XIIA

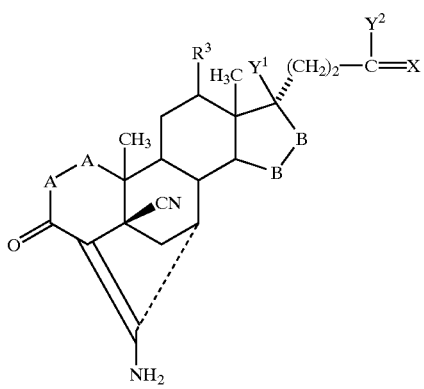

XIIA and the diketone product corresponds to Formula XIA

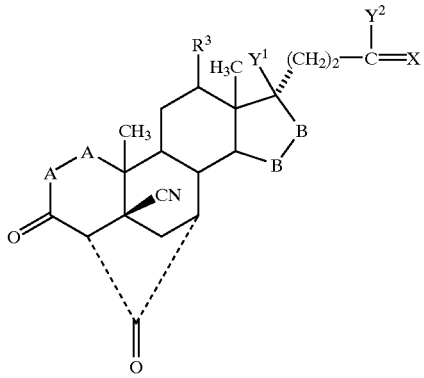

XIA in each of which —A—A—, —B—B—, $R^3$, $Y^1$, $Y^2$, and X are as defined in Formula XIIIA. Preferably, $R^3$ is hydrogen.

Further in accordance with reaction scheme 2, the diketone of Formula XI is reacted with an alkali metal alkoxide to form mexrenone or other product corresponding to Formula X,

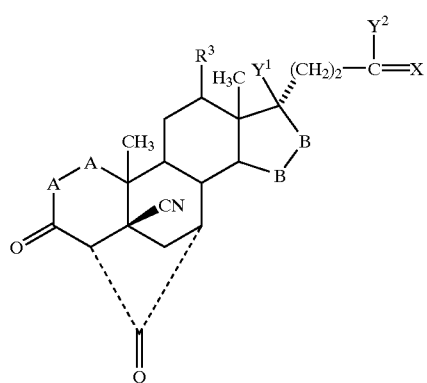

X in each of which —A—A—, —B—B—, $R^3$, $R^8$ and $R^9$ are as defined in Formula XIII, and $R^1$ is as defined in Formula V. The process is carried out using substantially the same reaction scheme that is described above for the conversion of the compounds of Formula VI to those of Formula V. Preferably, the substrate of Formula XI corresponds to Formula XIA

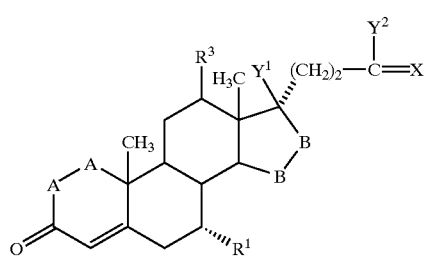

XIA and the intermediate product corresponds to Formula XA

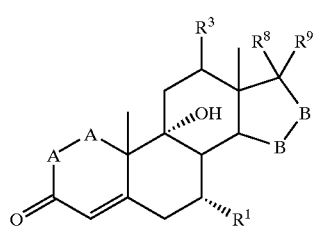

XA in each of which —A—A—, —B—B—, $R^3$, $Y^1$, $Y^2$, and X are as defined in Formula XIIIA, and $R^1$ is as defined in Formula V. Preferably, $R^3$ is hydrogen.

Mexrenone and other compounds of Formula X are next 9α-hydroxylated by a novel bioconversion process to yield products of Formula IX

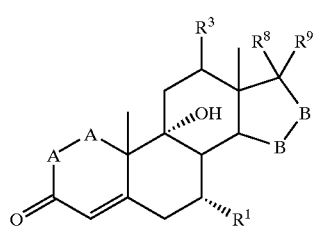

IX where —A—A—, —B—B—, $R^3$, $R^8$ and $R^9$ are as defined in Formula XIII, and $R^1$ is as defined in Formula V. Among the organisms that can be used in this hydroxylation step are *Nocardia conicruria* ATCC 31548, *Nocardia aurentia* ATCC 12674, *Corynespora cassiicola* ATCC 16718, *Streptomyces hydroscopicus* ATCC 27438, *Mortierella isabellina* ATCC 42613, *Beauvria bassiana* ATCC 7519, *Penicillum purpurogenum* ATCC 46581, *Hypomyces chrysospermus* IMI 109891, *Thamnostylum piriforme* ATCC 8992, *Cunninghamella blakesleeana* ATCC 8688a, *Cunninghamella echinulata* ATCC 3655, *Cunninghamella elegans* ATCC 9245, *Trichothecium roseum* ATCC 12543, *Epicoccum humicola* ATCC 12722, *Saccharopolyspora eythrae* ATCC 11635, *Beauvria bassiana* ATCC 13144, *Arthrobacter simplex*, *Bacterium cyclooxydans* ATCC 12673, *Cylindrocarpon radicicola* ATCC 11011, *Nocardia aurentia* ATCC 12674, *Norcardia restrictus* ATCC 14887, *Pseudomonas testosteroni* ATCC 11996, *Rhodococcus equi* ATCC 21329, *Mycobacterium fortuitum* NRRL B8119, and *Rhodococcus rhodochrous* ATCC 19150. The reaction is carried out substantially in the manner described above in connection with FIGS. 1 and 2. The process of FIG. 1 is particularly preferred.

Growth media useful in the bioconversions preferably contain between about 0.05% and about 5% by weight available nitrogen; between about 0.5% and about 5% by weight glucose; between about 0.25% and about 2.5% by weight of a yeast derivative; and between about 0.05% and about 0.5% by weight available phosphorus. Particularly preferred growth media include the following:

soybean meal: between about 0.5% and about 3% by weight glucose; between about 0.1% and about 1% by weight soybean meal; between about 0.05% and about 0.5% by weight alkali metal halide; between about 0.05% and about 0.5% by weight of a yeast derivative such as autolyzed yeast or yeast extract; between about 0.05% and about 0.5% by weight of a phosphate salt such as $K_2HPO_4$; pH=7;

peptone-yeast extract-glucose: between about 0.2% and about 2% by weight peptone; between about 0.05% and about 0.5% by weight yeast extract; and between about 2% and about 5% by weight glucose;

Mueller-Hinton: between about 10% and about 40% by weight beef infusion; between about 0.35% and about 8.75% by weight casamino acids; between about 0.15% and about 0.7% by weight starch.

Fungi can be grown in soybean meal or peptone nutrients, while actinomycetes and eubacteria can be grown in soybean meal (plus 0.5% to 1% by weight carboxylic acid salt such as sodium formate for biotransformations) or in Mueller-Hinton broth.

The production of 11β-hydroxymexrenone from mexrenone by fermentation is discussed in Example 19B. Similar bioconversion processes can be used to prepare other starting materials and intermediates. Example 19A discloses the bioconversion of androstendione to 11β-hydroxyandrostendione. Example 19C discloses the bioconversion of mexrenone to 11α-hydroxymexrenone, $\Delta^{1,2}$-mexrenone, 6β-hydroxymexrenone, 12β-hydroxymexrenone, and 9α-hydroxymexrenone. Example 19D discloses the bioconversion of canrenone to $\Delta^{9,11}$-canrenone.

The products of Formula IX are novel compounds, which may be separated by filtration, washed with a suitable organic solvent, e.g., ethyl acetate, and recrystallized from the same or a similar solvent. They have substantial value as intermediates for the preparation of compounds of Formula I, and especially of Formula IA. Preferably, the compounds of Formula IX correspond to Formula IXA in which —A—A— and —B—B— are —$CH_2$—$CH_2$—, $R^3$ is hydrogen, lower alkyl or lower alkoxy, and $R^8$ and $R^9$ together constitute the 20-spiroxane ring:

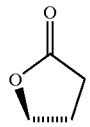

XXXIII

In the next step of the Scheme 2 synthesis, the product of Formula IX is reacted with a dehydration reagent (suitable dehydration reagents such as $PhSOCl$ or $ClSO_3H$ are known to persons skilled in the art) to produce a compound of Formula II

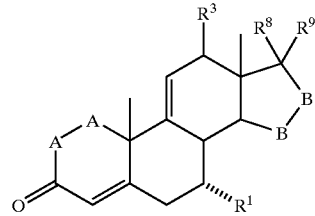

II wherein —A—A—, —B—B—, $R^3$, $R^8$ and $R^9$ are as defined in Formula XIII, and $R^1$ is as defined in Formula V. Preferably, the substrate of Formula IX corresponds to Formula IXA

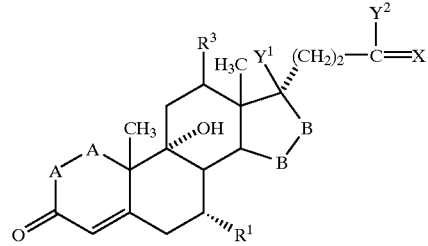

IXA and the intermediate product corresponds to Formula IIA

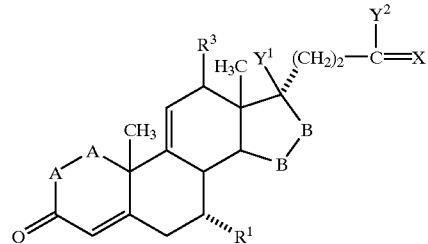

IIA in each of which —A—A—, —B—B—, $R^3$, $Y^1$, $Y^2$ and X are as defined in Formula XIIIA, and $R^1$ is as defined in Formula V. Preferably, $R^3$ is hydrogen.

In the final step of this synthesis scheme, the product of Formula II is converted to that of Formula I by epoxidation in accordance with the method described in U.S. Pat. No. 4,559,332; or preferably by the novel epoxidation method of the invention as described hereinabove.

In a particularly preferred embodiment, the overall process of Scheme 2 proceeds as follows:

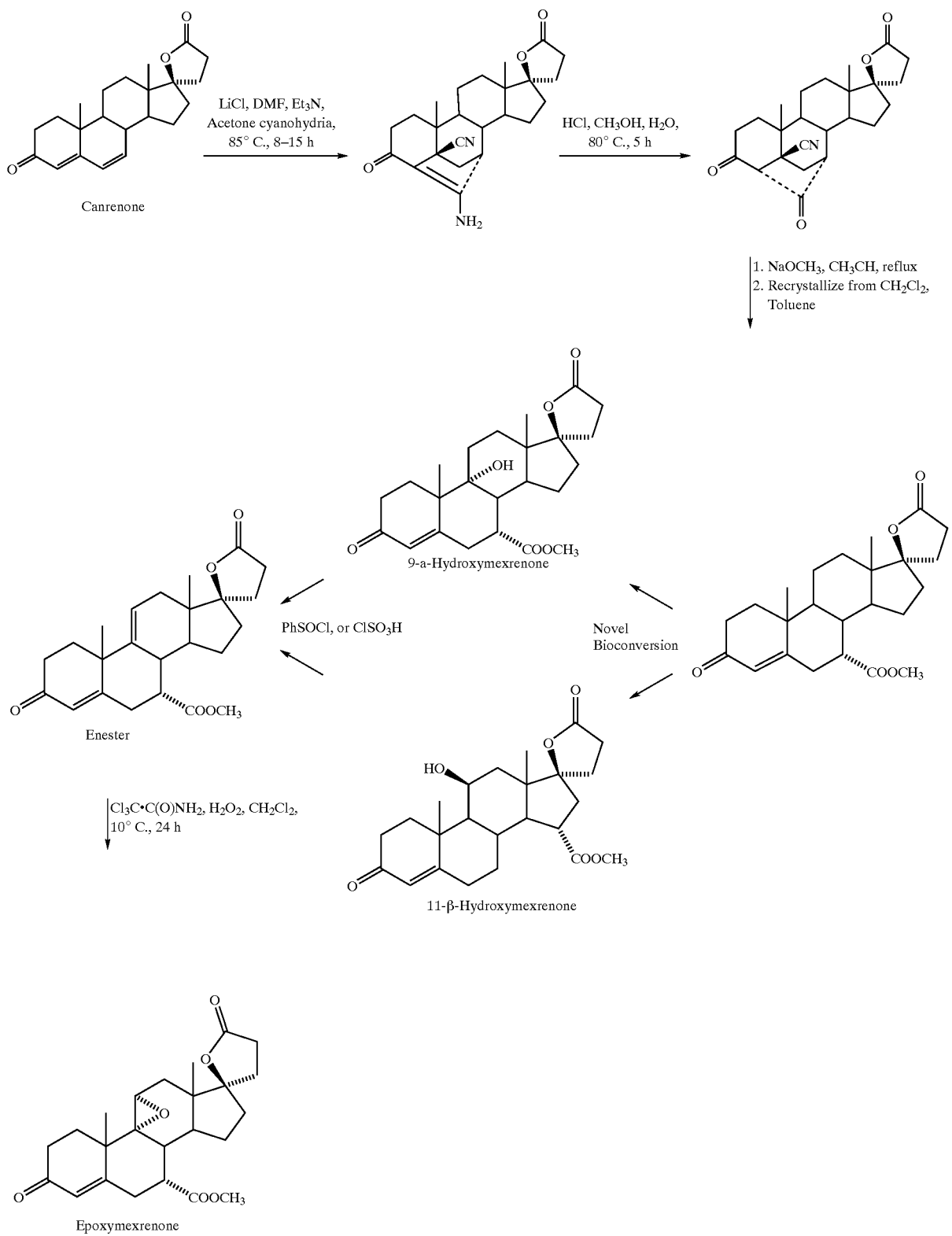

The synthesis in this case begins with a substrate corresponding to Formula XX

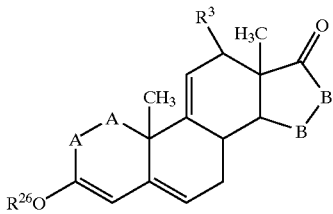

XX where —A—A— and R³ are as defined in Formula XIII, —B—B— is as defined in Formula XIII except that neither R⁶ nor R⁷ is part of a ring fused to the D ring at the 16,17 positions, and R²⁶ is lower alkyl, preferably methyl. Preferably, R³ is hydrogen. Reaction of the substrate of Formula XX with a sulfonium ylide produces the epoxide intermediate corresponding to Formula XIX

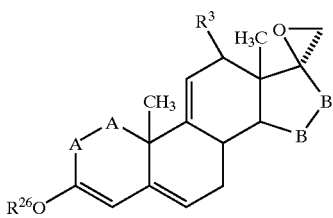

XIX wherein —A—A—, —B—B—, R³ and R²⁶ are as defined in Formula XX. Preferably, R³ is hydrogen.

In the next step of synthesis scheme 3, the intermediate of Formula XIX is converted to a further intermediate of Formula XVIII

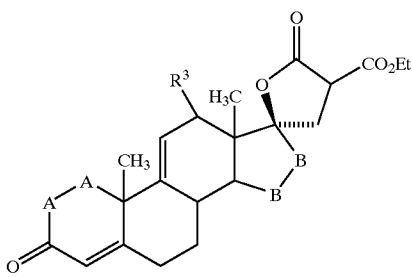

XVIII wherein —A—A—, —B—B— and R³ are as defined in Formula XX. Preferably, R³ is hydrogen. In this step, Formula XIX substrate is converted to Formula XVIII intermediate by reaction with NaCH(COOEt)₂ in the presence of a base in a solvent.

Exposure of the compound of Formula XVIII to heat, water and an alkali halide produces a decarboxylated intermediate compound corresponding to Formula XVII

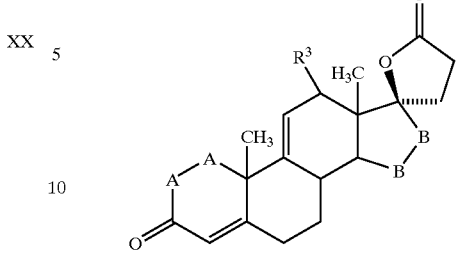

XVII wherein —A—A—, —B—B— and R³ are as defined in Formula XX. Preferably, R³ is hydrogen. The process for conversion of the compound of Formula XX to the compound of Formula XVII corresponds essentially to that described in U.S. Pat. Nos. 3,897,417, 3,413,288 and 3,300,489, which are expressly incorporated herein by reference. While the substrates differ, the reagents, mechanisms and conditions for introduction of the 17-spirolactone moiety are essentially the same.

Reaction of the intermediate of Formula XVII with a dehydrogenation reagent yields the further intermediate of Formula XVI.

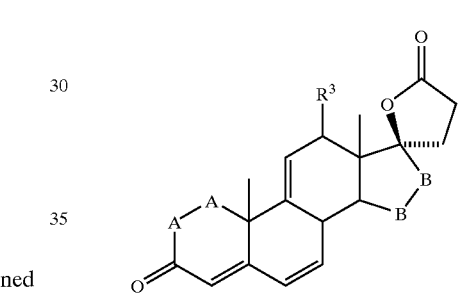

XVI where —A—A—, —B—B— and R³ are as defined in Formula XX. Preferably, R³ is hydrogen. Typically useful dehydrogenation reagents include dichlorodicyanobenzoquinone (DDQ) and chloranil (2,3,5,6-tetrachloro-p-benzoquinone). Alternatively, the dehydrogenation could be achieved by a sequential halogenation at the 6-position carbon followed by dehydrohalogenation reaction.

The intermediate of Formula XVI is next converted to the enamine of Formula XVB

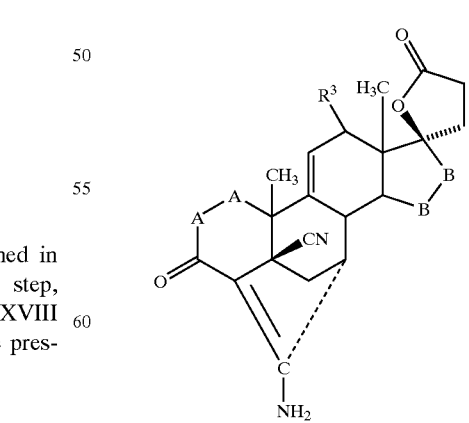

XVB wherein —A—A—, —B—B— and R³ are as defined in Formula XX. Preferably, R³ is hydrogen. Conversion is by cyanidation essentially in the manner described above for the conversion of the 11α-hydroxy compound of Formula VIII to the enamine of Formula VII. Typically, the cyanide ion source may be an alkali metal cyanide. The base is preferably pyrrolidine and/or tetramethylguanidine. A methanol solvent may be used.

The products of Formula XVB are novel compounds, which may be isolated by chromatography. These and other novel compounds of Formula XV have substantial value as intermediates for the preparation of compounds of Formula I, and especially of Formula IA. Compounds of Formula XV correspond to the structure

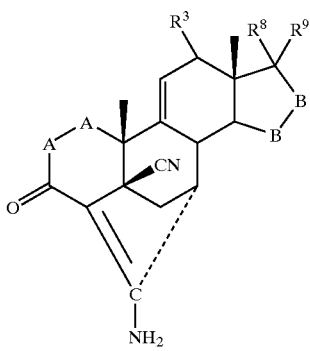

XV where —A—A—, —B—B—, $R^3$, $R^8$ and $R^9$ are as defined in Formula XIII. In the most preferred compounds of Formula XV and Formula XVB, —A—A— and —B—B— are —CH$_2$—CH$_2$—, and $R^3$ is hydrogen.

In accordance with the hydrolysis described above for producing the diketone compounds of Formula VI, the enamines of Formula XVB may be converted to the diketones of Formula XIVB

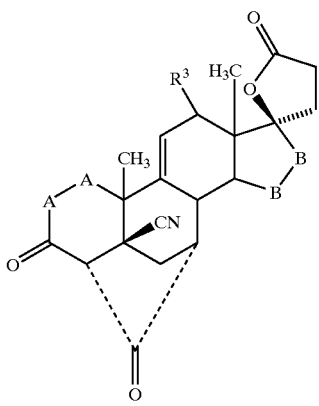

XIVB wherein —A—A—, —B—B— and $R^3$ are as defined in Formula XX. Preferably, $R^3$ hydrogen. Particularly preferred for the synthesis of epoxymexrenone are those compounds of Formula XIV which also fall within the scope of Formula XIVB as defined below.

The products of Formula XIVB are novel compounds, which may be isolated by precipitation. These and other novel compounds of Formula XIV have substantial value as intermediates for the preparation of compounds of Formula I, and especially of Formula IA. Compounds of Formula XIV correspond to the structure

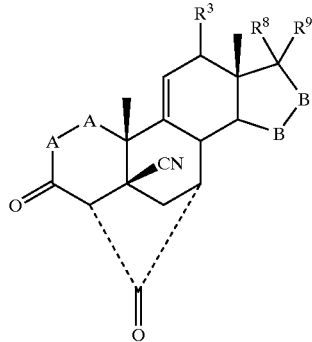

XIV where —A—A—, —B—B—, $R^3$, $R^8$ and $R^9$ are as defined in Formula XIII. In the most preferred compounds of Formula XIV and XIVB, —A—A— and —B—B— are —CH$_2$—CH$_2$—, and $R^3$ is hydrogen.

The compounds of Formula XIVB are further converted to compounds of Formula XXXI using essentially the process described above for converting the diketone of Formula VI to the hydroxyester of Formula V. In this instance, it is necessary to isolate the intermediate XXXI

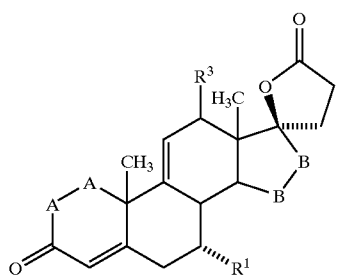

XXXI before further conversion to a product of Formula XXXII

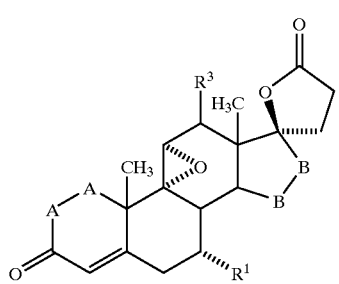

XXXII wherein —A—A—, —B—B— and $R^3$ are as defined in Formula XX, and $R^1$ is as defined in Formula V. Preferably, $R^3$ is hydrogen. Preferred compounds of Formula XXXI are those which fall within Formula IIA. The compounds of Formula XXXI are converted to compounds of Formula XXXII using the method described hereinabove or in U.S. Pat. No. 4,559,332.

Preferably, the compound of Formula XIV is 4'S(4'α), 7'α-1',2',3',4,4',5,5',6',7',8',10',12',13', 14',15',16'-hexadecahydro-10β-,13'β-dimethyl-3',5,20'-trioxospiro[furan-2(3H),17'β-[4,7]methano[17H]-cyclopenta[a]phenanthrene]5'-carbonitrile; and the compound of Formula XV is 5'R(5'α),7'β-20'-amino-1',2',3',4',5',6',7',8',10',12',13',14',15',16'-tetradecahydro-10'α,13'α-dimethyl-3',5-dioxospiro[furan-2(3H),17'α(5'H)-[7,4]metheno[4H]-cyclopenta[a]phenanthrene]-5'-carbonitrile. In a particularly preferred embodiment, the overall process of Scheme 3 proceeds as follows:

Scheme 4

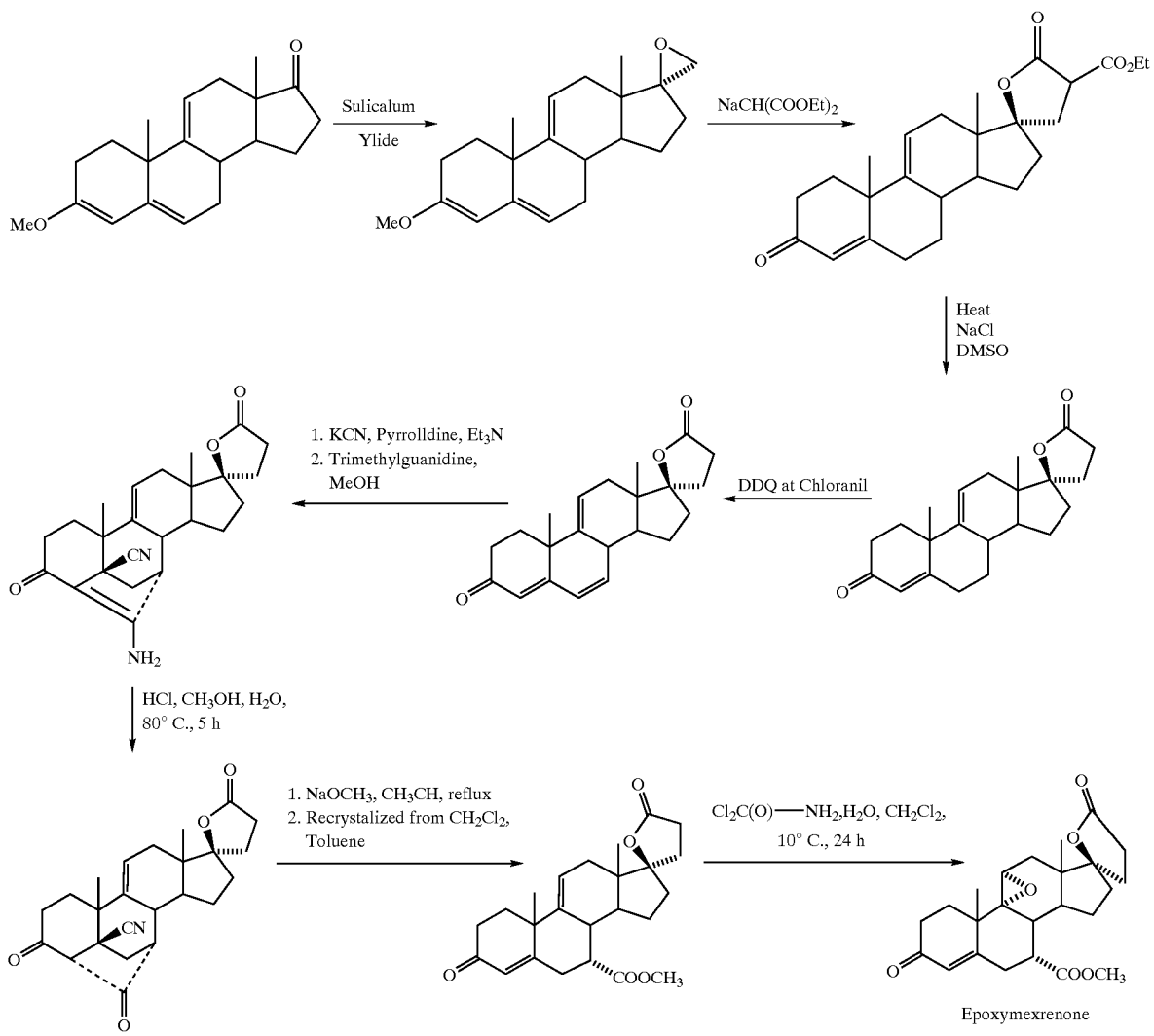

The first three steps of Scheme 4 are the same as those of Scheme 3, i.e., preparation of an intermediate of Formula XVII starting with a compound corresponding to Formula XX.

Thereafter, the intermediate of Formula XVII is epoxidized, for example, using the process of U.S. Pat. No. 4,559,332 to produce the compound of Formula XXIV

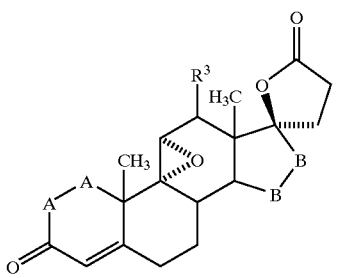

XXIV wherein —A—A—, —B—B— and $R^3$ are as defined in Formula XX. However, in a particularly preferred embodiment of the invention, the substrate of Formula XVII is epoxidized across the 9,11-double bond using an oxidation reagent comprising an amide type peroxide activator, most preferably trichloroacetamide, according to the process as described above in Scheme 1 for the conversion of the enester of Formula II to the product of Formula I. The conditions and proportions of reagents for this reaction are substantially as described for the conversion of the Formula II enester to epoxymexrenone. Particularly preferred compounds of Formula XXIV are those in which —A—A— and —B—B— are as defined in Formula XIII and $R^3$ is hydrogen.

It has been found that the epoxidation of the substrate of Formula XVII can also be effected in very good yield using a peracid such as, for example, m-chloroperoxybenzoic acid. However, the trichloroacetamide reagent provides superior results in minimizing the formation of Bayer-Villager oxidation by-product. The latter by-product can be removed, but this requires trituration from a solvent such as ethyl acetate, followed by crystallization from another solvent such as methylene chloride. The epoxy compound of Formula XXIV is dehydrogenated to produce a double bond between the 6- and 7-carbons by reaction with a dehydrogenation (oxidizing) agent such as DDQ or chloranil, or using the bromination/dehydrobromination (or other halogenation/dehydrohalogenation) sequence, to produce another novel intermediate of Formula XXIII

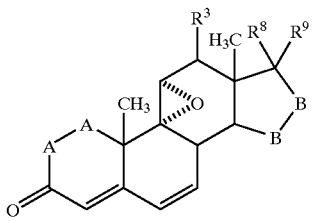

XXIII wherein —A—A—, —B—B—, $R^3$, $R^8$ and $R^9$ are as defined in Formula XX. Particularly preferred compounds of Formula XXIII are those in which —A—A— and —B—B— are as defined in Formula XIII and $R^3$ is hydrogen.

While direct oxidation is effective for the formation of the product of Formula XXIII, the yields are generally low. Preferably, therefore, the oxidation is carried out in two steps, first halogenating the substrate of Formula XXIV at the C-6 position, then dehydrohalogenating to the 6,7-olefin. Halogenation is preferably effected with an N-halo organic reagent such as, for example, N-bromosuccinamide. Bromination is carried out in a suitable solvent such as, for example, acetonitrile, in the presence of halogenation promoter such as benzoyl peroxide. The reaction proceeds effectively at a temperature in the range of about 50° to about 100° C., conveniently at atmospheric reflux temperature in a solvent such as carbon tetrachloride, acetonitrile or mixture thereof. However, reaction from 4 to 10 hours is typically required for completion of the reaction. The reaction solvent is stripped off, and the residue taken up in a water-immiscible solvent, e.g., ethyl acetate. The resulting solution is washed sequentially with a mild alkaline solution (such as an alkali metal bicarbonate) and water, or preferably saturated brine to minimize product losses, after which the solvent is stripped and a the residue taken up in another solvent (such as dimethylformamide) that is suitable for the dehydrohalogenation reaction.

A suitable dehydrohalogenation reagent, e.g., 1,4-diazabicyclo[2,2,2]octane (DABCO) is added to the solution, along with an alkali metal halide such as LiBr, the solution heated to a suitable reaction temperature, e.g., 60° to 80° C., and reaction continued for several hours, typically 4 to 15 hours, to complete the dehydrobromination. Additional dehydrobromination reagent may be added as necessary during the reaction cycle, to drive the reaction to completion. The product of Formula XXIII may then be recovered, e.g., by adding water to precipitate the product which is then separated by filtration and preferably washed with additional amounts of water. The product is preferably recrystallized, for example from dimethylformamide.

The products of Formula XXIII, such as 9,11-epoxycanrenone, are novel compounds, which may be isolated by extraction/crystallization. They have substantial value as intermediates for the preparation of compounds of Formula I, and especially of Formula IA. For example, they may be used as substrates for the preparation of compounds of Formula XXII.

Using substantially the process described above for the preparation of compounds of Formula VII, the compounds of Formula XXIII are reacted with cyanide ion to produce novel epoxyenamine compounds corresponding to Formula XXII

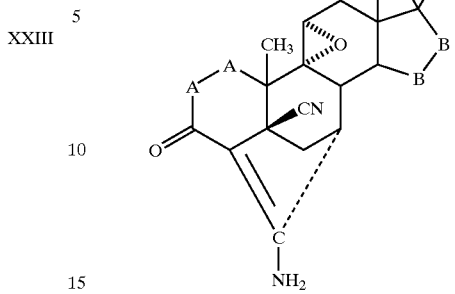

XXII wherein —A—A—, —B—B—, $R^3$, $R^8$ and $R^9$ are as defined in Formula XX. Particularly preferred compounds of Formula XXII are those in which —A—A— and —B—B— are as defined in Formula XIII and $R^3$ is hydrogen.

The products of Formula XXII are novel compounds, which may be isolated by precipitation and filtration. They have substantial value as intermediates for the preparation of compounds of Formula I, and especially of Formula IA. In the most preferred compounds of Formula XXII, —A—A— and —B—B— are —CH$_2$—CH$_2$—, and $R^3$ is hydrogen.

Using substantially the process described above for preparation of compounds of Formula VI, the epoxyenamine compounds of Formula XXII are converted to novel epoxydiketone compounds of Formula XXI

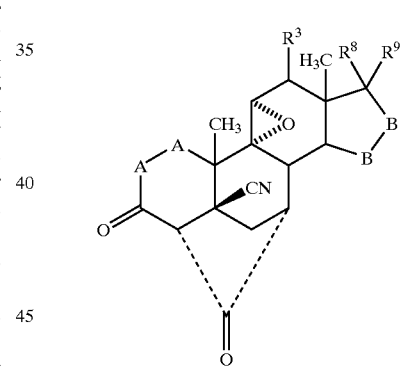

XXI wherein —A—A—, —B—B—, $R^3$, $R^8$ and $R^9$ are as defined in Formula XIII. In the most preferred compounds of Formula XXI, —A—A— and —B—B— are —CH$_2$—CH$_2$— and $R^3$ is hydrogen.

The products of Formula XXI are novel compounds, which may be isolated by precipitation and filtration. They have substantial value as intermediates for the preparation of compounds of Formula I, and especially of Formula IA. Particularly preferred compounds of Formula XXI are those in which —A—A— and —B—B— are as defined in Formula XIII. In the most preferred compounds of Formula XXI, —A—A— and —B—B— are —CH$_2$—CH$_2$— and $R_3$ is hydrogen.

Using substantially the process described above for preparation of the hydroxyester compounds of Formula V from the diketone compounds of Formula VI, the epoxydiketone compounds of Formula XXI are converted to compounds of Formula XXXII

XXXII

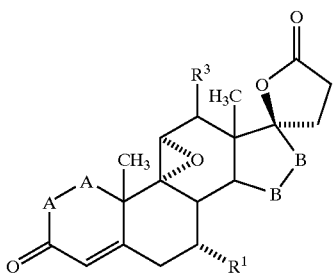

wherein —A—A—, —B—B— and $R^3$ are as defined in Formula XX, and $R^1$ is as defined in Formula V.

As in the conversion of the diketone of formula V to the hydroxyester of formula VI, a 5-β-cyano-7-ester intermediate is also formed in the conversion of the epoxydiketone of formula XXI to compounds of formula XXXII. The 5-β-cyano-7-ester intermediates in both series can be isolated by treatment of the corresponding diketone with an alcohol such as methanol in the presence of a base such as triethylamine. Preferably, the intermediates are prepared by refluxing a mixture of the diketone in an alcohol such as methanol containing about 0.1 to about 2 equivalents of triethylamine per mole of diketone for about 4 to about 16 hours. The products are isolated in pure form by cooling the mixture to about 25 degrees followed by filtration. The isolated intermediates can be converted to the compounds of Formula XXXII on treatment with a base such an alkali metal alkoxide in a solvent, preferably an alcohol such as methanol. Use of an alkoxide in an alcohol establishes an equilibrium mixture similar to that formed when the corresponding diketone of Formula XXI is treated under the same conditions.

In addition, the 7β-ester of the compound of Formula XXXII (for example 7-methyl hydrogen 9,11α-epoxy-17-hydroxy-3-oxo-17α-pregn-4-ene-7β,21-dicarboxylate, γ-lactone) has been observed by chromatography in the crude product of the final step of the process of Scheme 4. Alkoxide and/or cyanide in the solution reacts with and converts the 7α-ester into an epimeric mixture of the 7α-ester and its 7β-ester epimer. The pure 7β-ester can be isolated from the epimeric mixture by selective crystallization.

Preferably, the compound of Formula XXI is 4'S(4'α), 7'α-9',11α-epoxyhexadecahydro-10β-,13'β-dimethyl-3'5, 20'-trioxospiro[furan-2(3H),17'β-[4,7]methano[17H]-cyclopenta[a]phenanthrene-5'-carbonitrile; the compound of Formula XXII is 5'R(5'α),7'β-20'-amino-9,11β-epoxyhexadecahydro-10',13'-dimethyl-3',5-dioxospiro[furan-2(3H),17'a(5'H) [7,4]methene[4H]cyclopenta[a]phenanthrene-5'-carbonitrile; and the compound of Formula XXIII is 9,11α-epoxy-17α-hydroxy-3-oxopregna-4,6-diene-21-carboxylic acid, γ-lactone.

In a particularly preferred embodiment, the overall process of Scheme 4 proceeds as follows:

Scheme 5

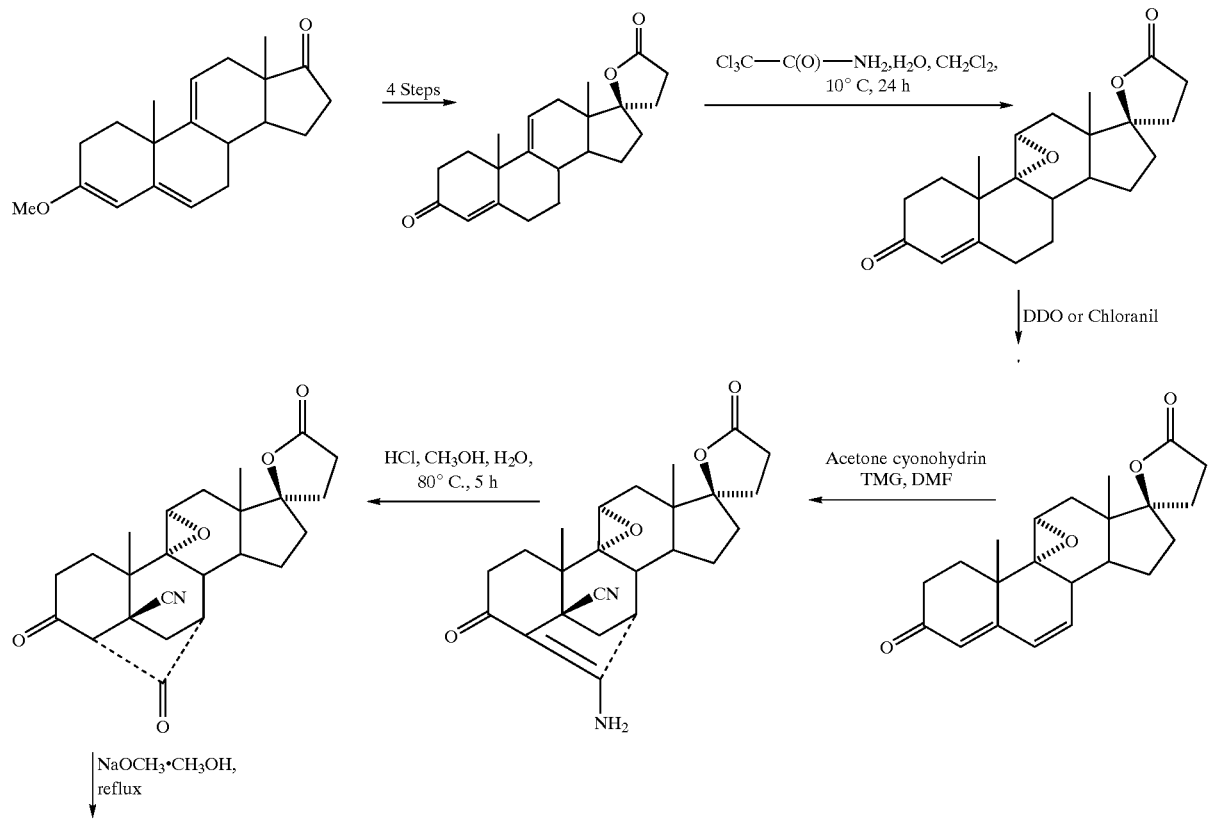

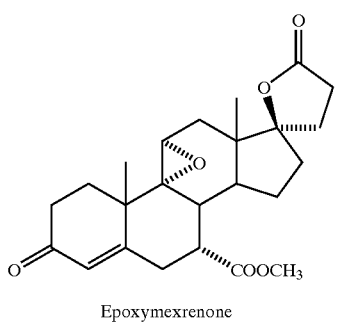

Epoxymexrenone

The process of scheme 5 begins with a substrate corresponding to Formula XXIX

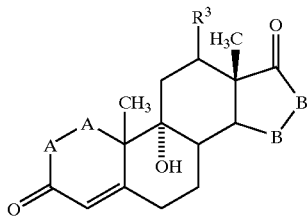

XXIX wherein —A—A—, —B—B— and R³ are as defined in Formula XX. The following microorganisms are capable of carrying out the 9α-hydroxylation of a compound of Formula XXXV (such as androstendione)

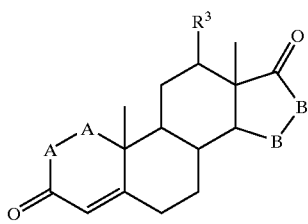

XXXV wherein —A—A—, —B—B— and R³ are as defined in Formula XIII, to a compound of Formula XXIX under conditions similar to those described in Example 19B:

*Asperigillus niger* ATCC 16888 and 26693, *Corynespora cassiicola* ATCC 16718, *Curvularia clavata* ATCC 22921, *Mycobacterium fortuitum* NRRL B8119, *Nocardia canicruria* ATCC 31548, Pycnosporium spp. ATCC 12231, *Stysanus microsporus* ATCC 2833, *Syncephalastrum racemosum* ATCC 18192, and *Thamnostylum piriforme* ATCC 8992.

The substrate corresponding to Formula XXIX is converted to a product of Formula XXVIII

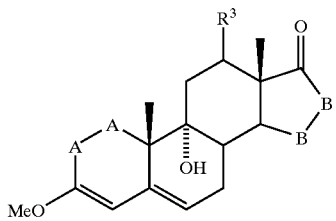

XXVIII by reaction with trimethylorthoformate, wherein —A—A—, —B—B— and R³ are as defined in Formula XX. Following the formation of the compounds of Formula XXVIII, those compounds are converted to the compounds of Formula XXVII using the method described above for conversion of the substrate of Formula XX to Formula XVII. Compounds of Formula XXVII have the structure:

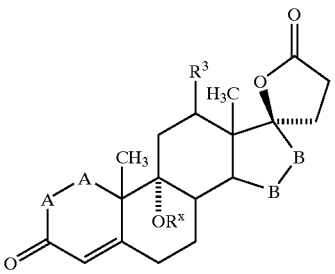

XXVII wherein —A—A—, —B—B— and R³ are as defined in Formula XX, and $R^x$ is any of the common hydroxy protecting groups. Alternatively, the C9 α-hydroxy group can be protected at an earlier step in this synthesis scheme if protection at that step is desired, i.e., the C9 hydroxy of the compound of Formula XXVIII or the C9 hydroxy of the compound of Formula XXIX can be protected with any of the common hydroxy protecting groups.

Using the method described above for the preparation of compounds of Formula XVI, compounds of Formula XXVII are oxidized to yield novel compounds corresponding to Formula XXVI

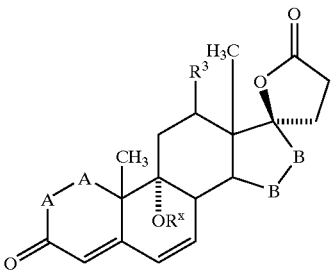

XXVI wherein —A—A—, —B—B— and R³ are as defined in Formula XX. Particularly preferred compounds of Formulae XXIX, XXVIII, XXVII and XXVI are those in which —A—A— and —B—B— are as defined in Formula XIII, and R³ is hydrogen.

The products of Formula XXVI are novel compounds, which may be isolated by precipitation/filtration. They have substantial value as intermediates for the preparation of compounds of Formula I, and especially of Formula IA. Particularly preferred compounds of Formula XXVI are those in which —A—A— and —B—B— are as defined in Formula XIII, and $R^3$ is hydrogen. In the most preferred compounds of Formula XXVI, and —A—A— and —B—B— are —CH$_2$—CH$_2$—, and $R^3$ is hydrogen.

Using the method defined above for cyanidation of compounds of Formula VIII, the novel intermediates of Formula XXVI are converted to the novel 9-hydroxyenamine intermediates of Formula XXV

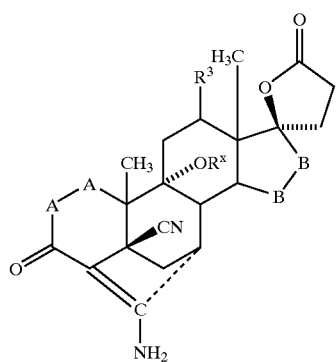

XXV wherein —A—A—, —B—B— and $R^3$ are as defined in Formula XX.

The products of Formula XXV are novel compounds, which may be isolated by precipitation/filtration. They have substantial value as intermediates for the preparation of compounds of Formula I, and especially of Formula IA. Particularly preferred compounds of Formula XXV are those in which —A—A— and —B—B— are as defined in Formula XIII, and $R^3$ is hydrogen. In the most preferred compounds of Formula XXVI, and —A—A— and —B—B— are —CH$_2$—CH$_2$—, and $R^3$ is hydrogen.

Using essentially the conditions described above for the preparation of the diketone compounds of Formula VI, the 9-hydroxyenamine intermediates of Formula XXV are converted to the diketone compounds of Formula XIVB. Note that in this instance the reaction is effective for simultaneous hydrolysis of the enamine structure and dehydration at the 9,11 positions to introduce the 9,11 double bond. The compound of Formula XIV is then converted to the compound of Formula XXXI, and thence to the compound of Formula XIII, using the same steps that are described above in scheme 3.

Preferably, the compound of Formula XIV is 4'S(4'α), 7'α-1',2',3',4,4',5,5',6',7',8',10', 12',13',14',15',16'-hexadecahydro-10β-,13'β-dimethyl-3',5,20'-trioxospiro[furan-2(3H),17'β-[4,7]methano[17H]-cyclopenta[a]phenanthrene]5'-carbonitrile; the compound of Formula XXV is 5'R(5'α),7'β-20'-aminohexadecahydro-9'β-hydroxy-10'a,13'α-dimethyl-3',5-dioxospiro[furan-2(3H),17'α(5'H)-[7,4]metheno[4H]cyclopenta[a]phenanthrene]-5'-carbonitrile; the compound of Formula XXVI is 9α,17α-dihydroxy-3-oxopregna-4,6-diene-21-carboxylic acid, γ-lactone; and the compound of Formula XXVII is 9α,17α-dihydroxy-3-oxopregn-4-ene-21-carboxylic acid, γ-lactone.

In a particularly preferred embodiment, the overall process of Scheme 5 proceeds as follows:

Scheme 6

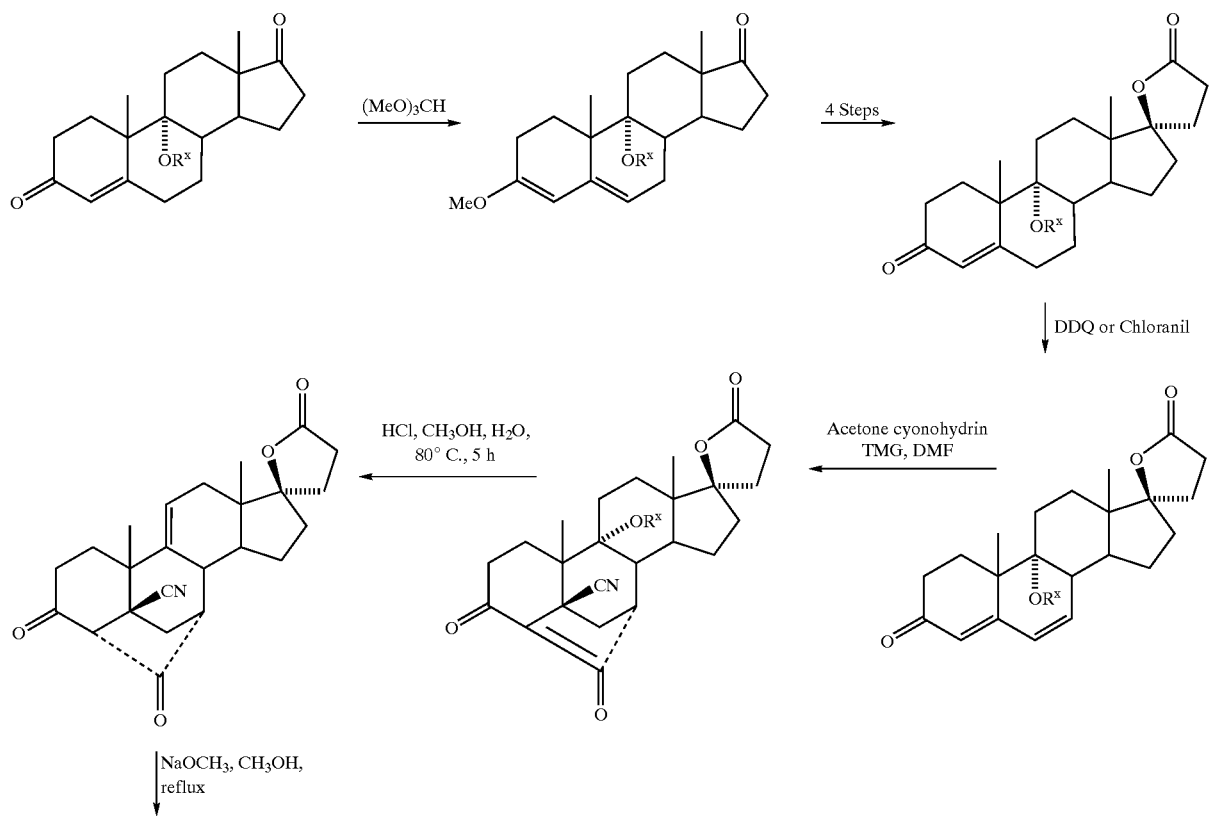

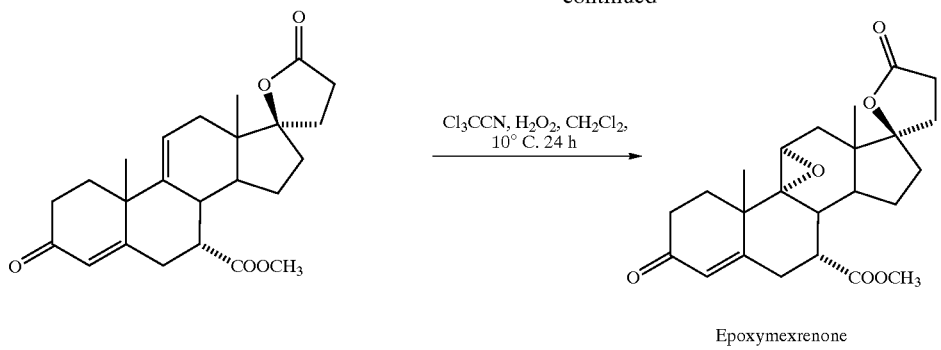

Epoxymexrenone

Scheme 6 provides an advantageous method for the preparation of epoxymexrenone and other compounds corresponding to Formula I, starting with 11α or 11β-hydroxylation of androstendione or other compound of Formula XXXV

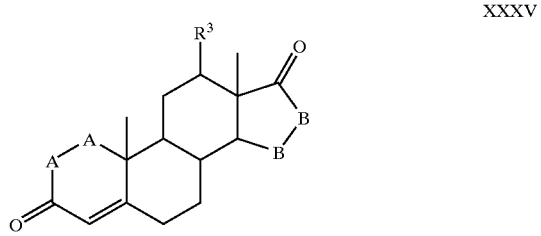

wherein —A—A—, —B—B— and $R^3$ are as defined in Formula XIII, producing an intermediate corresponding to the Formula XXXVI or its corresponding 11β-hydroxy isomer

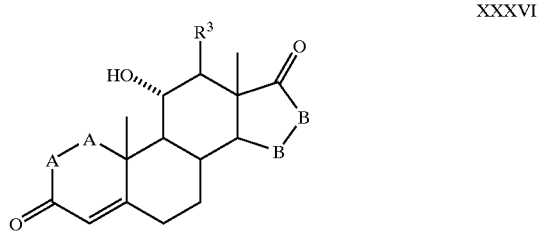

where —A—A—, —B—B— and $R^3$ are as defined in Formula XIII. Except for the selection of substrate, the process for conducting the 11α-hydroxylation is essentially as described hereinabove for Scheme 1. The following microorganisms are capable of carrying out the 11α-hydroxylation of androstendione or other compound of Formula XXXV:

*Absidia glauca* ATCC 22752, *Aspergillus flavipes* ATCC 1030, *Aspergillus foetidus* ATCC 10254, *Aspergillus fumigatus* ATCC 26934, *Aspergillus ochraceus* NRRL 405 (ATCC 18500), *Aspergillus niger* ATCC 11394, *Aspergillus nidulans* ATCC 11267, *Beauveria bassiana* ATCC 7159, *Fusarium oxysporum* ATCC 7601, *Fusarium oxysporum cepae* ATCC 11171, *Fusarium lini* ATCC IFO 7156, *Gibberella fujikori* ATCC 14842, *Hypomyces chyrsospermus* IMI 109891, *Mycobaterium fortuitum* NRRL B8119, *Penicillum patulum* ATCC 24550, Pycnosporium spp. ATCC 12231, *Rhizopus arrhizus* ATCC 11145, *Saccharopolyspora erythraea* ATCC 11635, *Thamnostylum piriforme* ATCC 8992, *Rhizopus oryzae* ATCC 11145, *Rhizopus stolonifer* ATCC 6227b, and *Trichothecium roseum* ATCC 12519 and ATCC 8685.

The following microorganisms are capable of carrying out the 11β-hydroxylation of androstendione or other compound of Formula XXXV:

*Aspergillus fumigatus* ATCC 26934, *Aspergillus niger* ATCC 16888 and ATCC 26693, *Epicoccum oryzae* ATCC 7156, *Curvularia lunata* ATCC 12017, *Cunninghamella blakesleeana* ATCC 8688a, and *Pithomyces atro-olivaceous* IFO 6651.

11α-Hydroxyandrost-4-ene-3,17-dione, or other compound of Formula XXXVI, is next converted to 11α-hydroxy-3,4-enol ether of Formula (101):

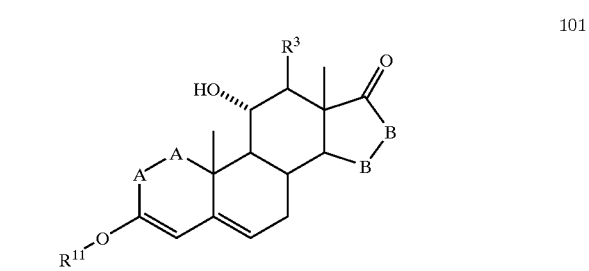

where —A—A—, —B—B— and $R^3$ are as defined in Formula XIII and $R^{11}$ is methyl or other lower alkyl ($C_1$ to $C_4$), by reaction with an etherifying reagent such as trialkyl orthoformate in the presence of an acid catalyst To carry out this conversion, the 11α-hydroxy substrate is acidified by mixing with an acid such as, e.g., benzene sulfonic acid hydrate or toluene sulfonic acid hydrate and dissolved in a lower alcohol solvent, preferably ethanol. A trialkyl orthoformate, preferably triethyl orthoformate is introduced gradually over a period of 5 to 40 minutes while maintaining the mixture in the cold, preferably at about 0° C. to about 15° C. The mixture is then warmed and the reaction carried out at a temperature of between 20° C. and about 60° C. Preferably the reaction is carried out at 30° to 50° C. for 1 to 3 hours, then heated to reflux for an additional period, typically 2 to 6 hours, to complete the reaction. Reaction mixture is cooled, preferably to 0° to 15°, preferably about 5° C., and the solvent removed under vacuum.

Using the same reaction scheme as described in Scheme 3, above, for the conversion of the compound of Formula XX to the compound of Formula XVII, a 17-spirolactone moiety of Formula XXXIII is introduced into the compound of Formula 101. For example, the Formula 101 substrate may be reacted with a sulfonium ylide in the presence of a base such as an alkali metal hydroxide in a suitable solvent such as DMSO, to produce an intermediate corresponding to Formula 102:

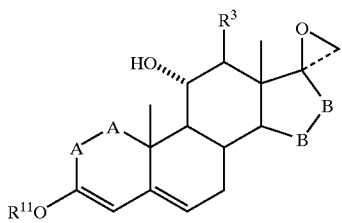

102 where —A—A—, $R^3$, $R^{11}$, and —B—B— are as defined in Formula 101. The intermediate of Formula 102 is then reacted with a malonic acid diester in the presence of an alkali metal alkoxide to form the five membered spirolactone ring and produce the intermediate of Formula 103

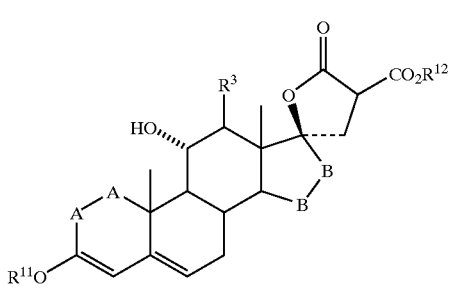

103 where —A—A—, $R^3$, $R^{11}$ and —B—B— are as defined in Formula 102, and $R^{12}$ is a $C_1$ to $C_4$ alkyl, preferably ethyl. Finally, the compound of Formula 103 in a suitable solvent, such as dimethylformamide, is subjected to heat in the presence of an alkali metal halide, splitting off the alkoxycarbonyl moiety and producing the intermediate of Formula 104:

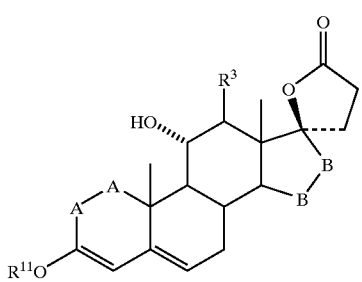

104 where again —A—A—, $R^3$, $R^{11}$ and —B—B— are as defined in Formula 102.

Next the 3,4-enol ether compound 104 is converted to the compound of Formula XXIII, i.e., the compound of Formula VIII in which $R^8$ and $R^9$ together form the moiety of Formula XXXIII. This oxidation step is carried out in essentially the same manner as the oxidation step for conversion of the compound of Formula XXIV to the intermediate of Formula XXIII in the synthesis of Scheme 4. Direct oxidation can be effected using a reagent such as 2,3-dichloro-5,6-dicyano-1,4-benzoquinone (DDQ) or tetrachlorobenzoquinone (chloranil), or preferably a two stage oxidation is effected by first brominating, e.g., with an N-halo brominating agent such as N-bromosuccinamide (NBS) or 1,3-dibromo-5,5-dimethyl hydantoin (DBDMH) and then dehydrobrominating with a base, for example with DABCO in the presence of LiBr and heat. Where NBS is used for bromination, an acid must also be employed to convert 3-enol ether to the enone. DBDMH, an ionic rather than free radical bromination reagent, is effective by itself for bromination and conversion of the enol ether to the enone.

The compound of Formula VIII is then converted to epoxymexrenone or other compound of Formula I by the steps described hereinabove for Scheme 1.

Each of the intermediates of Formulae 101, 102, 103 and 104 is a novel compound having substantial value as an intermediate for epoxymexrenone or other compounds of Formulae IA and I. In each of the compounds of Formulae 101, 102, 103 and 104, —A—A— and —B—B— are preferably —$CH_2$—$CH_2$— and $R^3$ is hydrogen, lower alkyl or lower alkoxy. Preferably, $R^3$ is hydrogen. Most preferably, the compound of Formula 101 is 3-ethoxy-11α-hydroxyandrost-3,5-dien-17-one, the compound of Formula 102 is 3-ethoxyspiro[androst-3,5-diene-17β,2'-oxiran]-11α-ol, the compound of Formula 103 is ethyl hydrogen 3-ethoxy-11α–17α-dihydroxypregna-3,5-diene-21,21-dicarboxylate, gamma-lactone, and the compound of Formula 104 is 3-ethoxy-11α–17α-dihydroxypregna-3,5-diene-21-carboxylic acid, gamma-lactone.

In a particularly preferred embodiment, the overall process of Scheme 6 proceeds as follows:

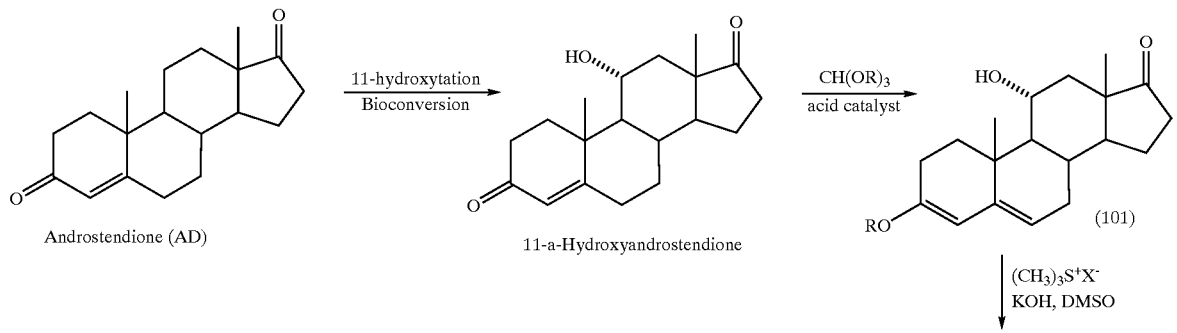

-continued

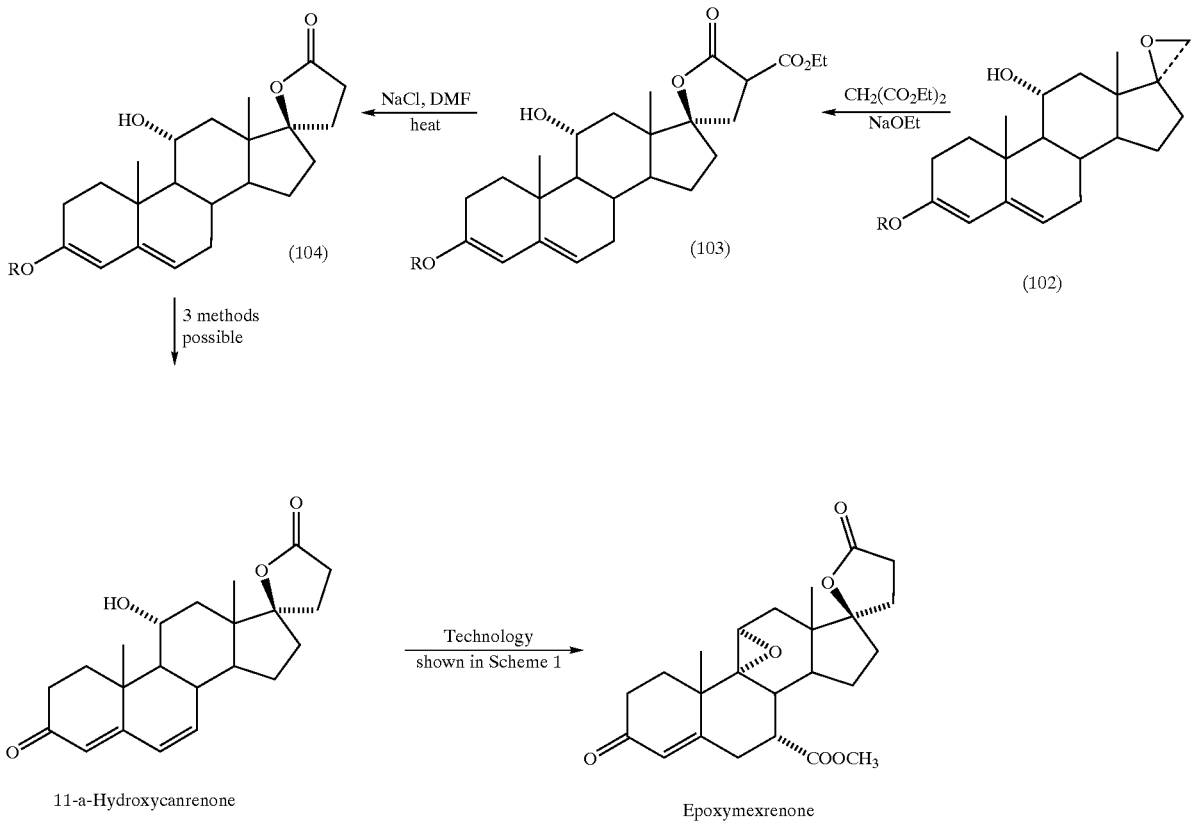

11-α-Hydroxycanrenone

Epoxymexrenone

It is hypothesized that epoxymexrenone and other compounds corresponding to Formula I likewise can be prepared from 11β-hydroxyandrostendione or other compounds of Formula XXXV which have been 11β-hydroxylated. In other words, epoxymexrenone and other compounds corresponding to Formula I can be prepared in accordance with the general process set forth in Scheme 6 using either an α-hydroxylated substrate of Formula XXXV or the corresponding β-hydroxylated substrate.

Scheme 7

Scheme 7 provides for the synthesis of epoxymexrenone and other compounds of Formula I using a starting substrate comprising β-sitosterol, cholesterol, stigmasterol or other compound of Formula XXXVII

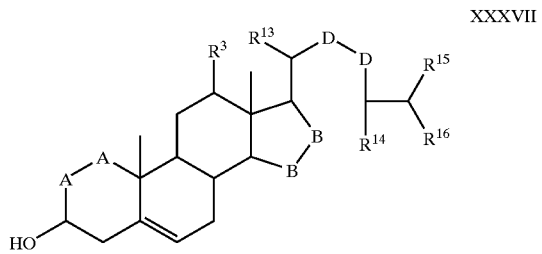

XXXVII where —A—A—, $R^3$, and —B—B— are as defined in Formula XIII; D—D is —$CH_2$—$CH_2$— or —CH=CH—; and each of $R^{13}$, $R^{14}$, $R^{15}$ and $R^{16}$ is independently selected from among hydrogen or $C_1$ to $C_4$ alkyl. $R^3$ is preferably hydrogen.

In the first step of the synthesis 11α-hydroxyandrostendione or other compound of Formula XXXVI is prepared by bioconversion of the compound of Formula XXXVII. The bioconversion process is carried out substantially in accordance with the method described hereinabove for the 11α-hydroxylation of canrenone (or other substrate of Formula XIII).

In the synthesis 11α-hydroxyandrostendione, 4-androstene-3,17-dione is initially prepared by bioconversion of the compound of Formula XXXVII. This initial bioconversion may be carried out in the manner described in U.S. Pat. No. 3,759,791, which is expressly incorporated herein by reference. Thereafter, 4-androstene-3,17-dione is converted to 11α-hydroxyandrostenedione substantially in accordance with the method described hereinabove for the 11α-hydroxylation of canrenone (or other substrate of Formula XIII).

The remainder of the synthesis of Scheme 7 is identical to Scheme 6. In a particularly preferred embodiment, the overall process of Scheme 7 proceeds as follows:

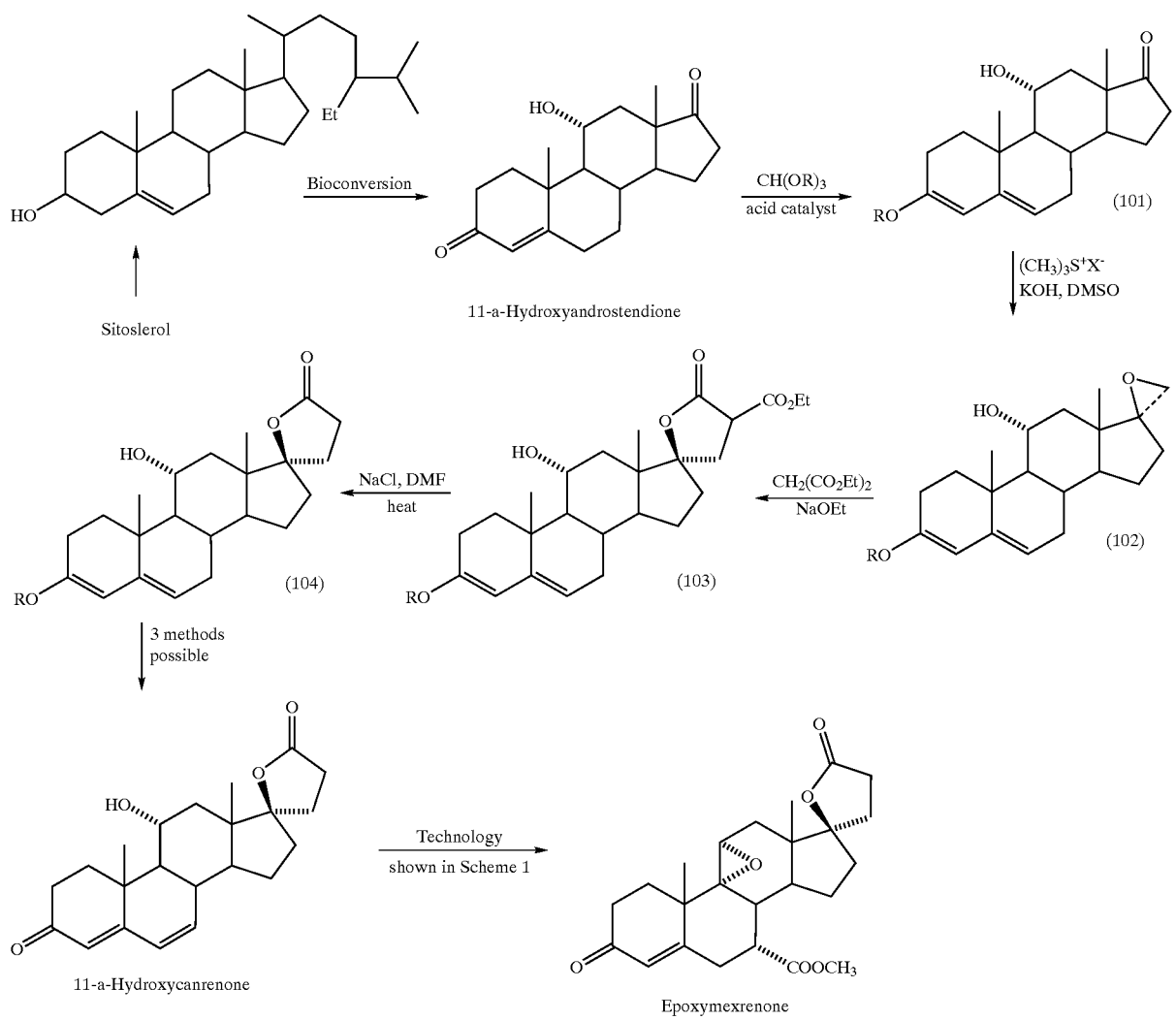

It is hypothesized that epoxymexrenone and other compounds corresponding to Formula I likewise can be prepared in accordance with the general process set forth in Scheme 7 when the product of the bioconversion of β-sitosterol or other compounds of Formula XXXVIII is 11β-hydroxyandrostendione or other compounds of Formula XXXV which have been 11β-hydroxylated. In other words, epoxymexrenone and other compounds corresponding to Formula I can be prepared in accordance with the general process set forth in Scheme 7 when the bioconversion of β-sitosterol or other compounds of Formula XXXVIII results in the preparation of either an α-hydroxylated substrate of Formula XXXV or the corresponding β-hydroxylated substrate.

Scheme 8

A significant complication in the synthesis of epoxymexrenone and related compounds is the need for stereoselective introduction of an α-alkoxycarbonyl substituent at the 7-carbon, without unwanted modifications at other sites of the steroidal structure. In accordance with the invention, it has been discovered that an effective synthesis path for introduction of a 7α-alkoxycarbonyl substituent involves the following steps: (i) initial cyanidation at the 7-carbon of the steroid, (ii) hydrolysis of the 7-cyano steroid to form a mixture of 7α-carboxylic acid and 7β-carboxylic acid steroids, (iii) formation of a 5,7-lactone steroid from the 7α-carboxylic acid steroid, and (iv) separation of the 7β-carboxylic acid steroid from the 5,7-lactone steroid. A base-mediated opening reaction of the 5,7-lactone steroid with an alkylating reagent produces the desired 7α-alkoxycarbonyl steroid.

Accordingly, the process of Scheme 8 is generally directed to a process for the preparation of a 3-keto-7α-alkoxycarbonyl substituted $\Delta^{4,5}$-steroid comprising reacting an alkylating reagent with a 3-keto-4,5-dihydro-5,7-lactone steroid substrate in the presence of a base. The lactone substrate is substituted with keto at the 3-carbon, and further comprises the moiety:

XXX

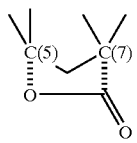

where C(5) represents the 5-carbon and C(7) represents the 7-carbon of the steroid structure of the substrate. Conversion of the 5,7-lactone to the 7α-alkoxycarbonyl is preferably effected by reaction with an alkyl halide in the presence of the base. The alkyl halide reagent is preferably an iodide, most preferably methyl iodide.

Further in accordance with the invention, an advantageous process has been discovered for the preparation of the 4,5-dihydro-5,7-lactone steroid compound described above. In this process, a 3-keto-$\Delta^{4,5}$-7α-cyano substituted steroid substrate is converted to the 7-carboxylic acid, and the acid in turn reacts with the trialkyl orthoformate in an acidified lower alcohol solvent to yield the 5,7-lactone. Reaction with be recovered in a conventional manner. Other methods known to the art are useful in this ancillary preparation.

Generally in accordance with Scheme 8, the 5,7-lactone may be formed from a 7-carboxy intermediate (which itself is prepared by hydrolyzing a 7-cyano intermediate) that is substituted at the 17-position with either keto, $R^8$ or $R^9$, where $R^8$ and $R^9$ are as described above, and having either an aliphatic, olefin, epoxide or hydroxy substituted configuration at C-9 and C-11, i.e.,

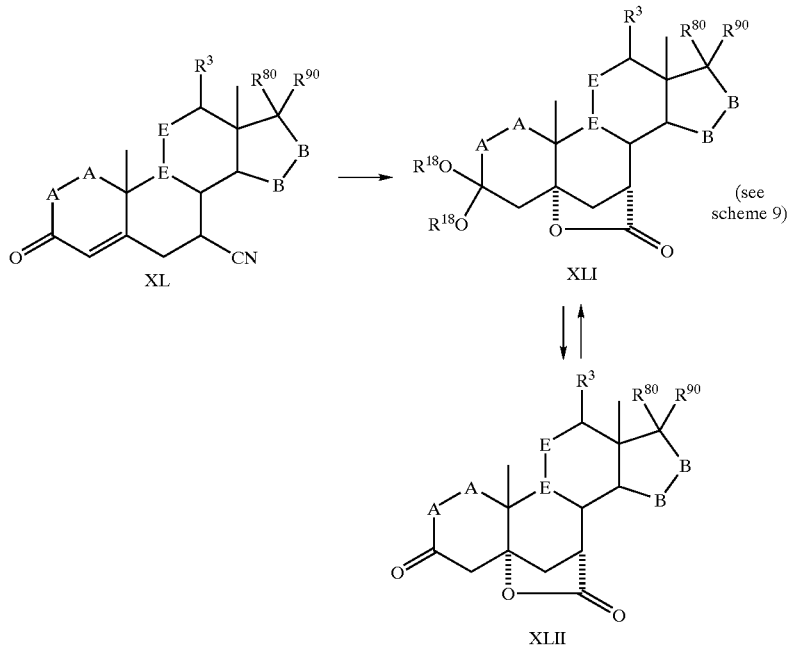

orthoformate esters also converts the 3-keto group to the 3-acyclic or cyclic ketal 5,7-lactone (the lactone is understood to form first). Preferably, the 3-ketal 5,7-lactone is a 3-dialkyl ketal 5,7-lactone. More preferably, the alkyl moiety of the alcohol solvent is the same as the alkyl moiety of the orthoformate alkoxy groups (and most preferably all are methyl) because: the alkoxy moieties of the ketal can derive either from the orthoformate or the alcohol; mixed ketals are not preferred; and 3-dimethoxy is preferred. Where the ketal is an ethylene ketal, the alkyl moiety of the alcohol solvent need not be the same as the alkyl moiety of the orthoformate alkoxy groups. The 3-ketal-5,7-lactone is readily hydrolyzed to the 3-keto-5,7-lactone, a crystalline compound which can be easily purified. Since only the 7α-carboxylic acid undergoes the lactonization reaction, complete stereospecificity is realized. The 7β-acid may then be removed from the reaction mixture in the form of its salt, e.g., by treating the 7β-acid with a mild base such as sodium bicarbonate.

The 7-cyano substrate for the formation of the 5,7-lactone can be prepared in a known manner. For example, a substrate unsubstituted at the 7-carbon may be reacted with a slight excess of cyanide ion, preferably about 1.05 to about 1.25 equivalents per equivalent substrate in a weakly acidic solution comprising a water/DMSO solvent mixture. Preferably, the reaction mixture includes a carboxylic acid, e.g., about one equivalent acetic acid per equivalent substrate. Both the 7α- and 7β-CN isomers are formed with the 7α-isomer as the major isomer. The 7α-cyano steroid may where —A—A—, —B—B— and $R^3$ are as defined above, $R^{80}$ and $R^{90}$ are the same as $R^8$ and $R^9$, or $R^{80}$ and $R^{90}$ together constitute keto, and $R^{18}$ is as described below regarding Scheme 9, and —E—E— is selected from among

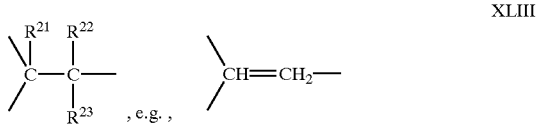

XLIII

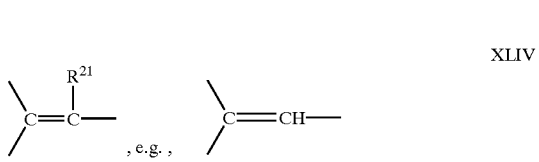

XLIV

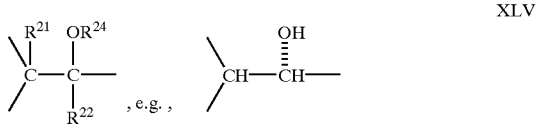

XLV

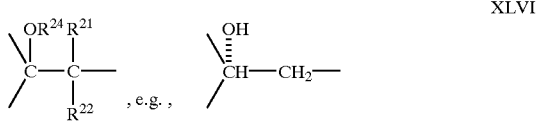

XLVI

-continued

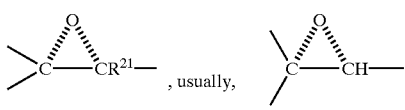, usually, XLVII

The compound of Formula XLII is then converted to the 7α-alkoxy-carbonyl:

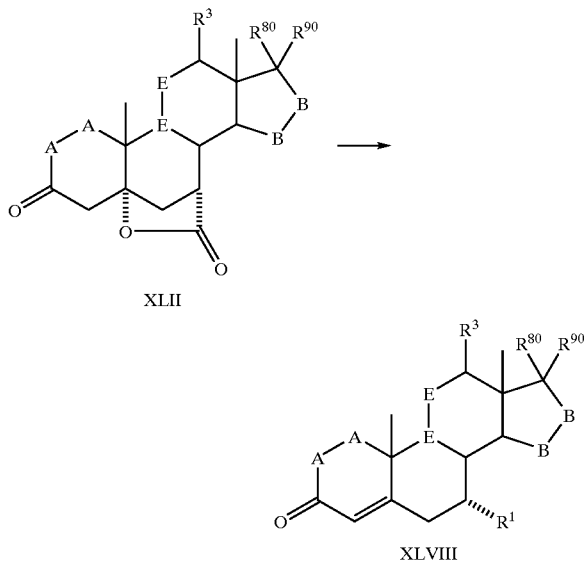

XLII

XLVIII

In each of XL, XLI, XLII and XLVIII, $R^{80}$ and $R^{90}$ together preferably comprise keto or

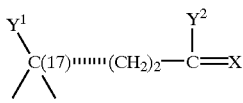 XXXIV where $Y^1$, $Y^2$, X and C(17) are as defined above, and most preferably $R^{80}$ and $R^{90}$ together comprise

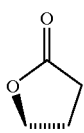 XXXIII $R^3$ is preferably H, $R^1$ is preferably methoxycarbonyl, and —A—A— and —B—B— are each preferably —CH$_2$—CH$_2$—. It will be understood that the reactions can also be carried out with the 3-keto group protected by converting it to and maintaining it in each ether or ketal form throughout the reaction sequence. Alternative processes of Scheme 8 comprise use of various intermediates within the scope of Formulae XLI and XLII as recited hereinabove.

Noting that the reagent for formation of the 5,7-lactone from the 3-keto-Δ$^{4,5}$-7-carboxylic acid per Scheme 8 is the trialkyl orthoformate, the same reagent used in conversion of the 11α-hydroxyandrostendione to the 3-enol ether-3,5-diene-11α-hydroxy intermediate 101 of Scheme 6, it is believed that the path of the Scheme 8 reaction is dependent on substitution at C-7. Reaction with orthoformate in the presence of H$^+$ forms an intermediate carbonium ion having a carboxyl at C-7 and its positive charge in equilibrium between C-3 and C-5. Upon loss of the proton, the C-3 carbonium ion yields the compound of Formula 101, while the C-5 carbonium ion yields the lactone. With hydrogen at C-7, it is believed that 3,5-dien-3-alkoxy (enol ether) is favored because of the double bond conjugation. With the 7α–CO$_2$ substituent at C-7, the C-5 carbonium ion is captured by the carboxy and the 5,7-lactone is formed. At this point the 3-keto group is preferentially converted to the ketal, thereby driving the reaction to completion.

Preferred embodiments of Scheme 8 are described in Schemes 9 and 10, infra.

Scheme 9

Scheme 9 begins with the same substrate as Scheme 4, i.e., the compound of Formula XX. This substrate is first oxidized to the compound of Formula B:

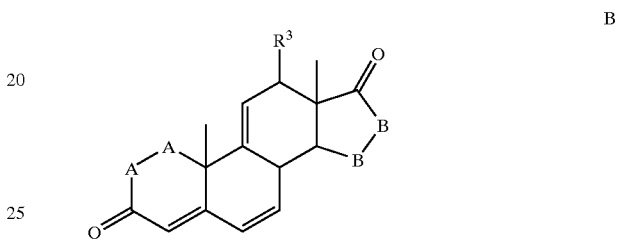 B where —A—A—, $R^3$, and —B—B— are as defined in Formula XIII. The oxidation reaction is conducted in accordance with any of the reaction schemes described above for conversion of the compound of Formula XXIV to the intermediate of Formula XXIII in the synthesis of Scheme 4. Using the methods described for Scheme 8, the compound of Formula B is converted to the 7-cyano intermediate of Formula C:

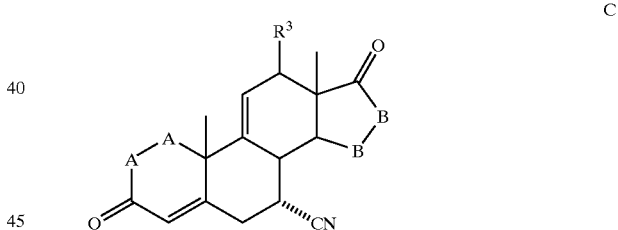 C where —A—A—, $R^3$, and —B—B— are as defined in Formula XIII. Next, the compound of Formula C is converted to the 5,7-lactone of Formula D:

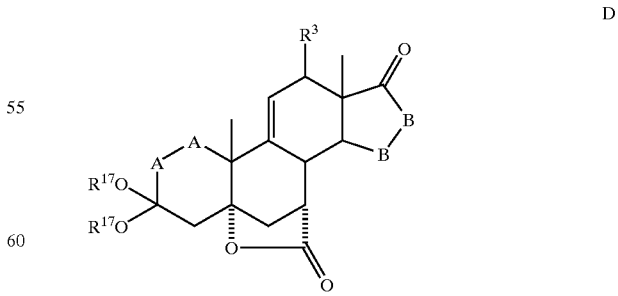 D where —A—A—, $R^3$, and —B—B— are as defined in Formula XIII and $R^{17}$ is $C_1$–$C_4$ alkyl, using the trialkyl orthoformate reagent utilized previously in Scheme 6. The 5,7-lactone of Formula D is readily separated from the unreacted 7-β-COOH, e.g., by removal of the acid via a bicarbonate wash, thereby establishing the desired C-7 stereochemistry and impeding epimerization in subsequent reactions that are conducted under basic conditions. Esterification of the lactone per reaction with alkyl halide, as described in Scheme 8, yields the enester intermediate of Formula II.

Continuing the Scheme 9 synthesis, the compound of Formula D is converted to a compound of Formula II. With the 3-keto group protected by having been converted to the ketal, a 20-spiroxane group of Formula XXXIII is selectively introduced at the 17-position in accordance with the reaction scheme described above for Schemes 3 and 6, supra, thereby producing a compound of Formula E

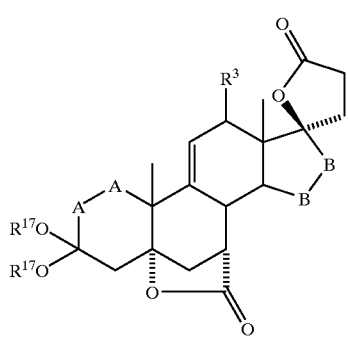

E

Because the 3-ketone is protected, hydrolysis conditions may be selected which are optimal for attacking the 17-ketone without concern for the formation of by-products through reaction at the 3-position. After hydrolysis of the 3-ketal compound of Formula E to the 3-keto group structure of Formula F

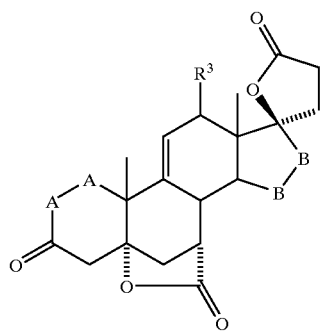

F the latter intermediate is reacted with alkyl iodide in the presence of base, per the conversion of Scheme 8, to produce the intermediate enester of Formula II. Finally, the latter intermediate is converted to epoxymexrenone or other compound of Formula I, using any of the methods described above for Scheme 1.

Scheme 9 benefits not only from the control of stereochemistry afforded by the 5,7-lactone intermediate, but enjoys the further advantage of allowing for a wider range of hydrolysis conditions without interference of the 17-spirolactone.

Like the reactions for other synthesis schemes of this invention, the reactions of Scheme 9 may be used for conversion of substrates other than those particularly described above. Thus, for example, the conversion of 3-keto- or 3-ketal-7-cyano steroids to 3-keto- or 3-ketal-5,7-lactone, or the conversion of the 3-keto- or 3-ketal-5,7-lactone to 7α-alkoxycarbonyl, may be carried out on compounds substituted at the 17-carbon by $R^8$ and $R^9$ as defined above, or more particularly by a substituent of Formula:

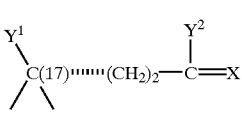

XXXIV where X, $Y^1$ and $Y^2$ are as defined above and C(17) indicates the 17-carbon. However, important advantages are realized, especially in process economics, by use of the specific reaction sequence using 17-keto substrates and following the specific reaction scheme described above for introduction of 17-spirolactone and 7α-alkoxycarbonyl into a 3-keto-$\Delta^{9,11}$ steroid.

The lactones of Formula D, E, and F are novel compounds which are useful in the preparation of epoxymexrenone and other compounds of Formula I and IA in accordance with the synthesis of Scheme 9. In these compounds —A—A— and —B—B— are preferably —CH$_2$—CH$_2$— and $R^3$ is hydrogen, lower alkyl or lower alkoxy. Most preferably the compound of Formula D is where $R^{17}$ is methoxy.

In a particularly preferred embodiment, the overall process of Scheme 9 proceeds as follows:

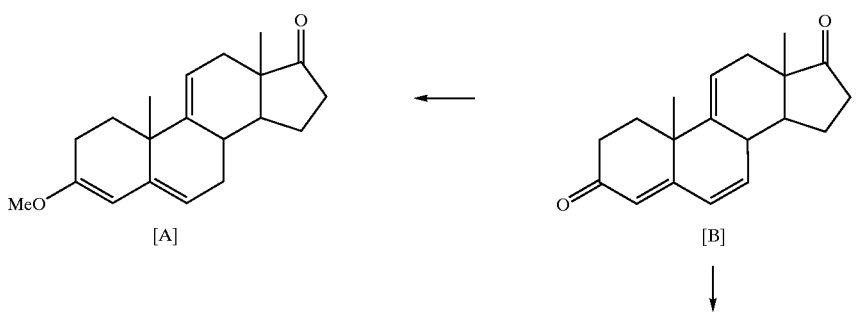

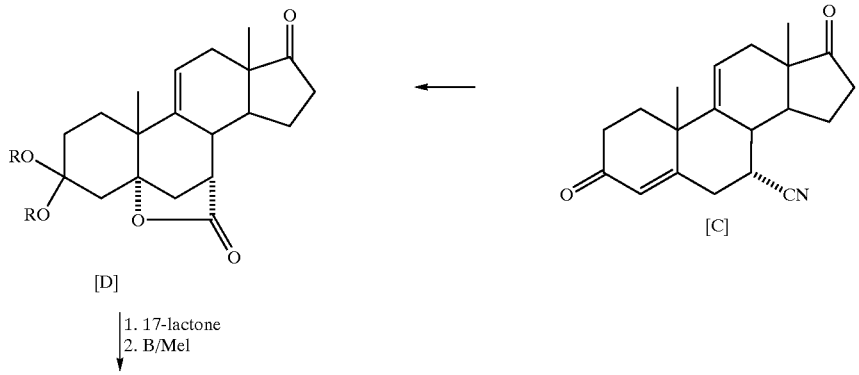

[D] ← [C]

1. 17-lactone
2. B/MeI

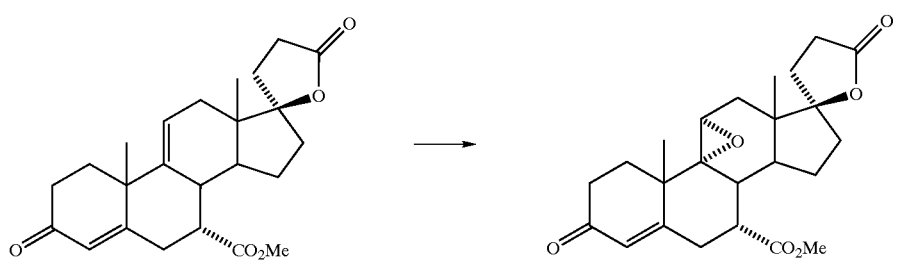

Scheme 10 is the same as Scheme 9 through the formation of the 7-cyano intermediate of Formula C. In the next step of Scheme 10, 7-cyano steroid is reacted with trialkyl orthoformate in an alkanol solvent, preferably trimethyl orthoformate in methanol, to simultaneously protect the 3-keto and 17-keto groups, by converting the former to the enol ether and the latter to the ketal. Thereafter the 7-cyano group is reduced to 7-formyl, e.g., by reaction with a dialkyl aluminum hydride, preferably diisobutyl aluminum hydride, thereby producing a compound of Formula 203:

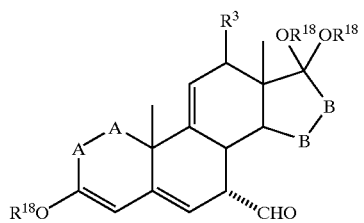

203 where —A—A—, $R^3$, and —B—B— are as defined in Formula XIII, and $R^{18}$ is $C_1$–$C_4$ alkyl. Prior protection of the keto groups, as described above, prevents their reduction by the dialkyl aluminum hydride. The intermediate of Formula 203 is next reacted with dilute aqueous acid to selectively hydrolyze the 17-ketal, in the presence of excess alcohol ($R^{19}OH$), producing the intermediate of Formula 204:

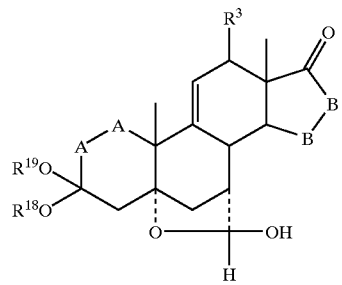

[204]

where $R^{19}$ is selected from among lower alkyl (preferably $C_1$ to $C_4$), or the $R^{19}$ groups at the 3-position forming a cyclic O,O-oxyalkyleneoxy substituent at the 3-carbon. The hemiacetal [204] is further protected by treatment with alkanol ($R^{19}OH$) in the presence of non-aqueous acid to produce the intermediate of Formula 205:

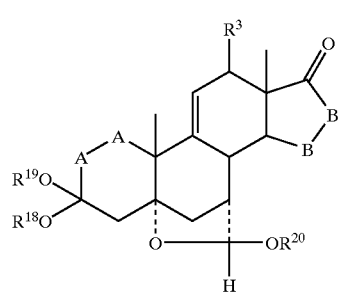

[205]

where —A—A—, —B—B—, $R^3$ and $R^{19}$ are as defined above, and $R^{20}$ is $C_1$ to $C_4$ alkyl. The 17-spirolactone moiety can then be introduced in accordance with the reaction steps described above for Schemes 3 and 6, thus proceeding through the sequence outlined below:

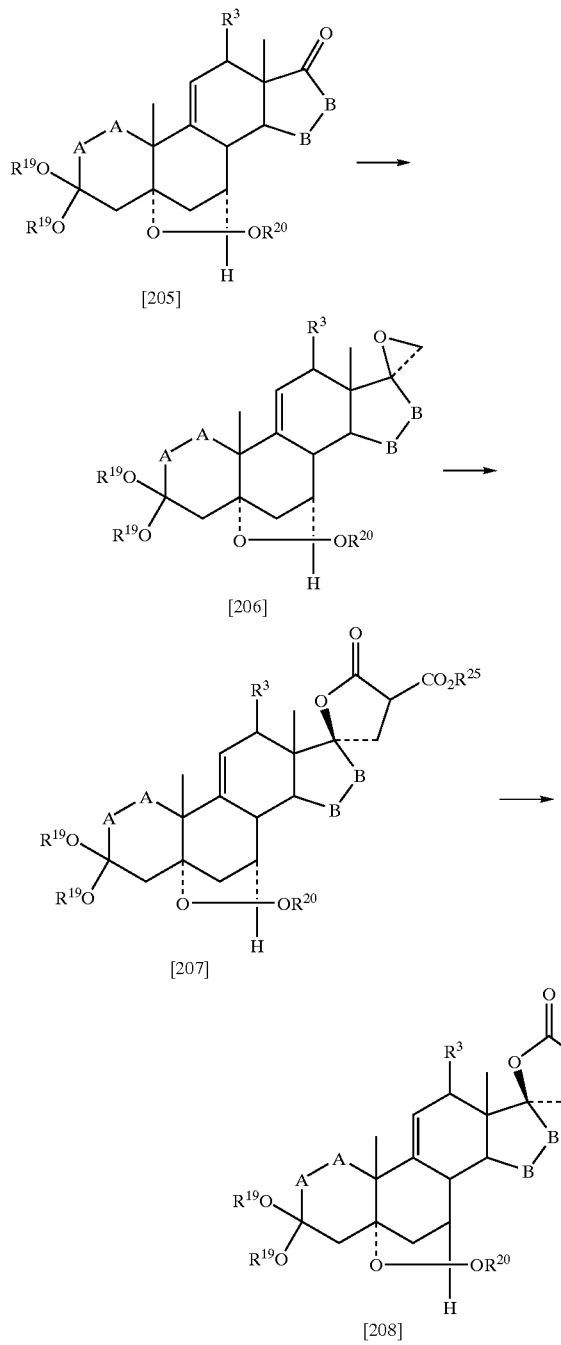

[205]

[206]

[207]

[208]

wherein —A—A—, —B—B—, $R^3$, $R^{19}$, and $R^{20}$ are as defined above and $R^{25}$ is $C_1$ to $C_4$ alkyl.

Thereafter the 3-position is deprotected by conventional hydrolysis to reintroduce the 3-keto group and 5,7-hemiacetal, producing the further intermediate corresponding to Formula 209:

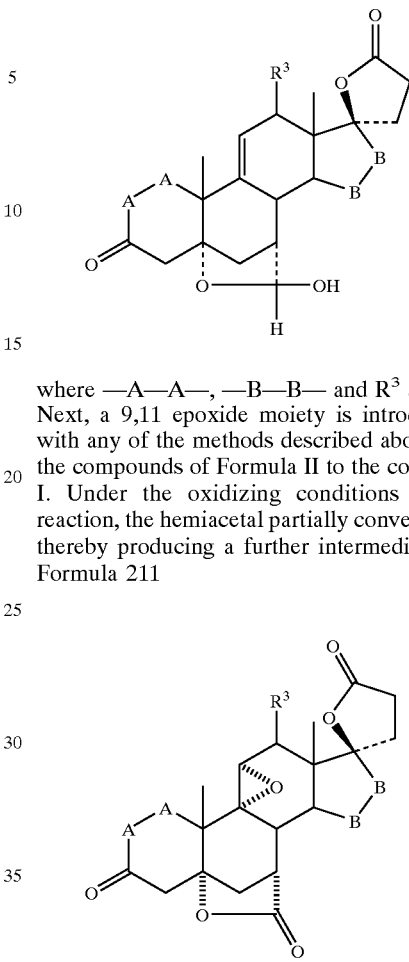

[209]

where —A—A—, —B—B— and $R^3$ are as defined above. Next, a 9,11 epoxide moiety is introduced in accordance with any of the methods described above for conversion of the compounds of Formula II to the compounds of Formula I. Under the oxidizing conditions of the epoxidation reaction, the hemiacetal partially converts to the 5,7-lactone, thereby producing a further intermediate corresponding to Formula 211

[211]

where —A—A—, —B—B— and $R^3$ are as defined above. Any remaining 9,11-epoxy-5,7-hemiacetal intermediate reaction product of Formula 210:

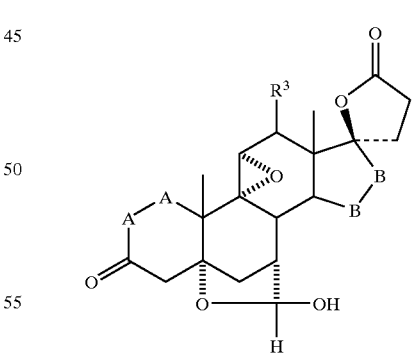

[210]

wherein —A—A—, —B—B— and $R^3$ are as defined, is readily oxidized by conventional means to the compound of Formula 211. Finally, the intermediate of Formula 211 is converted to epoxymexrenone or other compound of Formula I using the method described in Scheme 8 for the conversion of the 5,7-lactone to the 7α-alkoxycarbonyl compound. Thus, overall, Scheme 10 proceeds as follows, it being understood that at least the following steps may be carried out in situ without recovery of the intermediate.

Overall, the synthesis of Scheme 10 proceeds as follows:
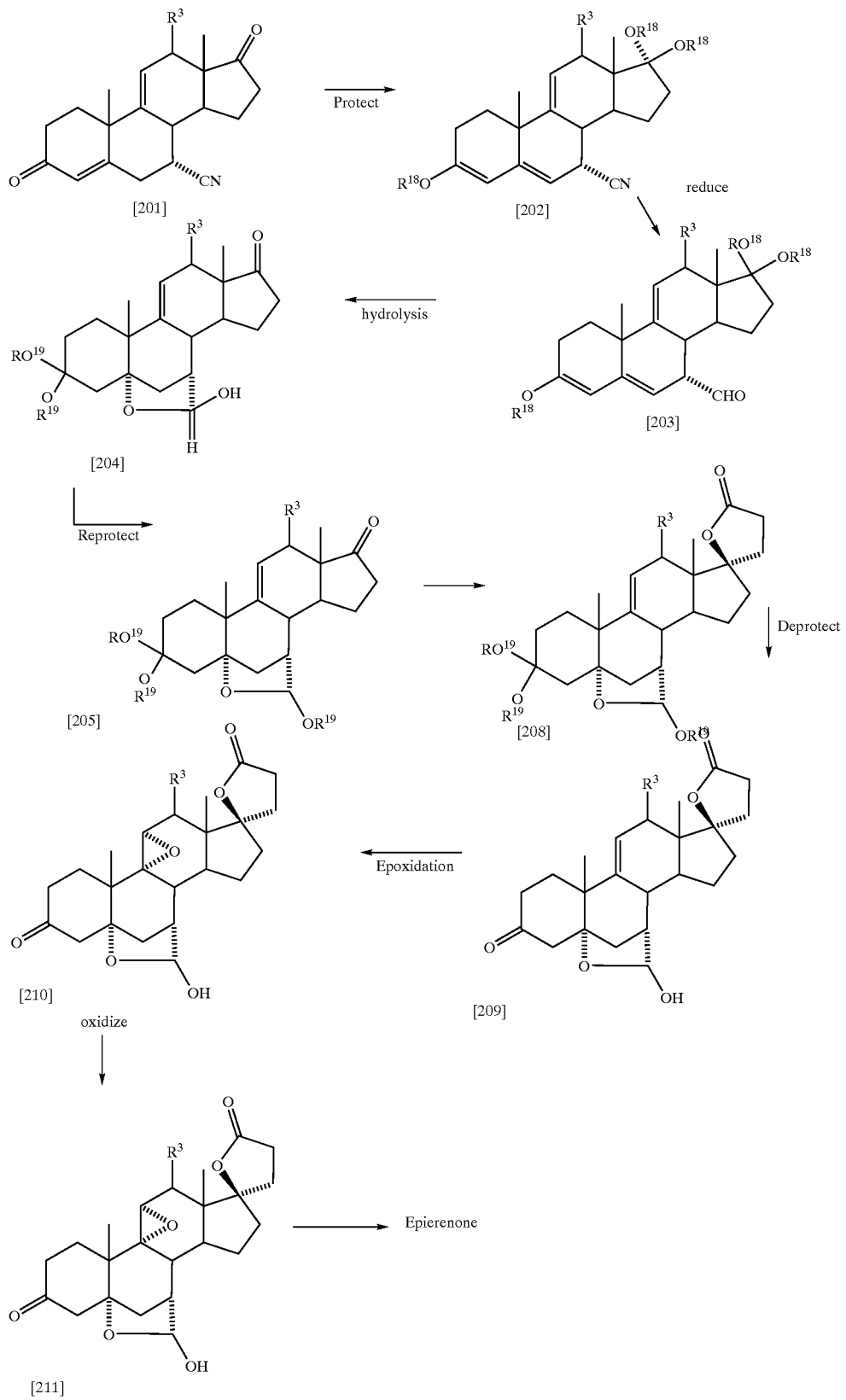
As in the case of Scheme 9 the reactions described above for Scheme 10 offer important advantages, especially with regard to process economics; but the novel reactions of Scheme 10 also have more generic application to substrates other than those particularly described. For example, introduction of the 7-formyl group into a 3-enol ether steroid, protection of the resulting 7-formyl-Δ-5,6-3,4-enol ether, hydrolysis to the 5,7-hemiacetal, and subsequent deprotection can be conducted on steroids substituted at the 17-position by $R^8$ and $R^9$ as defined above, or more particularly by a substituent of Formula:

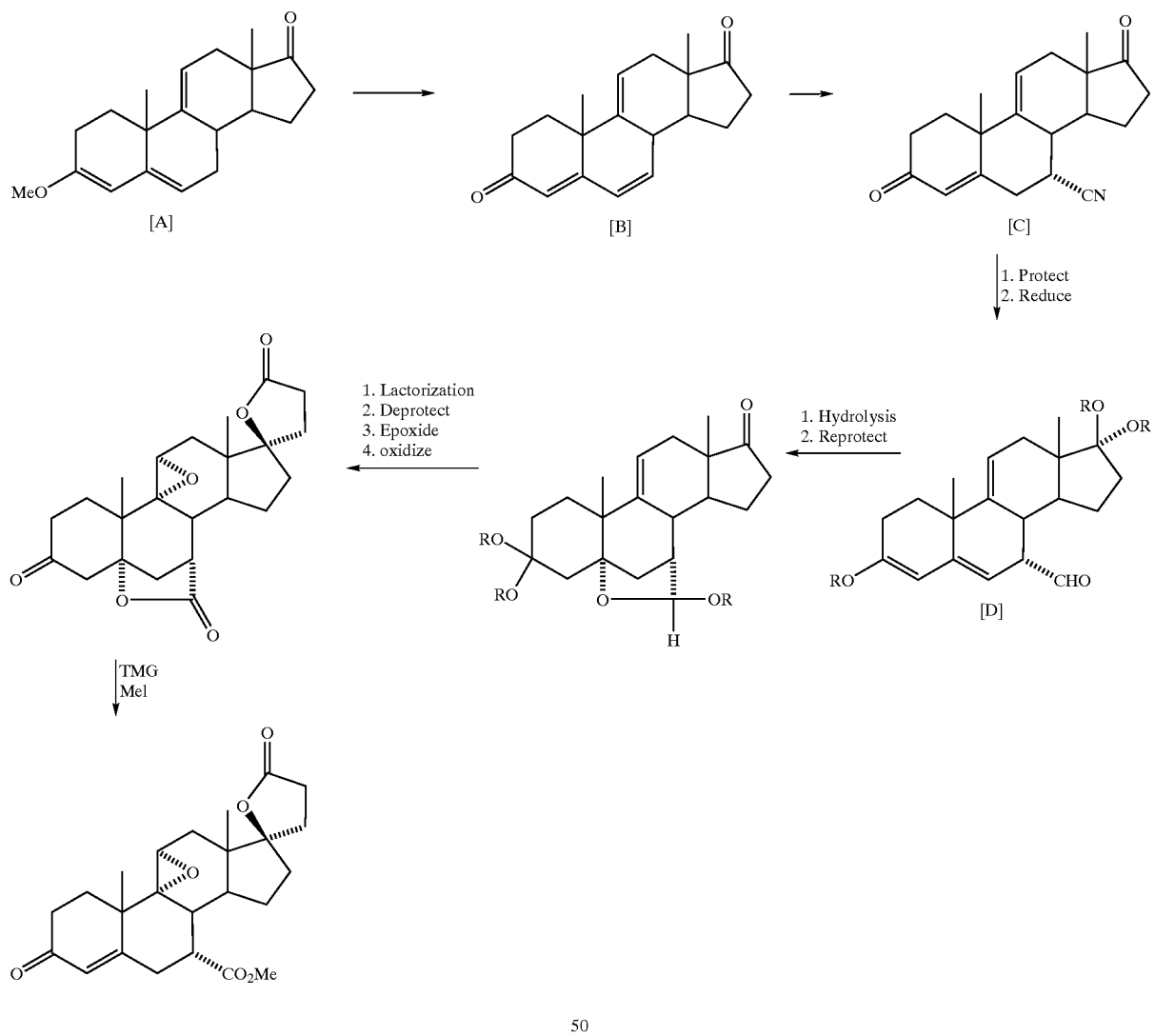

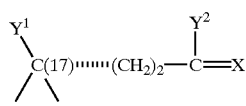

XXXIX where X, $Y^1$, $Y^2$, and C(17) are as defined above.

Alternative processes of Scheme 10 comprise use of the various intermediates within the scope of Formulae A203 through A210, respectively, hereinabove. Each of the intermediates of Formulae A203 through A211 is a novel compound which is useful in the preparation of epoxymexrenone and other compounds of Formula I and IA in accordance with the synthesis of Scheme 10.

In a particularly preferred embodiment, the overall process of Scheme 10 proceeds as follows:

From the several schemes that are illustrated above, it will be understood that the reaction steps selected for use in the processes of the invention provide substantial flexibility in the manufacture of epoxymexrenone and related compounds. The key features include, inter alia: (a) bioconversion of a substrate such as canrenone, androstendione, or β-sitosterol to an 11α- or 9α-hydroxy derivative (with simultaneous conversion of β-sitosterol to a 17-keto structure; (b) introduction of the 9,11 double bond by dehydration of a compound containing either an 11α- or 9α-hydroxy group, followed by introduction of the epoxy group by oxidation of the 9,11 double bond; (c) attachment of a 7α-alkoxycarbonyl by formation of the enamine, hydrolysis of the enamine to the diketone, and reaction of the diketone with an alkali metal alkoxide; (d) formation of the 20-spiroxane ring at the 17 position; (e) formation of the 5,7-lactone, and esterification of the lactone to the 7-alkoxycarbonyl; (f) protection of the 3-ketone by conversion to 3-enol ether or 3-ketal during various of the conversions at other positions (including formation of the 20-spiroxane ring at the 17-position. With few limitations, these four component process elements (b) to (d) can be conducted in almost any sequence. Process elements (e) and (f) offer comparable flexibility. They provide a route to epoxymexrenone and other compounds of Formula I which are much simplified as compared to the process of U.S. Pat. No. 4,559,332. Moreover, they provide important benefits in productivity and yield.

In the descriptions of the reaction schemes as set forth above, recovery, isolation and purification of reaction products can generally be carried out by methods well known to those skilled in the art. Except where otherwise indicated, conditions, solvents, and reagents are either conventional, not narrowly critical, or both. However, certain of the specific procedures as particularly described above provide advantages which contribute to the favorable overall yield and/or productivity of the various process steps and process schemes, and/or to high quality of the intermediates and ultimate 9,11-epoxy steroid products.

The utility of 20-Spiroxane compounds produced in accordance with the invention is described in Grob U.S. Pat. No. 4,559,332 which is expressly incorporated herein by reference.

20-Spiroxane compounds produced in accordance with the invention are distinguished by favorable biological properties and are, therefore, valuable pharmaceutical active ingredients. For example, they have a strong aldosterone-antagonistic action in that they reduce and normalize unduly high sodium retention and potassium excretion caused by aldosterone. They therefore have, as potassium-saving diuretics, an important therapeutic application, for example in the treatment of hypertension, cardiac insufficiency or cirrhosis of the liver.

20-Spiroxane derivatives having an aldosterone-antagonistic action are known, cf., for example, Fieser and Fieser: Steroids; page 708 (Reinhold Publ. Corp., New York, 1959) and British Patent Specification No. 1,041,534; also known are analogously active 17β-hydroxy-21-carboxylic acids and their salts, cf., for example, U.S. Pat. No. 3,849, 404. Compounds of this kind that have hitherto been used in therapy, however, have a considerable disadvantage in that they always possess a certain sexual-specific activity which has troublesome consequences sooner or later in the customary long-term therapy. Especially undesirable are the troublesome effects that can be attributed to the anti-androgenic activity of the known anti-aldosterone preparations.

The methods, processes and compositions of the invention, and the conditions and reagents used therein, are further described in the following examples.

EXAMPLE 1

Slants were prepared with a growth medium as set forth in Table 1

TABLE 1

Y P D A
(medium for slants and plates)

| yeast extract | 20 g |
|---|---|
| peptone | 20 g |
| glucose | 20 g |
| agar | 20 g |

TABLE 1-continued

Y P D A
(medium for slants and plates)

| distilled water, q.s. to | 1000 ml |
|---|---|
| pH as is 6.7 | |
| adjust at pH 5 with $H_3PO_4$ 10% w/v | |
| Distribute | |
| for slants: | |
| 7.5 ml in 180 × 18 mm tubes | |
| for plates (10 cm of φ) | |
| 25 ml in 200 × 20 mm tubes | |
| sterilize at 120° C. for 20 minutes | |
| pH after sterilization: 5 | |

To produce first generation cultures, a colony of *Aspergillus ochraceus* was suspended in distilled water (2 ml) in a test tube; and 0.15 ml aliquots of this suspension applied to each of the slants that had been prepared as described above. The slants were incubated for seven days at 25° C., after which the appearance of the surface culture was that of a white cottony mycelium. The reverse was pigmented in orange in the lower part, in yellow-orange in the upper part.

The first generation slant cultures were suspended in a sterile solution (4 ml) containing Tween 80 nonionic surfactant (3% by weight), and 0.15 ml aliquots of this suspension were used to inoculate second generation slants that had been prepared with the growth medium set forth in Table 2

TABLE 2

(for second generation and routine slants)

| malt extract | 20 g |
|---|---|
| peptone | 1 g |
| glucose | 20 g |
| agar | 20 g |
| distilled water q.s. to | 1000 ml |
| pH as is 5.3 | |
| distribute in tubes (180 × 18 mm) ml 7.5 | |
| sterilize at 120° C. for 20 minutes | |

The second generation slants were incubated for 10 days at 25° C., producing a heavy mass of golden-colored spores; reverse pigmented in brown orange.

A protective medium was prepared having the composition set forth in Table 3.

TABLE 3

PROTECTIVE MEDIUM

| Skim milk | 10 g |
|---|---|
| distilled water | 100 ml |
| In a 250 ml flask containing 100 ml of distilled water at 50° C., add skim milk. Sterilize at 120° C. for 15 minutes. Cool at 33° C. and use before the day is over | |

Cultures from five of the second generation slants were suspended in the protective solution (15 ml) in a 100 ml flask. The suspension was distributed in aliquots (0.5 ml each) among 100×10 mm tubes for lyophilization. These were pre-frozen at −70° to −80° C. in an acetone/dry ice bath for 20 minutes, then transferred immediately to a drying room pre-cooled to −40° to −50° C. The pre-frozen aliquots were lyophilized at a residual pressure of 50μ Hg and ≦−30° C. At the end of the lyophilization, two to three granules of sterile silica gel were added to each tube with moisture indicator and flame seal.

To obtain mother culture slants suitable for industrial scale fermentation, a single aliquot of lyophilized culture, which had been prepared in the manner described above, was suspended in distilled water (1 ml) and 0.15 ml aliquots of the suspension were used to inoculate slants that had been provided with a growth medium having the composition set forth in Table 2. The mother slants were incubated for seven days at 25° C. At the end of incubation, the culture developed on the slants was preserved at 4° C.

To prepare a routine slant culture, the culture from a mother slant was suspended in a sterile solution (4 ml) containing Tween 80 (3% by weight) and the resulting suspension distributed in 0.15 ml aliquots among slants which had been coated with the growth medium described in Table 2. The routine slant cultures may be used to inoculate the primary seed flasks for laboratory or industrial fermentations.

To prepare a primary seed flask culture, the culture from a routine slant, which had been prepared as described above, was removed and suspended in a solution (10 ml) containing Tween 80 (3% by weight). A 0.1 aliquot of the resulting suspension was introduced into a 500 ml baffled flask containing a growth medium having the composition set forth in Table 4.

TABLE 4

(for primary and transformation flask culture and round bottomed flask)

| | |
|---|---|
| glucose | 20 g |
| peptone | 20 g |
| yeast autolysate | 20 g |
| distilled water q.s to | |
| pH as is 5.2 | |
| adjust at pH 5.8 with NaOH 20% | |
| distribute in 500 ml baffled flask 100 ml | |
| distribute in 2000 ml round bottomed flasks (3 baffles) 500 ml | |
| sterilize 120° C. × 20 min. | |
| pH after sterilization about 5.7 | |

The seed flask was incubated on a rotating shaker (200 rpm, 5 cm displacement) for 24 hours at 28° C., thereby producing a culture in the form of pellet-like mycelia having diameters of 3 to 4 mm. On microscopic observation, the seed culture was found to be a pure culture, with synnematic growth, with big hyphae and well twisted. The pH of the suspension was 5.4 to 5.6. PMV was 5 to 8% as determined by centrifugation (3000 rpm×5 min.).

A transformation flask culture was prepared by inoculating a growth medium (100 ml) having the composition set forth Table 4 in a second 500 ml shaker flask with biomass (1 ml) from the seed culture flask. The resulting mixture was incubated on a rotating shaker (200 rpm, 5 cm displacement) for 18 hours at 28° C. The culture was examined and found to comprise pellet like mycelia with a 3–4 mm diameter. On microscopic examination, the culture was determined to be a pure culture, with synnematic and filamentous growth in which the apical cells were full of cytoplasm and the olden cells were little vacuolated. The pH of the culture suspension was 5 to 5.2 and the PMV was determined by centrifugation to be between 10% and 15%. Accordingly, the culture was deemed suitable for transformation of canrenone to 11α-hydroxycanrenone.

Canrenone (1 g) was micronized to about 5μ and suspended in sterile water (20 ml). To this suspension were added: a 40% (w/v) sterile glucose solution; a 16% (w/v) sterile solution of autolyzed yeast; and a sterile antibiotic solution; all in the proportions indicated for 0 hours reaction time in Table 5. The antibiotic solution had been prepared by dissolving kanamicyn sulfate (40 mg), tetracycline HCl (40 mg) and cefalexin (200 mg) in water (100 ml). The steroid suspension, glucose solution, and autolyzed yeast solution were added gradually to the culture contained in the shaker flask.

TABLE 5

Indicative Additions of Steroid and Solutions (additives and antibiotics) in the Course of Bioconversion of Canrenone in Shake Flask

| Reaction time hours | Steroid Suspension ml | approx. mg. | glucose solution ml | yeast auto- lised sol. ml. | anti- biotic solution ml |
|---|---|---|---|---|---|
| 0 | 1 | 50 | 1 | 0.5 | 1 |
| 8 | 2 | 100 | 2 | 1 | |
| 24 | 2 | 100 | 1 | 0.5 | 1 |
| 32 | 5 | 250 | 2 | 1 | |
| 48 | 2 | 100 | 1 | 0.5 | 1 |
| 56 | 5 | 250 | 2 | 1 | |
| 72 | 3 | 150 | 1 | 0.5 | 1 |
| 90 | | | | | |

As reaction proceeded, the reaction mixture was periodically analyzed to determine glucose content, and by thin layer chromatography to determine conversion to 11α-hydroxycanrenone. Additional canrenone substrate and nutrients were added to the fermentation reaction mixture during the reaction at rates controlled to maintain the glucose content in the range of about 0.1% by weight. The addition schedule for steroid suspension, glucose solution, autolyzed yeast solution and antibiotic solution is set forth in Table 5. The transformation reaction continued for 96 hours at 25° C. on a rotary shaker (200 rpm and 5 cm displacement). The pH ranged between 4.5 and 6 during the fermentation. Whenever the PMV rose to or above 60%, a 10 ml portion of broth culture was withdrawn and replaced with 10 ml distilled water. The disappearance of canrenone and appearance of 11α-hydroxycanrenone were monitored during the reaction by sampling the broth at intervals of 4, 7, 23, 31, 47, 55, 71, 80, and 96 hours after the start of the fermentation cycle, and analyzing the sample by TLC. The progress of the reaction as determined from these samples is set forth in Table 6

TABLE 6

Time Course of Bioconversion
of Canrenone in Shake Flask

| Time hours | Transformation Ratio | |
|---|---|---|
| | Canrenone Rf. RF. = 0.81 | 11αhydroxy Canrenone RF. = 0.29 |
| 0 | 100 | 0.0 |
| 4 | 50 | 50 |
| 7 | 20 | 80 |
| 23 | 20 | 80 |
| 31 | 30 | 70 |
| 47 | 20 | 80 |
| 55 | 30 | 70 |
| 71 | 25 | 75 |
| 80 | 15 | 85 |
| 96 | ~10 | ~90 |

EXAMPLE 2

A primary seed flask culture was prepared in the manner described in Example 1. A nutrient mixture was prepared having the composition set forth in Table 7

TABLE 7

For Transformation Culture
in 10 l glass fermenter

| | quantity | g/l |
|---|---|---|
| glucose | 80 g | 20 |
| peptone | 80 g | 20 |
| yeast autolyzed | 80 g | 20 |
| antifoam SAG 471 | 0.5 g | |
| deionized water q.s. to | 4 l | |
| sterilize the empty fermenter for 30 minutes at 130° C. load it with 3 l of deionized water, heat at 40° C. add while stirring the components of the medium stir for 15 minutes, bring to volume of 3.9 l pH as is 5.1 adjust of 5.8 with NaOH 20% w/v sterilize at 120° C. × 20 minutes pH after sterilization 5.5–5.7 | | |

An initial charge of this nutrient mixture (4 L) was introduced into a transformation fermenter of 10 L geometric volume. The fermenter was of cylindrical configuration with a height to diameter ratio of 2.58. It was provided with a 400 rpm turbine agitator having two No. 2 disk wheels with 6 blades each. The external diameter of the impellers was 80 mm, each of the blades was 25 mm in radial dimension and 30 mm high, the upper wheel was positioned 280 mm below the top of the vessel, the lower wheel was 365 mm below the top, and baffles for the vessel were 210 mm high and extended radially inwardly 25 mm from the interior vertical wall of the vessel.

Seed culture (40 ml) was mixed with the nutrient charge in the fermenter, and a transformation culture established by incubation for 22 hours at 28° C., and an aeration rate of 0.5 l/1-min. at a pressure of 0.5 kg/cm². At 22 hours, the PMV of the culture was 20–25% and the pH 5 to 5.2.

A suspension was prepared comprising canrenone (80 g) in sterile water (400 ml), and a 10 ml portion added to the mixture in the transformation fermenter. At the same time a 40% (w/v) sterile glucose solution, a 16% (w/v) sterile solution of autolyzed yeast, and a sterile antibiotic solution were added in the proportions indicated in Table 8 at 0 hours reaction time. The antibiotic solution was prepared in the manner described in Example 1.

TABLE 8

Indicative Additions of Steroid and Solutions
(additives and antibiotics) in the Course
of Bioconversion of Canrenone in
10 1 Glass Fermenter

| Reaction time hours | Steroid Suspension ml | approx gr | glucose solution ml | yeast autolyzed solution ml | anti-biotic solution ml |
|---|---|---|---|---|---|
| 0 | 10 | 4 | 25 | 12.5 | 40 |
| 4 | | | 25 | 12.5 | |
| 8 | 10 | 4 | 25 | 12.5 | |
| 12 | | | 25 | 12.5 | |
| 16 | 10 | 4 | 25 | 12.5 | |
| 20 | | | 25 | 12.5 | |
| 24 | 10 | 4 | 25 | 12.5 | 40 |
| 28 | 10 | 4 | 25 | 12.5 | |
| 32 | 12.5 | 5 | 25 | 12.5 | |
| 36 | 12.5 | 5 | 25 | 12.5 | |
| 40 | 12.5 | 5 | 25 | 12.5 | |
| 44 | 12.5 | 5 | 25 | 12.5 | |
| 48 | 12.5 | 5 | 25 | 12.5 | 40 |
| 52 | 12.5 | 5 | 25 | 12.5 | |
| 56 | 12.5 | 5 | 25 | 12.5 | |
| 60 | 12.5 | 5 | 25 | 12.5 | |
| 64 | 12.5 | 5 | 25 | 12.5 | |
| 68 | 12.5 | 5 | 25 | 12.5 | |
| 72 | 12.5 | 5 | 25 | 12.5 | 40 |
| 76 | 12.5 | 5 | 25 | 12.5 | |
| 80 | | | | | |
| 84 | | | | | |
| 88 | | | | | |

As reaction proceeded, the reaction mixture was periodically analyzed to determine glucose content, and by thin layer chromatography to determine conversion to 11α-hydroxycanrenone. Based on TLC analysis of reaction broth samples as described hereinbelow, additional canrenone was added to the reaction mixture as canrenone substrate was consumed. Glucose levels were also monitored and, whenever glucose concentration dropped to about 0.05% by weight or below, supplemental glucose solution was added to bring the concentration up to about 0.25% by weight. Nutrients and antibiotics were also added at discrete times during the reaction cycle. The addition schedule for steroid suspension, glucose solution, autolyzed yeast solution and antibiotic solution is set forth in Table 8. The transformation reaction continued for 90 hours at an aeration rate of 0.5 vol. air per vol. liquid per minute (vvm) at a positive head pressure of 0.3 kg/cm². The temperature was maintained at 28° C. until PVM reached 45%, then decreased to 26° C. and maintained at that temperature as PVM grew from 45% to 60%, and thereafter controlled at 24° C. The initial agitation rate was 400 rpm, increasing to 700 rpm after 40 hours. The pH was maintained at between 4.7 and 5.3 by additions of 2M orthophosphoric acid or 2M NaOH, as indicated. Foaming was controlled by adding a few drops of Antifoam SAG 471 as foam developed. The disappearance of canrenone and appearance of 11α-hydroxycanrenone were monitored at 4 hour intervals during the reaction by TLC analysis of broth samples. When most of the canrenone had disappeared from the broth, additional increments were added.

After all canrenone additions had been made, the reaction was terminated when TLC analysis showed that the concentration of canrenone substrate relative to 11α-hydroxycanrenone product had dropped to about 5%.

At the conclusion of the reaction cycle, the fermentation broth was filtered through cheese cloth for separation of the mycelium from the liquid broth. The mycelia fraction was resuspended in ethyl acetate using about 65 volumes (5.2 liters) per gram canrenone charged over the course of the reaction. The suspension of mycelia in ethyl acetate was refluxed for one hour under agitation, cooled to about 20° C., and filtered on a Buchner. The mycelia cake was washed sequentially with ethyl acetate (5 vol. per g canrenone charge; 0.4 L) and deionized water (500 ml) to displace the ethyl acetate extract from the cake. The filter cake was discarded. The rich extract, solvent washing and water washing were collected in a separator, then allowed to stand for 2 hours for phase separation.

The aqueous phase was then discarded and the organic phase concentrated under vacuum to a residual volume of 350 ml. The still bottoms were cooled to 15° C. and kept under agitation for about one hour. The resulting suspension was filtered to remove the crystalline product, and the filter cake was washed with ethyl acetate (40 ml). After drying, the yield of 11α-hydroxycanrenone was determined to be 60 g.

EXAMPLE 3

A spore suspension was prepared from a routine slant in the manner described in Example 1. In a 2000 ml baffled round bottomed flask (3 baffles, each 50 mm×30 mm), an aliquot (0.5 ml) of the spore suspension was introduced into a nutrient solution (500 ml) having the composition set forth in Table 4. The resulting mixture was incubated in the flask for 24 hours at 25° C. on an alternating shaker (120 strokes per min.; displacement 5 cm), thereby producing a culture which, on microscopic examination, was observed to appear as a pure culture with hyphae well twisted. The pH of the culture was between about 5.3 and 5.5, and the PMV (as determined by centrifugation at 3000 rpm for 5 min.) was 8 to 10%.

Using the culture thus prepared, a seed culture was prepared in a stainless steel fermenter of vertical cylindrical configuration, having a geometric volume of 160 L and an aspect ratio of 2.31 (height=985 mm; diameter=425 mm). The fermenter was provided with a disk turbine type agitator having two wheels, each wheel having six blades with an external diameter of 240 mm, each blade having a radial dimension of 80 mm and a height of 50 mm. The upper wheel was positioned at a depth of 780 mm from the top of the fermenter, and the second at a depth of 995 mm. Vertical baffles having a height of 890 mm extended radially inwardly 40 mm from the interior vertical wall of the fermenter. The agitator was operated at 170 rpm. A nutrient mixture (100 L) having the composition set forth in Table 9 was introduced into the fermenter, followed by a portion of preinoculum (1 L) prepared as described above and having a pH of 5.7.

TABLE 9

For Vegetative Culture in 160 L Fermenter About 8 L are needed to Seed Productive fermenter

|  | Quantity | g/L |
|---|---|---|
| glucose | 2 kg | 20 |
| peptone | 2 kg | 20 |
| yeast autolysed | 2 kg | 20 |
| antifoam SAG 471 | 0.010 Kg | traces |
| deionized water q.s. to sterilize the empty fermenter for 1 hour at 130° C. | 100 L | |
| load it with 6 L of deionized water; heat at 40° C. add while stirring the components of the medium stir for 15 minutes, bring to volume of 95 L sterilization at 121° C. for 30 minutes post sterilization pH is 5.7 add sterile deionized water to 100 L | | |

The inoculated mixture was incubated for 22 hours at an aeration rate of 0.5 L/L-min. at a head pressure of 0.5 kg/cm$^2$. The temperature was controlled at 28° C. until PMV reached 25%, and then lowered to 25° C. The pH was controlled in the range of 5.1 to 5.3. Growth of mycelium volume is shown in Table 10, along with pH and dissolved oxygen profiles of the seed culture reaction.

TABLE 10

Time Course for Mycelial Growth in Seed Culture Fermentation

| Fermentation period h | pH | packed mycelium volume (pmv) % (3000 rpms 5 min) | dissolved oxygen % |
|---|---|---|---|
| 0 | 5.7 ± 0.1 |  | 100 |
| 4 | 5.7 ± 0.1 |  | 100 |
| 8 | 5.7 ± 0.1 | 12 ± 3 | 85 ± 5 |
| 12 | 5.7 ± 0.1 | 15 ± 3 | 72 ± 5 |
| 16 | 5.5 ± 0.1 | 25 ± 5 | 40 ± 5 |
| 20 | 5.4 ± 0.1 | 30 ± 5 | 35 ± 5 |
| 22 | 5.3 ± 0.1 | 33 ± 5 | 30 ± 5 |
| 24 | 5.2 ± 0.1 | 35 ± 5 | 25 ± 5 |

Using the seed culture thus produced, a transformation fermentation run was carried out in a vertical cylindrical stainless steel fermenter having a diameter of 1.02 m, a height of 1.5 m and a geometric volume of 1.4 m$^3$. The fermenter was provided with a turbine agitator having two impellers, one positioned 867 cm below the top of the reactor and the other positioned 1435 cm from the top. Each wheel was provided with six blades, each 95 cm in radial dimension and 75 cm high. Vertical baffles 1440 cm high extended radially inwardly 100 cm from the interior vertical wall of the reactor. A nutrient mixture was prepared having the composition set forth in Table 11

TABLE 11

For Bioconversion Culture in 1000 L Fermenter

|  | Quantity | g/L |
|---|---|---|
| glucose | 16 kg | 23 |
| peptone | 16 kg | 23 |
| yeast autolysed | 16 kg | 23 |
| antifoam SAG 471 | 0.080 Kg | traces |
| deionized water q.s. to sterilize the empty fermenter for 1 hour at 130° C. load it with 600 L of deionized water; heat at 40° C. add while stirring the components of the medium stir for 15 minutes, bring to volume of 650 L sterilization at 121° C. for 30 minutes post sterilization pH is 5.7 add sterile deionized water to 700 L | 700 L | |

An initial charge (700 L) of this nutrient mixture (pH=5.7) was introduced into the fermenter, followed by the seed inoculum of this example (7 L) prepared as described above.

The nutrient mixture containing inoculum was incubated for 24 hours at an aeration rate of 0.5 L/L-min at a head pressure of 0.5 kg/cm$^2$. The temperature was controlled at 28° C., and the agitation rate was 110 rpm. Growth of mycelium volume is shown in Table 12, along with pH and dissolved oxygen profiles of the seed culture reaction.

TABLE 12

Time Course for Mycelial Growth in Fermenter of the Transformation Culture

| Fermentation period h | pH | packed mycelium volume (pmv) % (3000 rpmx5 min) | dissolved oxygen % |
|---|---|---|---|
| 0 | 5.6 ± 0.2 |  | 100 |
| 4 | 5.5 ± 0.2 |  | 100 |
| 8 | 5.5 ± 0.2 | 12 ± 3 | 95 ± 5 |
| 12 |  | 15 ± 3 | 90 ± 5 |
| 16 | 5.4 ± 0.1 | 20 ± 5 | 75 ± 5 |
| 20 | 5.3 ± 0.1 | 25 ± 5 | 60 ± 5 |
| 22 | 5.2 ± 0.1 | 30 ± 5 | 40 ± 5 |

At the conclusion of the incubation, pelleting of the mycelium was observed, but the pellets were generally small and relatively loosely packed. Diffuse mycelium was suspended in the broth. Final pH was 5.1 to 5.3.

To the transformation culture thus produced was added a suspension of canrenone (1.250 kg; micronized to 5μ) in sterile water (5 L). Sterile additive solution and antibiotic solution were added in the proportions indicated at reaction time 0 in Table 14. The composition of the additive solution is set forth in Table 13.

TABLE 13

ADDITIVE SOLUTION (for transformative culture)

|  | quantity |
|---|---|
| dextrose | 40 Kg |
| yeast autolysate | 8 Kg |
| antifoam SAG 471 | 0.010 Kg |
| deionized water q.s. to sterilize a 150 l empty fermenter for 1 hour at 130° C. load it with 70 l of deionized water; heat at 40° C. add while stirring the components of "additive solution" stir for 30 minutes, bring to volume of 95 l pH as is 4.9 sterilize at 120° C. × 20 minutes pH after sterilization about 5 | 100 l |

Bioconversion was carried out for about 96 hours with aeration at 0.5 L/L-min. at a head pressure of 0.5 kg/cm$^2$ and a pH of ranging between 4.7 and 5.3, adjusted as necessary by additions of 7.5 M NaOH or 4 M H$_3$PO$_4$. The agitation rate was initially 100 rpm, increased to 165 rpm at 40 hours and 250 rpm at 64 hours. The initial temperature was 28° C., lowered to 26° C. when PMV reached 45%, and lowered to 24° C. when PMV rose to 60%. SAG 471 in fine drops was added as necessary to control foaming. Glucose levels in the fermentation were monitored at 4 hour intervals and, whenever the glucose concentration fell below 1 gpl, an increment of sterile additive solution (10 L) was added to the batch. Disappearance of canrenone and appearance of 11α-hydroxycanrenone were also monitored during the reaction by HPLC. When at least 90% of the initial canrenone charge had been converted to 11α-hydroxycanrenone, an increment of 1.250 kg canrenone was added. When 90% of the canrenone in that increment was shown to have been converted, another 1.250 kg increment was introduced. Using the same criterion further increments (1.250 kg apiece) were added until the total reactor charge (20 kg) had been introduced. After the entire canrenone charge had been delivered to the reactor, reaction was terminated when the concentration of unreacted canrenone was 5% relative to the amount of 11α-hydroxycanrenone produced. The schedule for addition of canrenone, sterile additive solution, and antibiotic solution is as shown in Table 14.

TABLE 14

Additions of the Steroid and Solutions (additives and antibiotics) in the Course of Bioconversion of Canrenone in Fermenter

| Reaction time hours | CANRENONE in suspension | | Sterile additive solution liters | anti- biotic solution liters | volume liters about |
|---|---|---|---|---|---|
|  | Kg | Progress- ive Kg |  |  |  |
| 0 | 1.250 | 1.25 | 10 | 8 | 700 |
| 4 |  |  | 10 |  |  |
| 8 | 1.250 | 2.5 | 10 |  |  |
| 12 |  |  | 10 |  |  |

TABLE 14-continued

Additions of the Steroid and Solutions
(additives and antibiotics)
in the Course of Bioconversion of Canrenone
in Fermenter

| Reaction time hours | CANRENONE in suspension Kg | CANRENONE in suspension Progressive Kg | Sterile additive solution liters | anti-biotic solution liters | volume liters about |
|---|---|---|---|---|---|
| 16 | 1.250 | | 10 | | |
| 20 | | | 10 | | |
| 24 | 1.250 | 5 | 10 | 8 | 800 |
| 28 | 1.250 | | 10 | | |
| 32 | 1.250 | | 10 | | |
| 36 | 1.250 | | 10 | | |
| 40 | 1.250 | | 10 | | |
| 44 | 1.250 | | 10 | | |
| 48 | 1.250 | 12.5 | 10 | 6 | 900 |
| 52 | 1.250 | | 10 | | |
| 56 | 1.250 | | 10 | | |
| 60 | 1.250 | | 10 | | |
| 64 | 1.250 | | 10 | | |
| 68 | 1.250 | | 10 | | |
| 72 | 1.250 | 20 | 10 | 8 | 1050 |
| 76 | | | 0 | | |
| 80 | | | | | |
| 84 | | | | | |
| 88 | | | | | |
| 92 | | | | | |
| Total | | | | | |

When bioconversion was complete, the mycelia were separated from the broth by centrifugation in a basket centrifuge. The filtrate was determined by HPLC to contain only 2% of the total quantity of 11α-hydroxycanrenone in the harvest broth, and was therefore eliminated. The mycelia were suspended in ethyl acetate (1000 L) in an extraction tank of 2 m³ capacity. This suspension was heated for one hour under agitation and ethyl acetate reflux conditions, then cooled and centrifuged in a basket centrifuge. The mycelia cake was washed with ethyl acetate (200 L) and thereafter discharged. The steroid rich solvent extract was allowed to stand for one hour for separation of the water phase. The water phase was extracted with a further amount of ethyl acetate solvent (200 L) and then discarded. The combined solvent phases were clarified by centrifugation and placed in a concentrator (500 L geometric volume) and concentrated under vacuum to a residual volume of 100 L. In carrying out the evaporation, the initial charge to the concentrator of combined extract and wash solutions was 100 L, and this volume was kept constant by continual or periodic additions of combined solution as solvent was taken off. After the evaporation step was complete, the still bottoms were cooled to 20° C. and stirred for two hours, then filtered on a Buchner filter. The concentrator pot was washed with ethyl acetate (20 L) and this wash solution was then used to wash the cake on the filter. The product was dried under vacuum for 16 hours at 50° C. Yield of 11α-hydroxycanrenone was 14 kg.

EXAMPLE 4

Lyophilized spores of *Aspergillus ochraceus* NRRL 405 were suspended in a corn steep liquor growth medium (2 ml) having the composition set forth in Table 15:

TABLE 15

Corn Steep Liquor Medium
(Growth Medium for Primary Seed Cultivation)

| | |
|---|---|
| Corn steep liquor | 30 g |
| Yeast extract | 15 g |
| Ammonium phosphate Monobasic | 3 g |
| Glucose (charge after sterilization) | 30 g |
| distilled water, q.s. to 1000 ml | |
| pH as is: 4.6, adjust to pH 6.5 with 20% NaOH, distribute 50 ml to 250 ml Erlenmeyer flask sterilize 121° C. for 20 minutes. | |

The resulting suspension was used in an inoculum for the propagation of spores on agar plates. Ten agar plates were prepared, each bearing a solid glucose/yeast extract/phosphate/agar growth medium having the composition set forth in Table 16:

TABLE 16

GYPA
(Glucose/Yeast Extract/Phosphate
Agar for Plates)

| | |
|---|---|
| Glucose (charge after sterilization) | 10 g |
| Yeast extract | 2.5 g |
| K₂HPO₄ | 3 g |
| Agar | 20 g |
| distilled water, q.s. to 1000 ml | |
| adjust pH to 6.5 | |
| sterilize 121° C. for 30 minutes | |

A 0.2 ml aliquot of the suspension was transferred onto the surface of each plate. The plates were incubated at 25° C. for ten days, after which the spores from all the plates were harvested into a sterile cryogenic protective medium having the composition set forth in Table 17:

TABLE 17

GYP/Glycerol
(Glucose/Yeast Extract/
Phosphate/Glycerol
medium for stock vials)

| | |
|---|---|
| Glucose (charge after sterilization) | 10 g |
| Yeast extract | 2.5 g |
| K₂HPO₄ | 3 g |
| Glycerol | 20 g |
| Distilled water, q.s. to 1000 mL | |
| Sterilize at 121° C. for 30 minutes | |

The resulting suspension was divided among twenty vials, with one ml being transferred to each vial. These vials constitute a master cell bank that can be drawn on to produce working cell banks for use in generation of inoculum for bioconversion of canrenone to 11α-hydroxycanrenone. The vials comprising the master cell bank were stored in the vapor phase of a liquid nitrogen freezer at −130° C.

To begin preparation of a working cell bank, the spores from a single master cell bank vial were resuspended in a sterile growth medium (1 ml) having the composition set forth in Table 15. This suspension was divided into ten 0.2 ml aliquots and each aliquot used to inoculate an agar plate bearing a solid growth medium having the composition set forth in Table 16. These plates were incubated for ten days at 25° C. By the third day of incubation, the underside of the growth medium was brown-orange. At the end of the incubation there was heavy production of golden colored spores. The spores from each plate were harvested by the procedure described hereinabove for the preparation of the master cell bank. A total of one hundred vials was prepared, each containing 1 ml of suspension. These vials constituted the working cell bank. The working cell bank vials were also preserved by storage in the vapor phase of a liquid nitrogen freezer at −130° C.

Growth medium (50 ml) having the composition set forth in Table 15 was charged to a 250 ml Erlenmeyer flask. An aliquot (0.5 ml) of working cell suspension was introduced into the flask and mixed with the growth medium. The inoculated mixture was incubated for 24 hours at 25° C. to produce a primary seed culture having a percent packed mycelial volume of approximately 45%. Upon visual inspection the culture was found to comprise pellet-like mycelia of 1 to 2 mm diameter; and upon microscopic observation it appeared as a pure culture.

Cultivation of a secondary seed culture was initiated by introducing a growth medium having the composition set forth in Table 15 into a 2.8 L Fernbach flask, and inoculating the medium with a portion (10 ml) of the primary seed culture of this example, the preparation of which was as described above. The inoculated mixture was incubated at 25° C. for 24 hours on a rotating shaker (200 rpm, 5 cm displacement). At the end of the incubation, the culture exhibited the same properties as described above for the primary seed culture, and was suitable for use in a transformation fermentation in which canrenone was bioconverted to 11α-hydroxycanrenone.

Transformation was conducted in a Braun E Biostat fermenter configured as follows:

| | |
|---|---|
| Capacity: | 15 liters with round bottom |
| Height: | 53 cm |
| Diameter: | 20 cm |
| H/D: | 2.65 |
| Impellers: | 7.46 cm diameter, six paddles 2.2 × 1.4 cm each |
| Impeller spacing: | 65.5, 14.5 and 25.5 cm from bottom of tank |
| Baffles: | four 1.9 × 48 cm |
| Sparger: | 10.1 cm diameter, 21 holes ~1 mm diameter |
| Temperature control: | provided by means of an external vessel jacket |

Canrenone at a concentration of 20 g/L was suspended in deionized water (4 L) and a portion (2 L) of growth medium having the composition set forth in Table 18 was added while the mixture in the fermenter was stirred at 300 rpm.

TABLE 18

(Growth medium for bioconversion culture in 10 L fermenter)

| | Quantity | Amount/L |
|---|---|---|
| glucose (charge after sterilization) | 160 g | 20 g |
| peptone | 160 g | 20 g |
| yeast extract | 160 g | 20 g |
| antifoam SAF471 | 4.0 ml | 0.5 ml |
| Canrenone | 160 g | 20 g |
| deionized water q.s. to 7.5 L sterilize 121° C. for 30 minutes | | |

The resulting suspension was stirred for 15 minutes, after which the volume was brought up to 7.5 L with additional deionized water. At this point the pH of the suspension was adjusted from 5.2 to 6.5 by addition of 20% by weight NaOH solution, and the suspension was then sterilized by heating at 121° C. for 30 minutes in the Braun E fermenter. The pH after sterilization was 6.3±0.2, and the final volume was 7.0 L. The sterilized suspension was inoculated with a portion (0.5 L) of the secondary seed culture of this example that has been prepared as described above, and the volume brought up to 8.0 L by addition of 50% sterile glucose solution. Fermentation was carried out at a temperature of 28° C. until the PMV reached 50%, then lowered to 26° C., and further lowered to 24° C. when PMV exceeded 50% in order to maintain a consistent PMV below about 60%. Air was introduced through the sparger at a rate of 0.5 vvm based on initial liquid volume and the pressure in the fermenter was maintained at 700 millibar gauge. Agitation began at 600 rpm and was increased stepwise to 1000 rpm as needed to keep the dissolved oxygen content above 30% by volume. Glucose concentration was monitored. After the initial high glucose concentration fell below 1% due to consumption by the fermentation reaction, supplemental glucose was provided via a 50% by weight sterile glucose solution to maintain the concentration in the 0.05% to 1% range throughout the remainder of the batch cycle. Prior to inoculation the pH was 6.3±0.2. After the pH dropped to about 5.3 during the initial fermentation period, it was maintained in the range of 5.5±0.2 for the remainder of the cycle by addition of ammonium hydroxide. Foam was controlled by adding a polyethylene glycol antifoam agent sold under the trade designation SAG 471 by OSI Specialties, Inc.

Growth of the culture took place primarily during the first 24 hours of the cycle, at which time the PMV was about 40%, the pH was about 5.6 and the dissolved oxygen content was about 50% by volume. Canrenone conversion began even as the culture was growing. Concentrations of canrenone and 11α-hydroxycanrenone were monitored during the bioconversion by analyzing daily samples. Samples were extracted with hot ethyl acetate and the resulting sample solution analyzed by TLC and HPLC. The bioconversion was deemed complete when the residual canrenone concentration was about 10% of the initial concentration. The approximate conversion time was 110 to 130 hours.

When bioconversion was complete, mycelial biomass was separated from the broth by centrifugation. The supernatant was extracted with an equal volume of ethyl acetate, and the aqueous layer discarded. The mycelial fraction was resuspended in ethyl acetate using approximately 65 volumes per g canrenone charged to the fermentation reactor. The mycelial suspension was refluxed for one hour under agitation, cooled to about 20° C., and filtered on a Buchner funnel. The mycelial filter cake was washed twice with 5 volumes of ethyl acetate per g of canrenone charged to the fermenter, and then washed with deionized water (1 L) to displace the residual ethyl acetate. The aqueous extract, rich solvent, solvent washing and water washing were combined. The remaining exhausted mycelial cake was either discarded or extracted again, depending on analysis for residual steroids therein. The combined liquid phases were allowed to settle for two hours. Thereafter, the aqueous phase was separated and discarded, and the organic phase concentrated under vacuum until the residual volume was approximately 500 ml. The still bottle was then cooled to about 15° C. with slow agitation for about one hour. The crystalline product was recovered by filtration, and washed with chilled ethyl acetate (100 ml). Solvent was removed from the crystals by evaporation, and the crystalline product dried under vacuum at 50° C.

EXAMPLE 5

Lyophilized spores of *Aspergillus ochraceus* ATCC 18500 were suspended in a corn steep liquor growth medium (2 ml) as described in Example 4. Ten agar plates were prepared, also in the manner of Example 4. The plates were incubated and harvested as described in Example 4 to provide a master cell bank. The vials comprising the master cell bank were stored in the vapor phase of a liquid nitrogen freezer at −130° C.

From a vial of the master cell bank, a working cell bank was prepared as described in Example 4, and stored in the nitrogen freezer at −130° C.

Growth medium (300 mL) having the composition set forth in Table 19 was charged to a 2 L baffled flask. An aliquot (3 mL) of working cell suspension was introduced into the flask. The inoculated mixture was incubated for 20 to 24 hours at 28° C. on a rotating shaker (200 rpm, 5 cm displacement) to produce a primary seed culture having a percent packed mycelial volume of approximately 45%. Upon visual inspection the culture was found to comprise pellet like mycelia of 1 to 2 mm diameter; and upon microscopic observation it appeared as a pure culture.

TABLE 19

Growth medium for primary and secondary seed cultivation

| | Amount/L |
|---|---|
| glucose (charge after sterilization) | 20 g |
| peptone | 20 g |
| Yeast extract | 20 g |
| distilled water q.s. to 1000 mL | |
| sterilize 121° C. for 30 minutes | |

Cultivation of a secondary seed culture was initiated by introducing 8 L growth medium having the composition set forth in Table 19 into a 14 L glass fermenter. Inoculate the fermenter with 160 mL to 200 mL of the primary seed culture of this example. The preparation of which was as described above.

The inoculated mixture was cultivated at 28° C. for 18–20 hours, 200 rmp agitation, aeration rate was 0.5 vvm. At the end of the propagation, the culture exhibited the same properties as described above for the primary seed.

Transformation was conducted in a 60 L fermenter, substantially in the manner described in Example 4, except that the growth medium had the composition set forth in Table 20, and the initial charge of secondary seed culture was 350 mL to 700 mL. Agitation rate was initially 200 rpm, but increased to 500 rpm as necessary to maintain dissolved oxygen above 10% by volume. The approximate bioconversion time for 20 g/L canrenone was 80 to 160 hours.

TABLE 20

Growth Medium for Bioconversion Culture in 60 L Fermenter

| | Quantity | Amount/L |
|---|---|---|
| glucose (charge after sterilization) | 17.5 g | 0.5 g |
| peptone | 17.5 g | 0.5 g |
| yeast extract | 17.5 g | 0.5 g |
| Canrenone (charge as a 20% slurry in sterile water) | 700 g | 20 g | deionized water, q.s. to 35 L
sterilize 121° C. for 30 minutes

EXAMPLE 6

Using a spore suspension from the working cell bank produced in accordance with the method described in Example 4, primary and secondary seed cultures were prepared, also substantially in the manner described in Example 4. Using secondary seed culture produced in this manner, two bioconversion runs were made in accordance with a modified process of the type illustrated in FIG. 1, and two runs were made with the process illustrated in FIG. 2. The transformation growth medium, canrenone addition schedules, harvest times, and degrees of conversion for these runs are set forth in Table 21. Run R2A used a canrenone addition scheme based on the same principle as Example 3, while run R2C modified the Example 3 scheme by making only two additions of canrenone, one at the beginning of the batch, and one after 24 hours. In runs R2B and R2D, the entire canrenone charge was introduced at the beginning of the batch and the process generally carried in the manner described in Example 4, except that the canrenone charge was sterilized in a separate vessel before it was charged to the fermenter and glucose was added as the batch progressed. A Waring blender was used to reduce chunks produced on sterilization. In runs R2A and R2B, canrenone was introduced into the batch in methanol solution, in which respect these runs further differed from the runs of Examples 3 and 4, respectively.

TABLE 21

Descriptions of the Initial Canrenone Bioconversion Processes

| Run Number | R2A | R2B | R2C | R2D |
|---|---|---|---|---|
| Medium (g/L) | | | | |
| Corn steep liq. | 30 | the same as run R2A | 30 | the same as run R2C |
| Yeast extract | 15 | | 15 | |
| NH₄H₂PO₄ | 3 | | 3 | |
| Glucose | 15 | | 30 | |
| OSA | 0.5 ml | | 0.5 ml | |
| pH | adjusted to 6.0 with 2.5NNaOH | | adjusted to 6.5 with 2.5NNaOH | |
| Canrenone | 10 g/80 ml MEOH added at 0, 18, 24, 30, 36, 42, 50, 56, 62 and 68 hr. | 80 g/640 ml MEOH added at 0 hr all at once | Sterilized and blended; added at: 0 hr: 25 g 24 hr: 200 g | Sterilized and blended; added at: 0 hr: 200 g |

TABLE 21-continued

Descriptions of the Initial Canrenone Bioconversion Processes

| Run Number | R2A | R2B | R2C | R2D |
|---|---|---|---|---|
| Harvest time | 143 hrs. | 166 hrs. | 125 hrs. | 104 hrs. |
| Bioconversion | 45.9% | 95.6% | 98.1% | 95.1% |

In runs R2A and R2B, the methanol concentration accumulated to about 6.0% in the fermentation beer, which was found to be inhibitory to the growth of culture and bioconversion. However, based on the results of these runs, it was concluded that methanol or other water-miscible solvent could serve effectively at lower concentrations to increase the canrenone charge and provide canrenone as a fine particle precipitate providing a large interfacial area for supply of canrenone to the subject to the reaction.

Canrenone proved stable at sterilization temperature (121° C.) but aggregated into chunks. A Waring blender was employed to crush the lumps into fine particles, which were successfully converted to product.

EXAMPLE 7

Using a spore suspension from the working cell bank produced in accordance with the method described in Example 4, primary and secondary seed cultures were prepared, also substantially in the manner described in Example 4. The description and results of Example 7 are shown in Table 22. Using secondary seed culture produced in this manner, one bioconversion (R3C) was carried out substantially as described in Example 3, and three bioconversions were carried out in accordance with the process generally described in Example 5. In the latter three runs (R3A, R3B and R3D), canrenone was sterilized in a portable tank, together with the growth medium except for glucose. Glucose was aseptically fed from another tank. The sterilized canrenone suspension was introduced into the fermenter either before inoculation or during the early stage of bioconversion. In run R3B, supplemental sterile canrenone and growth medium was introduced at 46.5 hours. Lumps of canrenone formed on sterilization were delumped through a Waring blender thus producing a fine particulate suspension entering the fermenter. The transformation growth media, canrenone addition schedules, nutrient addition schedules, harvest times, and degrees of conversion for these runs are set forth in Tables 22 and 23.

TABLE 22

Descriptions of Process for Canrenone Bioconversion

| Run Number | R3A | R3B | R3C | R3D |
|---|---|---|---|---|
| Medium (g/L) | | | | |
| Corn steep liq. | 30 | the same as run R3A | Peptone: 20 | the same as run R3A |
| Yeast extract | 15 | | Yeast Ext.: 20 | |
| NH$_4$H$_2$PO$_4$ | 3 | | Glucose: 20 | |
| Glucose | 15 | | OSA: 3 ml | |
| OSA | 0.5 ml | | | |
| pH | adjusted to 6.5 with 2.5NNaOH | | adjusted to 6.5 with 2.5NNaOH | |
| Canrenone charge at | canrenone was sterilized and blended. BI: 50 g 16.5 hrs: 110 g | the same as run R3A BI: 50 g 16.5 hrs: 110 g 46.5 hrs: 80 g | Non-sterile canrenone: charged by the scheduled listed in Table 23 | The same as run R3A BI: 50 g 16.5 hrs: 110 g |
| Feedings | see Table 23 | see Table 23 | see Table 23 | see Table 23 |
| Harvest time | 118.5 hrs. | 118.5 hrs | 118.5 hrs | 73.5 hrs. |
| Bioconversion | 93.7% | 94.7% | 60.0% | 68.0% |

TABLE 23

The Feeding Schedule for Canrenone, Glucose and Growth Medium in the Development Experiment

| | R3C | | | | R3A | R3B | R3D |
|---|---|---|---|---|---|---|---|
| Addition Time hr. | canrenone 200 g/2 L sterile DI g | Glucose 50% solution g | Peptone & Yeast ext. 20 g each in IL water g | Antibiotics 20 mg kanamycin 20 mg tetracycline 100 mg cefalexin in 50 ml | Canrenone/ Growth Medium see Table 22 g/L | Canrenone/ Growth Medium see Table 22 g/L | Canrenone/ Growth Medium see Table 22 g/L |
| 0 | — | — | — | — | 50 g/0.4 L | 50 g/0.4 L | 50 g/0.4 L |
| 14.5 | 16 | 100 | 25 | 50 ml | — | — | — |

TABLE 23-continued

The Feeding Schedule for Canrenone, Glucose and
Growth Medium in the Development Experiment

| | R3C | | | | R3A | R3B | R3D |
|---|---|---|---|---|---|---|---|
| Addition Time hr. | canrenone 200 g/2 L sterile DI g | Glucose 50% solution g | Peptone & Yeast ext. 20 g each in 1L water g | Antibiotics 20 mg kanamycin 20 mg tetracycline 100 mg cefalexin in 50 ml | Canrenone/ Growth Medium see Table 22 g/L | Canrenone/ Growth Medium see Table 22 g/L | Canrenone/ Growth Medium see Table 22 g/L |
| 16.5 | — | — | — | — | 110 g/1.2 L | 110 g/1.2 L | 110 g/1.2 L |
| 20.5 | 16 | 140 | 25 | — | — | — | — |
| 28.5 | 16 | 140 | 25 | — | — | — | — |
| 34.5 | 16 | 150 | 25 | — | — | — | — |
| 40.5 | 16 | 150 | 25 | 50 ml | — | — | — |
| 46.5 | 880 | 130 | 25 | — | — | 80 g/0.8 L | — |
| 52.5 | 160 | 120 | 25 | — | — | — | — |
| 58.5 | 160 | 150 | 25 | — | — | — | — |
| 64.5 | 160 | 180 | 25 | 50 ml | — | — | — |
| 70.5 | 160 | 140 | 25 | — | — | — | — |

Due to filamentous growth, a highly viscous fermenter broth was seen in all four of the runs of this Example. To overcome obstacles which high viscosity created with respect to aeration, mixing, pH control and temperature control, the aeration rate and agitation speed were increased during these runs. Conversions proceeded satisfactorily under the more severe conditions, but a dense cake formed above the liquid broth surface. Some unreacted canrenone was carried out of the broth by this cake.

EXAMPLE 8

The description and results of Example 8 are summarized in Table 24. Four fermentation runs were made in which 11α-hydroxycanrenone was produced by bioconversion of canrenone. In two of these runs (R4A and R4D), the bioconversion was conducted in substantially the same manner as runs R3A and R3D of Example 6. In run R4C, canrenone was converted to 11α-hydroxycanrenone generally in the manner described in Example 3. In Run R4B, the process was carried out generally as described in Example 4, i.e., with sterilization of canrenone and growth medium in the fermenter just prior to inoculation, all nitrogen and phosphorus nutrients were introduced at the start of the batch, and a supplemental solution containing glucose only was fed into the fermenter to maintain the glucose level as the batch proceeded. In the latter process (run R4B), glucose concentration was monitored every 6 hours and glucose solution added as indicated to control glucose levels in the 0.5 to 1% range. The canrenone addition schedules for these runs are set forth in Table 25.

TABLE 24

Descriptions of the Process
Development Experiment of Canrenone Bioconversions

| Run Number | R4A | R4B | R4C | R4D |
|---|---|---|---|---|
| Medium (g/L) | | | | |
| Corn steep liq. | 30 | the same as run R4A | peptone: 20 | the same as run R4A |
| Yeast extract | 15 | | Yeast ext.: 20 | |
| NH4H2PO4 | 3 | | Glucose: 20 | |
| Glucose | 15 | | OSA 3 ml | |
| OSA | 0.5 ml | | | |
| pH | adjusted to 6.5 with 2.5NNaOH | | adjusted to 6.5 with 2.5NNaOH | |
| Canrenone charge at | Canrenone was sterilized and blended. BI: 40 g 23.5 hrs: 120 g | 160 g canrenone is sterilized in the fermenter | Nonsterile canrenone: charged by the schedule listed in Table 25 | Canrenone was sterilized and blended. BI: 40 g 23.5 hrs: 120 g |
| Medium charge | see Table 25 | see Table 25 | see Table 25 | see Table 25 |
| Harvest time | 122 hrs. | 122 hrs. | 122 hrs. | 122 hrs. |
| Bioconversion | 95.6% | 97.6% | 95.4% | 96.7% |

TABLE 25

The Feeding Schedule of Canrenone, Glucose and Growth Medium in the Development Experiment

| | R4C | | | | | | |
|---|---|---|---|---|---|---|---|
| Addition Time hr. | Canrenone 200 g /2 L sterile water g | Glucose 50% solution g | Peptone & Yeast ext. 20 g each in 1 L water g | Antibiotics 20 mg kanamycin 20 mg tetra-cycline 100 mg cefalexin in 50 ml (added in canrenone slurry) | R4A Growth Medium see Table 24 | R4B Growth Medium see Table 24 | R4D Growth Medium see Table 24 |
| 14 | 600 | 135 | 25 | 50 ml | — | — | — |
| 20 | — | 100 | — | — | — | — | — |
| 23 | — | — | — | — | 120 g/ 1.2 L | — | 120 g/ 1.2 L |
| 26 | — | 100 | 25 | — | — | — | — |
| 32 | — | 135 | 25 | — | — | — | — |
| 38 | 500 | 120 | 25 | 50 ml | — | — | — |
| 44 | — | 100 | 25 | — | — | — | — |
| 50 | — | 100 | 25 | — | — | — | — |
| 56 | — | 150 | 25 | — | — | — | — |
| 62 | 500 | 150 | 25 | 50 ml | — | — | — |
| 68 | — | 200 | 25 | — | — | — | — |
| 74 | — | 300 | 25 | — | — | — | — |
| 8- | — | 100 | 25 | — | — | — | — |
| 86 | — | 175 | 25 | — | — | — | — |
| 92 | — | 175 | 25 | — | — | — | — |
| 98 | — | 150 | — | — | — | — | — |
| 104 | — | 175 | — | — | — | — | — |
| 110 | — | 175 | — | — | — | — | — |
| 116 | — | 200 | — | — | — | — | — |

All fermenters were run under high agitation and aeration during most of the fermentation cycle because the fermentation beer had become highly viscous within a day or so after inoculation.

EXAMPLE 9

The transformation growth media, canrenone addition schedules, harvest times, and degrees of conversion for the runs of this Example are set forth in Table 26.

Four bioconversion runs were carried out substantially in the manner described for run R4B of Example 8, except as described below. In run R5B, the top turbine disk impeller used for agitation in the other runs was replaced with a downward pumping marine is impeller. The downward pumping action axially poured the broth into the center of the fermenter and reduced cake formation. Methanol (200 ml) was added immediately after inoculation in run R5D. Since canrenone was sterilized in the fermenter, all nutrients except glucose were added at the start of the batch, obviating the need for chain feeding of sources of nitrogen, sources of phosphorus or antibiotics.

TABLE 26

Process Description of the Process Development Experiment of 10 L Scale Bioconversions

| Run Number | R5A | R5B | R5C | R5D |
|---|---|---|---|---|
| Medium (g/L) | | | | |
| Corn steep liq. | 30 | the same as run R5A | Peptone: 20 | the same as run R5A |
| Yeast Extract | 15 | | Yeast Ext.: 20 | |
| NH$_4$H$_2$PO$_4$ | 3 | | Glucose: 20 | |
| Glucose | 15 | | OSA 3 ml | |
| OSA | 0.5 ml | | | |
| pH | adjusted to 6.5 with 2.5NNaOH | | adjusted to 6.5 with 2.5NNaOH | |
| Canrenone charge | 160 g canrenone sterilized in the fermenter | 160 g canrenone sterilized in the fermenter | 160 g canrenone sterilized in the fermenter | 160 g canrenone sterilized in the fermenter |
| Medium feeding | glucose feeding | glucose feeding | glucose feeding | glucose feeding |
| Harvest time | 119.5 hrs. | 119.5 hrs. | 106 | 119.5 hrs. |
| Bioconversion | 96% | 94.1% | 88.5% | 92.4% |

In order to maintain immersion of the solid phase growing above the liquid surface, growth medium (2 L) was added to each fermenter 96 hours after the beginning of the batch. Mixing problems were not entirely overcome by either addition of growth medium or use of a downward pumping impeller (run R5B) but the results of the runs demonstrated the feasibility and advantages of the process, and indicated that satisfactory mixing could be provided according to conventional practices.

EXAMPLE 10

Three bioconversion runs were carried out substantially in the manner described in Example 9. The transformation growth media, canrenone addition schedules, harvest times, and degrees of conversion for the runs of this Example are set forth in Table 27:

TABLE 27

Process Description of the
Experiment 10 L Scale Bioconversion

| Run Number | R6A | R6B | R6C |
|---|---|---|---|
| Medium (g/L) | | | |
| Corn steep liq. | 30 | the same as run R6A | Peptone: 20 |
| Yeast Extract | 15 | | Yeast Ext.: 20 |
| NH$_4$H$_2$PO$_4$ | 3 | | Glucose: 20 |
| Glucose | 15 | | OSA |
| OSA | 0.5 ml | | 0.5 ml |
| pH | adjusted to 6.5 with 2.5NNaOH | | adjusted to 6.5 with 2.5NNaOH |
| Canrenone charge | 160 g canrenone sterilized in the fermenter | 160 g canrenone sterilized in the fermenter | 160 g canrenone sterilized in the fermenter |
| Medium feeding | glucose feeding; 1.3 L medium and 0.8 L sterile water at 71 hrs. | glucose feeding; 0.5 L medium and 0.5 L sterile water at 95 hrs | glucose feeding; no other addition |
| Harvest time | 120 hrs. | 120 hrs. | 120 hrs. |
| Bioconversion | 95% | 96% | 90% |
| Mass Balance | 59% | 54% | 80% |

Growth medium (1.3 L) and sterile water (0.8 L) were added after 71 hours in run R6A to submerge mycelial cake which had grown above the surface of the liquid broth. For the same purpose, growth medium (0.5 L) and sterile water (0.5 L) were added after 95 hours in run R6B. Material balance data showed that a better mass balance could be determined where cake buildup above the liquid surface was minimized.

EXAMPLE 11

Fermentation runs were made to compare pre-sterilization of canrenone with sterilization of canrenone and growth medium in the transformation fermenter. In run R7A, the process was carried out as illustrated in FIG. 2, under conditions comparable to those of runs R2C, R2D, R3A, R3B, R3D, R4A, and R4D. Run R7B was as illustrated in FIG. 3 under conditions comparable to those of Examples 4, 9 and 10, and run R4B. The transformation growth media, canrenone addition schedules, harvest times, and degrees of conversion for the runs of this Example are set forth in Table 28:

TABLE 28

Process Description of the
Experiment of 10 L Scale Bioconversions

| Run Number | R7A | R7B |
|---|---|---|
| Medium (g/L) | | |
| corn steep liq. | 30 | the same as run R7A |
| Yeast extract | 15 | |
| NH$_4$H$_2$PO$_4$ | 3 | |
| Glucose | 15 | |
| OSA | 0.5 ml | |
| pH | adjusted to 6.5 with 2.5NNaOH | |
| Canrenone charge | 160 g canrenone was sterilized & blended outside the fermenter | 160 g canrenone was sterilized in the fermenter |
| Medium charge | Glucose feeding; canrenone was added with 1.6 L growth medium | Glucose feeding; no other addition |
| Harvest time | 118.5 hrs. | 118.5 hrs. |
| Bioconversion | 93% | 89% |

A mass balance based on the final sample taken from run R7B was 89.5%, indicating that no significant substrate loss or degradation in bioconversion. Mixing was determined to be adequate for both runs.

Residual glucose concentration was above the desired 5–10 g per liter control range during the initial 80 hours. Run performance was apparently unaffected by a light cake that accumulated in the head space of both the fermenters.

EXAMPLE 12

Extraction efficiency was determined in a series of 1 L extraction runs as summarized in Table 29. In each of these runs, steroids were extracted from the mycelium using ethyl acetate (1 L/L fermentation volume). Two sequential extractions were performed in each run. Based on RP-HPLC, About 80% of the total steroid was recovered in the first extraction; and recovery was increased to 95% by the second extraction. A third extraction would have recovered another 3% of steroid. The remaining 2% is lost in the supernatant aqueous phase. The extract was drawn to dryness using vacuum but was not washed with any additional solvent. Chasing with solvent would improve recovery from the initial extraction if justified by process economics.

TABLE 29

Recovery of 11α-Hydroxycanrenone
at 1 Liter Extraction (% of Total)

| Run Number | 1st Extract | 2nd Extract | 3rd Extract | Supernatant |
|---|---|---|---|---|
| R5A | 79% | 16% | 2% | 2% |
| R5A | 84% | 12% | 2% | 2% |
| R4A | 72% | 20% | 4% | 4% |
| R4A | 79% | 14% | 2% | 5% |
| R4B | 76% | 19% | 4% | 1% |
| R4B | 79% | 16% | 3% | 2% |
| R4B | 82% | 15% | 2% | 1% |
| Average | 79% | 16% | 3% | 2% |

Methyl isobutyl ketone (MIEK) and toluene were evaluated as extraction/crystallization solvents for 11α-hydroxycanrenone at the 1 L broth scale. Using the extraction protocol as described hereinabove, both MIBK and toluene were comparable to ethyl acetate in both extraction efficiency and crystallization performance.

EXAMPLE 13

As part of the evaluation of the processes of FIGS. 2 and 3, particle size studies were conducted on the canrenone substrate provided at the start of the fermentation cycle in each of these processes. As described above, canrenone fed to the process of FIG. 1 was micronized before introduction into the fermenter. In this process, the canrenone is not sterilized, growth of unwanted microorganisms being controlled by addition of antibiotics. The processes of FIGS. 2 and 3 sterilize the canrenone before the reaction. In the process of FIG. 2, this is accomplished in a blender before introduction of canrenone into the fermenter. In the process of FIG. 3, a suspension of canrenone in growth medium is sterilized in the fermenter at the start of the batch. As discussed hereinabove, sterilization tends to cause agglomeration of canrenone particles. Because of the limited solubility of canrenone in the aqueous growth medium, the productivity of the process depends on mass transfer from the solid phase, and thus may be expected to depend on the interfacial area presented by the solid particulate substrate which in turn depends on the particle size distribution. These considerations initially served as deterrents to the processes of FIGS. 2 and 3.

Figure 4:
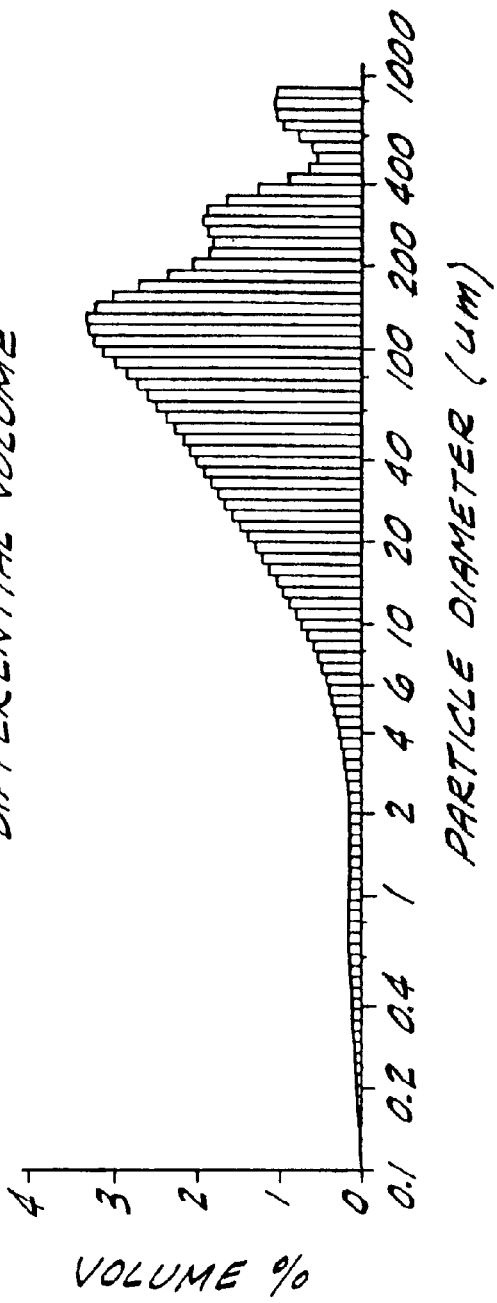
FIG. 4 shows the particle size distribution for canrenone as prepared in accordance with the process of FIG. 2.
Figure 5:
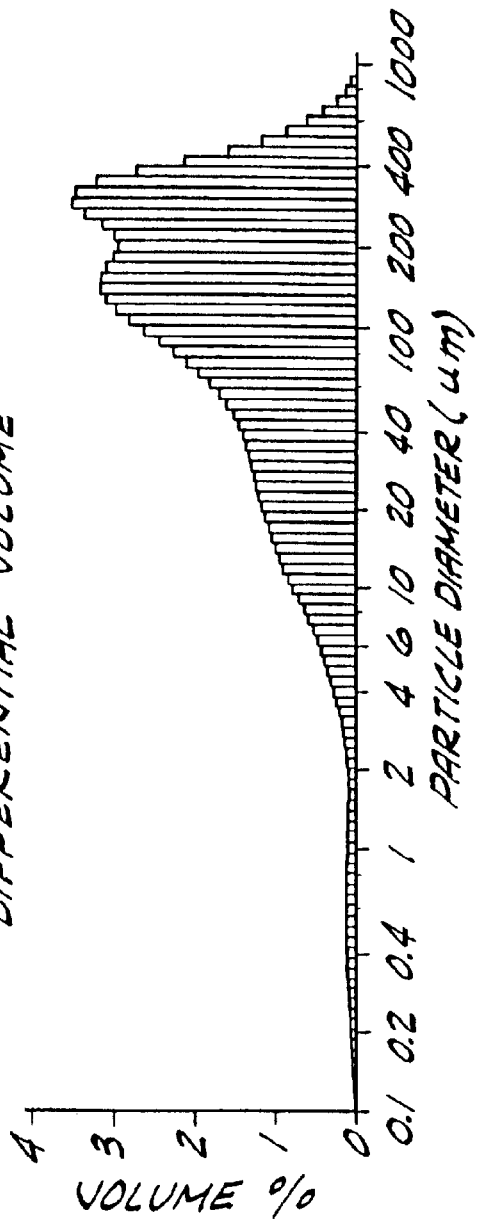
FIG. 5 shows the particle size distribution for canrenone as sterilized in the transformation fermenter in accordance with the process of FIG. 3.

However, agitation in the blender of FIG. 2 and the fermentation tank of FIG. 3, together with the action of the shear pump used for transfer of the batch in FIG. 2, were found to degrade the agglomerates to a particle size range reasonably approximate that of the unsterilized and micronized canrenone fed to the process of FIG. 1. This is illustrated by the particle size distributions for the canrenone as available at the outset of the reaction cycle in each of the three processes. See Table 30 and FIGS. 4 and 5.

TABLE 30

Particle Distributions of
Three Different Canrenone Samples

| Sample | 45–125 μ | <180 μ | mean size μ | Run #: % Bioconversion |
| --- | --- | --- | --- | --- |
| Canrenone shipment | 75% | 95% | — | R3C: 93.1% (120 h)<br>R4C: 96.3% (120 h) |
| Blended Sample | 31.2% | 77.2% | 139.5 | R3A: 94.6% (120 h)<br>R3B: 95.2% (120 h) |
| Sterilized Sample | 24.7% | 65.1% | 157.4 | R4B: 97.6% (120 h)<br>R5B: 93.8% (120 h) |

From the data in Table 30, it will be noted that agitators and shear pump were effective to reduce the average particle size of the sterilized canrenone to the same order of magnitude as the unsterilized substrate, but a significance size difference remained in favor of the unsterilized substrate. Despite this difference, reaction performance data showed that the pre-sterilization processes were at least as productive as the process of FIG. 1. Further advantages may be realized in the process of FIG. 2 by certain steps for further reducing and controlling particle size, e.g., wet milling of sterilized canrenone, and/or by pasteurizing rather than sterilizing.

EXAMPLE 14

A seed culture was prepared in the manner described in Example 5. At 20 hours, the mycelia in the inoculum fermenter was pulpy with a 40% PMV. Its pH was 5.4 and 14.8 gpl glucose remained unused.

A transformation growth medium (35 L) was prepared having the composition shown in Table 20. In the preparation of feeding medium, glucose and yeast extract were sterilized separately and mixed as a single feed at an initial concentration of 30% by weight glucose and 10% by weight yeast extract. pH of the feed was adjusted to 5.7.

Using this medium, (Table 20), two bioconversion runs were made for the conversion of canrenone to 11α-hydroxycanrenone. Each of the runs was conducted in a 60 L fermenter provided with an agitator comprising one Rushton turbine impeller and two Lightnin' A315 impellers.

Initial charge of the growth medium to the fermenter was 35 L. Micronized and unsterilized canrenone was added to an initial concentration of 0.5%. The medium in the fermenter was inoculated with a seed culture prepared in the manner described in Example 5 at an initial inoculation ratio of 2.5%. Fermentation was carried out at a temperature of 28° C., an agitation rate of 200 to 500 rpm, an aeration rate of 0.5 vvm, and backpressure sufficient to maintain a dissolved oxygen level of at least 20% by volume. The transformation culture developed during the production run was in the form of very small oval pellets (about 1–2 mm). Canrenone and supplemental nutrients were chain fed to the fermenter generally in the manner described in Example 1. Nutrient additions were made every four hours at a ratio of 3.4 g glucose and 0.6 g yeast extract per liter of broth in the fermenter.

Set forth in Table 31 are the aeration rate, agitation rate, dissolved oxygen, PMV, and pH prevailing at stated intervals during each of the runs of this Example, as well as the glucose additions made during the batch. Table 32 shows the canrenone conversion profile. Run R11A was terminated after 46 hours; Run R11B continued for 96 hours. In the latter run, 93% conversion was reached at 81 hours; one more feed addition was made at 84 hours; and feeding then terminated. Note that a significant change in viscosity occurred between the time feeding was stopped and the end of the run.

TABLE 31

| Time | air (1 pm) | rpm | % DO | Backpress | PMV (%) | pH | Gluc cc (g/l) |
| --- | --- | --- | --- | --- | --- | --- | --- |
| Fermentation R11A | | | | | | | |
| 0.1 | 20 | 200 | 93 | 0 | 2 | 6.17 | 5.8 |
| 7 | 20 | 200 | 85.1 | 0 | 5 | 6.03 | 5.5 |
| 12.4 | 20 | 300 | 50.2 | 0 | | 5.43 | |
| 21.8 | 20 | 400 | 25.5 | 0 | 38 | 6.98 | 0 |
| 29 | 20 | 500 | 17 | 0 | 35 | 5.22 | |
| 30.2 | 20 | 500 | 18.8 | 10 | | 5.01 | |
| 31 | 20 | 500 | 79 | 10 | | 4.81 | 1 |
| 35.7 | 20 | 500 | 100 | 10 | 45 | 5.57 | 0 |
| 46.2 | 20 | 500 | 23 | 6 | 45 | 5.8 | 1 |
| Total glucose: 27.5 g/l | | | | | | | |
| Total yeast extract: 8.75 g/l | | | | | | | |
| Fermentation R11B | | | | | | | |
| 0.1 | 20 | 200 | 92.9 | 0 | 2 | 5.98 | 5.4 |
| 7 | 20 | 200 | 82.3 | 0 | 5 | 5.9 | 5 |
| 12.4 | 20 | 300 | 49.5 | 0 | | 5.48 | |
| 21.8 | 20 | 400 | 18 | 0 | 40 | 7.12 | 0 |
| 29 | 20 | 500 | 36.8 | 0 | 35 | 5.1 | 3 |
| 35.7 | 20 | 500 | 94.5 | 10 | | 4.74 | 0 |
| 46.2 | 20 | 500 | 14.5 | 6 | 45 | 5.32 | 2 |
| 55 | 20 | 500 | 16.7 | 10 | | 5.31 | 0.5 |
| 58.6 | 20 | 500 | 19.4 | 15 | | 5.32 | 1 |
| 61.9 | 20 | 500 | 13 | 15 | 40 | 5.36 | 2 |

TABLE 31-continued

| Time | air (1 pm) | rpm | % DO | Backpress | PMV (%) | pH | Gluc cc (g/l) |
|---|---|---|---|---|---|---|---|
| 71.7 | 20 | 500 | 13 | 15 | 42 | 5.37 | 0 |
| 81.1 | 20 | 500 | 22.9 | 15 | | 5.42 | 2.5 |
| 85.6 | 20 | 500 | 22 | 15 | 45 | 6.47 | 0 |
| 97.5 | 20 | 500 | 108 | 15 | 45 | 6.47 | 0 |
| 117.7 | 20 | 500 | | 15 | | 7.38 | 0 |

Total glucose: 63 g/l
Total yeast extract: 14.5 g/l

TABLE 32

| Sample | Concentrations (g/l) | | | | Conversion (%) | Calc OH-can (g/l) | Conv. rates (g/l/h) | |
|---|---|---|---|---|---|---|---|---|
| | Time | OH-can | Canren. | Total | | | Calculated | Measured |
| Fermentation R11A: Canrenone conversion | | | | | | | | |
| R11A-0 | 0.10 | 0.00 | 5.41 | 5.41 | | | | |
| R11A-7 | 7.00 | 0.18 | 4.89 | 5.07 | 3.58 | 0.18 | 0.03 | 0.03 |
| R11A-22 | 21.80 | 2.02 | 2.12 | 4.14 | 48.75 | 2.44 | 0.15 | 0.12 |
| R11A-29 | 29.00 | 3.67 | 4.14 | 7.81 | 47.03 | 4.48 | 0.28 | 0.23 |
| R11A-36 | 35.70 | 6.68 | 1.44 | 8.12 | 82.27 | 7.74 | 0.49 | 0.45 |
| R11A-46 | 46.20 | 7.09 | 0.41 | 7.51 | 94.48 | 8.59 | 0.08 | 0.04 |
| Fermentation R11B: Canrenone conversion | | | | | | | | |
| R11B-0 | 0.1 | 0.00 | 5.60 | 5.60 | | | | |
| R11B-7 | 7.0 | 0.20 | 4.98 | 5.18 | 3.78 | 0.19 | 0.03 | 0.03 |
| R11B-22 | 21.8 | 2.51 | 2.46 | 4.97 | 50.49 | 2.52 | 0.16 | 0.16 |
| R11B-29 | 29.0 | 4.48 | 16.99 | 21.47 | 20.87 | 4.69 | 0.30 | 0.27 |
| R11B-36 | 35.7 | 8.18 | 10.35 | 18.53 | 44.16 | 9.70 | 0.75 | 0.55 |
| R11B-55 | 55.0 | 17.03 | 13.20 | 30.23 | 56.33 | 19.50 | 0.32 | 0.36 |
| R11B-59 | 58.6 | 20.80 | 11.73 | 32.53 | 63.95 | 21.97 | 0.69 | 1.05 |
| R11B-62 | 61.9 | 22.19 | 8.62 | 30.81 | 72.02 | 24.50 | 0.77 | 0.42 |
| R11B-72 | 71.7 | 26.62 | 3.61 | 30.23 | 88.06 | 29.46 | 0.51 | 0.45 |
| R11B-81 | 81.1 | 27.13 | 2.05 | 29.18 | 92.97 | 30.32 | 0.09 | 0.05 |
| R11B-86 | 85.6 | 26.87 | 2.02 | 28.88 | 93.02 | 30.11 | −0.04 | −0.06 |
| R11B-97 | 97.5 | 23.95 | 1.71 | 25.66 | 93.34 | 30.22 | 0.01 | −0.25 |
| R11B-118 | 117.7 | 24.10 | 1.68 | 25.79 | 93.47 | 30.26 | 0.00 | 0.01 |

EXAMPLE 15

Various cultures were tested for effectiveness in the bioconversion of canrenone to 11α-hydroxycanrenone according to the methods generally described above.

A working cell bank of each of *Aspergillus niger* ATCC 11394, *Rhizopus arrhizus* ATCC 11145 and *Rhizopus stolonifer* ATCC 6227b was prepared in the manner described in Example 5. Growth medium (50 ml) having the composition set forth in Table 18 was inoculated with a suspension of spores (1 ml) from the working cell bank and placed in an incubator. A seed culture was prepared in the incubator by fermentation at 26° C. for about 20 hours. The incubator was agitated at a rate of 200 rpm.

Aliquots (2 ml) of the seed culture of each microorganism were used to inoculate transformation flasks containing the growth medium (30 ml) of Table 18. Each culture was used for inoculation of two flasks, a total of six. Canrenone (200 mg) was dissolved in methanol (4 ml) at 36° C., and a 0.5 ml aliquot of this solution was introduced into each of the flasks. Bioconversion was carried out generally under the conditions described in Example 5 with additions of 50% by weight glucose solution (1 ml) each day. After the first 72 hours the following observations were made on the development of mycelia in the respective transformation fermentation flasks:

ATCC 11394—good even growth
ATCC 11145—good growth in first 48 hours, but mycelial clumped into a ball; no apparent growth in last 24 hours;
ATCC 6227b—good growth; mycelial mass forming clumped ball.

Samples of the broth were taken to analyze for the extent of bioconversion. After three days, the fermentation using ATCC 11394 provided conversion to 11α-hydroxycanrenone of 80 to 90%; ATCC 11145 provided a conversion of 50%; and ATCC 6227b provided a conversion of 80 to 90%.

EXAMPLE 16

Using the substantially the method described in Example 15, the additional microorganisms were tested for effectiveness in the conversion of canrenone to 11α-hydroxycanrenone. The organisms tested and the results of the tests are set forth in Table 33:

TABLE 33

Cultures tested for Bioconversion of canrenone to 11 alpha-hydroxy-canrenone

| Culture | ATTC# | media[1] | results | approximate conversion | |
|---|---|---|---|---|---|
| Rhizopus oryzae | 1145 | CSL | + | 50% | — |
| Rhizopus stolonifer | 6227b | CSL | + | 80–90% | — |
| Aspergillus nidulans | 11267 | CSL | + | 50% | 80% |
| Aspergillus niger | 11394 | CSL | + | 80–90% | — |
| Aspergillus ochraceus | NRRL 405 | CSL | + | | 90% |
| Aspergillus ochraceus | 18500 | CSL | + | | 90% |
| Bacillus subtilis | 31028 | P&CSL | − | 0% | 0% |
| Bacillus subtilis | 31028 | CSL | − | 0% | 0% |
| Bacillus sp. | 31029 | P&CSL | − | 0% | 0% |
| Bacillus sp. | 31029 | CSL | − | 0% | * |
| Bacillus megaterium | 14945 | P&CSL | + | 5% | 80%* |
| Bacillus megaterium | 14945 | CSL | + | 5% | 10%* |
| Trichothecium roseum | 12519 | CSL | + | 80%* | 90%* |
| Trichothecium roseum | 8685 | CSL | + | 80%* | 90%* |
| Streptomyces fradiae | 10745 | CSL | + | <5% | <10% |
| Streptomyces fradiae | 10745 | TSB | − | * | * |
| Streptomyces lavendulae | 13664 | CSL | − | 0% | * |
| Streptomyces lavendulae | 13664 | TSR | − | 0% | 0% |
| Nocardiodes simplex | 6946 | BP | − | 0% | 0% |
| Nocardiodes simplex | 13260 | BP | − | * | * |
| Pseudomonas sp. | 14696 | BP | − | * | * |
| Pseudomonas sp. | 14696 | CSL | + | <5* | <10% |
| Pseudomonas sp. | 14696 | TSR | − | 0% | * |
| Pseudomonas sp. | 13261 | BP | + | * | <10% |
| Pseudomonas cruciviae | 13262 | BP | | # | <10% |
| Pseudomonas putida | 15175 | BP | − | 0% | 0% |

*formation of other unidentified products
[1]Media: CSL - corn steep liquor; TSB - tryptic soy broth; P & CSL - peptone and acorn steep liquor; BP - beef extract and peptone.

EXAMPLE 17

Various microorganisms were tested for effectiveness in the conversion of canrenone to 9α-hydroxycanrenone. Fermentation media for the runs of this Example were prepared as set forth in Table 34:

TABLE 34

| Soybean Meal: | |
|---|---|
| dextrose | 20 g |
| soybean meal | 5 g |
| NaCl | 5 g |
| yeast extract | 5 g |
| KH$_2$PO$_4$ | 5 g |
| water | to 1 L |
| pH | 7.0 |
| Peptone/yeast extract/glucose: | |
| glucose | 40 g |
| bactopeptone | 10 g |
| yeast extract | 5 g |
| water | to 1 L |
| Mueller-Hinton: | |
| beef infusion | 300 g |
| casamino acids | 17.5 g |
| starch | 1.5 g |
| water | to 1 L |

Fungi were grown in soybean meal medium and in peptone-yeast extract glucose; atinomycetes and eubacteria were grown in soybean meal (plus 0.9% by weight Na formate for biotransformations) and in Mueller-Hinton broth.

Starter cultures were inoculated with frozen spore stocks (20 ml soybean meal in 250 ml Erlenmayer flask). The flasks were covered with a milk filter and bioshield. Starter cultures (24 or 48 hours old) were used to inoculate metabolism cultures (also 20 ml in 250 ml Erlenmeyer flask)—with a 10% to 15% crossing volume—and the latter incubated for 24 to 48 hours before addition of steroid substrate for the transformation reaction.

Canrenone was dissolved/suspended in methanol (20 mg/ml), filter sterilized, and added to the cultures to a final concentration of 0.1 mg/ml. All transformation fermentation flasks were shaken at 250 rpm (2" throw) in a controlled temperature room at 26° C. and 60% humidity.

Biotransformations were harvested at 5 and 48 hours, or at 24 hours, after addition of substrate. Harvesting began with the addition of ethyl acetate (23 ml) or methylene chloride to the fermentation flask. The flasks were then shaken for two minutes and the contents of each flask poured into a 50 ml conical tube. To separate the phases, tubes were centrifuged at 4000 rpm for 20 minutes in a room temperature unit. The organic layer from each tube was transferred to a 20 ml borosilicate glass vial and evaporated in a speed vac. Vials were capped and stored at −20° C.

To obtain material for structure determination, biotransformations were scaled up to 500 ml by increasing the number of shake flask fermentations to 25. At the time of harvest (24 or 48 hours after addition of substrate), ethyl acetate was added to each flask individually, and the flasks were capped and put back on the shaker for 20 minutes. The contents of the flasks were then poured into polypropylene bottles and centrifuged to separate the phases, or into a separatory funnel in which phases were allowed to separate by gravity. The organic phase was dried, yielding crude extract of steroids contained in the reaction mixture.

Reaction product was analyzed first by thin layer chromatography on silica gel (250 μm) fluorescence backed plates (254 nm). Ethyl acetate (500 μL was added to each vial containing dried ethyl acetate extract from the reaction mixture. Further analyses were conducted by high performance liquid chromatography and mass spectrometry. TLC plates were developed in a 95:5 v/v chloroform/methanol solvent mixture.

Further analysis was conducted by high performance liquid chromatography and mass spectrometry. A waters HPLC with Millennium software, photodiode array detector and autosampler was used. Reversed phase HPLC used a waters NovaPak C-18 (4 μm particle size) RadialPak 4 mm cartridge. The 25 minute linear solvent gradient began with the column initialized in water:acetonitrile (75:25), and ended at water:acetonitrile (25:75). This was followed by a three minute gradient to 100% acetonitrile and 4 minutes of isocratic wash before column regeneration in initial conditions.

For LC/MS, ammonium acetate was added to both the acetonitrile and water phases at a concentration of 2 nM. Chromatography was not significantly affected. Eluant from the column was split 22:1, with the majority of the material directed to the PDA detector. The remaining 4.5% of the material was directed to the electrospray ionizing chamber of an Sciex API III mass spectrometer. Mass spectrometry was accomplished in positive mode. An analog data line from the PDA detector on the HPLC transferred a single wave length chromatogram to the mass spectrometer for coanalysis of the UV and MS data.

Mass spectrometric fragmentation patterns proved useful in sorting from among the hydroxylated substrates. The two expected hydroxylated canrenones, 11α-hydroxy- and 9α-hydroxy, lost water at different frequencies in a consistent manner which could be used as a diagnostic. Also, the 9α-hydroxycanrenone formed an ammonium adduct more readily than did 11α-hydroxycanrenone. Set forth in Table 35 is a summary of the TLC, HPLC/UV and LC/MS data for canrenone fermentations, showing which of the tested microorganism were effective in the bioconversion of canrenone to 9α-hydroxycanrenone. Of these, the preferred microorganism was *Corynespora cassiicola* ATCC 16718.

TABLE 35

Summary of TLC, HPLC/UV, and LC/MS Data for Canrenone Fermentations

| Culture | Evidence for 9αOH-canrenone | | |
|---|---|---|---|
| | TLC spot at 9αQH-AD | HPLC-peak at 9αOH-canrenone w/UV | MS: 357 (M + H), 339 (−H$_2$O) & 375 (+NH$_4$) |
| *Absidia coerula* ATCC 6647 | n | y | y/n |
| *Absidia glauca* ATCC 22752 | n | | |
| *Actinomucor elegans* ATCC 6476 | tr | y | tr |
| *Aspergillus flavipes* ATCC 1030 | tr | | |
| *Aspergillus fumigatus* ATCC 26934 | tr | y | n |
| *Aspergillus nidulans* ATCC 11267 | tr | y | y |
| *Aspergillus niger* ATCC 16888 | n | y | y |
| *Aspergillus niger* ATCC 26693 | n | y | n |
| *Aspergillus ochraceus* ATCC 18500 | n | y | n |
| *Bacterium cyclo-oxydans* (Searle) ATCC 12673 | n | tr | n |
| *Beauveria bassiana* ATCC 7159 | tr | y | y |
| *Beauveria bassiana* ATCC 13144 | y | y | y |
| *Botryosphaeria obtusa* IMI 038560 | y | tr | tr |
| *Calonectria decora* ATCC 14767 | n | tr | y |
| *Chaetomium cochliodes* ATCC 10195 | tr | tr | y/n |
| *Comomonas testosteroni* (Searle) ATCC 11996 | tr | tr | n |
| *Corynespora cassiicola* ATCC 16718 | y | y | y |
| *Cunninghamella blakesleana* ATCC 8688a | y | y | y |
| *Cunninghamella echinulata* ATCC 3655 | y | y | y |
| *Cunninghamella elegans* ATCC 9245 | y | y | y |
| *Curcularia clavata* ATCC 22921 | n | y | y/n |
| *Curvularia lunata* ATCC 12071 | y | n | n |
| *Cylindrocarpon radicicola* (Searle) ATCC 11011 | tr | n | n |
| *Epicoccum humucola* ATCC 12722 | y | y | y |
| *Epicoccum oryzae* ATCC 12724 | tr | tr | tr |
| *Fusarium oxysporum* ATCC 7601 | tr | | |
| *Fusarium oxysporum* f. sp. cepae ATCC 11171 | n | | |
| *Gibberella fujikuroi* ATCC 14842 | tr | y | y |
| *Gliocladium deliguescens* ATCC 10097 | y | tr | tr |
| *Gongronella butieri* ATCC 22822 | y | y UV? | y |
| *Hypomyces chrysospermus* Tul. IMI 109891 | y | y | y |
| *Lipomyces lipofer* ATCC 10792 | n | | |
| *Melanospora ornata* ATCC 26180 | tr | n | n |
| *Mortierella isabellinay* ATCC 42613 | y | y | n |
| *Mucor grisco-cyanus* ATCC 1207a | n | | |
| *Mucor mucedo* ATCC 4605 | tr | y | y |
| *Mycobacterium fortuitumn* NRRL B8119 | | | |
| *Myrothecium verrucaria* ATCC 9095 | tr | tr | y |
| *Nocardia aurentia* (Searle) ATCC 12674 | n | tr | n |
| *Nocardia cancicruria* ATCC 31548 | y | y | n |
| *Nocardia corallina* ATCC 19070 | n | | |
| *Paecilomyces carneus* ATCC 46579 | n | y | n |
| *Penicillium chrysogenum* ATCC 9480 | n | | |
| *Penicillium patulum* ATCC 24550 | y | y | y/n |
| *Penicillium purpurogenum* ATCC 46581 | tr | y | y |
| *Pithomyces atro-olivaceus* ATCC 6651 | tr | y | tr |
| *Pithomyces cynodontis* ATCC 26150 | n | tr | tr |
| *Phycomyces blakesleeanus* IMI 118496 | y | y | y/n |
| *Pycnosporium sp.* ATCC 12231 | y | y | y/n |
| *Rhizopogon sp.* ATCC 36060 | | | |
| *Rhizopus arrhizus* ATCC 11145 | tr | y | n |
| *Rhizopus stolonifer* ATCC 6227b | n | | |
| *Rhodococcus equi* ATCC 14887 | n | tr | n |
| *Rhodococcus equi* ATCC 21329 | tr | tr | n |
| *Rhodococcus sp.* ATCC 19070 | n | n | n |
| *Rhodococcus rhodochrous* ATCC 19150 | n | tr | n |
| *Saccharopolyspora erythaea* ATCC 11635 | y | y | y |
| *Sepedonium ampullosporum* IMI 203033 | n | n | n |
| *Sepedonium chrysospermum* ATCC 13378 | n | | |
| *Septomyxa affinis* ATCC 6737 | n | y UV? | y/n |
| *Stachylidium bicolor* ATCC 12672 | y | y | y/n |
| *Streptomyces californicus* ATCC 15436 | n | | |
| *Streptomyces cinereocrocatus* ATCC 3443 | n | | |

TABLE 35-continued

Summary of TLC, HPLC/UV, and LC/MS Data for Canrenone Fermentations

| | | Evidence for 9αOH-canrenone | |
|---|---|---|---|
| Culture | TLC spot at 9αQH-AD | HPLC-peak at 9αOH-canrenone w/UV | MS: 357 (M + H), 339 (-H$_2$O) & 375 (+NH$_4$) |
| *Streptomyces coelicolor* ATCC 10147 | n | | |
| *Streptomyces flocculus* ATCC 25453 | | | |
| *Streptomyces fradiae* ATCC 10745 | n | | |
| *Streptomyces griseus* subsp. *griseus* ATCC 13968 | n | | |
| *Streptomyces griseus* ATCC 11984 | n | | |
| *Streptomyces hydrogenans* ATCC 19631 | n | | |
| *Streptomyces hygroscopicus* ATCC 27438 | y | y | y |
| *Streptomyces lavendulae* Panlab 105 | n | | |
| *Streptomyces paucisporogenes* ATCC 25489 | n | | |
| *Streptomyces purpurascens* ATCC 25489 | n | tr | tr |
| *Streptomyces roseochromogenes* ATCC 13400 | | | |
| *Streptomyces spectabilis* ATCC 27465 | n | | |
| *Stysanus microsporus* ATCC 2833 | | | |
| *Syncephalastrum racemosum* ATCC 18192 | n | | |
| *Thamnidium elegans* ATCC 18191 | | | |
| *Thamnostylum piriforme* ATCC 8992 | y | tr | y |
| *Thielavia terricolan* ATCC 13807 | | | n |
| *Trichoderma viride* ATCC 26802 | n | | |
| *Trichothecium roseum* ATCC 12543 | tr | y | y/n |
| *Verticillium theobromae* ATCC 12474 | y | tr | tr |

EXAMPLE 18

Various cultures were tested for effectiveness in the bioconversion of androstendione to 11α-hydroxyandrostendione according to the methods generally described above.

A working cell bank of each of *Aspergillus ochraceus* NRRL 405 (ATCC 18500); *Aspergillus niger* ATCC 11394; *Aspergillus nidulans* ATCC 11267; *Rhizopus oryzae* ATCC 11145; *Rhizopus stolonifer* ATCC 6227b; *Trichothecium roseum* ATCC 12519 and ATCC 8685 was prepared essentially in the manner described in Example 4. Growth medium (50 ml) having the composition set forth in Table 18 was inoculated with a suspension of spores (1 ml) from the working cell bank and placed in an incubator. A seed culture was prepared in the incubator by fermentation at 26° C. for about 20 hours. The incubator was agitated at a rate of 200 rpm.

Aliquots (2 ml) of the seed culture of each microorganism were used to inoculate transformation flasks containing the growth medium (30 ml) of Table 15. Each culture was used for inoculation of two flasks, a total of 16. Androstendione (300 mg) was dissolved in methanol (6 ml) at 36° C., and a 0.5 ml aliquot of this solution was introduced into each of the flasks. Bioconversion was carried out generally under the conditions described in Example 6 for 48 hours. After 48 hours samples of the broth were pooled and extracted with ethyl acetate as in Example 17. The ethyl acetate was concentrated by evaporation, and samples were analyzed by thin layer chromatography to determine whether a product having a chromatographic mobility similar to that of 11α-hydroxy-androstendione standard (Sigma Chemical Co., St. Louis) was present. The results are shown in Table 36. Positive results are indicated as "+".

TABLE 36

Bioconversion of androstendione to 11 alpha-hydroxy-androstendione

| Culture | ATTC# | media | TLC results |
|---|---|---|---|
| *Rhizopus oryzae* | 11145 | CSL | + |
| *Rhizopus stolonifer* | 6227b | CSL | + |
| *Aspergillus nidulans* | 11267 | CSL | + |
| *Aspergillus niger* | 11394 | CSL | + |
| *Aspergillus ochraceus* | NRRL 405 | CSL | + |
| *Aspergillus ochraceus* | 18500 | CSL | + |
| *Trichothecium roseum* | 12519 | CSL | + |
| *Trichothecium roseum* | 8685 | CSL | + |

The data in Table 36 demonstrate that each of listed cultures was capable of producing a compound from androstendione having the same Rf value as that of the 11α-hydroxyandrostendione standard.

*Aspergillus ochraceus* NRRL 405 (ATCC 18500) was retested by the same procedure described above, and the culture products were isolated and purified by normal phase silica gel column chromatography using methanol as the solvent. Fractions were analyzed by thin layer chromatography. TLC plates were Whatman K6F silica gel 60 Å, 10×20 size, 250µ thickness. The solvent mixture was chloroform:methanol, 95:5, v/v. The crystallized product and 11α-hydroxyandrostendione standard were both analyzed by LC-MS and NMR spectroscopy. Both compounds yielded similar profiles and molecular weights.

EXAMPLE 19A

Various microorganisms were tested for effectiveness in the bioconversion of androstendione to 11β-hydroxyandrostendione essentially by the methods described above in Examples 17 and 18.

Cultures of each of *Aspergillus fumigatus* ATCC 26934, *Aspergillus niger* ATCC 16888 and ATCC 26693, *Epicoccum oryzae* ATCC 7156, *Curvularia lunata* ATCC 12017, *Cunninghamella blakesleeana* ATCC 8688a, and *Pithomyces atro-olivaceus* IFO 6651 were grown essentially in the manner described in Example 17. Growth and fermentation media (30 ml) had the composition shown in Table 34.

The 11β-hydroxylation of androstendione by the above-listed microorganisms was analyzed using essentially the same methods of product identification described in Examples 17 and 18. The results are set forth in Table 19A-1.

TABLE 19A-1

11β-Hydroxylation of Androstendione by Various Microorganisms

| Organism | TLC | LC/MS |
|---|---|---|
| Aspergillus fumigatus ATCC 26934 | + | + |
| Aspergillus niger ATCC 16888 and ATCC 26693 | + | + |
| Epicoccum oryzae ATCC 7156 | + | + |
| Curvularia lunata ATCC 12017 | + | + |
| Cunninghamella blakesleeana ATCC 8688a | + | + |
| Pithomyces atro-olivaceus IFO 6651 | + | + |

In Table 19A-1, a "+" indicates a positive result, i.e., an $R_f$ as expected in thin layer chromatography and an approximately correct molecular weight upon LC/MS.

These results demonstrate that the listed micro-organisms are capable of carrying out the 11β-hydroxylation of androstendione.

EXAMPLE 19B

Various microorganisms were tested for effectiveness in the conversion of mexrenone to 11β-hydroxymexrenone. Fermentation media for this example were prepared as described in Table 34.

The fermentation conditions and analytical methods were the same as those in Example 17. TLC plates and the solvent system were as described in Example 18. The rationale for chromatographic analysis is as follows: 11α-hydroxymexrenone and 11α-hydroxycanrenone have the same chromatographic mobility. 11α-hydroxycanrenone and 9α-hydroxycanrenone exhibit the same mobility pattern as 11α-hydroxyandrostendione and 11β-hydroxyandrostendione. Therefore, 11β-hydroxymexrenone should have the same mobility as 9α-hydroxycanrenone. Therefore, compounds extracted from the growth media were run against 9α-hydroxycanrenone as a standard. The results are shown in Table 36.

TABLE 37

Summary of TLC Data for 11β-hydroxymexrenone Formation from Mexrenone

| Microorganism | Medium[1] | Spot Character[2] |
|---|---|---|
| Absidia coerula ATCC 6647 | M, S | strong |
| Aspergillus niger ATCC 16888 | S, P | faint (S) ? (P) |
| Beauveria bassiana ATCC 7159 | P | strong |
| Beauveria bassiana ATCC 13144 | S, P | ?, ? |
| Botryosphaeria obtusa IMI 038560 | | faint |
| Cunninghamella blakesleeana ATCC 8688a | S, P | strong |
| echinulata ATCC 3655 | S, P | strong |
| elegans ATCC 9245 | S, P | strong |
| Curvularia lunata ATCC 12017 | S | strong |

TABLE 37-continued

Summary of TLC Data for 11β-hydroxymexrenone Formation from Mexrenone

| Microorganism | Medium[1] | Spot Character[2] |
|---|---|---|
| Gongronella butleri ATCC 22822 | S, P | strong |
| Penicillium patulum ATCC 24550 | S, P | strong |
| Penicillium purpurogenum ATCC 46581 | S, P | strong |
| Pithomyces atro-olivaceus IFO 6651 | S, P | faint |
| Rhodococcus equi ATCC 14887 | M | faint |
| Saccharopolyspora erythaea ATCC 11635 | M, SF | faint |
| Streptomyces hygroscopicus ATCC 27438 | M, SF | strong |
| Streptomyces purpurascens ATCC 25489 | M, SF | faint |
| Thamnidium elegans ATCC 18191 | S, P | faint |
| Thamnostylum piriforme ATCC 8992 | S, P | faint |
| Trichothecium roseum ATCC 12543 | P, S | faint (P) ? (S) |

[1]M = Mueller-Hinton
P = PYG (peptone/yeast extract/glucose)
S = soybean meal
SF = soybean meal plus formate
[2]? = questionable difference from no substrate control These data suggest that the majority of the organisms listed in this table produce a product similar or identical to 11β-hydroxymexrenone from mexrenone.

EXAMPLE 19C

Various microorganisms were tested for effectiveness in the conversion of mexrenone to 11α-hydroxymexrenone, $\Delta^{1,2}$-mexrenone, 6β-hydroxymexrenone, 12β-hydroxymexrenone, and 9α-hydroxymexrenone. Mexrenone can be prepared in the manner set forth in Weier, U.S. Pat. No. 3,787,396 and R. M. Weier et al., J.Med.Chem., Vol. 18, pp. 817–821 (1975), which are incorporated herein by reference. Fermentation media were prepared as described in Example 17, except that mexrenone was included. The fermentation conditions were essentially the same as those in Example 17; analytical methods were also the same as those in Examples 17 and 18. TLC plates and the solvent system were as described in Examples 17 and 18.

The microorganisms tested and results obtained therewith are shown in Table 19C-1.

TABLE 19C-1

Production of 11α-hydroxymexrenone from Mexrenone by Various Microorganisms

| Organism | TLC | HPLC | m/z |
|---|---|---|---|
| 457:399 | | | |
| Beauveria bassiana ATCC 7159 | + | + | 5:1 |
| Beauveria bassiana ATCC 13144 | + | + | 10:1 |
| Mortierella isabella ATCC 42613 | + | + | 1:1 |

TABLE 19C-1-continued

Production of 11α-hydroxymexrenone from Mexrenone by Various Microorganisms

| Organism | TLC | HPLC | m/z |
|---|---|---|---|
| Cunninghamella blakesleeana ATCC 8688a | + | + | 1:1 |
| Cunninghamella echinulata ATCC 3655 | + | + | 1:2 |
| Cunninghamella elegans ATCC 9245 | + | + | 1:1 |
| Absidia coerula ATCC 6647 | + | + | 1:1 |
| Aspergillus niger ATCC 16888 | + | + | 4:1 |
| Gongronella butieri ATCC 22822 | + | + | 3:1 |
| Pithomyces atro-olivaceus ATCC 6651 | + | + | 3:1 |
| Streptomyces hygroscopicus ATCC 27438 | + | + | 3:1 |

In Table 19C-1, a "+" indicates a positive result, i.e., an $R_f$ as expected in thin layer chromatography and a retention time as expected in HPLC. m/z 417:399 indicates the peak height ratio of the 417 molecule (hydroxymexrenone) and the 399 molecule (mexrenone). The standard has a 10:1 ratio of peak height for m/z 417 to m/z 399.

The product obtained from *Beauveria bassiana* ATCC 13144 was isolated from the incubation mixture and analyzed by NMR, and the structural profile thereby confirmed to be 11α-hydroxymexrenone. By analogy, the products obtained from the other microorganisms listed in Table 19C-1 were also presumed to be 11α-hydroxymexrenone.

TABLE 19C-2

Production of $\Delta^{1,2}$-Mexrenone from Mexrenone by Various Microorganims

| Organism | m/z 399 | HPLC | TLC |
|---|---|---|---|
| Rhodococcus equi ATCC 148875 | + | + | + |
| Bacterium cyclo-oxydans ATCC 12673 | + | + | + |
| Comomonas testosteroni ATCC 11996 | + | + | + |
| Nocardia aurentia ATCC 12674 | + | + | + |
| Rhodococcus equi ATCC 21329 | + | + | + |

In Table 19C-2, a "+" indicates a positive result, e.g., an $R_f$ as expected in thin layer chromatography, a retention time as expected in HPLC, etc.

The product obtained from *Bacterium cyclo-oxydans* ATCC 12673 was isolated from the incubation mixture and analyzed by NMR, and the structural profile thereby confirmed to be $\Delta^{1,2}$-mexrenone. By analogy, the products obtained from the other microorganisms listed in Table 19C-2 were also presumed to be $\Delta^{1,2}$-mexrenone.

Production of 6β- and 12β-hydroxymexrenone

*Mortierella isabella* ATCC 42613 was grown as in Example 17 in the presence of mexrenone. The fermentation products were isolated and purified by flash chromatography. The purified products were analyzed by LC/MS as in Examples 17 and 18, and proton NMR and carbon-13 NMR. The data indicated that the products included 6β- and 12β-hydroxymexrenone.

TABLE 19C-3

Production of 9α-Hydroxymexrenone from Mexrenone by Various Microorganisms

| Organism | m/z 417 | HPLC | TLC |
|---|---|---|---|
| Streptomyces hygroscopicus ATCC 27438 | + | + | + |
| Gongronella butleri ATCC 22822 | + | + | + |
| Cunninghamella blakesleeana ATCC 8688a | + | + | + |
| Cunninghamella echinulata ATCC 3655 | + | + | + |
| Cunninghamella elegans ATCC 9245 | + | + | + |
| Mortierella isabellina ATCC 42613 | + | + | + |
| Absidia coerula ATCC 6647 | + | + | + |
| Beauveria bassiana ATCC 7159 | + | + | + |
| Beauveria bassiana ATCC 13144 | + | + | + |
| Aspergillus niger ATCC 16888 | + | + | + |

The microorganisms listed in Table 19C-3 were grown under the same conditions as in Example 17, in the presence of mexrenone. The fermentation products were analyzed by TLC and LC/MS as in Examples 17 and 18. A "+" indicates a positive result, e.g., an $R_f$ as expected in thin layer chromatography, a retention time as expected in HPLC, etc. The data suggest that the products include 9α-hydroxymexrenone.

EXAMPLE 19D

Various microorganisms were tested for effectiveness in the conversion of canrenone to $\Delta^{9,11}$-canrenone. The fermentation media and growth conditions were essentially the same as in Example 17, except that canrenone was included in the medium. The analytical methods were as described in Examples 17 and 18. The microorganisms and results are shown in Table 19D-1, below.

TABLE 19D-1

Production of $\Delta^{9,11}$-Canrenone from Canrenone by Various Microorganisms

| Organism | m/z 339 | HPLC | TLC |
|---|---|---|---|
| Bacterium cyclo-oxydans ATCC 12673 | + | + | + |
| Comomonas testosteroni ATCC 11996 | + | + | + |
| Cylindrocarpon radicicola ATCC 11011 | + | + | + |
| Paecilomyces carneus ATCC 46579 | + | + | + |
| Septomyxa affinis ATCC 6737 | + | + | + |
| Rhodococcus spp. ATCC 19070 | + | + | + |

The fermentation products were analyzed by TLC and LC/MS as in Examples 17 and 18. A "+" indicates a positive result, e.g., an $R_f$ as expected in thin layer chromatography, a retention time as expected in HPLC, etc.

The product obtained from *Comomonas testosteroni* ATCC 11996 was isolated from the growth medium and analyzed by UV spectroscopy. The spectroscopic profile confirmed the presence of $\Delta^{9,11}$-canrenone. By analogy, the products obtained from the other microorganisms listed in Table 19D-1 were also presumed to be $\Delta^{9,11}$-canrenone.

EXAMPLE 20A

Scheme 1: Step 1: Method A: Preparation of 5'R (5'α),7'β-20'-Aminohexadecahydro-11'β-hydroxy-10'a,13'α-dimethyl-3',5-dioxospirofuran-2(3H),17'α (5'H)-[7,4]metheno[4H[cyclopenta[a]phenanthrene]-5'-carbonitrile Into a 50 gallon glass-line reactor was charged 61.2 L (57.8 kg) of DMF followed by 23.5 Kg of 11-hydroxycanrenone 1 with stirring. To the mixture was added 7.1 kg of lithium chloride. The mixture was stirred for 20 minutes and 16.9 kg of acetone cyanohydrin was charged followed by 5.1 kg of triethylamine. The mixture was heated to 85° C. and maintained at this temperature for 13–18 hours. After the reaction 353 L of water was added followed by 5.6 kg of sodium bicarbonate. The mixture was cooled to 0° C., transferred to a 200 gallon glass-lined reactor and quenched with 130 kg of 6.7% sodium hypochlorite solution slowly. The product was filtered and washed with 3×40 L portions of water to give 21.4 kg of the product enamine.

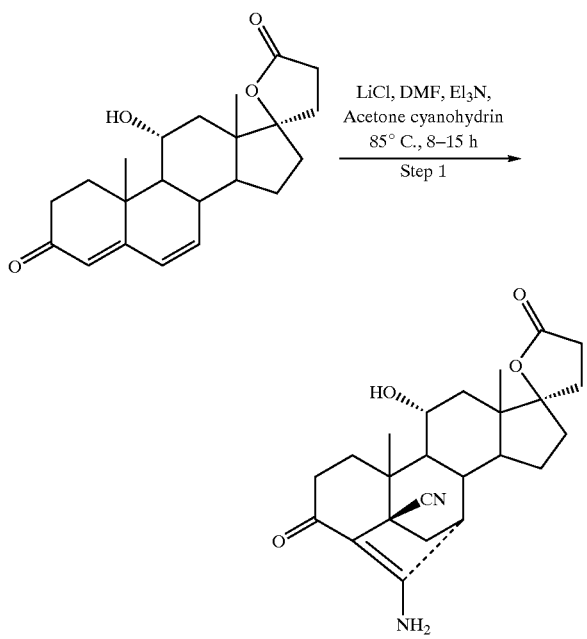

$H^1$ NMR (DMSO-$d_6$): 7.6 (2H, bd), 4.53 (1H, d, J=5.9), 3.71 (1H, m), 3.0–1.3 (17H, m), 1.20 (5H, m), 0.86 (3H,s), 0.51 (1H,t, J=10).

EXAMPLE 20B

Preparation of 7α-cyano-11α,17-dihydroxy-3-oxo-17α-pregn-4-ene-21-carboxylic acid, γ-lactone

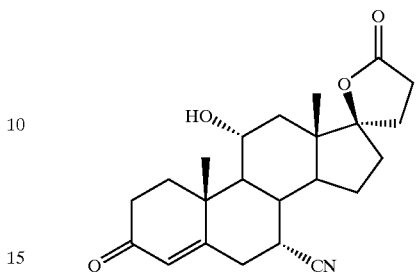

50.0 g of 11-hydroxycanrenone and 150.0 mL of dimethylacetamide were added to a clean, dry three-necked flask equipped with a mechanical stirrer, condenser, thermocouple and heating mantle. 16.0 mL of a sulfuric acid solution (prepared by mixing 50.0 mL of sulfuric acid (98.7% Baker grade) with 50.0 mL of water) was added to this mixture. A sodium cyanide solution comprising 15.6 g of sodium cyanide and 27.0 mL of water was then added.

The resulting mixture was heated at 80° C. for 7 hours, the degree of conversion being periodically checked by TLC or HPLC. After approximately 7 hours, HPLC of the mixture indicated the presence of the 7-cyano compound. The mixture was then stirred overnight and allowed to cool to room temperature (about 22° C.). 200 mL of water was added to the mixture followed by 200 mL of methylene chloride and the resulting two phase mixture stirred and the phases were then allowed to separate. The aqueous layer was a gel. 100 mL of sodium bicarbonate solution was added to the aqueous layer in an unsuccessful attempt to break up the gel. The aqueous layer was then discarded.

The separated methylene chloride layer was washed with 100 mL of water and the resulting two phase mixture stirred. The phases were then allowed to separate and the separated methylene chloride layer was filtered through 200 g of silica gel (Aldrich 200–400 mesh, 60 Å). The filtrate was concentrated to dryness under reduced pressure at 45° C. using a water aspirator to provide about 53.9 g of a crude solid product. The crude solid product then was dissolved in 50 mL of methylene chloride and treated with 40 mL of 4N hydrochloric acid in a separatory funnel and the two phase mixture allowed to separate. The methylene chloride layer was washed with 50 mL of water. The combined aqueous layers were extracted with 50 mL of methylene chloride. The combined methylene chloride layers were then dried over sodium sulfate to provide 45 g of a solid which was a mixture of 11α-hydroxycanrenone and the product, 7α-cyano-11α,17-dihydroxy-3-oxo-17α-pregn-4-ene-21-carboxylic acid, γ-lactone.

A sample of the product was analyzed by HPLC (column: 25 cm×4.6 mm, 5μ Altima $C_{18}$LL); solvent gradient: solvent A=water/trifluoroacetic acid=99.9/0.1, solvent B=acetonitrile/trifluoroacetic acid=99.9/0.1, flow rate=1.00 mL/minute, gradient=65:30 (v/v) (A:B—initial), 35:65 (v/v) (A:B—after 20 minutes), 10:90 (v/v) (A:B—after 25 minutes); diode array detector) which revealed a $\lambda_{max}$ of 238 nm.

The reaction mixture was analyzed by HPLC-NMR using the following conditions: HPLC—column: Zorbax RX-C8 (25 cm×4.6 mm, 5μ) using a solvent gradient from 75%

D₂O, 25% acetonitrile to 25% D2O, 75% acetonitrile over 25 minutes with a flow of 1 mL/minute; ¹H NMR (obtained using WET solvent suppression): 5.84 (s,1H), 4.01 (m,1H), 3.2 (m,1H), 2.9–1.4 (m, integral not meaningful due to solvent suppression of acetonitrile), 0.93–0.86 (s, overlapping 3H, and t,2H).

EXAMPLE 20C

Preparation of 5β,7α-dicyano-17-hydroxy-3-oxo-17α-pregnane-21-carboxylic acid, γ-lactone

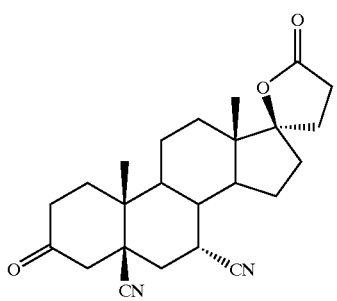

102 g (0.3 mol) of 17-hydroxy-3-oxo-17α-pregna-4,6-diene-21-carboxylic acid, γ-lactone (canrenone) was slurried with 46.8 g (0.72 mol) of potassium cyanide, 78.6 mL (1.356 mols) of acetic acid, and 600 mL of methanol in a three liter, three neck, round bottom flask. 64.8 mL (0.78 mol) of pyrrolidine was added to the mixture and the combined slurry heated to reflux (64° C.) and maintained for about 1.5 hours. The temperature of the slurry was then lowered to 25° C. to 30° C. over a ten minute period with a cooling bath. 120 mL of a concentrated hydrochloric acid was slowly added during the cooldown as a tan colored solid precipitated.

The mixture was stirred at 25° C. to 30° C. for 1.5 hours, then an additional 500 mL of water added in 30 minutes. The mixture was cooled to 5° C. with an ice bath and the pH adjusted from 3 to 5.5 (monitored using pH strips) with the addition of 100 mL of aqueous 9.5M sodium hydroxide (0.95 mol). Excess cyanide was destroyed with the addition of household bleach. 25 mL (0.020 mol) was added to achieve a negative starch iodide test. The cold mixture (10° C.) was filtered and the solid washed with water until the rinse exhibited a neutral pH (pH strips). The solid was dried at 60° C. to a constant weight of 111.4 g.

The isolated solid melted at 244° C. to 246° C. on a Fisher Johns block. A methanol solution containing the solid exhibited no absorption throughout the UV region of 210 to 240 nm. IR (CHCl₃)cm⁻¹2222 (cyanide), 1775 (lactone), 1732 (3-keto). ¹H NMR (pyridine d₅) ppm 0.94 (s,3H), 1.23 (s,3H).

EXAMPLE 21A

Scheme 1: Step 2: Preparation of 4'S(4'α),7'α-Hexadecahydro-11'α-hydroxy-10'β,13'β-dimethyl-3',5,20'-trioxospiro[furan-2(3H),17'β-[4,7]methano[17H]cyclopenta[a]phenanthrene]-5'β(2'H)-carbonitrile Into a 200 gallon glass-lined reactor was charged 50 kg of enamine 2, approximately 445 L of 0.8 N dilute hydrochloric acid and 75 L of methanol. The mixture was heated to 80° C. for 5 hours, cooled to 0° C. for 2 hours. The solid product was filtered to give 36.5 kg of dry product diketone.

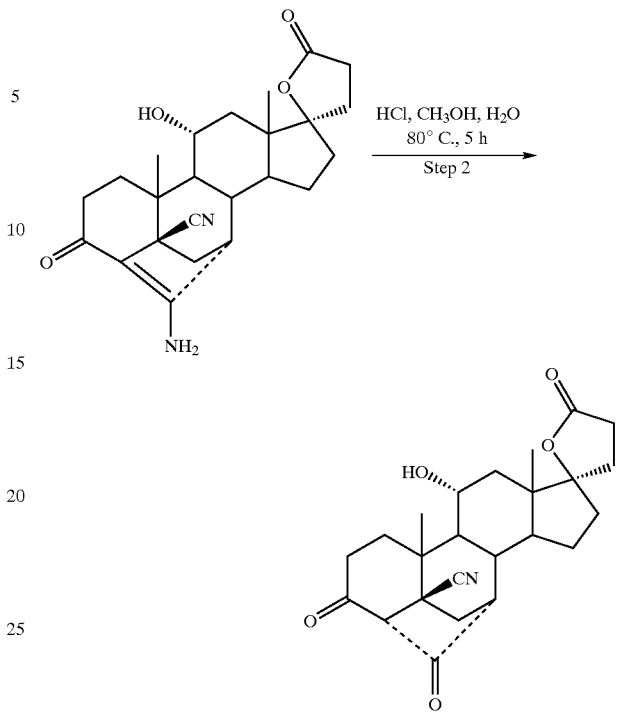

H¹ NMR (DMSO-d₆) 4.53(1H, d, J=6) 3.74 (2H, m), 2.73 (1H,dd, J=14,7) 2.65–2.14 (8H, m), 2.05 (1H, t, J=11), 1.98–1.71 (4H,m), 1.64 (1H, m), 1.55 (1H, dd, J=13, 5), 1.45–1.20 (7H, m), 0.86 (3H,s).

EXAMPLE 21B

Scheme 1: Steps 1 and 2: In Situ Preparation of 4'S (4'α),7'α-Hexadecahydro-11'α-hydroxy-10'β,13'β-dimethyl-3',5,20'-trioxospiro[furan-2(3H),17'β-[4,7]methano-[17H]cyclopenta[a]phenanthrene]-5'β(2'H)-carbonitrile from 11α-hydroxycanrenone Into a reactor fitted with a cooling condenser, mechanical stirrer, heating mantle and controller, and funnel was charged 100 g (280.54 mmol) of 11-hydroxycanrenone prepared prepared as in the manner of Example 1 followed by 300 mL of dimethylacetamide (Aldrich). The mixture was stirred until the 11-hydroxycanrenone dissolved. To this mixture was added 31.5 mL of 50% sulfuric acid (Fisher) which caused the temperature of the resulting mixture to rise about 10° C. to 15° C. A sodium cyanide solution prepared by dissolving 31.18 g (617.20 mmol) (Aldrich) of sodium cyanide in 54 mL of deionized water was then added to the 11α-hydroxycanrenone mixture over a 2 to 3 minute period. The temperature of the resulting mixture rose about 20° C. to 25° C. after addition of the sodium cyanide solution.

The mixture was heated to 80° C. and maintained at this temperature for 2–3 hours. Once HPLC analysis indicated the reaction for the conversion of the 11α-hydroxycanrenone to the enamine was substantially complete (greater than 98% conversion), the heat source was removed. Without isolation of the enamine contained in the mixture, an additional 148 mL of 50% sulfuric acid was added to the mixture over a 3–5 minute period. Over a 10 minute period 497 mL of deionized water was then added to the mixture.

The mixture was heated to 102° C. and maintained at that temperature until approximately 500 g of distillate had been removed from the mixture. During the reaction/distillation, 500 mL of deionized water was added to the mixture in four separate 125 mL portions. Each portion was added to the mixture after an equivalent amount of distillate (approximately 125 mL) had been removed. The reaction continued for over 2 hours. When HPLC analysis indicated that the reaction hydrolyzing the enamine to the diketone was substantially completed (greater than 98% conversion), the mixture was cooled to about 80° C. over a 20 minute period.

The mixture was filtered through a glass funnel. The reactor was rinsed with 1.2 L of deionized water to remove residual product. The solid on the filter was washed three times using approximately equal portions (about 0.4 L) of the rinse water. A 1 L solution of methanol and deionized water (1:1 v/v) was prepared in the reactor and the filtrate was washed with 500 mL of this solution. The filtrate was then washed a second time with the remaining 500 mL of the methanol/water solution. Vacuum was applied to the funnel to dry the filtrate sufficiently for transfer. The filtrate was transferred to a drying oven where it was dried under vacuum for 16 hours to yield 84 g of dry product diketone, 4'S(4'α),7'α-Hexadecahydro-11'α-hydroxy-10'β,13'β-dimethyl-3',5,20'-trioxospiro[furan-2(3H),17'β-[4,7]methano-[17H]cyclopenta[a]phenanthrene]-5'β(2'H)-carbonitrile. HPLC assay indicated 94% of the desired diketone.

EXAMPLE 22

Scheme 1: Step 3A: Method A: Preparation of Methyl Hydrogen 11α,17α-Dihydroxy-3-oxopregn-4-ene-7α,21-dicarboxylate, γ-Lactone A 4-neck 5-L bottom flask was equipped with mechanical stirrer, pressure equalizing addition funnel with nitrogen inlet tube, thermometer and condenser with bubbler. The bubbler was connected via tygon tubing to two 2-L traps, the first of which was empty and placed to prevent back-suction of the material in the second trap (1 L of concentrated sodium hypochlorite solution) into the reaction vessel. The diketone 3 (79.50 g; [weight not corrected for purity, which was 85%]) was added to the flask in 3 L methanol. A 25% methanolic sodium methoxide solution (64.83 g) was placed in the funnel and added dropwise, with stirring under nitrogen, over a 10 minute period. After the addition was complete, the orangish yellow reaction mixture was heated to reflux for 20 hours. After this period, 167 mL of 4 N HCl was added (Caution: HCN evolution at this point!) dropwise through the addition funnel to the still refluxing reaction mixture. The reaction mixture lightened in color to a pale golden orange. The condenser was then replaced with a take-off head and 1.5 L of methanol was removed by distillation while 1.5 L of water was simultaneously added to the flask through the funnel, in concert with the distillation rate. The reaction mixture was cooled to ambient temperature and extracted twice with 2.25 L aliquots of methylene chloride. The combined extracts were washed successively with 750 mL aliquots of cold saturated NaCl solution, 1N NaOH and again with saturated NaCl. The organic layer was dried over sodium sulfate overnight, filtered and reduced in volume to ~250 mL in vacuo. Toluene (300 mL) was added and the remaining methylene chloride was stripped under reduced pressure, during which time the product began to form on the walls of the flask as a white solid. The contents of the flask were cooled overnight and the solid was removed by filtration. It was washed with 250 mL toluene and twice with 250 mL aliquots of ether and dried on a vacuum funnel to give 58.49 g of white solid was 97.3% pure by HPLC. On concentrating the mother liquor, an additional 6.76 g of 77.1% pure product was obtained. The total yield, adjusted for purity, was 78%.

H$^1$ NMR (CDCl$_3$): 5.70 (1H,s), 4.08 (1H,s), 3.67 (3H,s), 2.9–1.6 (19H, m), 1.5–1.2 (5H, m), 1.03 (3H.s).

EXAMPLE 23

Scheme 1: Step 3B: Conversion of Methyl Hydrogen 11α,17α-Dihydroxy-3-oxopregn-4-ene-7α,21-dicarboxylate, γ-Lactone to Methyl Hydrogen 17α-Hydroxy-11α-(methylsulfonyl)oxy-3-oxopregn-4-ene-7α,21-dicarboxylate, γ-Lactone A 5-L four neck flask was equipped as in the above example, except that no trapping system was installed beyond the bubbler. A quantity of 138.70 g of the hydroxyester was added to the flask, followed by 1425 mL methylene chloride, with stirring under nitrogen. The reaction mixture was cooled to –5° C. using a salt/ice bath. Methanesulfonyl chloride (51.15 g, 0.447 mole) was added rapidly, followed by the slow dropwise addition of triethylamine (54.37 g) in 225 mL methylene chloride. Addition, which required ~30 minutes, was adjusted so that the temperature of the reaction never rose about 5° C. Stirring was continued for 1 hour post-addition, and the reaction contents were transferred to a 12-L separatory funnel, to which was added 2100 mL methylene chloride. The solution was washed successively with 700 mL aliquots each of cold 1N HCl, 1N NaOH, and saturated aqueous NaCl solution. The aqueous washes were combined and back-extracted with 3500 mL methylene chloride. All of the organic washes were combined in a 9-L jug, to which was added 500 g neutral alumina, activity grade II, and 500 g anhydrous sodium sulfate. The contents of the jug were mixed well for 30 minutes and filtered. The filtrate was taken to dryness in vacuo to give a gummy yellow foam. This was dissolved in 350 mL methylene chloride and 1800 mL ether was added dropwise with stirring. The rate of addition was adjusted so that about one-half of the ether was added over 30 minutes. After about 750 mL had been added, the product began to separate as a crystalline solid. The remaining ether was added in 10 minutes. The solid was removed by filtration, and the filter cake was washed with 2 L of ether and dried in a vacuum oven at 50° C. overnight, to give 144.61 g (88%) nearly white solid, m.p. 149°–150° C. Material prepared in this fashion is typically 98–99% pure by HPLC (area %). In one run, material having a melting point of 153°–153.5° C. was obtained, with a purity, as determined by HPLC area, of 99.5%.

H$^1$ NMR (CDCl$_3$): 5.76 (1H,s), 5.18 (1H,dt), 3.68(3H,s), 3.06 (3H,s), 2.85 (1H,m), 2.75–1.6 (19H, m), 1.43 (3H,s), 1.07 (3H,s).

EXAMPLE 24

Scheme 1: Step 3C: Method A: Preparation of 7-Methyl Hydrogen 17α-Hydroxy-3-oxopregna-4,9 (11)-diene-7α,21-dicarboxylate, γ-Lactone A 1-L four neck flask was equipped as in the second example. Formic acid (250 mL) and acetic anhydride (62 mL) were added to the flask with stirring under nitrogen. Potassium formate (6.17 g) was added and the reaction mixture was heated with an oil bath to an internal temperature of 40° C. (this was later repeated at 70° C. with better results) for 16 hours. After 16 hours, the mesylate was added and the internal temperature was increased to 100° C. Heating and stirring were continued for 2 hours, after which the solvent was removed in vacuo on a rotavap. The residue was stirred with 500 mL ice water for fifteen minutes, then extracted twice with 500 mL aliquots of ethyl acetate. The organic phases were combined and washed successively with cold 250 mL aliquots of saturated sodium chloride solution (two times), 1 N sodium hydroxide solution, and again with saturated sodium chloride. The organic phase was then dried over sodium sulfate, filtered and taken to dryness in vacuo to give a yellowish white foam, which pulverized to a glass when touched with a spatula. The powder that formed, 14.65 g analyzed (by HPLC area %) as a mixture of 82.1% 7-Methyl Hydrogen 17α-Hydroxy-3-oxopregna-4,9 (11)-diene-7α,21-dicarboxylate, γ-Lactone; 7.4% 7-Methyl Hydrogen 17α-Hydroxy-3-oxopregna-4,11-diene-7α,21-dicarboxylate, γ-Lactone; and 5.7% 9α,17-dihydroxy-3-oxo-17α-pregn-4-ene-7α,21-dicarboxylic acid, bis(γ-lactone).

$H^1$ NMR (CDCl$_3$): 5.74 (1H, s), 5.67 (1H,m), 3.61 (3H,s), 3.00 (1H,m), 2.84 (1H, ddd, J=2,6,15), 2.65–2.42 (6H,m), 2.3–2.12 (5H,m), 2.05–1.72 (4H,m), 1.55–1.45 (2H,m), 1.42 (3H,s), 0.97 (3H,s).

EXAMPLE 25

Scheme 1: Step 3C: Method B: Preparation of Methyl Hydrogen 17α-Hydroxy-3-oxopregna-4,9 (11)-diene-7α,21-dicarboxylate, γ-Lactone A 5-L four neck flask was equipped as in the above example and 228.26 g acetic acid and 41.37 g sodium acetate were added with stirring under nitrogen. Using an oil bath, the mixture was heated to an internal temperature of 100° C. The mesylate (123.65 g) was added, and heating was continued for thirty minutes. At the end of this period, heating was stopped and 200 mL of ice water was added. The temperature dropped to 40° C. and stirring was continued for 1 hour, after which the reaction mixture was poured slowly into 1.5 L of cold water in a 5-L stirred flask. The product separated as a gummy oil. The oil was dissolved in 1 L ethyl acetate and washed with 1 L each cold saturated sodium chloride solution, 1 N sodium hydroxide, and finally saturated sodium chloride again. The organic phase was dried over sodium sulfate and filtered. The filtrate was taken to dryness in vacuo to give a foam which collapsed to a gummy oil. This was triturated with ether for some time and eventually solidified. The solid was filtered and washed with more ether to afford 79.59 g of a yellow white solid. This consisted of 70.4% of the desired $\Delta^{9,11}$ enester 6, 12.3% of the $\Delta^{11,12}$ enester 8, 10.8% of the 7-α,9-α-lactone 9 and 5.7% unreacted 5.

EXAMPLE 26

Scheme 1: Step 3D: Method A: Synthesis of Methyl Hydrogen 9,11α-Epoxy-17α-hydroxy-3-oxopregn-4-ene-7α,21-dicarboxylate, γ-Lactone A 4-neck jacketed 500 mL reactor was equipped with mechanical stirrer, condenser/bubbler, thermometer and addition funnel with nitrogen inlet tube. The reactor was charged with 8.32 g of the crude enester in 83 mL methylene chloride, with stirring under nitrogen. To this was added 4.02 g dibasic potassium phosphate, followed by 12 mL of trichloroacetonitrile. External cooling water was run through the reactor jacket and the reaction mixture was cooled to 8° C. To the addition funnel 36 mL of 30% hydrogen peroxide was added over a 10 minute period. The initially pale yellow colored reaction mixture turned almost colorless after the addition was complete. The reaction mixture remained at 9±1° C. throughout the addition and on continued stirring overnight (23 hours total) Methylene chloride (150 mL) was added to the reaction mixture and the entire contents were added to ~250 mL ice water. This was extracted three times with 150 mL aliquots of methylene chloride. The combined methylene chloride extracts were washed with 400 mL cold 3% sodium sulfite solution to decompose any residual peroxide. This was followed by a 330 mL cold 1 N sodium hydroxide wash, a 400 mL cold 1 N hydrochloric acid wash, and finally a wash with 400 mL brine. The organic phase was dried over magnesium sulfate, filtered, and the filter cake was washed with 80 mL methylene chloride. Solvent was removed in vacuo to give 9.10 g crude product as a pale yellow solid. This was recrystallized from ~25 mL 2-butanone to give 5.52 g nearly white crystals. A final recrystallization from acetone (~50 mL gave 3.16 g long, acicular crystals, mp 241–243° C.

$H^1$ NMR (CDCl$_3$): 5.92 (1H,s), 3.67(3H,s), 3.13 (1H,d, J=5), 2.89 (1H, m), 2.81–2.69 (15H,m), 1.72 (1H, dd, J=5,15), 1.52–1.22 (5H,m), 1.04 (3H,s).

EXAMPLE 27

Scheme 1: Step 3: Option 1: From 4'S(4'α),7'α-Hexadecahydro-11'α-hydroxy-10'β,13'β-dimethyl-3', 5,20'-trioxospiro[furan-2(3H),17'β-[4,7]methano [17H]cyclopenta[a]phenanthrene]-5'β(2'H)-carbonitrile to Methyl Hydrogen 9,11α-Epoxy-17α-hydroxy-3-oxopregn-4-ene-7α,21-dicarboxylate, γ-Lactone Diketone (20 g) was charged into a clean and dried reactor followed by the addition of 820 ml of MeOH and 17.6 ml of 25% NaOMe/MeOH solution. The reaction mixture was heated to reflux condition (~67° C.) for 16–20 hours. The product was quenched with 40 mL of 4N HCl. The solvent was removed at atmospheric pressure by distillation. 100 mL of toluene was added and the residual methanol was removed by azeotrope distillation with toluene. After concentration, the crude hydroxyester 4 was dissolved in 206 mL of methylene chloride and cooled to 0° C. Methanesulfonyl chloride (5 mL) was added followed by a slow addition of 10.8 ml of triethylamine. The product was stirred for 45 minutes. The solvent was removed by vacuum distillation to give the crude mesylate 5.

In a separate dried reactor was added 5.93 g of potassium formate, 240 mL of formic acid and followed by 118 mL of acetic anhydride. The mixture was heated to 70° C. for 4 hours.

The formic acid mixture was added to the concentrated mesylate solution 5 prepared above. The mixture was heated to 95–105° C. for 2 hours. The product mixture was cooled to 50° C. and the volatile components were removed by vacuum distillations at 50° C. The product was partitioned between 275 ml of ethyl acetate and 275 ml of water. The aqueous layer was back extracted with 137 ml of ethyl acetate, washed with 240 ml of cold 1N sodium hydroxide solution and then 120 ml of saturated NaCl. After phase separation, the organic layer was concentrated to under vacuum distillation to give crude enester.

The product was dissolved in 180 mL of methylene chloride and cooled to 0 to 15° C. 8.68 g of dipotassium hydrogen phosphate was added followed by 2.9 mL of trichloroacetonitrile. A 78 mL solution of 30% hydrogen peroxide was added to the mixture over a 3 minute period. The reaction mixture was stirred at 0–15° C. for 6–24 hours. After the reaction, the two phase mixture was separated. The organic layer was washed with 126 mL of 3% sodium sulfite solution, 126 mL of 0.5 N sodium hydroxide solution, 126 mL of 1 N hydrochloric acid and 126 mL of 10% brine. The product was dried over anhydrous magnesium sulfate or filtered over Celite and the solvent methylene chloride was removed by distillation at atmospheric pressure. The product was crystallized from methylethyl ketone twice to give 7.2 g of epoxymexrenone.

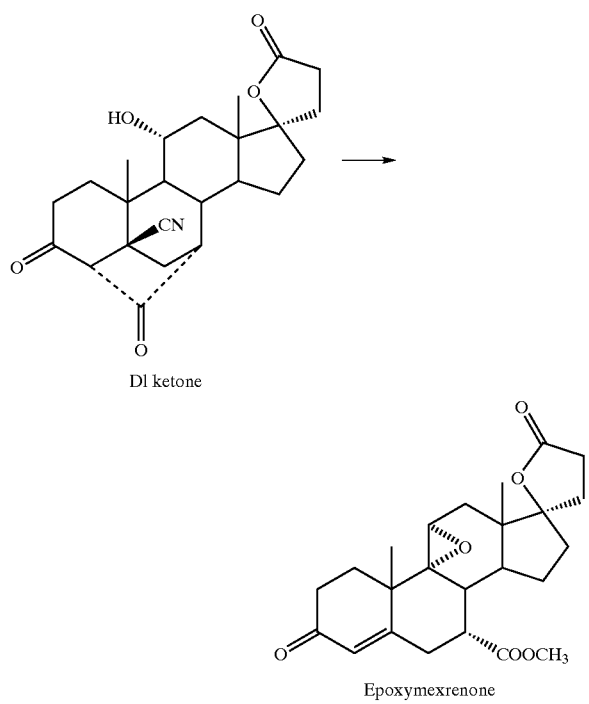

D1 ketone

Epoxymexrenone

EXAMPLE 28

Scheme 1: Step 3: Option 2: Conversion of 1'S (4'α),7'α-Hexadecahydro-11'α-hydroxy-10'β,13'β-dimethyl-3',5,20'-trioxospiro[furan-2(3H),17'β-[4,7]methano[17H]cyclopenta[a]phenanthrene]-5'β(2'H)-carbonitrile to Methyl Hydrogen 9,11α-Epoxy-17α-hydroxy-3-oxopregn-4-ene-7α,21-dicarboxylate, γ-Lactone without intermediate isolation A 4-neck 5-L round bottom flask was equipped with mechanical stirrer, addition funnel with nitrogen inlet tube, thermometer and condenser with bubbler attached to a sodium hypochlorite scrubber. The diketone (83.20 g) was added to the flask in 3.05 L methanol. The addition funnel was charged with 67.85 g of a 25% (w:w) solution of sodium methoxide in methanol. With stirring under nitrogen, the methoxide was added dropwise to the flask over a 15 minute period. A dark orange/yellow slurry developed. The reaction mixture was heated to reflux for 20 hours and 175 mL 4 N hydrochloric acid was added dropwise while refluxing continued. (Caution, HCN evolution during this operation!) The reflux condenser was replaced with a takeoff head and 1.6 L of methanol was removed by distillation while 1.6 L of aqueous 10% sodium chloride solution was added dropwise through the funnel, at a rate to match the distillation rate. The reaction mixture was cooled to ambient temperature and extracted twice with 2.25 L of aliquots of methylene chloride. The combined extracts were washed with cold 750 mL aliquots of 1 N sodium hydroxide and saturated sodium chloride solution. The organic layer was dried by azeotropic distillation of the methanol at one atmosphere, to a final volume of 1 L (0.5% of the total was removed for analysis).

The concentrated organic solution (hydroxyester) was added back to the original reaction flask equipped as before, but without the HCN trap. The flask was cooled to 0° C. and 30.7 g methanesulfonyl chloride was added with stirring under nitrogen. The addition funnel was charged with 32.65 g triethylamine, which was added dropwise over a 15 minute period, keeping the temperature at 5° C. Stirring was continued for 2 hours, while the reaction mixture warmed to ambient. A column consisting of 250 g Dowex 50 W×8–100 acid ion exchange resin was prepared and was washed before using with 250 mL water, 250 mL methanol and 500 mL methylene chloride. The reaction mixture was run down this column and collected. A fresh column was prepared and the above process was repeated. A third 250 g column, consisting of Dowex 1×8–200 basic ion exchange resin was prepared and pretreated as in the acid resin treatment described above. The reaction mixture was run down this column and collected A fourth column of the basic resin was prepared and the reaction mixture again was run down the column and collected. Each column pass was followed by two 250 mL methylene chloride washes down the column, and each pass required ~10 minutes. The solvent washes were combined with the reaction mixture and the volume was reduced in vacuo to ~500 mL and 2% of this was removed for qc. The remainder was further reduced to a final volume of 150 mL (crude mesylate solution).

To the original 5-L reaction set-up was added 960 mL formic acid, 472 mL acetic anhydride and 23.70 g potassium formate. This mixture was heated with stirring under nitrogen to 70° C. for 16 hours. The temperature was then increased to 100° C. and the crude mesylate solution was added over a thirty minute period via the addition funnel. The temperature dropped to 85° C. as methylene chloride was distilling out of the reaction mixture. After all of it had been removed, the temperature climbed back to 100° C., and was held there for 2.5 hours. The reaction mixture was cooled to 40° C. and the formic acid was removed under pressure until the minimum stir volume had been reached (~150 mL). The residue was cooled to ambient and 375 mL methylene chloride was added. The diluted residue was washed with cold 1 L portions of saturated sodium chloride solution, 1 N sodium carbonate, and again with sodium chloride solution. The organic phase was dried over magnesium sulfate (150 g), and filtered to give a dark reddish brown solution (crude enester solution).

A 4-neck jacketed 1 L reactor was equipped with mechanical stirrer, condenser/bubbler, thermometer and addition funnel with nitrogen inlet tube. The reactor was charged with the crude enester solution (estimated 60 g) in 600 mL methylene chloride, with stirring under nitrogen. To this was added 24.0 g dibasic potassium phosphate, followed by 87 mL trichloroacetonitrile. External cooling water was run through the reactor jacket and the reaction mixture was cooled to 10° C. To the addition funnel 147 mL 30% hydrogen peroxide was added mixture over a 30 minute period. The initially dark reddish brown colored reaction mixture turned a pale yellow after the addition was complete. The reaction mixture remained at 10±1° C. throughout the addition and on continued stirring overnight (23 hours total). The phases were separated and the aqueous portion was extracted twice with 120 mL portions of methylene chloride. The combined organic phases were then washed with 210 mL 3% sodium sulfite solution was added. This was repeated a second time, after which both the organic and aqueous parts were negative for peroxide by starch/iodide test paper. The organic phase was successively washed with 210 mL aliquots of cold 1 N sodium hydroxide, 1 N hydrochloric acid, and finally two washes with brine. The organic phase was dried azeotropically to a volume of ~100 mL, fresh solvent was added (250 mL and distilled azeotropically to the same 100 mL and the remaining solvent was removed in vacuo to give 57.05 g crude product as a gummy yellow foam. A portion (51.01 g) was further dried to a constant weight of 44.3 g and quantitatively analyzed by HPLC. It assayed at 27.1% epoxymexrenone.

EXAMPLE 29

Formation of 3-ethoxy-11α-hydroxy-androsta-3,5-diene-17-one from 11α-hydroxyandrostendione 11α-Hydroxyandrostendione (429.5 g) and toluene sulfonic acid hydrate (7.1) were charged to a reaction flask under nitrogen. Ethanol (2.58 L) was added to the reactor, and the resulting solution cooled to 5° C. Triethyl orthoformate (334.5 g) was added to the solution over a 15 minute period at 0° to 15° C. After the triethyl orthoformate addition was complete the reaction mixture was warmed to 40° C. and reacted at that temperature for 2 hours, after which the temperature was increased to reflux and reaction continued under reflux for an additional 3 hours. The reaction mixture was cooled under vacuum and the solvent removed under vacuum to yield 3-ethoxy-11α-hydroxy-androsta-3,5-diene-17-one.

EXAMPLE 30

Formation of Enamine from 11α-hydroxycanrenone

Scheme 1: Step 3A: Method B: Preparation of 5'R(5'α),7'β-20'-Aminohexadecahydro-11'β-hydroxy-10'a,13'α-dimethyl-3',5dioxospiro[furan-2(3H),17'α(5'H)-[7,4]metheno[4H[cyclopenta[a]phenanthrene[-5'-carbonitrile.

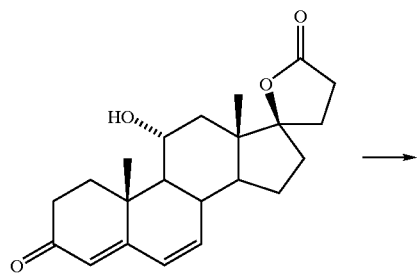

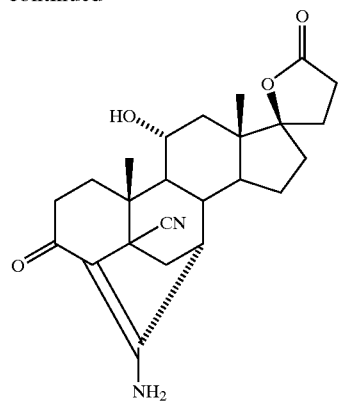

Sodium cyanide (1.72 g) was placed in 25 mL 3-neck flask fitted with a mechanical stirrer. Water (2.1 mL) was added and the mixture was stirred with heating until the solids dissolved. Dimethylformamide (15 mL) was added followed by 11α-hydroxycanrenone (5.0 g). A mixture of water (0.4 mL) and sulfuric acid (1.49 g) was added to mixture. The mixture was heated to 85° C. for 2.5 hours at which time HPLC analysis showed complete conversion to product. The reaction mixture was cooled to room temperature. Sulfuric acid (0.83 g) was added and the mixture stirred for one half hour. The reaction mixture was added to 60 mL water cooled in an ice bath. The flask was washed with 3 mL DMF and 5 mL water. The slurry was stirred for 40 min. and filtered. The filter cake was washed twice with 40 mL water and dried in a vacuum oven at 60° C. overnight to yield the 11α-hydroxy enamine, i.e., 5'R(5'α),7'β-20'-aminohexadecahydro-11'β-hydroxy-10'α,13'α-dimethyl-3',5-dioxospiro[furan-2(3H),17'α(5'H)-[7,4]metheno [4H] cyclopenta[a]phenanthrene]-5'-carbonitrile (4.9 g).

EXAMPLE 31

One-pot Conversion of 11α-hydroxycanrenone to Diketone

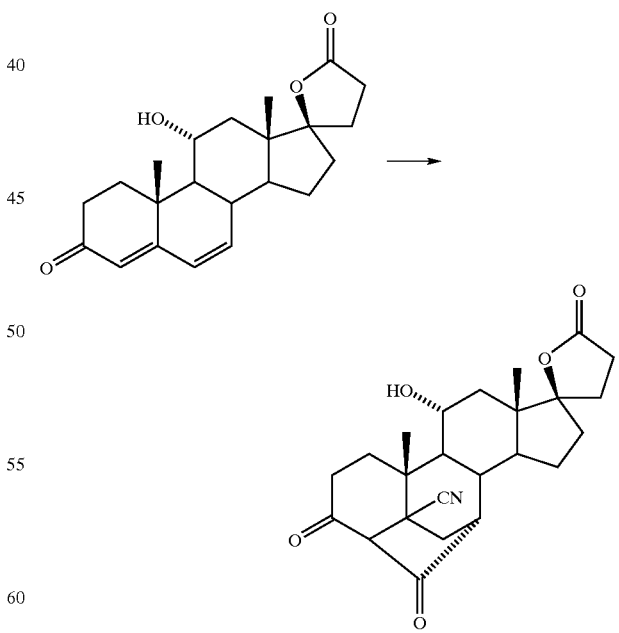

Sodium cyanide (1.03 g) was added to a 50 mL 3-neck flask fitted with a mechanical stirrer. Water (1.26 mL) was added and the flask was heated slightly to dissolve the solid. Dimethylacetamide [or dimethyformamide] (9 mL) was added followed by 11α-hydroxycanrenone (3.0 g). A mixture of sulfuric acid (0.47 mL) and water (0.25 mL) was added to the reaction flask while stirring. The mixture was heated to 95° C. for 2 hours. HPLC analysis indicated that the reaction was complete. Sulfuric acid (0.27 mL) was added and the mixture stirred for 30 min. Additional water (25 mL) and sulfuric acid (0.90 mL) were introduced and the reaction mixture stirred for 16 hours. The mixture was then cooled in an ice bath to 5–10° C. The solid was isolated by filtering through a sintered glass filter followed by washing twice with water (20 mL). The solid diketone, i.e., 4'S(4'α), 7'α-Hexadecahydro-11'α-hydroxy-10'β,13'β-dimethyl-3',5, 20'-trioxospiro[furan-2(3H),17'β-[4,7]methano[17H]cyclopenta[a]phenanthrene]-5'β(2'H)-carbonitrile was dried in a vacuum oven to yield 3.0 g of a solid.

EXAMPLE 32A-1

Scheme 1: Step 3A: Method B: Preparation of Methyl Hydrogen 11α,17α-Dihydroxy-3-oxopregn-4-ene-7α,21-dicarboxylate, γ-Lactone A suspension of 5.0 g of the diketone produced in the manner described in Example 31 in methanol (100 mL) was heated to reflux and a 25% solution of potassium methoxide in methanol (5.8 mL) was added over 1 min. The mixture became homogeneous. After 15 min., a precipitate was present. The mixture was heated at reflux and again became homogeneous after about 4 hours. Heating at reflux was continued for a total of 23.5 hours and 4.0 N HCl (10 mL) was added. A total of 60 mL of a solution of hydrogen cyanide in methanol was removed by distillation. Water (57 mL) was added to the distillation residue over 15 min. The temperature of the solution was raised to 81.5° C. during water addition and an additional 4 mL of hydrogen cyanide/methanol solution was removed by distillation. After water addition was complete, the mixture became cloudy and the heat source was removed. The mixture was stirred for 3.5 hours and product slowly crystallized. The suspension was filtered and the collected solid was washed with water, dried in a stream of air on the funnel, and dried at 92° (26 in. Hg) for 16 hours to give 2.98 g of an off-white solid. The solid was 91.4% of the hydroxyester, i.e., methyl hydrogen 11α,17α-dihydroxy-3-oxopregn-4-ene-7α,21-dicarboxylate, γ-lactone by weight. The yield was 56.1%.

EXAMPLE 32A-2

Preparation of Methyl Hydrogen 11α,17α-Dihydroxy-3-oxopregn-4-ene-7α,21-dicarboxylate, γ-Lactone The diketone (40 g) produced in the manner described in Example 31 is charged to a clean, dry, jacketed 1 L reactor equipped with a bottom drain, condenser, RTD probe and fraction collecting receiver. Methanol (800 mL) is then charged to the reactor and the mixture stirred. The resulting slurry is heated to about 60° C. to 65° C. and a 25% solution of potassium methoxide (27.8 mL) is added. The mixture becomes homogeneous.

The mixture is heated at reflux. After about 1.5 hours at reflux an additional 16.7 mL of 25% potassium methoxide solution is added to the mixture while maintaining reflux. The mixture is maintained at reflux for an additional 6 hours. Conversion of diketone to hydroxyester is analyzed by HPLC. Once HPLC indicates the ratio of diketone to hydroxyester is less than about 10%, a charge of 77 mL of 4M HCl (a comparable amount of 1.5 M to 3 M sulfuric acid could be substituted for the hydrochloric acid) is added to the mixture over a period of about 15 minutes as refluxing is continued.

The mixture is then distilled and about 520 mL of methanol/HCN distillate is collected and discarded. The concentrated mixture is cooled to about 65° C. About 520 mL of water is added to the mixture over a period of about 90 minutes and the temperature is maintained at about 65° C. during the addition. The mixture is gradually cooled to about 15° C. over a period of about four hours, and then is stirred and maintained at about 15° C. for an additional two hours. The mixture is filtered and the filtered product is washed twice with about 200 mL of water each time. The filtered product is dried in vacuo (90° C., 25 mm Hg). Approximately 25 to 27 g of an off-white solid comprising principally methyl hydrogen 11α,17α-dihydroxy-3-oxopregn-4-ene-7α,21-dicarboxylate, γ-lactone is obtained.

EXAMPLE 32B-1

Preparation of 7-methyl hydrogen 5β-cyano-11α, 17-dihydroxy-3-oxo-17α-pregnane-7α,21-dicarboxylate, γ-lactone

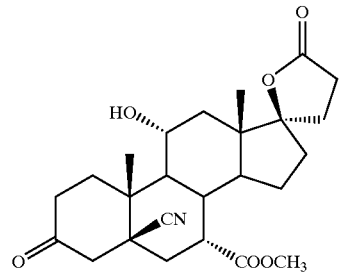

A reaction flask was charged with 4.1 g of the diketone produced in the manner described in Example 31, 75 mL of methanol and 1 mL of 1N methanolic sodium hydroxide. The suspension was stirred at room temperature. A homogeneous solution was obtained within minutes and a precipitate observed after about 20 minutes. Stirring was continued for 70 minutes at room temperature. At the end of this time the solid was filtered and washed with methanol. The solid was dried in a steam cabinet resulting in 3.6 g of 7-methyl hydrogen 5β-cyano-11α,17-dihydroxy-3-oxo-17α-pregnane-7α,21-dicarboxylate, γ-lactone.

1H NMR (CDCl$_3$) ppm 0.95 (s,3H), 1.4 (s,3H), 3.03 (d,1H,J15), 3.69 (s,3H), 4.1 (m,1H).

13C NMR (CDCl$_3$) ppm 14.6, 19.8, 22.6, 29.0, 31.0, 33.9, 35.17, 35.20, 36.3, 37.7, 38.0, 38.9, 40.8, 42.8, 43.1, 45.3, 45.7, 47.5, 52.0, 68.0, 95.0, 121.6, 174.5, 176.4, 207.0.

EXAMPLE 32B-2

Preparation of 7-methyl hydrogen 5β-cyano-9,11α-epoxy-17-hydroxy-3-oxo-17α-pregnane-7α,21-dicarboxylate, γ-lactone

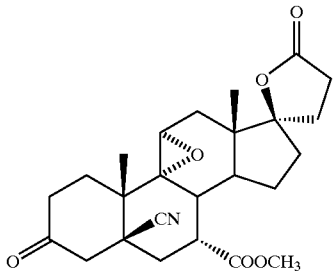

To 2.0 g (4.88 mmol) of the 9,11-epoxydiketone of Formula 21 suspended in 30 mL of anhydrous methanol was added 0.34 mL (2.4 mmol) of triethylamine. The suspension was heated to reflux and after 4.5 hours no starting material remained as judged by HPLC (Zorbax SB-C8 150×4.6 mm, 2 ml/min., linear gradient 35:65 A:B to 45:55 A:B over 15 min, A=acetonitrile/methanol 1:1, B=water/0.1% trifluoroacetic acid, detection at 210 nm). The mixture was allowed to cool and maintained at about 25 degrees for about 16 hours. The resulting suspension was filtered to give 1.3 g of 7-methyl hydrogen 5β-cyano-9,11α-epoxy-17-hydroxy-3-oxo-17α-pregnane-7α,21-dicarboxylate, γ-lactone as a white solid. The filtrate was concentrated to dryness on a rotary evaporator and the residue was triturated with 3–5 mL of methanol. Filtration gave an additional 260 mg of 7-methyl hydrogen 5β-cyano-9,11α-epoxy-17-hydroxy-3-oxo-17α-pregnane-7α,21-dicarboxylate, γ-lactone. The yield was 74.3%.

1H-nmr (400 MHz, deuterochloroform) d 1.00 (s,3H), 1.45 (m, 1H), 1.50 (s,3H), 1.65 (m, 2H), 2.10 (m, 2H), 2.15–2.65 (m, 8H), 2.80 (m, 1H), 2.96 (m, 1H), 3.12 (d, J=13, 1H), 3.35, (d, J=7, 1H), 3.67 (s, 3H).

EXAMPLE 32C

Preparation of 5β-cyano-11-α,17-dihydroxy-3-oxo-17α-pregnane-7α,21-dicarboxylic acid, γ-lactone

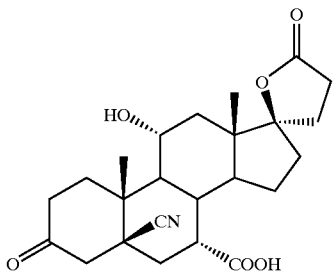

A reaction flask was charged with 6.8 g of the diketone (prepared in the manner described in Example 31), 68 mL of acetonitrile, 6.0 g of sodium acetate and 60 mL of water. The mixture was warmed and stirred at reflux. After about 1.5 hours the mixture was almost homogeneous. At the end of three hours 100 mL of water was added as 50 mL of acetonitrile was distilled. The mixture was cooled and the precipitated solid (1.7 g) was removed via filtration. The filtrate (pH=5.5) was treated with hydrochloric acid to reduce the pH to about 4.5 and a solid precipitated. The solid was isolated, washed with water and dried to give 4.5 g of 5β-cyano-11-α,17-dihydroxy-3-oxo-17α-pregnane-7α,21-dicarboxylic acid, γ-lactone.

$^1$H NMR (DMSO) ppm 0.8 (s,3H), 1.28 (s,3H), 3.82 (m,1H).

$^{13}$C NMR (DMSO) ppm 14.5, 19.5, 22.0, 28.6, 30.2, 33.0, 34.1, 34.4, 36.0, 37.5, 37.7, 38.5, 42.4, 42.6, 45.08, 45.14, 47.6, 94.6, 122.3, 176.08, 176.24, 207.5.

EXAMPLE 33

Scheme 1: Step 3A: Method C: Preparation of Methyl Hydrogen 11α,17α-Dihydroxy-3-oxopregn-4-ene-7α,21-dicarboxylate, γ-Lactone Diketone (30 g) prepared in the manner described in Example 31 was charged into a cleaned and dried 3-neck reaction flask equipped with a thermometer, a Dean Stark trap and a mechanical stirrer. Methanol (24 mL) was charged to the reactor at room temperature (22° C.) and the resulting slurry stirred for 5 min. A 25% by weight solution of sodium methoxide in methanol (52.8 mL) was charged to the reactor and the mixture stirred for 10 min. at room temperature during which the reaction mixture turned to a light brown clear solution and a slight exotherm was observed (2–3° C.). The addition rate was controlled to prevent the pot temperature from exceeding 30° C. The mixture was thereafter heated to reflux conditions (about 67° C.) and continued under reflux for 16 hrs. A sample was then taken and analyzed by HPLC for conversion. The reaction was continued under reflux until the residual diketone was not greater than 3% of the diketone charge. During reflux 4 N HCl (120 mL) was charged to the reaction pot resulting in the generation of HCN which was quenched in a scrubber.

After conclusion of the reaction, 90–95% of the methanol solvent was distilled out of the reaction mixture at atmospheric pressure. Head temperature during distillation varied from 67–75° C. and the distillate which contained HCN was treated with caustic and bleach before disposal. After removal of methanol the reaction mixture was cooled to room temperature, solid product beginning to precipitate as the mixture cooled in the 40–45° C. range. An aqueous solution containing optionally 5% by weight sodium bicarbonate (1200 mL) at 25° C. was charged to the cooled slurry and the resultant mixture then cooled to 0° C. in about 1 hr. Sodium bicarbonate treatment was effective to eliminate residual unreacted diketone from the reaction mixture. The slurry was stirred at 0° C. for 2 hrs. to complete the precipitation and crystallization after which the solid product, Methyl Hydrogen 11α,17α-Dihydroxy-3-oxopregn-4-ene-7α,21-dicarboxylate, γ-Lactone, was recovered by filtration and the filter cake washed with water (100 mL). The product was dried at 80–90° C. under 26" mercury vacuum to constant weight. Water content after drying was less than 0.25% by weight. Adjusted molar yield was around 77–80% by weight.

EXAMPLE 34

Scheme 1: Step 3A: Method D: Preparation of Methyl Hydrogen 11α,17α-Dihydroxy-3-oxopregn-4-ene-7α,21-dicarboxylate, γ-Lactone Diketone as prepared in accordance with Example 31 (1 eq.) was reacted with sodium methoxide (4.8 eqs.) in a methanol solvent in the presence of zinc iodide (1 eq.). Work up of the reaction product can be either in accordance with the extractive process described herein, or by a non-extractive process in which methylene chloride extractions, brine and caustic washes, and sodium sulfate drying steps are eliminated. Also in the non-extractive process, toluene was replaced with 5% by weight sodium bicarbonate solution. Methyl Hydrogen 11α,17α-Dihydroxy-3-oxopregn-4-ene-7α,21-dicarboxylate, γ-Lactone was isolated as the product.

EXAMPLE 35

Scheme 1: Step 3C: Method C: Preparation of Methyl Hydrogen 17α-Hydroxy-3-oxopregna-4,9(11)-diene-7α,21-dicarboxylate, γ-Lactone The hydroxyester prepared as by Example 34 (1.97 g) was combined with tetrahydrofuran (20 mL) and the resulting mixture cooled to −70° C. Sulfuryl chloride (0.8 mL) was added and the mixture was stirred for 30 min., after which imidazole (1.3 g) was added. The reaction mixture was warmed to room temperature and stirred for an additional 2 hrs. The mixture was then diluted with methylene chloride and extracted with water. The organic layer was concentrated to yield crude product Methyl Hydrogen 17α-Hydroxy-3-oxopregna-4,9(11)-diene-7α,21-dicarboxylate, γ-Lactone (1.97 g). A small sample of the crude product was analyzed by HPLC. The analysis showed that the ratio of 9,11-olefin: 11,12-olefin: 7,9-lactone was 75.5:7.2:17.3. When carried out at 0° C. but otherwise as described above, the reaction yielded a product in which the 9,11-olefin: 11,12-olefin: 7,9-lactone distribution was 77.6:6.7:15.7. This procedure combines into one step the introduction of a leaving group and elimination thereof for the introduction of the 9,11-olefin structure of the enester, i.e., reaction with sulfuryl chloride causes the 11α-hydroxy group of the hydroxy ester of Formula V to be replaced by halide and this is followed by dehydrohalogenation to the $\Delta^{9,11}$ structure. Thus formation of the enester is effected without the use of a strong acid (such as formic) or a drying agent such as acetic anhydride. Also eliminated is the refluxing step of the alternative process which generates carbon monoxide.

EXAMPLE 36A

Scheme 1: Step 3C: Method D: Preparation of Methyl Hydrogen 17α-Hydroxy-3-oxopregna-4,9(11)-diene-7α,21-dicarboxylate, γ-Lactone Hydroxyester (20 g) prepared as by Example 34, and methylene chloride (400 mL) were added to a clean dry three-neck round bottom flask fitted with a mechanical stirrer, addition funnel and thermocouple. The resulting mixture was stirred at ambient temperature until complete solution was obtained. The solution was cooled to 5° C. using an ice bath. Methanesulfonyl chloride (5 mL) was added to the solution of $CH_2Cl_2$ containing the hydroxyester, rapidly followed by the slow dropwise addition of triethylamine (10.8 mL). The addition rate was adjusted so that the temperature of the reaction did not exceed 5° C. The reaction was very exothermic; therefore cooling was necessary. The reaction mixture was stirred at about 5° C. for 1 h. When the reaction was complete (HPLC and TLC analysis), the mixture was concentrated at about 0° C. under 26 in Hg vacuum until it became a thick slurry. The resulting slurry was diluted with $CH_2Cl_2$ (160 mL), and the mixture was concentrated at about 0° C. under 26 in Hg vacuum to obtain a concentrate. The purity of the concentrate (mesylate product of Formula IV wherein $R^3$=H and —A—A— and —B—B— are both —$CH_2$—$CH_2$—, i.e., methyl hydrogen 11α,17α-dihydroxy-3-oxopregn-4-ene-7α,21-dicarboxylate, γ-lactone to methyl hydrogen 17α-hydroxy-11α-(methylsulfonyl)oxy-3-oxopregn-4-ene-7α,21-dicarboxylate, γ-lactone was found to be 82% (HPLC area %). This material was used for the next reaction without isolation.

Potassium formate (4.7 g), formic acid (16 mL) and acetic anhydride (8 mL, 0.084 mol) were added to a clean dry reactor equipped with mechanical stirrer, condenser, thermocouple and heating mantle. The resulting solution was heated to 70° C. and stirred for about 4–8 hours. The addition of acetic anhydride is exothermic and generated gas (CO), so that the rate of addition had to be adjusted to control both temperature and gas generation (pressure). The reaction time to prepare the active eliminating reagent was dependent on the amount of water present in the reaction (formic acid and potassium formate contained about 3–5% water each). The elimination reaction is sensitive to the amount of water present; if there is >0.1% water (KF), the level of the 7,9-lactone impurity may be increased. This by product is difficult to remove from the final product. When the KF showed <0.1% water, the active eliminating agent was transferred to the concentrate of mesylate (0.070 mol) prepared in the previous step. The resulting solution was heated to 95° C. and the volatile material was distilled off and collected in a Dean Stark trap. When volatile material evolution ceased, the Dean Stark trap was replaced with the condenser and the reaction mixture was heated for additional 1 h at 95° C. Upon completion (TLC and HPLC analysis; <0.1% starting material) the content was cooled to 50° C. and vacuum distillation was started (26 in Hg/50° C.). The mixture was concentrated to a thick slurry and then cooled to ambient temperature. The resulting slurry was diluted with ethyl acetate (137 mL) and the solution was stirred for 15 min. and diluted with water (137 mL). The layers were separated, and the aqueous lower layer was re-extracted with ethyl acetate (70 mL). The combined ethyl acetate solution was washed once with brine solution (120 mL) and twice with ice cold 1N NaOH solution (120 mL each). The pH of aqueous was measured, and the organic layer rewashed if the pH of the spent wash liquor was <8. When the pH of the spent wash was observed to be >8, the ethyl acetate layer was washed once with brine solution (120 mL) and concentrated to dryness by rotary evaporation using a 50° C. water bath. The resulting enester, solid product i.e., methyl hydrogen 17α-hydroxy-3-oxopregna-4,9(11)-diene-7α,21-dicarboxylate, γ-lactone weighed 92 g (77% mol yield).

EXAMPLE 36B

Preparation of Methyl Hydrogen 17α-Hydroxy-3-oxopregna-4,9(11)-diene-7α,21-dicarboxylate, γ-Lactone To a clean dry 250 mL three-neck round bottom flask fitted with a mechanical stirrer, addition funnel and thermocouple was added 25 g (53.12 mmol) of the hydroxyester Methyl Hydrogen 11α,17α-Dihydroxy-3-oxopregn-4-ene-7α,21-dicarboxylate, γ-Lactone prepared as by Example 34, followed by 150 mL of methylene chloride (Burdick & Johnson). The resulting mixture was stirred at ambient temperature until a light slurry was obtained. The solution was cooled to −5° C. using an ice bath. Methanesulfonyl chloride (7.92 g, 69.06 mmol) (Aldrich) was added to the solution of methylene chloride containing the hydroxyester, rapidly followed by the slow dropwise addition of triethylamine (7.53 g) (Aldrich). The addition rate was adjusted so that the temperature of the reaction did not exceed 0° C. The reaction was very exothermic; therefore cooling was necessary. Addition time was 35 minutes. The reaction mixture was stirred at about 0° C. for an additional 45 minutes. When the reaction was complete (less than 1% hydroxyester remaining indicated by HPLC and TLC analysis), the mixture was concentrated by stripping approximately 110 mL to 125 mL of the methylene chloride solvent at atmospheric pressure. The reactor temperature reached approximately 40° C. to 45° C. during stripping. Where the reaction is not complete after the additional 45 minutes, an additional 0.1 equivalent of methanesulfonyl chloride and an additional 0.1 equivalent triethylamine can be charged to the reactor and the reaction checked for completion. The resulting mixture contained the crude product methyl hydrogen 17α-hydroxy-11α-(methylsulfonyl)oxy-3-oxopregn-4-ene-7α,21-dicarboxylate, γ-lactone. This material was used for the next reaction without isolation.

Anhydrous sodium acetate (8.7 g)(Mallinkrodt), glacial acetic acid (42.5 mL) (Fisher) and acetic anhydride (0.5 mL) (Fisher) were added to a second 250 mL clean dry reactor equipped with mechanical stirrer, condenser, thermocouple and heating mantle. The resulting solution was heated to 90° C. and stirred for about 30 minutes. The addition of acetic anhydride is exothermic, so that the rate of addition had to be adjusted to control both temperature and pressure. Acetic anhydride was added to reduce the water content of the solution to an acceptable level (less than about 0.1%). When the KF showed <0.1% water, the acetic acid solution was transferred to the concentrate of mesylate prepared as discussed in the first paragraph of this example. The temperature of the resulting mixture was about 55° C. to 60° C. after the transfer. By using acetic acid and sodium acetate instead of formic acid and potassium formate as in Example 36A, gas generation was reduced.

The mixture was heated to 135° C. and maintained at that temperature for about 60 to 90 minutes until volatile material evolution ceased. The volatile material distilled from the mixture was collected in a Dean Stark trap. Upon completion (TLC and HPLC analysis; <0.1% starting material) the heat source was removed. When the temperature of the mixture reached 80° C., 150 mL of water was slowly added to the mixture over 60 to 90 minutes. At the end of the water addition, the mixture had cooled to a temperature of about 35° C. to 45° C. and a slurry had begun to form. The mixture was further cooled to 15° C. and maintained at that temperature for about 30 to 60 minutes.

The mixture was filtered through a glass funnel. The filtrate was rinsed with 100 mL of water. The filtrate was then washed a second time with an additional 100 mL of water. The resulting filtrate was dried at 70° C. in vacuo to yield 25.0 g of dry product enester, methyl hydrogen 17α-hydroxy-3-oxopregna-4,9(11)-diene-7α,21-dicarboxylate, γ-lactone. HPLC assay indicated 70% of the desired 9,11-olefin, 15% of the 11,12-olefin, and 5% of the 7,0-lactone.

This method had the beneficial result (relative to similar processes) of (i) reducing solvent volumes, (ii) reducing the number of separate operational steps needed to produce the enester from the hydroxyester, (iii) reducing the washes needed, (iv) replacing extraction with water precipitation in isolating the final product, and (v) eliminating safety concerns previously associated with mixed anhydride formation and gas generation when formic acid is used instead of acetic acid.

EXAMPLE 37A

Scheme 1: Step 3C: Method E: Preparation of Methyl Hydrogen 17α-Hydroxy-3-oxopregna-4,9 (11)-diene-7α,21-dicarboxylate, γ-Lactone Hydroxyester (100 g; 0.22 mol) prepared as by Example 34 was charged to a 2 L 3-neck round bottom flask equipped with mechanical stirrer, addition funnel, and thermocouple. A circulating cooling bath was used with automatic temperature control. The flask was dried prior to reaction because of the sensitivity of methanesulfonyl chloride to water.

Methylene chloride (1 L) was charged to the flask and the hydroxyester dissolved therein under agitation. The solution was cooled to 0° C. and methane sulfonyl chloride (25 mL; 0.32 mol) was charged to the flask via the addition funnel. Triethylamine (50 mL; 0.59 mol) was charged to the reactor via the addition funnel and the funnel was rinsed with additional methylene chloride (34 mL). Addition of triethylamine was highly exothermic. Addition time was around 10 min. under agitation and cooling. The charge mixture was cooled to 0° C. and held at that temperature under agitation for an additional 45 min. during which the head space of the reaction flask was flushed with nitrogen. A sample of the reaction mixture was then analyzed by thin layer chromatography and high performance liquid chromatography to check for reaction completion. The mixture was thereafter stirred at 0° C. for an additional 30 min. and checked again for reaction completion. Analysis showed the reaction to be substantially complete at this point; the solvent methylene chloride was stripped at 0° C. under 26" mercury vacuum. Gas chromatography analysis of the distillate indicated the presence of both methane sulfonyl chloride and triethylamine. Methylene chloride (800 mL) was thereafter charged to the reactor and the resulting mixture was stirred for 5 min. at a temperature in the range of 0–15° C. The solvent was again stripped at 0–5° C. under 26" mercury vacuum yielding the mesylate of Formula IV wherein $R^3$ is H, —A—A— and —B—B— are —$CH_2$—$CH_2$— and $R^1$ is methoxy carbonyl. The purity of the product was about 90–95 area %.

To prepare an elimination reagent, potassium formate (23.5 g; 0.28 mol), formic acid (80 mL) and acetic anhydride (40 mL) were mixed in a separate dried reactor. Formic acid and acetic anhydride were pumped into the reactor and the temperature was maintained not greater than 40° C. during addition of acetic anhydride. The elimination reagent mixture was heated to 70° C. to scavenge water from the reaction system. This reaction was continued until the water content was lower than 0.3% by weight as measured by Karl Fisher analysis. The elimination reagent solution was then transferred to the reactor containing the concentrated crude mesylate solution prepared as described above. The resulting mixture was heated to a maximum temperature of 95° C. and volatile distillate collected until no further distillate was generated. Distillation ceased at about 90° C. After distillation was complete, the reaction mixture was stirred at 95° C. for an additional 2 hrs. and completion of the reaction was checked for thin layer chromatography. When the reaction was complete, the reactor was cooled to 50° C. and the formic acid and solvent removed from the reaction mixture under 26" mercury vacuum at 50° C. The concentrate was cooled to room temperature and thereafter ethyl acetate (688 mL) was introduced and the mixture of ethyl acetate and concentrate stirred for 15 min. At this point, a 12% brine solution (688 mL) was introduced to assist in removing water soluble impurities from the organic phase. The phases were then allowed to settle for 20 min. The aqueous layer was transferred to another vessel to which an additional amount of ethyl acetate (350 mL) was charged. This back extraction of the aqueous layer was carried out for 30 min. after which the phases were allowed to settle and the ethyl acetate layers combined. To the combined ethyl acetate layers, saturated sodium chloride solution (600 mL) was charged and stirring carried out for 30 min. The phases were then allowed to settle. The aqueous layer was removed. An additional sodium chloride (600 mL) wash was carried out. The organic phase was separated from the second spent wash liquor. The organic phase was then washed with 1 N sodium hydroxide (600 mL) under stirring for 30 min. The phases were settled for 30 min. to remove the aqueous layer. The pH of the aqueous layer was checked and it found to be >7. A further wash was carried out with saturated sodium chloride (600 mL) for 15 min. The organic phase was finally concentrated under 26" mercury vacuum at 50° C. and the product recovered by filtration. The final product was a foamy brown solid when dried. Further drying at 45° C. under reduced pressure for 24 hrs. yielded 95.4 g of the enester product Methyl Hydrogen 17α-Hydroxy-3-oxopregna-4,9(11)-diene-7α,21-dicarboxylate, γ-Lactone which assayed at 68.8%. The molar yield was 74.4% corrected for both the starting hydroxy ester and the final enester.

EXAMPLE 37B

Preparation of 7-methyl hydrogen 17-methyl-3-oxo-18-norpregna-4,9(11),13-triene-7α,21-dicarboxylate

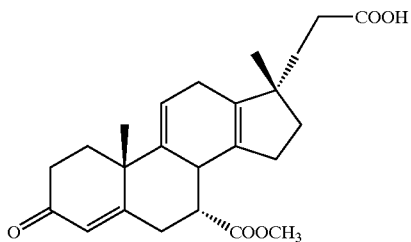

A reaction flask was charged with 5.5 g of the mesylate prepared in the manner of Example 23, 55 mL of 94.3% formic acid and 1.38 g of potassium formate. The mixture was heated and stirred at reflux (104° C.) for two hours. At the end of the two hour period the formic acid was distilled under reduced pressure. The residue was dissolved in ethyl acetate and washed with 10% potassium carbonate (50 mL). The recovered aqueous portion was yellow in color. The ethyl acetate was washed with 5% sodium hydroxide (50 mL). The aqueous portions were combined and acidified with dilute hydrochloric acid and the insoluble material extracted with ethyl acetate. The ethyl acetate was evaporated to dryness under reduced pressure to give 1.0 g of a residue, 7-methyl hydrogen 17-methyl-3-oxo-18-norpregna-4,9(11),13-triene-7α,21-dicarboxylate.

$^1$H NMR (CDCl$_3$) ppm 1.5 (s,3H), 1.4 (s,3H), 3.53 (s,3H), 5.72 (m,1H).

$^{13}$C NMR (CDCl3) ppm 25.1 and 25.4 (18 CH$_3$ and 19 CH$_3$), 40.9 (10 C), 48.5 (17 C), 51.4 (OCH$_3$), 118.4 (11 CH), 125.4 (4 CH), 132.4 (9 C), 138.5 and 139.7 (13 C and 14 C), 168.2 (5 C), 172.4 (7 CO), 179.6 (22 CO), 198.9 (3 CO).

EXAMPLE 37C

Preparation of 7-methyl hydrogen 5β-cyano-17-hydroxy-3-oxo-17α-pregn-11-ene-7α,21-dicarboxylate, γ-lactone

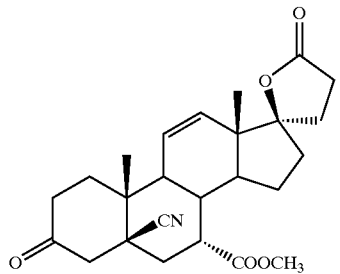

A reaction flask was charged with 5.5 g of the mesylate prepared in the manner of Example 23, 55 mL of 94.3% formic acid and 1.38 g of potassium formate. The mixture was heated and stirred at reflux (104° C.) for two hours. At the end of the two hour period the formic acid was distilled under reduced pressure. The residue was dissolved in ethyl acetate and washed with 10% potassium carbonate (50 mL). The recovered aqueous portion was yellow in color. The ethyl acetate was washed with 5% sodium hydroxide (50 mL). The ethyl acetate was evaporated to dryness under reduced pressure to give a 3.7 g residue. A 3.4 g portion of the residue was chromatographed on 267 g of Merck silica gel (40–63μ). The product was recovered with an elution scheme of ethyl acetate and toluene 37:63 (v/v). After drying this product, 0.0698 g of a residue, 7-methyl hydrogen 5β-cyano-17-hydroxy-3-oxo-17α-pregn-11-ene-7α,21-dicarboxylate, γ-lactone, was obtained.

$^1$H NMR (CDCl$_3$) ppm 1.03 (s,3H), 1.22 (s,3H), 3.70 (s,3H), 5.60 (d,1H,J10), 5.98 (d,1H,J10).

MIR cm$^{-1}$ 2229 (CN), 1768 (lactone), 1710 (ester).

EXAMPLE 37D

Isolation of 9α,17-dihydroxy-3-oxo-17α-pregn-4-ene-7α,21-dicarboxylic acid, bis(γ-lactone)

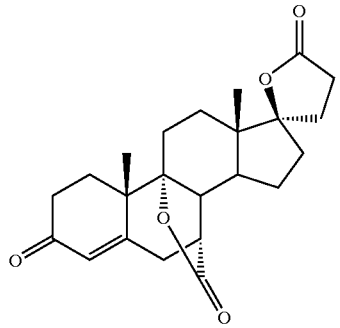

9α,17-dihydroxy-3-oxo-17α-pregn-4-ene-7α,21-dicarboxylic acid, bis(γ-lactone) is a byproduct of the 11-mesylate elimination. A pure sample was isolated from the reaction mixture of Example 37A via preparative liquid chromatography followed by reverse phase preparative HPLC. Thus, a 73 g residue was chromatographed over 2.41 kg of Merck silica gel (40–63μ) with a gradient elution scheme of ethyl acetate and toluene (20:80, 30:70, 40:60, 60:40, v/v). An enriched mixture (10.5 g) of the enamine and the 7,9-lactone was obtained in the 60:40 fractions. The progress of the purification was observed via TLC on EMF plates with a 60:40 (v/v) ethyl acetate, toluene eluent and visualization via sulfuric acid, SWUV. A portion (10.4 g) of the mixture was further purified via reverse phase HPLC on Kromasil C8 (7μ) and a 30:70 (v/v) milliQ water and acetonitrile mobile phase. The 7,9-lactone (2.27 g) was isolated as crystals from the mobile phase.

MIR cm$^{-1}$ 1762 (7,9-lactone and 17-lactone), 1677, 1622 (3-keto-Δ$^{4,5}$).

$^1$H NMR (CDCl$_3$) ppm 1.00 (s,3 H), 1.4 (s,3H), 2.05 (d,1H), 2.78 (d,1H), 5.87 (s,1H).

$^{13}$C NMR (CDCl$_3$) ppm 13.2, 19.0, 22.2, 23.2, 26.8, 28.8, 29.5, 30.8, 33.1, 34.4, 35.1, 42.5, 43.6, 43.9, 45.0, 45.3, 89.9, 94.7, 129.1, 161.5, 176.0, 176.4, 196.9.

Theory C, 71.85 and H, 7.34; Found C, 71.68 and H, 7.30.

EXAMPLE 37E

Isolation of 7-methyl hydrogen 5-cyano-17-hydroxy-3-oxo-17α-pregn-11-ene-7α,21-dicarboxylate, γ-lactone

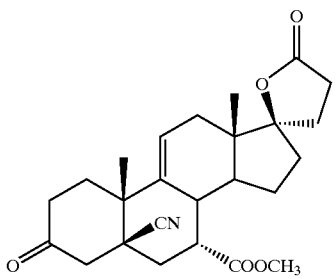

The compound 7-methyl hydrogen 5-cyano-17-hydroxy-3-oxo-17α-pregn-11-ene-7α,21-dicarboxylate, γ-lactone was isolated after multiple preparative liquid chromatography on the reaction mixture obtained after elimination of the 11-mesyloxy group (Example 24). It was part of a cluster of less polar impurities as viewed via TLC on EMF plates with a 30:70 (v/v) ethyl acetate and methylene chloride eluting system and visualized via sulfuric acid, SWUV. Generally, these less polar impurities were separated from the crude enamine via preparative liquid chromatography. Specifically, 9.6 g of the crude enamine solution was chromatographed over 534 g of Merck silica gel (40–63μ) using an ethyl acetate and toluene gradient elution scheme (20:80, 30:70, 40:60, 60:40, v/v). The less polar impurities were concentrated in the 30:70 fractions. A 12.5 g pool of the less polar impurities was collected in this fashion. This material was further chromatographed over 550 g of Merck silica gel (40–63μ) using an ethyl acetate and methylene chloride gradient elution scheme (5:95, 10:90, 20:80, 30:70, v/v). An enriched portion of the 20:80 fractions yielded 1.2 g of residue. Additional chromatography of the 1.2 g residue over 53 g of Merck silica gel (40–63μ) using an acetone and methylene chloride gradient (3:97, 6:94, 10:90, 15:85, v/v) yielded 0.27 g of 7-methyl hydrogen 5-cyano-17-hydroxy-3-oxo-17α-pregn-11-ene-7α,21-dicarboxylate, γ-lactone from an enriched portion of the 10:90 fractions.

MS M+425, calculated for C$_{25}$H$_{31}$NO$_5$ (425.52).

MIR 2222 cm$^{-1}$ (nitrile), 1767 cm$^{-1}$ (lactone), 1727 cm$^{-1}$ (ester and 3-ketone).

$^1$H NMR (CDCl$_3$) ppm 0.92 (s,3H), 1.47 (s,3H), 2.95 (m,1H), 3.65 (s,3H), 5.90 (m,1H).

$^{13}$C NMR (CDCl$_3$) ppm 14.0 (18 CH$_3$), 23.5 (15 CH$_2$), 27.0 (19 CH$_3$), 37.8, 38.5 and 40.9 (7, 8 and 14 CH), 52.0 (OCH$_3$), 95.0 (17 C), 121.5 (23 CN), 123.5 (11 CH), 135.3 (9 C), 174.2 and 176.2 (22 and 24 CO), 206 (3CO).

EXAMPLE 37F

Preparation of 7-methyl hydrogen 17-hydroxy-3-oxo-11α-(2,2,2-trifluoro-1-oxoethoxy)-17α-pregn-4-ene-7α,21-dicarboxylate

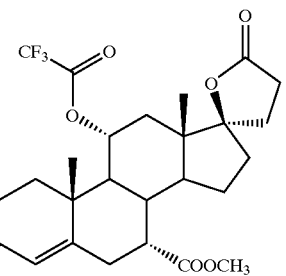

Hydroxyester (2.0 g, 4.8 mmols) prepared in the manner of Example 34 was added to 40 mL of methylene chloride in a clean, dry 3-neck, round bottom flask equipped with a mechanical stirrer. Triethyl amine (0.61 g, 6.10 mmols) and trifluoroacetic anhydride (1.47 g, 7.0 mmols) were then added to the solution. This mixture was stirred at ambient temperature overnight.

The mixture then was diluted with an additional 40 mL of methylene chloride. The mixture then was washed successively with 40 mL of water, 40 mL of 1N HCl, and 40 mL of 1N NaOH solution. The resulting solution was then dried over magnesium sulfate and concentrated to dryness to afford 3.2 g of a light brown solid, 7-methyl hydrogen 17-hydroxy-3-oxo-11α-(2,2,2-trifluoro-1-oxoethoxy)-17α-pregn-4-ene-7α,21-dicarboxylate.

The residue was further analyzed and purified by chromatography. HPLC conditions: column—Waters Symmetry C18 (150 mm×4.6 mm i.d., 5 micron particle size); column temperature—ambient; mobile phase—acetonitrile/water, 30/70 by volume; flow rate—1.0 mL/minute; injection volume—20 microliters; sample concentration—1.0 mg/ml; detection—UV at 210 nm; pressure—1500 psi; and run time—45 minutes. TLC conditions: adsorbent—Merck Silica Gel 60 F$_{254}$; solvent system—ethyl acetate/toluene, 65/35 by volume; visualization technique—shortwave; and application amount—100 micrograms.

EXAMPLE 37G

Preparation of 7-methyl hydrogen 11α-(acetyloxy)-17-hydroxy-3-oxo-17α-pregn-4-ene-7,21-dicarboxylate, γ-lactone

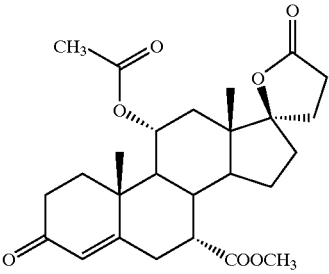

Hydroxyester (2.86 g, 6.87 mmole) prepared in the manner of Example 34 was added to 15 mL of methylene chloride in a clean, dry 3-neck, round bottom flask equipped with a mechanical stirrer. Triethyl amine (1.39 g, 13.7 mmol), dimethylaminopyridine (0.08 g, 0.6 mmol) and acetic anhydride (1.05 g, 10.3 mmol) were then added to the solution. This mixture was stirred at ambient temperature overnight.

The mixture then was diluted with 150 mL of ethyl acetate and 25 mL of water. This ethyl acetate solution then was washed 25 mL of citric acid solution. The solution was then dried over magnesium sulfate and concentrated to dryness to afford 3.33 g of a light brown solid, 7-methyl hydrogen 11α-(acetyloxy)-17-hydroxy-3-oxo-17α-pregn-4-ene-7,21-dicarboxylate, γ-lactone.

The residue was further analyzed and purified by chromatography. HPLC conditions: column—Waters Symmetry C18 (150 mm×4.6 mm i.d., 5 micron particle size); column temperature—ambient; mobile phase—acetonitrile/water, 30/70 by volume; flow rate—1.0 mL/minute; injection volume—20 microliters; sample concentration—1.0 mg/mL; detection—UV at 210 nm; pressure—1500 psi; and run time—45 minutes. TLC conditions: adsorbent—Merck Silica Gel 60 $F_{254}$; solvent system—methylene chloride/methanol, 95/5 by volume; visualization technique—shortwave; and application amount—100 micrograms.

EXAMPLE 37H

Scheme 1: Step 3C: Method F: Preparation of 7-methyl hydrogen 17-hydroxy-3-oxo-17α-pregna-4,9(11)-diene-7,21-dicarboxylate, γ-lactone

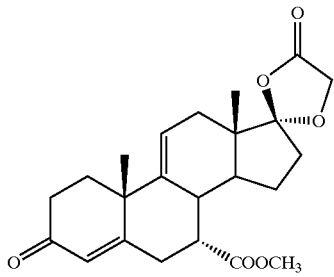

Potassium formate (1.5 g, 0.018 mol), formic acid 60 mL, 1.6 mol) and acetic anhydride (29.5 mL, 0.31 mol) were added to a clean, dry 250 mL reactor equipped with a mechanical stirrer, condenser, thermocouple and heating mantle. The solution was then was stirred at 70° C. for 4 hours and cooled to ambient temperature to provide an elimination reagent useful for converting the mesylate of Formula IV to the product of this example.

The preformed TFA/TFA anhydride elimination reagent was added to 70.0 g (0.142 mol) of the mesylate prepared in the manner of Example 23. The resulting mixture was heated to 95° C. to 105° C. for 2.5 hrs., the degree of conversion being periodically checked by TLC or HPLC. The resulting residue was cooled to 50° C., diluted with ice water (1.4 L) and stirred for 1 hour. The mixture was left standing overnight at ambient temperature. The layers were separated and aqueous phase was re-extrated with ethyl acetate (75 mL). The ethyl acetate solution was then successively washed with a water/brine mixture (70 mL), another water/brine mixture (60 mL), 1N sodium hydroxide (60 mL), and a third water/brine mixture (60 mL). Brine strength was 12% by weight. The ethyl acetate solution was then dried over sodium sulfate, filtered and concentrated to dryness by rotary evaporator to afford a 4.5 g mixture of both the desired product and an unknown impurity. The ratio of the impurity/product by HPLC area was about 50/15 respectively. The major product from this reaction was the impurity which was identified as 7-methyl hydrogen 17-hydroxy-3-oxo-17α-pregna-4,9(11)-diene-7,21-dicarboxylate, γ-lactone.

The mixture was purified by column chromatography to afford 1.9 g of analytically pure 7-methyl hydrogen 17-hydroxy-3-oxo-17α-pregna-4,9(11)-diene-7,21-dicarboxylate, γ-lactone.

The residue was further analyzed and purified by chromatography. HPLC conditions: column—Waters Symmetry C18 (150 mm×4.6 mm i.d., 5 micron particle size); column temperature—ambient; mobile phase—acetonitrile/water, 30/70 by volume; flow rate—1.0 mL/minute; injection volume—20 microliters; sample concentration—1.0 mg/mL; detection—UV at 210 nm; pressure—1500 psi; and run time—45 minutes. TLC conditions: adsorbent—Merck Silica Gel 60 $F_{254}$; solvent system—chloroform/methyl t-butyl ether/isopropanol, 70/28/2 by volume; visualization technique—50% by volume aqueous $H_2SO_4$/LWUV and 50% by volume $H_2SO_4$/phosphomolybdic acid; and application amount—100 micrograms.

EXAMPLE 37I

Preparation of 7-methyl hydrogen 17-hydroxy-3,11-dioxo-17α-pregn-4-ene-7α,21-dicarboxylate, γ-lactone

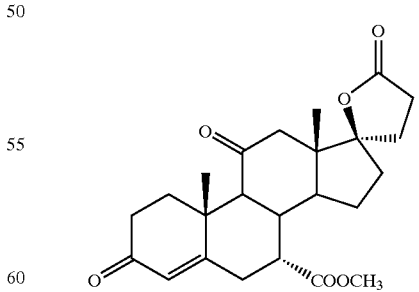

A Jones Reagent was prepared by dissolving 6.7 g of chromic anhydride ($CrO_3$) in 6 mL of concentrated sulfuric acid and carefully diluting that mixture with distilled water to 50 mL. One mL of this reagent is sufficient to oxidize 2 mmol of a secondary alcohol to a ketone.

Hydroxyester (10.0 g, 24.0 mmole) prepared in the manner of Example 34 was dissolved/suspended in 1200 mL of acetone. To this mixture was added 8.992 mL of the Jones Reagent and the combined mixture was stirred for 10 minutes. An aliquot of the reaction mixture, after being treated with water and extracted with methylene chloride, was analyzed by HPLC (column: Beckman Ultrasphere ODS C18, 4.6 mm×250 mm, 5 micron; solvent gradient: acetonitrile/water=1/99 to 100/0 in 20 minutes at a flow rate of 1.5 mL/minute; detector: UV210 nm). The reaction was complete as evidenced by the lack of any significant amount of the starting material in the reaction mixture. The HPLC retention time for the starting material (hydroxester) is 13.37 minute and for the product ketone was 14.56 min.

The reaction was worked up by adding 200 mL of water and 300 mL of methylene chloride. The organic layer was separated from the aqueous layer and washed again with 200 mL of water. The organic layer was separated from the aqueous layer and dried over magnesium sulfate. The solvent was evaporated to provide 9.52 g of the off-white solid (95.6% crude yield) 7-methyl hydrogen 17-hydroxy-3,11-dioxo-17α-pren-4-ene-7α,21-dicarboxylate, γ-lactone.

The structure assignment was based on the mass spectrum (m/e 414), HNMR (DMF-d7) and CNMR (DMF-d7). In HNMR, the characteristic peak of the 11-H (4.51 ppm, doublet, j=5.8 Hz) found in the hydroxester was absent. In CNMR, a peak appeared at 208.97 ppm which is expected for the 11-keto carbon.

CNMR (400 MHz, DMF-d7) 208.97 (11-keto), 197.70 (3-keto), 176.00 (22-lactone), 173.34 (7–COOMe), 167.21 (C5), 125.33 (C4), 93.63 (C17), and other peaks in the region of 15 to 57 ppm.

EXAMPLE 37J

Preparation of dimethyl 11α,17-dihydroxy-3-oxo-17α-pregn-4-ene-7α,21-dicarboxylate, γ-lactone

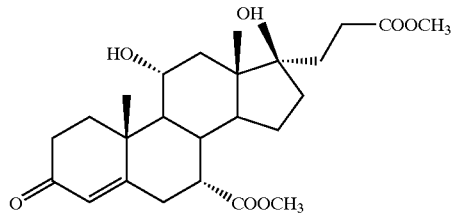

A solution of 3.5 g (8.4 mmols) of the hydroxyester prepared in the manner of Example 34 in 42 mL of methanol was mixed with 4 mL of methanolic 4N potassium hydroxide (8 mmols). The slurry was stirred at room temperature overnight and heated to reflux for one hour. The methanol was evaporated under vacuum and the residue mixed with 50 mL of ethyl acetate. The ethyl acetate was evaporated under vacuum and the residue digested with 50 mL of ethyl acetate. The dried solid was combined with 50 mL of acetone and 2 mL of methyl iodide (32.1 mmols). The mixture was stirred at room temperature for 18 hours. During this time most of the solids dissolved. The mixture was filtered and the filtrate evaporated to dryness under vacuum. The residue was digested with ethyl acetate, the solids then removed via filtration and the solvent removed under vacuum distillation. The residue was determined to be a 78:22 (v/v) mixture of dimethyl 11α,17-dihydroxy-3-oxo-17α-pregn-4-ene-7α,21-dicarboxylate, γ-lactone and the starting material hydroxyester via H¹ NMR. This mixture was adequate for use as an HPLC marker without further purification.

¹H NMR (CDCl₃) indicated the following features: ppm 0.93 (s,3H), 1.37 (s,3H), 3.64 (s,3H) 3.69 (s,3H).

EXAMPLE 37K

Preparation of 11α,17-dihydroxy-3-oxo-17α-pregn-4-ene-7α,21-dicarboxylate, γ-lactone

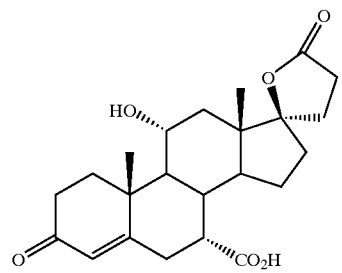

To 11.86 g (28.5 mmol) of the hydroxyester prepared in the manner of Example 34 was added 50 mL of methanol and 20 mL of 2.5 M NaOH. The suspension was heated to reflux. After 25 minutes, a portion of the starting ester remained unreacted as judged by HPLC (Zorbax SB-C8 150×4.6 mm, 2 ml/min., linear gradient 35:65 A:B to 45:55 A:B over 15 min, A=acetonitrile/methanol 1:1, B=water/ 0.1% trifluoroacetic acid, detection at 210 nm) and 10 mL of 10 M NaOH was added. After 1.5 hours, a trace of ester remained unreacted as judged by HPLC. The reaction mixture was allowed to stand at about 25 degrees for 64 hours.

The mixture was diluted with 100 mL of water and then made strongly acidic with 20 mL of concentrated HCl. The resulting gummy precipitate was stirred until the precipitate became a suspension. The solid was isolated by filtration, resuspended in methanol and filtered to give 3.75 g of a brown solid. The material was dissolved in 8 mL of hot DMF and the mixture was diluted with 40 mL of methanol. The acid crystallized and was isolated by filtration to give 1.7 g of a fluffy white solid, 11α,17-dihydroxy-3-oxo-17α-pregn-4-ene-7α,21-dicarboxylate, γ-lactone.

1H-nmr (400 MHz, deuterodimethyl sulfoxide) d 0.80 (s, 3H), 1.25 (s, 3H), 1.2–2.7 (m, 20H), 3.8 (brs, 1H), 4.45 (m, 1H), 5.50 (s, 1H). The carboxyl proton was not observed due to the presence of an HOD peak at 3.4 ppm.

EXAMPLE 38

Scheme 1: Step 3C: Method G: Preparation of 7-methyl hydrogen 17-hydroxy-3-oxo-17α-pregna-4,9 (11)-diene-7,21-dicarboxylate, γ-lactone The procedure of Example 37A was repeated except that the multiple washing steps were avoided by treating the reaction solution with an ion exchange resin, basic alumina or basic silica. Conditions for treatment with basic alumina or basic silica are set forth in Table 38. Each of these treatments was found effective for removal of impurities without the multiple washes of EXAMPLE 44 to produce 7-methyl hydrogen 17-hydroxy-3-oxo-17α-pregna-4,9(11)-diene-7,21-dicarboxylate, γ-lactone.

TABLE 38

| Factor | Set point | Purpose of Experiment | Key results |
|---|---|---|---|
| Basic alumina | 2 g/125 g product | Treating the reaction mixture with basic alumina to remove Et₃N.HCl salt and to eliminate the 1 N NaOH and 1 N HCl washes | The yield was 93% |
| Basic silica | 2 g/125 g product | Treating the reaction mixture with basic silica which is cheaper to remove Et₃N.HCl salt and eliminate 1 N NaOH and 1 N HCl washes | The yield was 95% |

EXAMPLE 39

Scheme 1: Step 3C: Method H: Preparation of 7-methyl hydrogen 17-hydroxy-3-oxo-17α-pregna-4,9(11)-diene-7,21-dicarboxylate, γ-lactone Potassium acetate (4 g) and trifluoroacetic acid (42.5 mL) were mixed in a 100 mL reactor. trifluoroacetic anhydride (9.5 mL) was added to the mixture at a rate controlled to maintain temperature during addition below 30° C. The solution was then heated to 30° C. for 30 min. to provide an elimination reagent useful for converting the mesylate of Formula IV to the enester of Formula II.

The preformed TFA/TFA anhydride elimination reagent was added to a solution of the mesylate of Formula IV previously prepared as in Example 37A. The resulting mixture was heated at 40° C. for 4½ hrs., the degree of conversion being periodically checked by TLC or HPLC. When the reaction was complete, the mixture was transferred to a 1-neck flask and concentrated to dryness under reduced pressure at room temperature (22° C.). Ethyl acetate (137 mL) was added to the mixture to obtain complete dissolution of solid phase material after which a water/brine mixture (137 mL) was added and the resulting two phase mixture stirred for 10 min. The phases were then allowed to separate for 20 min. Brine strength was 24% by weight. The aqueous phase was contacted with an additional amount of ethyl acetate (68 mL) and the two phase mixture thus prepared was stirred for 10 min. after which it was allowed to stand for 15 min. for phase separation. The ethyl acetate layers from the two extractions were combined and washed with 24% by weight brine (120 mL), another aliquot of 24% by weight brine (60 mL), 1 N sodium hydroxide solution (150 mL) and another portion of brine (60 mL). After each aqueous phase addition, the mixture was stirred for 10 min. and allowed to stand for 15 min. for separation. The resulting solution was concentrated to dryness under reduced pressure at 45° C. using a water aspirator. The solid product (8.09 g) was analyzed by HPLC and found to include 83.4 area % of the enester 7-methyl hydrogen 17-hydroxy-3-oxo-17α-pregna-4,9(11)-diene-7,21-dicarboxylate, γ-lactone; 2.45 area % of the 11,12-olefin; 1.5% of the 7,9-lactone; and 1.1% of unreacted mesylate.

EXAMPLE 40

Scheme 1: Step 3C: Method I: Preparation of 7-methyl hydrogen 17-hydroxy-3-oxo-17α-pregna-4,9(11)-diene-7,21-dicarboxylate, γ-lactone The mesylate having the structure prepared per Example 23 (1.0 g), isopropenyl acetate (10 g) and p-toluenesulfonic acid (5 mg) were placed in a 50 ml flask and heated to 90° C. with stirring. After 5 hours the mixture was cooled to 25° C. and concentrated in vacuo at 10 mm of Hg. The residue was dissolved in CH₂Cl₂ (20 ml) and washed with 5% aqueous NaHCO₃. The CH₂Cl₂ layer was concentrated in vacuo to give 1.47 g of a tan oil. This material was recrystallized from CH₂Cl₂/Et₂O to give 0.50 g of enol acetate of Formula IV(Z).

This material was added to a mixture of sodium acetate (0.12 g) and acetic acid (2.0 ml) that had been previously heated to 100° C. with stirring. After 60 minutes the mixture was cooled to 25° C. and diluted with CH₂Cl₂ (20 ml). The solution was washed with water (20 ml) and dried over MgSO₄. The drying agent was removed by filtration and the filtrate was concentrated in vacuo to give 0.4 g of the desired 9,11-olefin, 7-methyl hydrogen 17-hydroxy-3-oxo-17α-pregna-4,9(11)-diene-7,21-dicarboxylate, γ-lactone. The crude product contained less than 2% of the 7,9-lactone impurity.

EXAMPLE 41

Thermal Elimination of Mesylate in DMSO

Scheme 1: Step 3C: Method J: Preparation of 7-methyl hydrogen 17-hydroxy-3-oxo-17α-pregna-4,9(11)-diene-7,21-dicarboxylate, γ-lactone

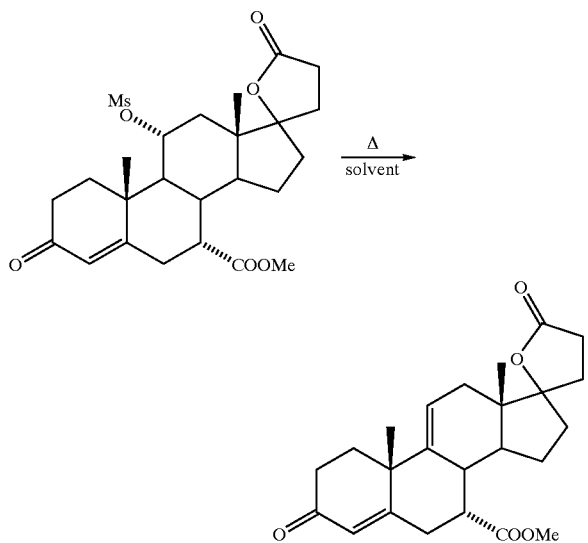

A mixture of 2 g of mesylate and 5 ml of DMSO in a flask was heated at 80° C. for 22.4 hours. HPLC analysis of the reaction mixture indicated no starting material was detected. To the reaction was added water (10 ml) and the precipitate was extracted with methylene chloride three times. The combined methylene chloride layers were washed with water, dried over magnesium sulfate, and concentrated to give the enester 7-methyl hydrogen 17-hydroxy-3-oxo-17α-pregna-4,9(11)-diene-7,21-dicarboxylate, γ-lactone.

EXAMPLE 42

Scheme 1: Step 3D: Method B: Synthesis of Methyl Hydrogen 9,11α-Epoxy-17α-hydroxy-3-oxopregn-4-ene-7α,21-dicarboxylate, γ-Lactone In a 50 mL pear-shaped flask under stirring the enester of Formula IIA (1.07 g assaying 74.4% enester), trichloroacetamide (0.32 g), dipotassium hydrogen phosphate (0.70 g) as solid were mixed with methylene chloride (15.0 mL).

Hydrogen peroxide (30% by weight; 5.0 mL) was added via a pipet over a 1 min. period. The resulting mixture was stirred for 6 hrs. at room temperature at which point HPLC analysis showed that the ratio of epoxymexrenone to enester in the reaction mixture was approximately 1:1. Additional trichloroacetamide (0.32 g) was added to the reaction mixture and reaction continued under agitation for 8 more hours after which time the remaining proportion of enester was shown to have been reduced to 10%. Additional trichloroacetamide (0.08 g) was added and the reaction mixture was allowed to stand overnight at which point only 5% of unreacted enester remained relative to epoxymexrenone in the mixture.

EXAMPLE 43

Scheme 1: Step 3D: Method C: Synthesis of
Methyl Hydrogen 9,11α-Epoxy-17α-hydroxy-3-
oxopregn-4-ene-7α,21-dicarboxylate, γ-Lactone Enester of Formula IIA (5.4 g, assaying 74.4% enester) was added to a 100 mL reactor. Trichloroacetamide (4.9 g) and dipotassium hydrogen phosphate (3.5 g) both in solid form were added to the enester followed by methylene chloride (50 mL). The mixture was cooled to 15° C. and a 30% hydrogen peroxide (25 g) was added over a ten min. period. The reaction mixture was allowed to come to 20° C. and stirred at that temperature for 6 hrs., at which point conversion was checked by HPLC. Remaining enester was determined to be less than 1% by weight.

The reaction mixture was added to water (100 mL), the phases were allowed to separate, and the methylene chloride layer was removed. Sodium hydroxide (0.5 N; 50 mL) was added to the methylene chloride layer. After 20 min. the phases were allowed to separate HCl (0.5 N; 50 mL) was added to the methylene chloride layer after which the phases were allowed to separate and the organic phase was washed with saturated brine (50 mL). The methylene chloride layer was dried over anhydrous magnesium sulfate and the solvent removed. A white solid (5.7 g) was obtained. The aqueous sodium hydroxide layer was acidified and extracted and the extract worked up to yield an additional 0.2 g of product. Yield of epoxymexrenone was 90.2%.

EXAMPLE 44

Scheme 1: Step 3D: Method D: Synthesis of
Methyl Hydrogen 9,11α-Epoxy-17α-hydroxy-3-
oxopregn-4-ene-7α,21-dicarboxylate, γ-Lactone Enester of Formula IIA was converted to epoxymexrenone in the manner described in Example 43 with the following differences: the initial charge comprised of enester (5.4 g assaying 74.4% enester), trichloroacetamide (3.3 g), and dipotassium hydrogen phosphate (3.5 g). Hydrogen peroxide solution (12.5 mL) was added. The reaction was conducted overnight at 20° C. after which HPLC showed a 90% conversion of enester to epoxymexrenone. Additional trichloroacetamide (3.3 g) and 30% hydrogen peroxide (5.0 mL) was added and the reaction carried out for an additional 6 hrs. at which point the residual enester was only 2% based on the enester charge. After work up as described in Example 43, 5.71 g of epoxymexrenone resulted.

EXAMPLE 45

Scheme 1: Step 3D: Method E: Synthesis of
Methyl Hydrogen 9,11α-Epoxy-17α-hydroxy-3-
oxopregn-4-ene-7α,21-dicarboxylate, γ-Lactone The enester of Formula IIA was converted to epoxymexrenone in the manner generally described in Example 43. In the reaction of this Example, enester charge was 5.4 g (assaying 74.4% enester), the trichloroacetamide charge was 4.9 g, hydrogen peroxide charge was 25 g, dipotassium hydrogen phosphate charge was 3.5 g. The reaction was run at 20° C. for 18 hrs. The residual enester was less than 2%. After work up, 5.71 g of epoxymexrenone resulted.

EXAMPLE 46

Scheme 1: Step 3D: Method F: Synthesis of
Methyl Hydrogen 9,11α-Epoxy-17α-hydroxy-3-
oxopregn-4-ene-7α,21-dicarboxylate, γ-Lactone Enester of Formula IIA was converted to epoxymexrenone in the manner described in Example 43 except that the reaction temperature in this Example was 28° C. The materials charged in the reactor included enester (2.7 g), trichloroacetamide (2.5 g), dipotassium hydrogen phosphate (1.7 g), hydrogen peroxide (17.0 g) and methylene chloride (50 mL). After 4 hrs. reaction, unreacted enester was only 2% based on the enester charge. After work up as described in Example 43, 3.0 g of epoxymexrenone was obtained.

EXAMPLE 47–1

Scheme 1: Step 3D: Method G: Synthesis of
Methyl Hydrogen 9,11α-Epoxy-17α-hydroxy-3-
oxopregn-4-ene-7α,21-dicarboxylate, γ-Lactone Enester of Formula IIA (40.0 g, assaying 68.4% enester) was charged into a 1000 mL, jacketed reactor and dissolved in 175 mL of methylene chloride. The solution was stirred as trichloroacetamide (22.3 g) and dipotassium hydrogen phosphate (6.0 g) were added as solids. The mixture was stirred at 400 RPM and the temperature adjusted to 27° C. with a constant temperature bath to control the liquid circulating through the reactor jacket. Hydrogen peroxide (72.8 mL at 30% assay) was added over a 3 to 5 minute period. Following the hydrogen peroxide addition, the mixture was stirred at 400 RPM and 27° C. HPLC assay indicated that the reaction was 99% complete within 5 hours. At the end of six hours, 72.8 mL of water was added. The aqueous hydrogen peroxide was separated and back extracted one time with 50 mL of methylene chloride. The combined methylene chloride was washed with 6% sodium sulfite (62.3 mL) to destroy any contained peroxide. The methylene chloride removal was started with atmospheric distillation and concluded under vacuum. A yellowish residue (48.7 g, 55.4% assay) was obtained. This correlated with a 94.8% assay adjusted molar yield.

A portion (47.8 g) of the residue was combined with 498 mL of ethanol 3A (95% ethanol denatured with 5% methanol). The mixture was heated to reflux and 249 mL of distillate removed at atmospheric pressure. The mixture was cooled to 25° C. and filtered. An ethanol 3A rinse (53 mL) was used to assist the transfer. The dried solid weighed 27.6 g (87.0% assay) which correlated with a 91% recovery. A portion of the solid (27.0 g) was dissolved in 292 mL of methyl ethyl ketone at reflux. The hot solution was filtered through a pad of solka floc (powdered cellulose) with another 48.6 mL of methyl ethyl ketone used to assist the transfer. A 146 mL portion of the methyl ethyl ketone was removed via atmospheric distillation. The solution was cooled to 50° C. and stirred for one hour as the product crystallized. After one hour the mixture was cooled to 25° C. Stirring was continued for one hour and the solid filtered with 48.6 mL of methyl ethyl ketone used as a rinse. The solid was dried to a constant weight of 20.5 g which represented an 87.2% recrystallization recovery. The reaction yield and ethanol, methyl ethyl ketone recoveries combined for a 75% overall yield.

The methyl ethyl ketone mother liquor was suitable for recycling with an incoming methylene chloride solution from a subsequent reaction. The combined methylene chloride and methyl ethyl ketone mixture was evaporated to dryness with atmospheric and vacuum distillation. The residue was combined with 19 volumes of ethanol 3A based on epoxymexrenone content. One half of the solvent was removed under atmospheric distillation. After cooling to 25° C. the solid was filtered and dried. The dry solid was dissolved in 12 volumes of methyl ethyl ketone at reflux. The hot solution was filtered through a solka floc pad with 2 volumes of methyl ethyl ketone added as a rinse. The filtrate was concentrated with the atmospheric distillation of 6 volumes of methyl ethyl ketone. The solution was cooled to 50° C. and stirred for one hour as the product crystallized. After one hour the mixture was cooled to 25° C. Stirring was continued for one hour and the solid filtered with 2 volumes of methyl ethyl ketone used as a rinse. The solid was dried to a constant weight. The incorporation of the methyl ethyl ketone mother liquor raised the overall yield to 80–85%.

This method appears particularly suited for scaleup since it maximizes throughput and minimizes washing volumes and waste.

EXAMPLE 47A

Scheme 1: Step 3D: Method H: Synthesis of Methyl Hydrogen 9,11α-Epoxy-17α-hydroxy-3-oxopregn-4-ene-7α,21-dicarboxylate, γ-Lactone Enester of Formula IIA (17 g, assaying 72% enester) was dissolved in methylene chloride (150 mL) after which trichloroacetamide (14.9 g) was added under slow agitation. The temperature of the mixture was adjusted to 25° C. and a solution of dipotassium hydrogen phosphate (10.6 g) in water (10.6 mL) was stirred into the enester substrate solution under 400 rpm agitation. Hydrogen peroxide (30% by weight solution; 69.4 mL) was added to the substrate/phosphate/trichloroacetamide mixture over a 3–5 min. period. No exotherm or oxygen evolution was observed. The reaction mixture thus prepared was stirred at 400 rpm and 25° C. for 18.5 hrs. No oxygen evolution was observed throughout the course of the reaction, but analysis of the hydrogen peroxide consumption indicated that some oxygen was formed during the reaction. The reaction mixture was diluted with water (69.4 mL) and the mixture stirred at about 250 rpm for 15 min. No temperature control was necessary for this operation and it was conducted essentially at room temperature (any temperature in the range of 5–25° C. being acceptable). The aqueous and organic layers were allowed to separate and the lower methylene chloride layer was removed.

The aqueous layer was back extracted with methylene chloride (69.4 mL) for 15 min. under agitation of 250 rpm. The layers were allowed to separate and the lower methylene chloride layer was removed. The aqueous layer (177 g; pH=7) was submitted for hydrogen peroxide determination. The result (12.2%) indicated that 0.0434 mol of hydrogen peroxide were consumed in the reaction of 0.0307 mol of olefin. The excess hydrogen peroxide consumption was a measure of oxygen generation in the reaction. Back extraction with a small amount of methylene chloride volume was sufficient to insure no loss of epoxymexrenone in the aqueous layer. This result was confirmed with the application of a second large methylene chloride extraction in which only trichloroacetamide was recovered.

The combined methylene chloride solutions from the above described extractions were combined and washed with 3% by weight sodium sulfite solution (122 mL) for at least 15 min. at about 250 rpm. A negative starch iodide test (KI paper; no color observed; in a positive test a purple coloration indicates the presence of peroxide) was observed at the end of the stir period.

The aqueous and organic layers were allowed to separate and the lower methylene chloride layer removed. The aqueous layer (pH=6) was discarded. Note that addition of sodium sulfite solution can cause a slight exotherm so that such addition should be carried out under temperature control.

The methylene chloride phase was washed with 0.5 N sodium hydroxide (61 mL) for 45 min. at about 250 rpm and a temperature in the range of 15–25° C. (pH=12–13). Impurities derived from trichloroacetamide were removed in this process. Acidification of the alkaline aqueous fraction followed by extraction of the methylene chloride confirmed that very little epoxymexrenone was lost in this operation.

The methylene chloride phase was washed once with 0.1 N hydrochloric acid (61 mL) for 15 min. under 250 rpm agitation at a temperature in the range 15–25° C. The layers were then allowed to separate and the lower methylene chloride layer removed and washed again with 10% by weight aqueous sodium chloride (61 mL) for 15 min at 250 rpm at a temperature in the range of 15–25° C. Again the layers were allowed to separate and the organic layer removed. The organic layer was filtered through a pad of Solkafloc and then evaporated to dryness under reduced pressure. Drying was completed with a water bath temperature of 65° C. An off-white solid (17.95 g) was obtained and submitted for HPLC assay. Epoxymexrenone assay was 66.05%. An adjusted molar yield for the reaction was 93.1%.

The product was dissolved in hot methyl ethyl ketone (189 mL) and the resulting solution was distilled at atmospheric pressure until 95 mL of the ketone solvent had been removed. The temperature was lowered to 50° C. as the product crystallized. Stirring was continued at 50° C. for 1 hr. The temperature was then lowered to 20–25° C. and stirring continued for another 2 hrs. The solid was filtered and rinsed with MEK (24 mL) and the solid dried to a constant weight of 9.98 g, which by HPLC assay contain 93.63% epoxymexrenone. This product was re-dissolved in hot MEK (106 mL) and the hot solution filtered through a 10 micron line filter under pressure. Another 18 mL of MEK was applied as a rinse and the filtered MEK solution distilled at atmospheric pressure until 53 mL of solvent had been removed. The temperature was lowered to 50° C. as the product crystallized; and stirring was continued at 50° C. for 1 hr. The temperature was then lowered to 20–25° C. and held at that temperature while stirring was continued for another 2 hrs. The solid product was filtered and rinsed with MEK (18 mL). The solid product was dried to a constant weight of 8.32 g which contained 99.6% epoxymexrenone per quantitative HPLC assay. The final loss on drying was less than 1.0%. Overall yield of epoxymexrenone in accordance with the reaction and work up of this Example is 65.8%. This overall yield reflected a reaction yield of 93%, an initial crystallization recovery of 78.9%, and a recrystallization recovery of 89.5%.

EXAMPLE 47B

Preparation of 7-methyl hydrogen 11α,12α-epoxy-17-hydroxy-3-oxo-17α-pregn-4-ene-7α,21-dicarboxylate, γ-lactone

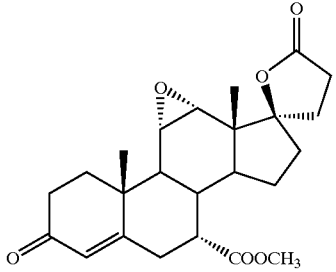

The $\Delta^{11,12}$ olefin of the enester is a byproduct of the 11-mesylate elimination. A pure sample was isolated from a a reaction mixture prepared in the the manner of Example 37A via repetitive preparative liquid chromatography. Thus, a 73 g residue (prepared as described in Example 37A) was chromatographed over 2.41 kg of Merck silica gel (40–63μ) with an ethyl acetate, toluene gradient elution scheme (20:80, 30:70, 40:60, 60:40, v/v). Enriched $\Delta^{11,12}$ olefin portions were combined from selected 30:70 fractions. TLC on EMF plates using ethyl acetate/toluene 60:40 (v/v) with sulfuric acid SWUV visualization served as a guide for choosing the appropriate fractions. The 7.9 g of crude $\Delta^{11,12}$ olefin (80 area % via HPLC) obtained after the removal of solvent was chromatographed over 531 g of Merck silica gel (40–63μ) with an ethyl acetate/methylene chloride gradient elution scheme (10:90, 20:80, 35:65, v/v). Pure 7-methyl hydrogen 17-hydroxy-3-oxo-17α-pregna-4,11-diene-7α,21-dicarboxylate, γ-lactone (3.72 g) was obtained from selected 20:80 fractions. The selection of fractions was based on TLC evaluation as in the previous situation.

MIR cm$^{-1}$ 1767 (lactone), 1727 (ester), 1668 and 1616 (3-Keto-$\Delta^{4,5}$).

$^1$H NMR (CDCl$_3$) ppm 1.05 (s,3H), 1.15 (s,3H), 3.66 (s,3H), 5.58 (dd,1H), 5.80 (s,1H), 5.88 (dd,1H).

$^{13}$C NMR (CDCl$_3$) ppm 17.41, 18.58, 21.73, 28.61, 32.28, 33.63, 34.91, 35.64, 35.90, 38.79, 42.07, 44.12, 48.99, 49.18, 51.52, 93.81, 126.43, 126.69, 133.76, 166.24, 172.91, 176.64, 198.56.

A solution of 1.6 g (3.9 mmols) of 7-methyl hydrogen 17-hydroxy-3-oxo-17α-pregna-4,11-diene-7α,21-dicarboxylate, γ-lactone in 16 mL of methylene chloride was mixed with 2.2 mL of trichloroacetonitrile (22.4 mmols) and 0.75 g of dipotassium phosphate (4.3 mmols). The mixture was stirred and combined with 6.7 mL of 30% hydrogen peroxide (66 mmols). Stirring was continued at 25° C. for 45 hours. At the end of this time 28 mL of methylene chloride and 39 mL of water were added. The organic portion was isolated and washed in succession with a) 74 mL of 3% sodium sulfite, b) 62 mL of 1 N sodium hydroxide, c) 74 mL of 1 N hydrochloric acid, and d) 31 mL of 10% brine. The organic portion was separated again, dried over magnesium sulfate, and evaporated to dryness under vacuum. The 1.25 g residue was chromatographed over 138.2 g of Merck silica gel (40–63μ) using a methyl-t-butyl ether and toluene gradient system (40:60, 60:40, 75:25, v/v). Appropriate portions of the 60:40 and 75:25 fractions were combined after TLC evaluation to give 0.66 g of pure 7-methyl hydrogen 11α,12α-epoxy-17-hydroxy-3-oxo-17α-pregn-4-ene-7α,21-dicarboxylate, γ-lactone. The TLC system utilized EMF plates and a 75:25 (v/v) methyl-t-butyl ether and toluene elution scheme with sulfuric acid and SWUV for visualization.

$^1$H NMR (CDCl$_3$) ppm 1.09 (s,3H), 1.30 (s,3H) 3.05 (AB$^{11,12}$ 2H for), 3.67 (s,3H), 5.80 (s,1H).

$^{13}$C NMR (CDCl$_3$) ppm 14.2, 18.0, 21.2, 28.8, 31.9, 33.5, 34.6, 34.7, 35.1, 35.5, 37.4, 38.3, 41.8, 46.0, 47.2, 50.4, 51.7, 56.7, 94.0, 126.7, 165.2, 172.5, 176.7, 198.1.

Theory: C, 69.54 and H, 7.30; Found: C, 69.29 and H, 7.17.

EXAMPLE 47C

Isolation of 7-methyl hydrogen 4α,5α:9α,11α-diepoxy-17-hydroxy-3-oxo-17α-pregnane-7α,21-dicarboxylate, γ-lactone

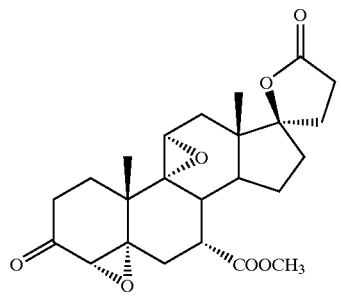

Crude epoxymexrenone (157 g) prepared from 200 g of the enester in the manner of Example 26 was subjected to chromatography over 4.4 kg of Merck silica gel (40–63μ). An 88.1 g portion was recovered with an is acetonitrile and toluene 10:90 (v/v) elution scheme. The isolated solid was dissolved in 880 mL of hot methyl ethyl ketone and filtered through a pad of solka floc. Another 88 mL of methyl ethyl ketone was applied as a rinse. The filtrate was concentrated via the removal of 643 mL of solvent and the mixture cooled to room temperature. The solids were filtered and rinsed with methyl ethyl ketone. After drying, 60.2 g of epoxymexrenone assaying 96.8% via HPLC was obtained. The filtrate was concentrated to dryness under reduced pressure. The 9.3 g residue was recrystallized from 99 mL of methyl ethyl ketone to yield 2.4 g of dry solid. A 400 mg portion of the solid was subjected to reverse phase preparative HPLC on a YMC ODS AQ column. Pure 7-methyl hydrogen 4α,5α:9α,11α-diepoxy-17-hydroxy-3-oxo-17α-pregnane-7α,21-dicarboxylate, γ-lactone (103 mg) was isolated with an elution scheme of acetonitrile (24%), methanol (4%) and water (72%).

$^1$H NMR (CDCl$_3$) ppm 0.98 (s,3H), 1.32 (s,3H), 2.89 (m,1 H), 3.07 (s,d,2H), 3.73 (s,3H).

MS, M+430, calculated for $C_{24}H_{30}O_7$(430.50).

EXAMPLE 47D

Isolation of 7-methyl hydrogen 17-hydroxy-3,12-dioxo-17α-pregna-4,9(11)-diene-7α,21-dicarboxylate, γ-lactone

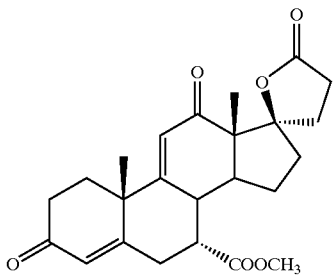

A methyl ethyl ketone mother liquor obtained in the manner of Example 26 was evaporated to dryness under reduced pressure. A 4.4 g portion of the residue was subjected to chromatography on 58.4 g of BTR Zorbax LP (40μ). Elution with a gradient of methyl ethyl ketone and methylene chloride (25:75 to 50:50, v/v) yielded 1.38 g of material. A 1.3 g portion of this material was further purified via reverse phase preparative HPLC using acetonitrile (30%), methanol (5%) and water (65%) as the mobile phase and a YMC ODS AQ column (10μ). The product was obtained from the enriched fractions via methylene chloride extraction. The methylene chloride was evaporated to dryness and the 175 mg residue repurified via reverse phase preparative HPLC using acetonitrile (24%), methanol (4%) and water (72%) as the mobile phase and a YMC ODS AQ column. Methylene chloride extraction of enriched fractions yielded 30.6 mg of pure 7-methyl hydrogen 17-hydroxy-3, 12-dioxo-17α-pregna-4,9(11)-diene-7α,21-dicarboxylate, γ-lactone.

$^1$H NMR (CDCl$_3$) ppm 1.17 (s,3H), 1.49 (s,3H), 3.13 (m,1H), 3.62 (s,3H), 5.77 (s,1H), 5.96 (s,1H).

$^{13}$C NMR (CDCl$_3$) ppm 13.1, 21.0, 28.0, 29.4, 33.1, 33.4, 33.9, 35.5, 36.7, 40.3, 41.5, 43.0, 43.4, 52.0, 55.0, 91.0, 123.7, 126.7, 163.2, 167.9, 171.8, 176.8, 197.4, 201.0.

EXAMPLE 47E

Preparation of 9,11α-epoxy-17-hydroxy-3-oxo-17α-pregn-4-ene-7α,21-dicarboxylic acid, dihydrate, dipotassium salt

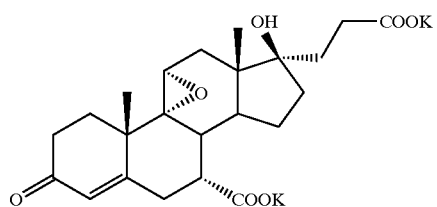

A suspension containing 2.0 g (4.8 mmol) of epoxymexrenone prepared in the manner of Example 43, 10 mL of water, 3 mL of dioxane and 9.3 mL of 1.04 N aqueous potassium hydroxide (9.7 mmol) was prepared. The mixture was stirred at 25° C. for 3 hours. A yellow, homogenous solution was formed during the first two hours. The temperature was raised to 70° C. and stirring continued for an additional 3 hours. The solvent was removed via vacuum distillation and the residue purified via reverse phase chromatography over 90 g of C18 silica gel using water as the eluent. The desired fractions were combined after review via TLC on EMF plates using methylene chloride, methanol (7:3) as the eluent and SWUV for visualization. The combined fractions were concentrated to dryness under vacuum and the residue subjected to reverse phase purification was repeated as previously described. The desired fractions were concentrated to dryness under reduced pressure and the residue dissolved in ethanol. Ethyl acetate was added to the cloud point, then heptane added to complete the precipitation. 0.55 g of the product, 9,11α-epoxy-17-hydroxy-3-oxo-17α-pregn-4-ene-7α,21-dicarboxylic acid, dihydrate, dipotassium salt, was isolated as a yellow solid. The carbon analysis correlated with a hydrated structure C$_{23}$H$_{28}$O$_7$K$_2$·1.75 H$_2$O: Theory C, 52.50 vs 55.85 for anhydrous form; Found C, 52.49. After TLC on EMF plates with methylene chloride, methanol, water (6:3:0.5, v/v) as the eluent and visualization via SWUV, an R$_f$ of 0.29 was observed.

EXAMPLE 47F

Preparation of 9,11α-epoxy-17-hydroxy-3-oxo-17α-pregn-4-ene-7α,21-dicarboxylic acid, disodium salt

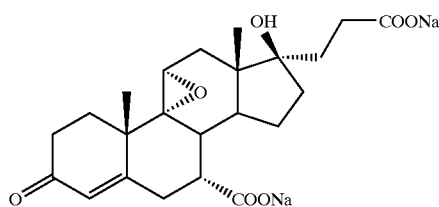

About 5 mg (0.01 mmol) of epoxymexrenone prepared in the manner of Example 43 was suspended in about 200 μL of methanol in a 4 mL vial and diluted with about 200 μL of 2.5 N NaOH. The resulting mixture was yellow and homogeneous. The mixture was then heated in an oil bath at 70° C. After 10 minutes a 1 μm sample from the mixture was analyzed by HPLC (Zorbax SB-C8 150×4.6 nn, 2 mL/minute, gradient=35:65 (v/v) A:B, A=acetonitrile/methanol (1:1), B=water/0.1% trifluoroacetic acid, detection at 210 nm) showed two materials at 4.86 and 2.93 minute retention times consistent with the hydroxyacid (open lactone) and the open lactone 7-carboxylic acid, respectively. After 30 minutes a second (0.05 mL) sample was removed and acidified with 0.05 mL of 3 N HCl followed by neutralization with about 0.5 mL of sodium bicarbonate. HPLC analysis as above showed the expected ring-closed steroids with retention times of 6.59 and 10.71 minutes. The ratio of 7-methyl hydrogen 9,11α-epoxy-17-hydroxy-3-oxo-17α-pregn-4-ene-7α,21-dicarboxylate, γ-lactone (10.71 minutes) to the corresponding 7-carboxylic acid was 7:89.

Selective hydrolysis of the lactone was possible under mild conditions. A second 4 mL vial was prepared as above but was not heated. The mixture was sonicated for 5 minutes. A 0.05 mL sample was diluted in 0.5 mL of a 1:1 (v/v) mixture of methanol/acetonitrile and was analyzed by HPLC without prior acidification. The resulting open lactone carboxylic acid 7-ester had a retention time of 4.85 minutes as observed above and was uncontaminated by the 7-carboxylic acid.

EXAMPLE 47G

Isolation of 7-methyl hydrogen 9α,11β,17-trihydroxy-3-oxo-17α-pregn-4-ene-7α,21-dicarboxylate, γ-lactone

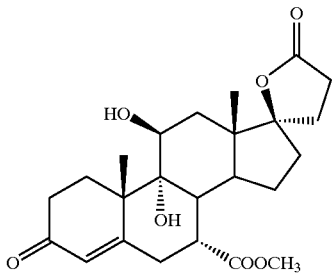

and 7-methyl hydrogen 12α,17-dihydroxy-3-oxo-17α-pregna-4,9(11)-diene-7α,21-dicarboxylate, γ-lactone

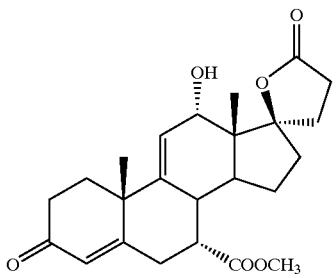

7-methyl hydrogen 9α,11β,17-trihydroxy-3-oxo-17α-pregn-4-ene-7α,21-dicarboxylate, γ-lactone and 7-methyl hydrogen 12α,17-dihydroxy-3-oxo-17α-pregna-4,9(11)-diene-7α,21-dicarboxylate, γ-lactone were isolated after preparative liquid chromatography of the 2-butanone mother liquor recovered from the epoxidation of the enester as described in example 26 (trichloroacetonitrile protocol). Thus, the first crystallization was carried out using 2-butanone as indicated. The recrystallization, however, utilized 2-butanone (10 vols per g) in place of acetone. A 2.8 g residue was obtained in this manner and was purified via reverse phase preparative HPLC. Cromasil C8 (10μ) was used as the stationary phase with a mobile phase composed of milliQ water and acetonitrile in a ratio of 70:30 (v/v). Crystallization was observed in one of the enriched fractions. The solid (46.7 mg) was isolated and identified as 7-methyl hydrogen 9α,11β,17-trihydroxy-3-oxo-17α-pregn-4-ene-7α,21-dicarboxylate, γ-lactone. The mother liquor was evaporated to dryness under reduced pressure and the residue (123 mg) identified as 7-methyl hydrogen 12α,17-dihydroxy-3-oxo-17α-pregna-4,9(11)-diene-7α,21-dicarboxylate, γ-lactone.

7-methyl hydrogen 9α,11β,17-trihydroxy-3-oxo-17α-pregn-4-ene-7α,21-dicarboxylate, γ-lactone:

MS M+432, calculated for $C_{24}H_{32}O_5$ (432.51).

$^1$H NMR (CDCl$_3$) ppm 1.23 (s,3H), 1.54 (s,3H), 3.00 (m,1H), 3.14 (m,1H), 3.74 (s,3H), 5.14 (s,1H, slowly exchangeable), 5.79 (s,1H).

$^{13}$C NMR (CDCl$_3$) ppm 16.8, 22.7, 24.8, 29.0, 29.3, 32.1, 34.1, 34.7, 35.2, 35.7, 36.8, 40.7, 43.0, 45.0, 45.9, 52.9, 72.8, 77.4, 95.9, 127.4, 163.7, 176.7, 177.3, 199.4.

7-methyl hydrogen 12α,17-dihydroxy-3-oxo-17α-pregna-4,9(11)-diene-7α,21-dicarboxylate, γ-lactone:

MS M+ 441, calculated for $C_{24}H_{30}O_6$ (414.50).

$^1$H NMR (CDCl$_3$) ppm 0.87 (s,1H), 1.40 (s,1H), 3.05 (m,1H), 3.63 (s,3H), 3.99 (m,1H), 5.72 (s,1H), 5.96 (m,1H).

$^{13}$C NMR (CDCl$_3$) ppm 14.8, 24.0, 26.1, 29.7, 33.6, 33,8, 34.0, 36.3, 37.0, 37.4, 40.7, 40.9, 43.8, 48.1, 51.9, 69.1, 95.5, 122.7, 126.3, 145.9, 164.5, 173.2, 177.6, 198.2.

EXAMPLE 47H

Preparation of 7-methyl hydrogen 9,11α-epoxy-3-ethoxy-17-hydroxy-17α-pregn-4-ene-7α,21-dicarboxylate, γ-lactone

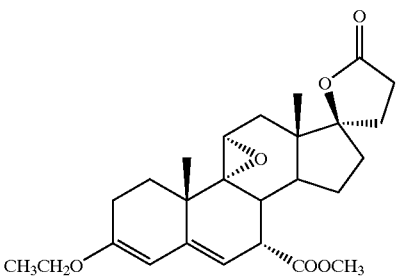

and 7-methyl hydrogen 6β,17-dihydroxy-9,11α-epoxy-3-oxo-17α-pregn-4-ene-7α,21-dicarboxylate, γ-lactone

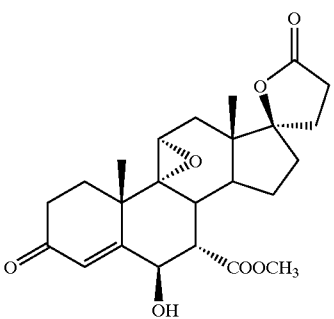

7-methyl hydrogen 9,11α-epoxy-3-ethoxy-17-hydroxy-17α-pregn-4-ene-7α,21-dicarboxylate, γ-lactone was prepared according to the method of R. M. Weier and L. M. Hofmann (J. Med Chem 1977, 1304) which is incorporated by reference. 148 g (357 mmols) of 7-methyl hydrogen 9,11α-epoxy-17-hydroxy-3-oxo-17α-pregn-4-ene-7α,21-dicarboxylate, γ-lactone prepared in the manner of Example 43 were combined with 311 mL of absolute ethanol and 155 mL (932 mmols) of triethylorthoformate. The slurry was stirred at room temperature and 10.4 g (54.7 mmols) of toluene sulfonic acid (monohydrate) added as a catalyst. Stirring was continued for 30 minutes and the reaction quenched with the addition of 41.4 g (505 mmols) of powdered sodium acetate and 20.7 mL (256 mmols) of pyridine. Solids (70.2 g) were removed by filtration and the filtrate concentrated to dryness under vacuum. The residue was digested with 300 mL of ethyl acetate and 9.8 g of solids were removed via filtration.

The filtrate was concentrated to dryness and the residue digested with 100 mL of methanol containing 2 mL of pyridine. 29.7 g of solids were removed via filtration. Additional precipitation was observed in the filtrate. Therefore, the filtrate was refiltered to remove an additional 21.9 g of solids. The filtrate was concentrated to dryness and the residue digested with 50 mL of methanol containing 1 mL of pyridine. 33.8 g of solids were isolated via filtration. Qualitative HPLC indicated that this last portion of solids was sufficiently pure (90 area percent of 7-methyl hydrogen 9,11α-epoxy-3-ethoxy-17-hydroxy-17α-pregn-4-ene-7α, 21-dicarboxylate, γ-lactone) for use in the next step of the reaction.

7-methyl hydrogen 9,11α-epoxy-3-ethoxy-17-hydroxy-17α-pregn-4-ene-7α,21-dicarboxylate, γ-lactone:

$^1$H NMR (CDCl$_3$) ppm 1.02 (s,3H), 1.27 (s,3H), 1.30 (t,3H), 3.12 (m,1H), 3.28 (m,1H), 3.66 (s,3H), 3.78 (m,2H), 5.20 (s,1H), 5.29 (d,1H).

An 8 g portion of the enol ether (7-methyl hydrogen 9,11α-epoxy-3-ethoxy-17-hydroxy-17α-pregn-4-ene-7α, 21-dicarboxylate, γ-lactone) (18 mmols) prepared in the prior step was dissolved in 120 mL of 1,4-dioxane. The solution was combined with a mixture of 6.8 g of 53% m-chloroperbenzoic acid (20.9 mmols), 18.5 mL of 1.0 N sodium hydroxide (18.5 mmols) and 46 mL of dioxane/water (9:1). The temperature was maintained at −3° C. and the mixture stirred for two hours. The temperature was raised to 25° C. and stirring continued for another twenty hours. The mixture was combined with 400 mL of cold water (10° C.) and 23.5 mL of 1.0 N sodium hydroxide (23.5 mmols). The mixture was extracted four times with 100 mL portions of methylene chloride each time. The combined methylene chloride portions were dried over magnesium sulfate and the supernatant solvent removed under vacuum distillation. The 13.9 g residue was triturated with 50 mL of ethyl ether to give 2.9 g of a white solid. A 2.4 g portion of the solid was chromatographed over 100 g of Merck silica gel (60μ). After an initial washing with 1 L of 1:1 ethyl acetate/heptane, the product was eluted with a 7:3 ratio of ethyl acetate/heptane. Enriched fractions were combined on the basis of TLC evaluation (EMF plates; ethyl acetate/heptane 7:3 (v/v) eluent; SWUV visualization). Thus, 0.85 g of enriched material was obtained and recrystallized from 10 mL of isopropanol to give 0.7 g of 7-methyl hydrogen 6β,17-dihydroxy-9,11α-epoxy-3-oxo-17α-pregn-4-ene-7α, 21-dicarboxylate, γ-lactone. The more contaminated fractions were combined and 0.87 g of crude 7-methyl hydrogen 6β,17-dihydroxy-9,11α-epoxy-3-oxo-17α-pregn-4-ene-7α, 21-dicarboxylate, γ-lactone obtained. This material was chromatographed over 67.8 g of Merck silica gel (40–63μ). An additional 0.69 g of product was recovered with toluene containing 0.5 to 2.5% methanol.

7-methyl hydrogen 6β,17-dihydroxy-9,11α-epoxy-3-oxo-17α-pregn-4-ene-7α,21-dicarboxylate, γ-lactone:

Theory: C, 66.96 and H, 7.02: Found: C, 66.68 and H, 7.16.

$^1$H NMR (CDCl$_3$) ppm 1.06 (s,3H), 1.36 (dm,1H), 1.63 (s,3H), 2.92 (m,1H), 3.02 (dd,1H), 3.12 (d,1H), 3.64 (s,3H), 4.61 (d,1H), 5.96 (s,1H).

$^{13}$C NMR (CDCl$_3$) ppm 16.17, 21.32, 21.79, 24.36, 27.99, 28.94, 30.86, 31.09, 32.75, 33.19, 34.92, 36.77, 39.16, 43.98, 47.74, 51.56, 51.66, 65.36, 72.23, 94.79, 165.10, 171.36, 176.41, 199.59.

EXAMPLE 47I

Preparation of 7-methyl hydrogen 9,11α-epoxy-17-hydroxy-3-oxo-17α-pregn-4-ene-7β,21-dicarboxylate, γ-lactone

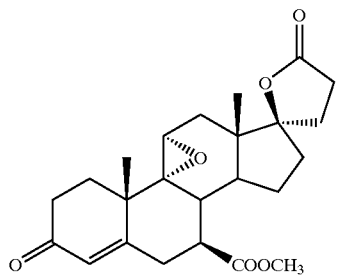

To 2 g (4.8 mmol) of 7-methyl hydrogen 9,11α-epoxy-17-hydroxy-3-oxo-17α-pregn-4-ene-7α,21-dicarboxylate, γ-lactone prepared in the manner of Example 43 was added 3.3 mL (14.4 mmol) of 25% sodium methoxide in methanol. The resulting yellow suspension was heated to 50° C. The solid did not dissolve. To the mixture was added 3.3 ml of methanol (Aldrich anhydrous). The mixture was heated to reflux conditions (65° C.) and became homogeneous. After 30 minutes a solid precipitate prevented stirring.

About 25 ml of anhydrous methanol was added and the mixture was transferred to a 100 mL flask. The mixture was heated at reflux conditions for 16 hours at which time the mixture was dark and homogeneous. The mixture was cooled to 25° C. and 70 ml of 3N HCl was added (exothermic). Several grams of ice were added to cool the mixture and the solution was extracted with two successive 25 mL portions of methylene chloride. The dark solution was dried over sodium sulfate and filtered through a 2.5 cm pad of silica gel (E. Merck, 70–230 mesh 60 Å pore size). The silica was eluted with 100 mL of methylene chloride. The eluted methylene chloride was then concentrated in vacuo to give 1 g of a brown foam which crystallized upon addition of ethyl acetate. The silica pad was eluted a second time with 100 ml of 10% ethyl acetate/methylene chloride and the eluted solution was concentrated to give 650 mg of a brown foam.

Thin layer chromatography (E. Merck 60 F-254 silica gel 0.25 mm, toluene/ethyl acetate (1:1, v/v)) revealed the presence of 7-methyl hydrogen 9,11α-epoxy-17-hydroxy-3-oxo-17α-pregn-4-ene-7α,21-dicarboxylate, γ-lactone and 7-methyl hydrogen 9,11α-epoxy-17-hydroxy-3-oxo-17α-pregn-4-ene-7β,21-dicarboxylate, γ-lactone in both samples, although very little of the 7α-carboxy epimer was present in the first sample. The first sample was triturated with hot ethyl acetate (77° C.) and allowed to cool to 25° C. The mixture then was filtered to give 400 mg of an off-white solid, mp 254–258° C. H, $^{13}$C and $^{13}$C-APT were consistent with the assigned structure. A small amount of ethyl acetate remained in the sample but no starting material was evident by HPLC (Zorbax SB-C8 150×4.6 nn, 2 mL/minute, isocratic 40:60 (v/v) A:B, A=acetonitrile/methanol (1:1), B=water/0.1% trifluoroacetic acid, detection at 210 nm) (HPLC showed 98.6 area percent), and by TLC (toluene-ethyl acetate 1:1, v/v).

FAB-MS confirmed a molecular weight of 414 with M$_+$H at 415.2.

$^1$H NMR (400 MHz, deuterochloroform) δ 0.95 (s,3H), 1.50 (s,3H), 1.45 (m,3H), 1.55–2.7 (m,15H), 2.85 (t,J=13, 1H), 3.25 (d,J=6,1H), 3.65 (s,3H), 5.78 (s,1H).

EXAMPLE 47J

Preparation of 9,11α-epoxy-17-hydroxy-3-oxo-17α-pregn-4-ene-7α,21-dicarboxylic acid, γ-lactone

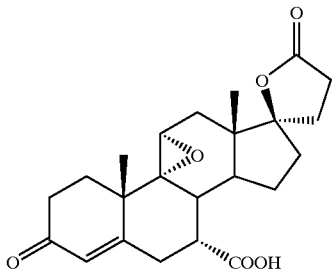

To 774 mg (1.82 mml) of 7-methyl hydrogen 9,11α-epoxy-17-hydroxy-3-oxo-17α-pregn-4-ene-7α,21-dicarboxylate, γ-lactone prepared in the manner of Example 43 and suspended in 3 ml of acetonitrile was added 3 mL (7.5 mmol, 2.0 equivalents) of 2.5 M sodium hydroxide. The mixture became yellow and after 10 minutes was homogeneous.

To monitor the progress of the reaction, aliquots (0.1 mL) of the mixture were quenched in 0.01 mL of 3M sulfuric acid and extracted in a 4 mL glass vial with ethyl acetate (0.2 ml). The phases were separated by removal of the lower aqueous phase with a pipette. The organic phase was stripped and the residue analyzed by HPLC using the method described in Example 47H. After 50 minutes at 25° C. there was little change in the composition of the mixture.

The mixture was heated to reflux conditions (about 90° C.) for 50 minutes. HPLC analysis of the mixture showed 6 area percent of the starting material remained. The mixture was stirred at 25° C. for 65 hours. Acidification, extraction and HPLC analysis of an aliquot as described above confirmed that no starting material remained.

The mixture was made strongly acidic by addition of about 4 mL of 3M sulfuric acid and was extracted with two portions (about 10 mL) of methylene chloride. The organic phases were combined and dried over sodium sulfate. Concentration on a rotary evaporator yielded 780 g of a solid. The solid was recrystallized from dimethyl formamide/methanol to give 503 mg (67%) of a tan crystalline solid. The sample melted with gas evolution near 260° C. when heated rapidly. The sample slowly darkened but remained solid when slowly heated to 285° C.

$^1$H NMR (dimethylsulfoxide d-6, 400 MHz) δ 0.85 (s,3H), 1.4 (s,3H), 1.3–2.9 (m,19H), 3.15 (m,1H), 5.55 (s,1H), 11.8 (br,1H).

EXAMPLE 47K

Scheme 1: Step 3D: Method I: Synthesis of Methyl Hydrogen 9,11α-Epoxy-17α-hydroxy-3-oxopregn-4-ene-7α,21-dicarboxylate, γ-Lactone A 0.2 M solution of the enester of Formula IIA in methylene chloride was combined with 2 equivalents of dipotassium phosphate dissolved in an equal weight of water (50% w/w aqueous solution), 3 equivalents of chlorodifluoroacetamide and 22 equivalents of hydrogen peroxide (added as a 30% aqueous solution). The mixture was stirred at 25° C. for 23 hours. The reaction was diluted with an amount of water equal to the hydrogen peroxide charge and the methylene chloride separated. The methylene chloride portion was washed one time with a 3% sodium sulfite solution (volume equal to 1.75 times the hydrogen peroxide charge). The methylene chloride portion was separated and dried over sodium sulfate. The solution was concentrated under atmospheric distillation until a head temperature of 70° C. was achieved. The residue was evaluated via HPLC, $_1$H and $^{13}$C NMR (CDCl$_3$) The yield of epoxymexrenone was determined to be 54.2 area % by HPLC.

EXAMPLE 47L

Scheme 1: Step 3D: Method J: Synthesis of Methyl Hydrogen 9,11α-Epoxy-17α-hydroxy-3-oxopregn-4-ene-7α,21-dicarboxylate, γ-Lactone The procedure of Example 47K was repeated using heptafluorobutyramide (CF$_3$CF$_2$CF$_2$CONH$_2$) instead of chlorodifluoroacetamide. The yield of epoxymexrenone was determined to be 58.4 area % by HPLC.

EXAMPLE 48

Epoxidation of Enester of Formula IIA Using Toluene

Scheme 1: Step 3D: Method K: Synthesis of Methyl Hydrogen 9,11α-Epoxy-17α-hydroxy-3-oxopregn-4-ene-7α,21-dicarboxylate, γ-Lactone The enester of Formula IIA was converted to epoxymexrenone in the method generally described in Example 46 except that toluene was used as the solvent. The materials charged to the reactor included enester (2.7 g) trichloroacetamide (2.5 g), dipotassium hydrogen phosphate (1.7 g), hydrogen peroxide (17.0 g) and toluene (50 ml). The reaction was allowed to exotherm to 28° C. and was complete in 4 hours. The resulting three phase mixture was cooled to 15° C., filtered, washed with water and dried in vacuo to yield 2.5 g of product.

EXAMPLE 49

Scheme 4: Method A: Epoxidation of 9,11-Dienone

A compound designated XVIIA (compound XVII wherein —A—A— and —B—B— are both —CH$_2$—CH$_2$—) (40.67 g) was dissolved in methylene chloride (250 mL) in a one liter 3 necked flask and cooled by ice salt mixture externally. Dipotassium phosphate (22.5 g), and trichloroacetonitrile (83.5 g) were added and mixture cooled to 2° C. after which 30% Hydrogen peroxide (200 g) was slowly added over a period of 1 hour. The reaction mixture was stirred at 12° for 8 hours and 14 hours at room temperature. A drop of the organic layer was taken and checked for any starting enone and was found to be <0.5%. Water (400 mL) was added, stirred for 15 min. and layers separated. The organic layer was washed successively with 200 mL of potassium iodide (10%), 200 mL of sodium thiosulfate (10%) and 100 mL of saturated sodium bicarbonate solution separating layers each time. The organic layer was dried over anhydrous magnesium sulfate and concentrated to yield crude epoxide (41 g). The product crystallized from ethyl acetate:methylene chloride to give 14.9 g of pure material.

EXAMPLE 50

Scheme 4: Method B: Epoxidation of Compound XVIIA Using m-chloroperbenzoic Acid

Compound XVIIA (18.0 g) was dissolved in 250 mL of methylene chloride and cooled to 10° C. Under stirring solid m-chloroperbenzoic acid, (50–60% pure, 21.86 g) was added during 15 min. No rise in temperature was observed. The reaction mixture was stirred for 3 hours and checked for the presence of the dienone. The reaction mixture was treated successively with sodium sulfite solution (10%), sodium hydroxide solution (0.5N), hydrochloric acid solution (5%) and finally with 50 mL of saturated brine solution. After drying with anhydrous magnesium sulfate and evaporation, 17.64 g of the epoxide resulted and was used directly in the next step. The product was found to contain Baeyer-Villiger oxidation product that had to be removed by trituration from ethyl acetate followed by crystallization from methylene chloride. On a 500 g scale, the precipitated m-chlorobenzoic acid was filtered followed by the usual work up.

EXAMPLE 51

Scheme 4: Method C: Epoxidation of Compound XVIIA Using Trichloroacetamide

Compound XVIIA (2 g) was dissolved in 25 mL of methylene chloride. Trichloroacetamide (2 g), dipotassium phosphate (2 g) were added. Under stirring at room temperature 30% hydrogen peroxide (10 mL) was added and stirring continued for 18 hours to yield the epoxide (1.63 g). Baeyer-Villiger product was not formed.

EXAMPLE 52

Potassium hydroxide (56.39 g; 1005.03 mmol; 3.00 eq.) was charged to a 2000 mL flask and slurried with dimethylsulfoxide (750.0 mL) at ambient temperature. A trienone corresponding to Formula XX (wherein $R^3$ is H and —A—A— and —B—B— are each —$CH_2$—$CH_2$—) (100.00 g; 335.01 mmol; 1.00 eq.) was charged to the flask together with THF (956.0 mL). Trimethylsulfonium methylsulfate (126.14 g; 670.02 mmol; 2.00 eq.) was charged to the flask and the resulting mixture heated at reflux, 80 to 85° C. for 1 hr. Conversion to the 17-spirooxymethylene was checked by HPLC. THF approximately 1 L was stripped from the reaction mixture under vacuum after which water (460 mL) was charged over a 30 min. period while the reaction mixture was cooled to 15° C. The resulting mixture was filtered and the solid oxirane product washed twice with 200 mL aliquots of water. The product was observed to be highly crystalline and filtration was readily carried out. The product was thereafter dried under vacuum at 40° C. 104.6 g of the 3-methyl enol ether Δ-5,6,9,11,-17-oxirane steroid product was isolated.

EXAMPLE 53

Sodium ethoxide (41.94 g; 616.25 mmol; 1.90 eq.) was charged to a dry 500 mL reactor under a nitrogen blanket. Ethanol (270.9 mL) was charged to the reactor and the sodium methoxide slurried in the ethanol. Diethyl malonate (103.90 g; 648.68 mmol; 2.00 eq.) was charged to the slurry after which the oxirane steroid prepared in the manner described in Example 52 (104.60 g; 324.34 mmol; 1.00 eq.) was added and the resulting mixture heated to reflux, i.e., 80 to 85° C. Heating was continued for 4 hrs. after which completion of the reaction was checked by HPLC. Water (337.86 mL) was charged to the reaction mixture over a 30 min. period while the mixture was being cooled to 15° C. Stirring was continued for 30 min. and then the reaction slurry filtered producing a filter cake comprising a fine amorphous powder. The filter cake was washed twice with water (200 mL each) and thereafter dried at ambient temperature under vacuum. 133.8 g of the 3-methyl enolether-Δ5,6,9,11,-17-spirolactone-21-ethoxycarbonyl intermediate was isolated.

EXAMPLE 54

The 3-methyl enolether-Δ5,6,9,11,-17-spirolactone-21-ethoxycarbonyl intermediate (Formula XVIII where $R^3$ is H and —A—A— and —B—B— are each —$CH_2$—$CH_2$—; 133.80 g; 313.68 mmol; 1.00 eq., as produced in Example 53, was charged to the reactor together with sodium chloride (27.50 g; 470.52 mmol; 1.50 eq.) dimethyl formamide (709 mL) and water (5 mL) were charged to a 2000 mL reactor under agitation. The resulting mixture was heated to reflux, 138 to 142° C. for 3 hrs. after which the reaction mixture was checked for completion of the reaction by HPLC. Water was thereafter added to the mixture over a 30 min. period while the mixture was being cooled to 15° C. Agitation was continued for 30 min. after which the reaction slurry was filtered recovering amorphous solid reaction product as a filter cake. The filter cake was washed twice (200 mL aliquots of water) after which it was dried. The product 3-methylenolether-17-spirolactone was dried yielding 91.6 g (82.3% yield; 96 area % assay).

EXAMPLE 55

The enol ether produced in accordance with Example 54 (91.60 g; 258.36 mmol; 1.00 eq.) ethanol (250 mL) acetic acid (250 mL) and water (250 mL) were charged to a 2000 mL reactor and the resulting slurry heated to reflux for 2 hrs. Water (600 mL) was charged over a 30 min. period while the reaction mixture was being cooled to 15° C. The reaction slurry was thereafter filtered and the filter cake washed twice with water (200 mL aliquots). The filter cake was then dried; 84.4 g of product 3-keto Δ4,5,9,11,-17-spirolactone was isolated (compound of Formula XVII where $R^3$ is H and —A—A— and —B—B— are —$CH_2$—$CH_2$—; 95.9% yield).

EXAMPLE 56

Compound XVIIA (1 kg; 2.81 moles) was charged together with carbon tetrachloride (3.2 L) to a 22 L 4-neck flask. N-bromo-succinamide (538 g) was added to the mixture followed by acetonitrile (3.2 L). The resulting mixture was heated to reflux and maintained at the 68° C. reflux temperature for approximately 3 hrs. producing a clear orange solution. After 5 hrs. of heating, the solution turned dark. After 6 hrs. the heat was removed and the reaction mixture was sampled. The solvent was stripped under vacuum and ethyl acetate (6 L) added to the residue in the bottom of the still. The resultant mixture was stirred after which a 5% sodium bicarbonate solution (4 L) was added and the mixture stirred for 15 min. after which the phases were allowed to settle. The aqueous layer was removed and saturated brine solution (4 L) introduced into the mixture which was then stirred for 15 min. The phases were again separated and the organic layer stripped under vacuum producing a thick slurry. Dimethylformamide (4 L) was then added and stripping continued to a pot temperature of 55° C. The still bottoms were allowed to stand overnight and DABCO (330 g) and lithium bromide (243 g) added. The mixture was then heated to 70° C. After one and one-half hrs. heating, a liquid chromatography sample was taken and after 3.50 hrs. heating, additional DABCO (40 g) was added. After 4.5 hrs. heating, water (4 L) was introduced and the resulting mixture was cooled to 15° C. The slurry was filtered and the cake washed with water (3 L) and dried on the filter overnight. The wet cake (978 g) was charged back into the 22 L flask and dimethylformamide (7 L) added. The mixture thus produced was heated to 105° C. at which point the cake had been entirely taken up into solution. The heat was removed and the mixture in the flask was stirred and cooled. Ice water was applied to the reactor jacket and the mixture within the reactor cooled to 14° C. and held for two hours. The resulting slurry was filtered and washed twice with 2.5 L aliquots of water. The filter cake was dried under vacuum overnight. A light brown solid product 510 g was obtained.

EXAMPLE 57

To a 2 L 4-neck flask were charged: 9,11-epoxy canrenone as produced in Example 56 (100.00 g; 282.1 mmol; 1.00 eq.), dimethylformamide (650.0 mL), lithium chloride (30.00 g; 707.7 mmol; 2.51 eq.), and acetone cyanohydrin (72.04 g; 77.3 mL; 846.4 mmol; 3.00 eq.). The resulting suspension was mechanically stirred and treated with tetramethyl guanidine (45.49 g; 49.6 mL; 395.0 mmol; 1.40 eq.). The system was then filtered with a water cooled condenser and a dry ice condenser (filled with dry ice in acetone) to prevent escape of HCN. The vent line from the dry ice condenser passed into a scrubber filled with a large excess of chlorine bleach. The mixture was heated to 80° C.

After 18 hrs., a dark reddish-brown solution was obtained which was cooled to room temperature with stirring. During the cooling process, nitrogen was sparged into the solution to remove residual HCN with the vent line being passed into bleach in the scrubber. After two hrs. the solution was treated with acetic acid (72 g) and stirred for 30 min. The crude mixture was then poured into ice water (2 L) with stirring. The stirred suspension was further treated with 10% aqueous HCl (400 mL) and stirred for 1 hr. Then the mixture was filtered to give a dark brick-red solid (73 g). The filtrate was placed in a 4 L separatory funnel and extracted with methylene chloride (3×800 mL); and the organic layers were combined and back extracted with water (2×2 L). The methylene chloride solution was concentrated in vacuo to give 61 g of a dark red oil.

After the aqueous wash fractions were allowed to sit overnight, a considerable precipitate developed. This precipitate was collected by filtration and determined to be pure product enamine (14.8 g).

After drying the original red solid (73 g) was analyzed by HPLC and it was determined that the major component was the 9,11-epoxyenamine. HPLC further showed that enamine was the major component of the red oil obtained from methylene chloride workup. Calculated molar yield of enamine was 46%.

EXAMPLE 58

9,11-epoxyenamine (4.600 g; 0.011261 mol; 1.00 eq.) as prepared in accordance with Example 57 was introduced into a 1000 mL round bottom flask. Methanol (300 mL) and 0.5% by weight aqueous HCl (192 mL) were added to the mixture which was thereafter refluxed for 17 hrs. Methanol was thereafter removed under vacuum reducing the amount of material in the still pot to 50 mL and causing a white precipitate to be formed. Water (100 mL) was added to the slurry which was thereafter filtered producing a white solid cake which was washed three times with water. Yield of solid 9,11-epoxydiketone product was 3.747 g (81.3%).

EXAMPLE 59

The epoxydiketone prepared in accordance with Example 58 (200 mg; 0.49 mmol) was suspended in methanol (3 mL) and 1,8-diazabicyclo[5.4.0]undec-7-ene(DBU) added to the mixture. Upon heating under reflux for 24 hrs. the mixture became homogeneous. It was then concentrated to dryness at 30° C. on a rotary evaporator and the residue partitioned between methylene chloride and 3.0 N HCl. Concentration of the organic phase yielded a yellow solid (193 mg) which was determined to be 22% by weight epoxy mexrenone. The yield was 20%.

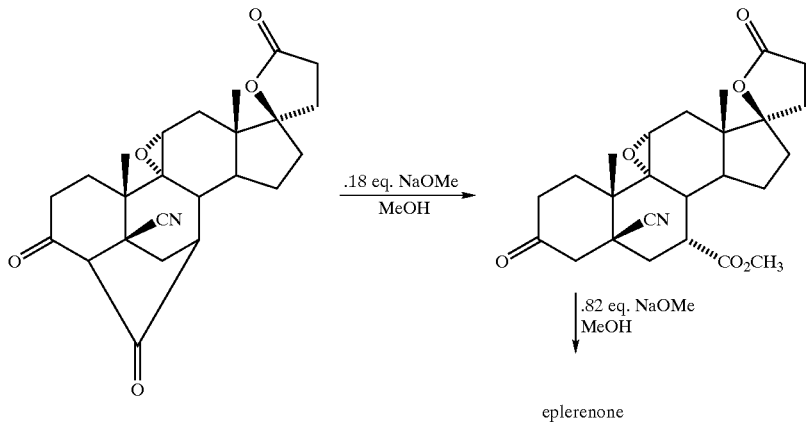

eplerenone

EXAMPLE 60

To 100 mg of diketone (prepared in accordance with Example 58) suspended in 1.5 mL of methanol was added 10 microliters (0.18 eq) of a 25% (w/w) solution of sodium methoxide in methanol. The solution was heated to reflux. After 30 min. no diketone remained and the 5-cyanoester was present. To the mixture was added 46 microliters of 25% (w/w) sodium methanol solution in methanol. The mixture was heated at reflux for 23 hours at which time the major product was epoxymexrenone as judged by HPLC.

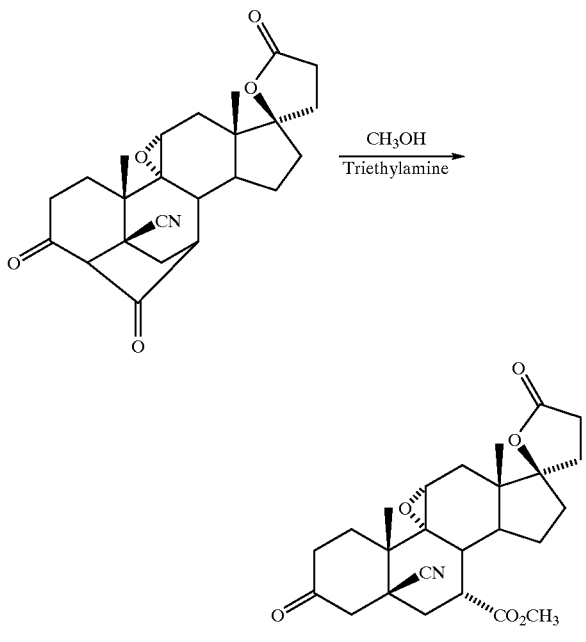

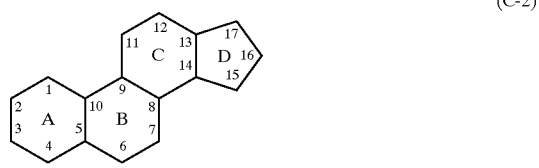

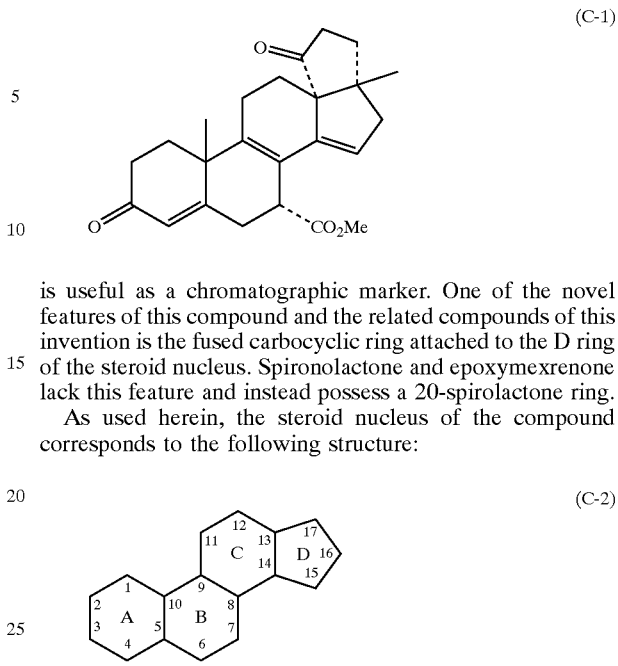

is useful as a chromatographic marker. One of the novel features of this compound and the related compounds of this invention is the fused carbocyclic ring attached to the D ring of the steroid nucleus. Spironolactone and epoxymexrenone lack this feature and instead possess a 20-spirolactone ring.

As used herein, the steroid nucleus of the compound corresponds to the following structure:

(C-2)

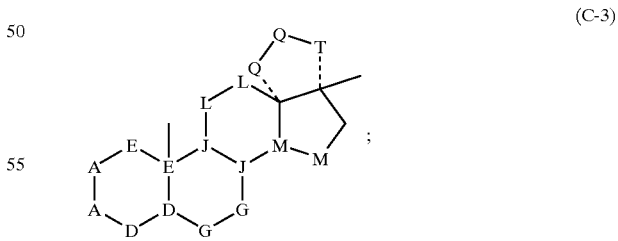

EXAMPLE 61

To 2 g of diketone (prepared in accordance with Example 58) suspended in 30 ml of dry methanol was added 0.34 mL of triethylamine. The suspension was heated at reflux for 4.5 hours. The mixture was stirred at 25° C. for 16 hours. The resulting suspension was filtered to give 1.3 g of the 5-cyanoester as a white solid.

To 6.6 g of the diketone suspended in 80 mL of methanol was added 2.8 mL of triethylamine. The mixture was heated at reflux for 4 hours and was stirred at 25 rpm for 88 hours during which time the product crystallized from solution. Filtration followed by a methanol wash gave 5.8 g of the cyanoester as a white powder. The material was recrystallized from chloroform/methanol to give 3.1 g of crystalline material which was homogeneous by HPLC.

In view of the above, it will be seen that the several objects of the invention are achieved and other advantageous results attained.

As various changes could be made in the above compositions and processes without departing from the scope of the invention, it is intended that all matter contained in the above description and shown in the accompanying drawings shall be interpreted as illustrative and not in a limiting sense.

The Novel Compounds

The present invention is further directed to additional polycyclic organic moieties useful as chromatographic markers in the preparation of steroid compounds having favorable biological activity such as spironolactone or epoxymexrenone.

In brief, it has been discovered that certain compounds comprising a substituted or unsubstituted steroid nucleus and a substituted or unsubstituted carbocyclic ring fused to the 13,17 position of the steroid nucleus can used as internal or chromatographic markers in the preparation of steroids such as spironolactone and epoxymexrenone. In particular, the compound methyl 2,3,3a,4,6,7,9,10,11, 11a,12,13-dodecahydro-3aβ,11aβ-dimethyl-1,9-dioxo-1H-pentaleno[1,6a-a]phenanthrene-6α-carboxylate:

This structure reflects the conventional numbering and ring designation for steroid compounds. The steroid nucleus may be saturated, unsaturated, substituted or unsubstituted. Preferably, it contains at least one to four unsaturated bonds. More preferably, the A, C and D rings each contain at least one unsaturated bond. The steroid nucleus also may be substituted as more specifically discussed below. Preferably, the nucleus is substituted with at least a C7 ester group.

As used herein, the carbocyclic ring fused to the steroid nucleus corresponds to a four, five or six carbon cyclic skeleton. It may be saturated, unsaturated, substituted or unsubstituted. Preferably, it is saturated or has one double bond, and it is substituted with a hydroxy or keto group. In addition, the carbocyclic ring preferably has the α-orientation relative to the steroid nucleus.

In a preferred embodiment, the carbocyclic ring comprises a five carbon cyclic skeleton and has the α-orientation, and the compound is selected from the group consisting of those compounds corresponding to the following formulae:

(C-3)

wherein
—A—A— represents the group —$CR^{102}R^{102a}$—$CR^{103}R^{103a}$— or —$CR^{102}$=$CR^{103}$—, wherein —$CR^{102}R^{102a}$— and —$CR^{102}$= correspond to the C2 carbon, and —$CR^{103}R^{103a}$— and =$CR^{103}$— correspond to the C3 carbon;
—D—D— represents the group —$CHR^{104}$—CH— or —$CR^{104}$=C—;

—E—E— represents the group —CH$_2$—CR$^{110}$— or —CH=C—;

—A—E— represents the group —CR$^{102}$R$^{102a}$—CH$_2$— or —CR$^{102}$=CH, wherein —CR$^{102}$R$^{102a}$— and —CR$^{102}$= correspond to the C2 carbon and —CH$_2$— and =CH— correspond to the C1 carbon;

—G—G— represents the group —CR$^{106}$R$^{106a}$—CHR$^{107}$— or —CR$^{106}$=CR$^{107}$—, wherein —CR$^{106}$R$^{106a}$— and —CR$^{106}$= correspond to the C6 carbon and —CHR$^{107}$— and =CR$^{107}$— correspond to the C7 carbon;

—J—J— represents the group —CR$^{108}$—CR$^{109}$— or —C=C—, wherein —CR$^{108}$— corresponds to the C8 carbon and —CR$^{109}$— corresponds to the C9 carbon;

—L—L— represents the group —CR$^{111}$R$^{111a}$—CH$_2$— or —CR$^{111}$=CH—, wherein —CR$^{111}$R$^{111a}$— and —CR$^{111}$= correspond to the C11 carbon and —CHR$^2$— and =CH— correspond to the C12 carbon;

—J—L— represents the group —CR$^{109}$—CR$^{111}$R$^{111a}$— or —C=CR$^{111}$—, wherein —CR$^{109}$— and —C= correspond to the C9 carbon, and —CR$^{111}$R$^{111a}$— and —CR$^{111}$— correspond to the C11 carbon;

—M—M— represents the group —CR$^{114}$—CH$_2$— or —C=CH—, wherein —CR$^{114}$— and —C= correspond to the C14 carbon, and —CH$_2$— and —C=H— correspond to the C15 carbon;

—J—M— represents the group —CR$^{108}$—CR$^{114}$— or —C=C—, wherein —CR$^{108}$— corresponds to the C8 carbon and —CR$^{114}$— corresponds to the C14 carbon;

—Q—Q— represents the group —CR$^{120}$R$^{120a}$—CR$^{119}$R$^{119a}$— or —CR$^{120}$=CR$^{119}$—, wherein —CR$^{120}$R$^{120a}$— and —CR$^{120}$=CR$^{119}$— correspond to the C20 carbon, and —CR$^{119}$R$^{119a}$— and =CR$^{119}$— correspond to the C19 carbon;

—Q— T—represents the group —CR$^{119}$R$^{119a}$—CHR$^{118}$— or —CR$^{119}$=CR$^{118}$—, wherein —CR$^{119}$R$^{119a}$— and —CR$^{119}$= correspond to the C19 carbon, and —CHR$^{118}$— and =CR$^{118}$— correspond to the C18 carbon;

R$^{102}$ is hydrogen, alkyl, alkenyl or alkynyl;

R$^{102a}$ is hydrogen; or represents a bond between the C2 carbon atom and the C3 carbon atom when —A—A— represents the group —CR$^{102}$=CR$^{103}$— and —A—E— represents the group —CR$^{102}$R$^{102a}$—CH$_2$—; or represents a bond between the C1 carbon atom and the C2 carbon atom when —A—E— represents the group —CR$^{102}$=CH— and —A—A— represents the group —CR$^{102}$R$^{102a}$—CR$^{103}$R$^{103a}$—;

R$^{103}$ is hydrogen, hydroxy, protected hydroxy, R$^{130}$O—, R$^{130}$C(O)O—, R$^{130}$OC(O)O—, or together with R$^{103a}$ forms an oxo; provided that —A—A— is —CR$^{102}$R$^{102a}$—CR$^{103}$R$^{103a}$— when R$^{103}$ together with R$^{103a}$ form an oxo;

R$^{103a}$ is hydrogen or together with R$^{103}$ forms an oxo; provided that —A—A— is —CR$^{102}$R$^{102a}$—CR$^{103}$R$^{103a}$— when R$^{103a}$ together with R$^{103}$ form an oxo;

R$^{104}$ is hydrogen, alkyl, alkenyl or alkynyl;

R$^{106}$ is hydrogen, hydroxy or protected hydroxy, or together with R$^{106a}$ forms an oxo, or together with R$^{106a}$ and the carbon atom to which they are attached form a cyclopropyl, cyclobutyl or cyclopentyl ring; provided that —G—G— is —CR$^{106}$R$^{106a}$—CR$^{107}$R$^{107a}$— when R$^{106}$ together with R$^{106a}$ form an oxo;

R$^{106a}$ is hydrogen, hydroxy or protected hydroxy, or together with R$^{106a}$ forms an oxo, or together with R$^{106}$ and the carbon atom to which they are attached form a cyclopropyl, cyclobutyl or cyclopentyl ring, or R$^{106a}$ together with R$^{107}$ and the carbon atoms to which they are attached form a cyclopropyl, cyclobutyl or cyclopentyl ring;

R$^{107}$ is hydrogen; hydroxycarbonyl; lower alkyl, alkenyl, alkynyl, aryl, heteroaryl or aralkyl; haloalkyl; hydroxyalkyl; alkoxyalkyl; lower alkanoyl, alkenoyl, alkynoyl, aryloyl, heteroaryloyl or aralkanoyl; lower alkoxycarbonyl, alkenoxycarbonyl, alkynoxycarbonyl, aryloxycarbonyl, heteroaryloxycarbonyl or aralkoxycarbonyl; lower alkanoylthio, alkenoylthio, alkynoylthio, aryloylthio, heteraroylthio or aralkanoylthio; lower alkylthio, alkenylthio, alkynylthio, arylthio, heteroarylthio or aralkylthio; carbamyl; alkoxycarbonylamino; or cyano; or R$^{107}$ together with R$^{106a}$ and the carbon atoms to which they are attached form a cyclopropyl, cyclobutyl or cyclopentyl ring; or R$^{107}$ and R$^{114}$ together with the C7, C8 and C14 carbon atoms form a γ-lactone;

R$^{108}$ is hydrogen, hydroxy, protected hydroxy, alkyl, alkenyl, alkynyl, R$^{140}$O—, R$^{140}$C(O)O—, or R$^{140}$OC(O)O—; or represents a bond between the C8 carbon atom and the C9 carbon atom when —J—J— represents the group —C=C— and —J—M— represents the group —CR$^{108}$—CR$^{114}$—; or represents a bond between the C8 carbon atom and the C14 carbon atom when —J—M— represents the group —C=C— and —J—J— represents the group —CR$^{108}$—CR$^{114}$—;

R$^{109}$ is hydrogen, hydroxy, protected hydroxy, alkyl, alkenyl, alkynyl, R$^{150}$O—, R$^{150}$C(O)O—, or R$^{150}$OC(O)O—; or represents a bond between the C9 carbon atom and the C11 carbon atom when —J—L— represents the group —C=CR$^{111}$— and —J—J— represents the group —CR$^{108}$—CR$^{109}$—; or represents a bond between the C9 carbon atom and the C8 carbon atom when —J—J— represents the group —C=C— and —J—L— represents the group —CR$^{109}$—CR$^{111a}$—;

R$^{110}$ is hydrogen or methyl;

R$^{111}$ is hydrogen, hydroxy or protected hydroxy, or together with R$^{111a}$ form an oxo, provided that —J—L— represents the group —CR$^{109}$—CR$^{111}$R$^{111a}$— and —L—L— represents the group —CR$^{111}$R$^{111a}$—CH$_2$— when R$^{111}$ together with R$^{111a}$ form an oxo;

R$^{111a}$ is hydrogen, or together with R$^{111}$ form an oxo, provided that —J—L— represents the group —CR$^{109}$—CR$^{111}$R$^{111a}$— and —L—L— represents the group —CR$^{111}$R$^{111a}$—CH$_2$— when R$^{111a}$ together with R$^{111}$ form an oxo; or R$^{111a}$ represents a bond between the C11 carbon atom and the C9 carbon atom when —J—L— represents the group —C=CR$^{111}$— and —L—L— represents the group —CR$^{111}$R$^{111a}$—CH$_2$—; or R$^{111a}$ represents a bond between the C11 carbon atom and the C12 carbon atom when —L—L— represents the group —CR$^{111}$=CH— and —J—L— represents the group —CR$^{109}$R$^{109a}$—CR$^{111}$R$^{111a}$—;

R$^{114}$ is hydrogen, hydroxy, protected hydroxy, alkyl, alkenyl, alkynyl, R$^{160}$O—, R$^{160}$C(O)O—, or R$^{160}$OC(O)O—; or R$^{114}$ and R$^{107}$ together with the C7, C8 and C14 carbons form a γ-lactone; or R$^{114}$ represents a bond between the C14 carbon atom and the C8 carbon atom when —J—M— represents the group —C=C— and —M—M— represents the group —CR$^{114}$—CH$_2$—; or R$^{114}$ represents a bond between the C14 carbon atom and the C15 carbon atom when —M—M— represents the group —C=CH— and —J—M— represents the group —CR$^{108}$—CR$^{114}$—;

R$^{118}$ is hydrogen, alkyl, alkenyl, alkynyl, aryl, heteroaryl, alkylthio, alkenylthio or cyano;

R$^{118a}$ is hydrogen, or represents a bond between the C18 carbon atom and the C19 carbon atom when —Q—T— represents the group —CR$^{118}$=CR$^{119}$— and —Q—Q— represents the group —CR$^{119}$R$^{119a}$—CR$^{120}$R$^{120a}$—;

R$^{119}$ is hydrogen, alkyl or alkenyl;

R$^{119a}$ is hydrogen, or represents a bond between the C19 carbon atom and the C20 carbon atom when —Q—Q— represents the group —CR$^{120}$=CR$^{119}$— and —Q—T— represents the group —CR$^{119}$R$^{119a}$—CR$^{118}$R$^{118a}$—; or represents a bond between the C19 carbon atom and the C18 carbon atom when —Q—T— represents —CR$^{119}$=CR$^{118}$— and —Q—Q— represents the group —CR$^{119}$R$^{119a}$—CR$^{120}$R$^{120a}$—;

R$^{120}$ is hydrogen, hydroxy, protected hydroxy, or together with R$^{120a}$ forms an oxo; provided that —Q—Q— represents the group —CR$^{119}$R$^{119a}$—CR$^{120}$R$^{120a}$ when R$^{120}$ together with R$^{120a}$ form an oxo;

R$^{120a}$ is hydrogen or together with R$^{120}$ form an oxo; provided that —Q—Q— represents the group —CR$^{119}$R$^{119a}$—CR$^{120}$R$^{120a}$ when R$^{120a}$ together with R$^{120}$ forms an oxo; and R$^{130}$, R$^{140}$, R$^{150}$ and R$^{160}$ are independently alkyl, alkenyl, alkynyl, aryl or heteroaryl.

More preferably, the compound corresponds to the compound of Formula C-3 wherein R$^{107}$ is hydrogen, hydroxycarbonyl, lower alkyl, lower alkanoyl, lower alkoxycarbonyl, lower alkanoylthio, lower alkylthio, carbamyl, or R$^{107}$ together with R$^{106a}$ and the carbon atoms to which they are attached form a cyclopropyl ring; R$^{106}$ is hydrogen, hydroxy, or together with R$^{106a}$ and the carbon atom to which they are attached form a cyclopropyl ring; R$^{106a}$ is hydrogen, hydroxy, or together with R$^{106}$ and the carbon atom to which they are attached form a cyclopropyl ring; or R$^{106a}$ together with R$^{107}$ and the carbon atoms to which they are attached form a cyclopropyl ring; and R$^{120}$ is keto.

The following definitions apply to the discussion relating to the 13,17-fused ring compounds disclosed in the present specification:

The term "lower alkyl" means an alkyl radical having from 1 to 6 carbon atoms, such as methyl, ethyl, propyl, isopropyl, butyl, isobutyl, sec.-butyl and tert.-butyl, pentyl and hexyl. The radical may be straight, branched chain or cyclic and substituted (particularly with aryl), unsubstituted or heterosubstituted.

The term "lower alkanoyl" means a radical preferably derived from a straight-chain alkyl having from 1 to 7 carbon atoms and attached to the parent molecular moiety via a carbonyl group. Especially preferred are formyl and acetyl.

The term "lower alkoxycarbonyl" means a radical preferably derived from a straight-chain alkyl having from 1 to 7 carbon atoms and attached to an oxygen atom, said oxygen atom being attached to the parent molecular moiety via a carbonyl group. Especially preferred are methoxycarbonyl, ethoxycarbonyl, isopropoxycarbonyl and n-hexyloxycarbonyl.

The term "lower alkenyl" means an alkenyl radical having from 2 to 6 carbon atoms, such as ethenyl, propenyl, isopropenyl, butenyl, isobutenyl, sec.-butenyl and tert.-butenyl, pentenyl and hexenyl. The radical may be straight or branched chain and substituted, unsubstituted or heterosubstituted. The terms "lower alkenoyl" and "lower alkenoxycarbonyl" are defined in the same manner as "lower alkanoyl" and "lower alkoxycarbonyl", respectively, except that they are derived from straight chain alkenyl instead of straight chain alkyl. Preferably, the oxygen attached to the alkenyl radical of any alkenoxycarbonyl group is separated from any unsaturated carbon by at least one methylene group.

The term "lower alkynyl" means an alkynyl radical having from 2 to 6 carbon atoms, such as ethynyl, propynyl, isopropynyl, butynyl, isobutynyl, sec.-butynyl and tert.-butynyl, pentynyl and hexynyl. The radical may be straight or branched chain and substituted, unsubstituted or heterosubstituted. The terms "lower alkynoyl" and "lower alkynoxycarbonyl" are defined in the same manner as "lower alkanoyl" and "lower alkoxycarbonyl", respectively, except that they are derived from straight chain alkynyl instead of straight chain alkyl. Preferably, the oxygen attached to the alkynyl radical of any alkynoxycarbonyl group is separated from any unsaturated carbon by at least one methylene group.

An "aryl" moiety preferably contains, either alone or with various substituents, from 5 to 15 atoms and includes phenyl.

The term "lower alkylthio" means a radical preferably derived from a straight-chain alkyl having from 1 to 7 carbon atoms and attached to the parent molecular moiety via a sulfur atom. Especially preferred is methylthio.

The term "lower alkanoylthio" means a radical preferably derived from a straight-chain alkyl having from 1 to 7 carbon atoms and attached to a carbonyl group, said carbonyl group being attached to the parent molecular moiety via a sulfur atom. Especially preferred is acetylthio.

The terms "lower alkenylthio" and "lower alkenoylthio" are defined in the same manner as "lower alkylthio" and "lower alkanoylthio", respectively, except that they are derived from straight chain alkenyl instead of straight chain alkyl. Preferably, the sulfur atom of any alkenylthio group is separated from any unsaturated carbon by at least one methylene group.

The terms "lower alkynylthio" and "lower alkynoylthio" are defined in the same manner as "lower alkylthio" and "lower alkanoylthio", respectively, except that they are derived from straight chain alkynyl instead of straight chain alkyl. Preferably, the sulfur atom of any alkynylthio group is separated from any unsaturated carbon by at least one methylene group.

The term "carbamyl" means an —NH$_2$ radical attached to the parent molecular moiety via a carbonyl group. The carbamyl group may be mono-substituted or di-substituted and the substituents may include alkyl, alkenyl, alkynyl and aryl radicals.

The groups defined above may be unsubstituted or additionally substituted. Such additional substituents can include alkyl, alkenyl, alkynyl, aryl, heteroaryl, carboxy such as alkoxy, carboxyalkyl, acyl, acyloxy, halo such as chloro or fluoro, haloalkoxy, nitro, amino, amido, and keto. The groups defined above, as well as the additional substituents, also may contain oxygen, sulfur, phosphorus and/or nitrogen.

As used herein, "Me" means methyl; "Et" means ethyl; and "Ac" means acetyl.

In a still more preferred embodiment, the compound is selected from the group consisting of compounds having the following formulae:
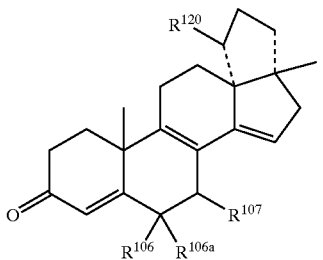
(C-5)
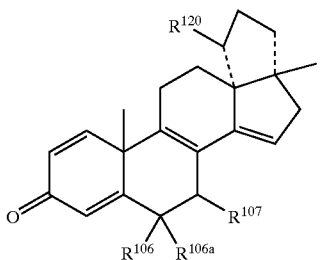
(C-6)
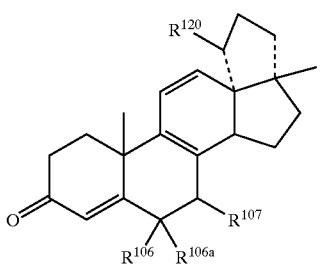
(C-7)
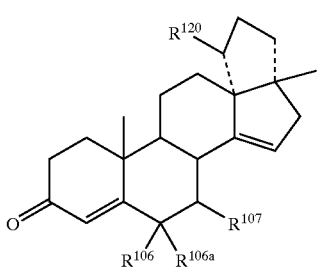
(C-8)
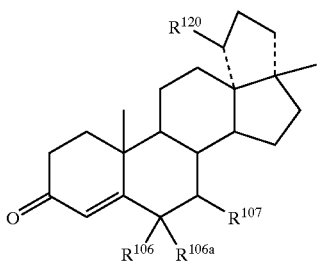
(C-9)
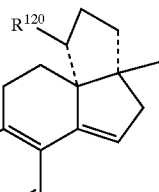
(C-10)
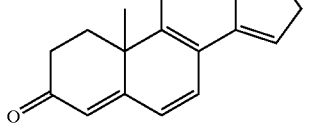
(C-11)
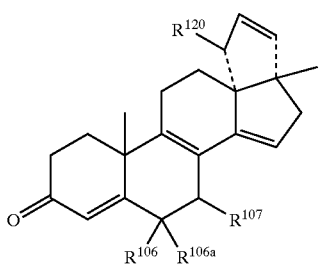
(C-12)
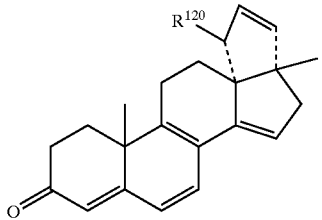
(C-13a)
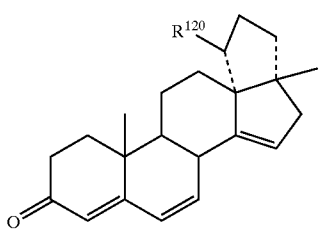
(C-13b)
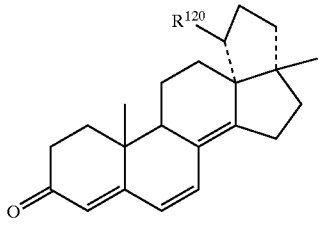
(C-13c)
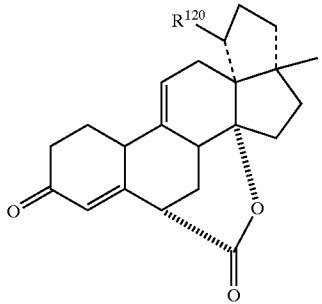

(C-13d)

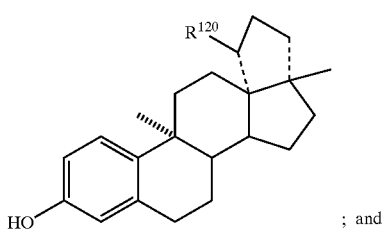

; and (C-13e)

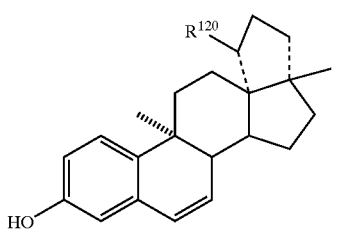

wherein $R^{107}$, $R^{106}$, $R^{106a}$ and $R^{120}$ are as defined above. Preferably, $R^{107}$ is hydrogen, hydroxycarbonyl, lower alkyl, lower alkanoyl, lower alkoxycarbonyl, lower alkanoylthio, lower alkylthio, carbamyl, or together with $R^{106a}$ and the carbon atoms to which they are attached form a cyclopropyl ring; $R^{106}$ is hydrogen, hydroxy, or together with $R^{106a}$ and the carbon atom to which they are attached form a cyclopropyl ring; $R^{106a}$ is hydrogen, hydroxy, or together with $R^{106}$ and the carbon atom to which they are attached form a cyclopropyl ring; or together with $R^{107}$ and the carbon atoms to which they are attached form a cyclopropyl ring; and $R^{120}$ is keto. Still more preferably, the compound further corresponds to the compound of Formula C-5.

In an even more preferred embodiment, the compound of Formula C-3 is selected from the group consisting of the following compounds:

(C-14)

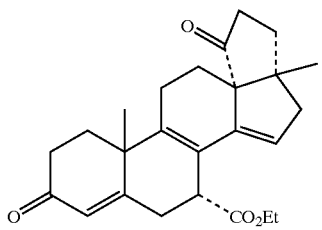

ethyl 3′,4′,5′,17-tetrahydro-17β–methyl-
3,5′-dioxocyclopenta [13R, 17]-18-norandrosta-
4,8,14-triene-7α-carboxylate (C-15)

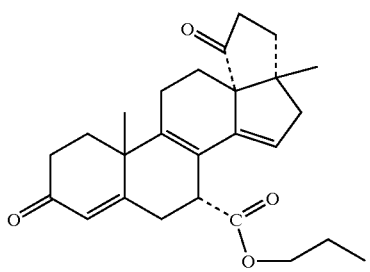

propyl 3′,4′,5′,17-tetrahydro-17β-methyl-3,5′-
dioxocyclopenta [13R, 17]-18-norandrosta-
4,8,14-triene-7α-carboxylate (C-16)

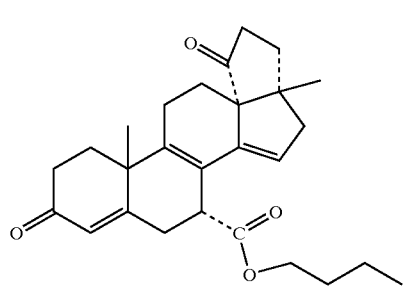

butyl 3′,4′,5′,17-tetrahydro-17β-methyl-
3,5′-dioxocyclopenta [13R,17]-18-norandrosta-
4,8,14-triene-7α-carboxylate (C-17)

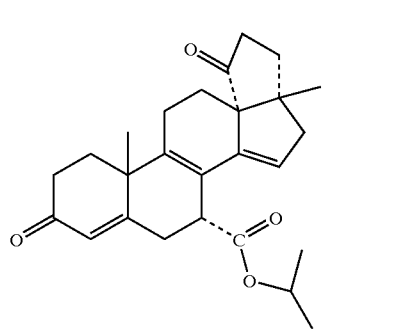

1-methylethyl 3′,4′,5′,17-tetrahydro-17β-methyl-3,5′-
dioxocyclopenta [13R,17]-18-norandrosta-4,8,14-
triene-7α-carboxylate (C-18)

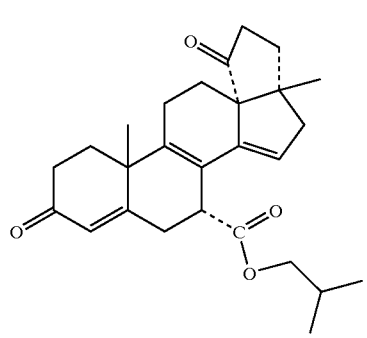

2-methylpropyl 3′,4′,5′,17-tetrahydro-
17β-methyl-3,5′-dioxocyclopenta [13R,17]-
18-norandrosta-4,8,14-triene-7α-carboxylate (C-19)

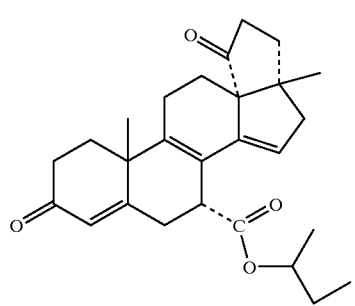

1-methylpropyl 3′,4′,5′,17-tetrahydro-17β-methyl-3,5′-
dioxocyclopenta [13R,17]-18-norandrosta-4,8,14-triene-7α-
carboxylate

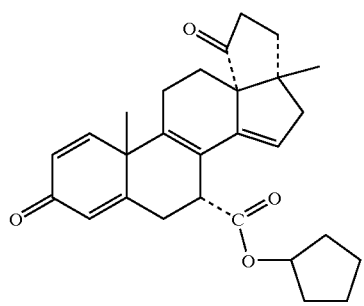

cyclopentyl 3',4',5',17-tetrahydro-17β-methyl-
3,5'-dioxocyclopenta [13R,17]-18-norandrosta-
1,4,8,14-tetraene-7α-carboxylate (C-20)

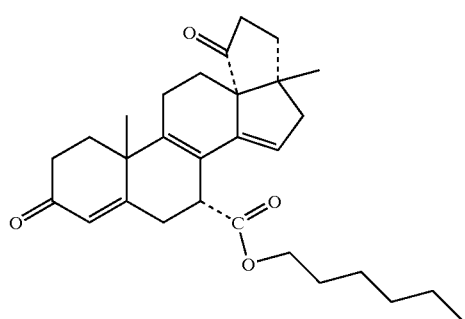

hexyl 3',4',5',17-tetrahydro-17β-methyl-3,5'-
dioxocyclopenta [13R,17]-18-norandrosta-4,
8,14-triene-7α-carboxylate (C-21)

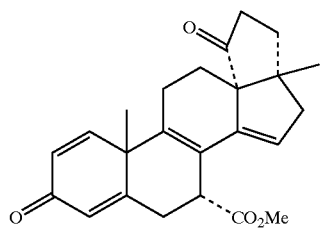

methyl 3',4',5',17-tetrahydro-17β-methyl
3,5'-dioxocyclopenta [13R,17]-18-norandrosta-
1,4,8,14-tetraene-7α-carboxylate (C-22)

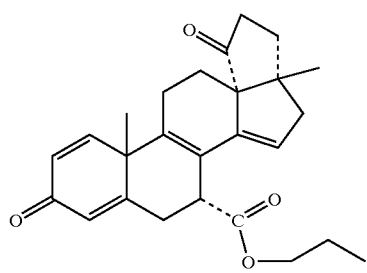

propyl 3',4',5',17-tetrahydro-17β-methyl-3,5'-
dioxocyclopenta [13R,17]-18-norandrosta-1,4,8,14-
tetraene-7α-carboxylate (C-23)

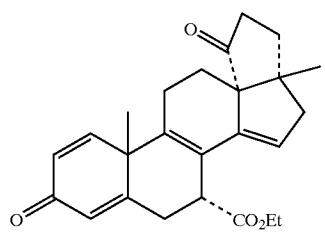

ethyl 3',4',5',17-tetrahydro-17β-methyl
3,5'-dioxocyclopenta [13R,17]-18-norandrosta-
1,4,8,14-tetraene-7α-carboxylate (C-24)

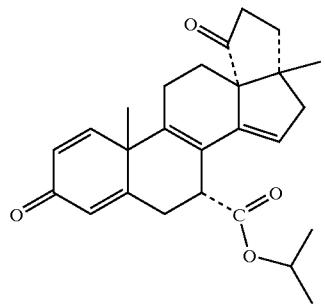

1-methylethyl 3',4',5',17-tetrahydro-17β-methyl-3,5'-
dioxocyclopenta [13R,17]-18 norandrosta-1,4,8,14-
tetraene-7α-carboxylate (C-25)

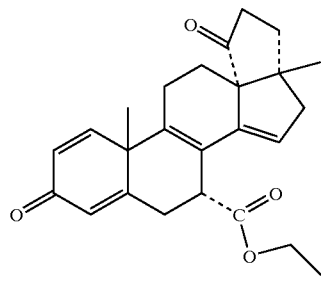

butyl 3',4',5',17-tetrahydro-17β-methyl3,5'-dioxocyclopenta
[13R,17]-18-norandrosta-1,4,8,14-tetraene-7α-carboxylate (C-26)

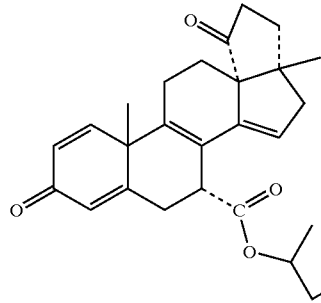

1-methylpropyl 3',4',5',17-tetrahydro-17β-methyl-3,5'-
dioxocyclopenta [13R,17]-18- norandrosta-1,4,8,14-
tetraene-7α-carboxylate (C-27)

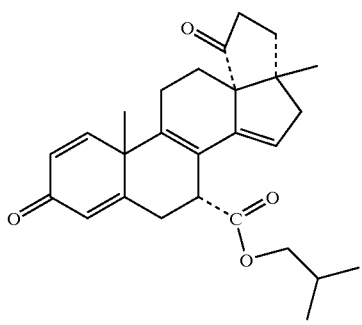

2-methylpropyl3',4',5',17-tetrahydro-17β-methyl 3,5'-dioxocyclopenta [13R,17]-18-norandrosta-1,4,8,14-tetraene-7α-carboxylate (C-28)

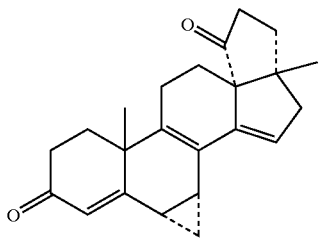

1,2,4bS(4bR*),5,5aS*,8,9,11,12,12bR*-dodecahydro-7a,12b-dimethyl-10aS*-cy-clopropal [1]pentaleno[1,6a-a] phenanthrene-3,10-dione (C-32)

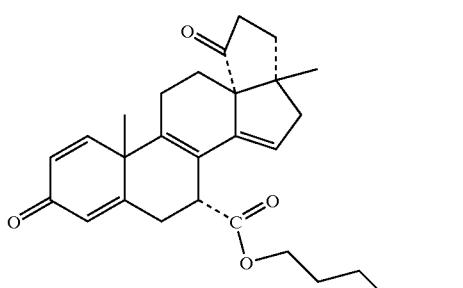

hexyl 3',4',5',17-tetrahydro-17β-methyl-3,5'-dioxocyclopenta [13R,17]-18- norandrosta-1,4,8,14-tetraene-7α-carboxylate (C-29)

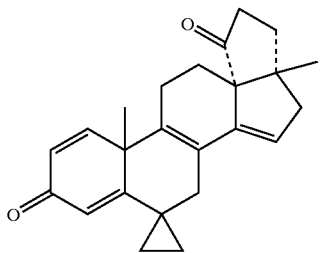

2',3',3'aα,4',6',11'aα,12',13'-octahydro-3'aR, 3'a,11'a-dimethyl-13'aR*-spiro[cyclopropane-1,7'(9'H)-[1H]pentaleno[1,6,a-a]phenanthrene-1',9'-dione (C-33)

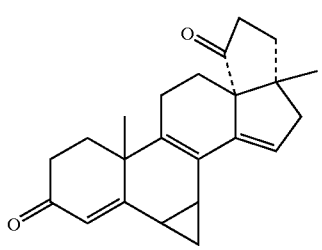

1,2,4bR(4bR*),5,5aS*,7,7aR*,8,9,11,12bS*-dodecahydro-7a,12b-dimethyl-10aR*-cyclo-propal[1] pentaleno[1,6a-a]phenanthrene-3,10-dione (C-30)

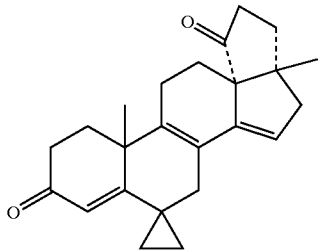

2',3',3'aα, 4',6',10',11',11'aα,12',13'-decahydro-3'aR,3'a,11'a-dimethyl-13'aR*-spiro[cyclopropane-1,7'(9'H)-[1H]pentaleno[1,6a-a]phenanthrene]-1',9'-dione (C-34)

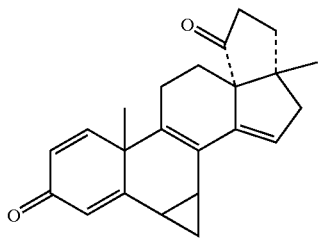

4bR(4bR*),5,5aS*,7,7aR*,8,9,11,12,12bS*-decahydro-7A,12b-dimethyl-10R*-cyclopropal (1)pentaleno [1,6a- a]phenanthrene-3,10-dione (C-31)

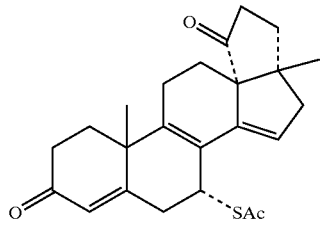

7α-(acetylthio)- 3',4'-dihydro-17-methyl-cyclopenta [13,17]-18-norandrosta-4,8,14-triene-3,5'(2'H)-dione (C-35)

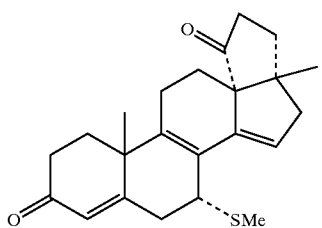

3',4'-dihydro-17-methyl-7α-(methylthio)-cyclopenta
[13,17]-18-norandrosta-4,8,14-triene-3,5'(2'H)-dione

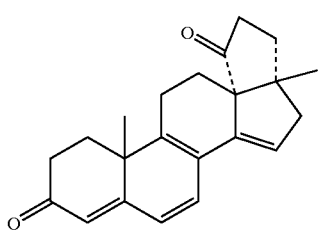

3',4',5,5',6,17-hexahydro-17β-methylcyclopenta
[13R,17]-18-norandrosta-4,8,14-triene-3, 5'(2'H)-dione

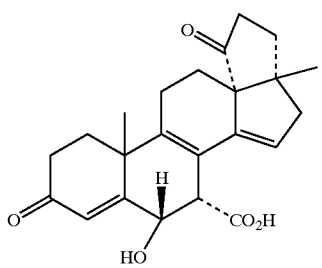

3',4',5',17-tetrahydro-6α,hydroxy-17β-methyl-
3,5'-dioxocyclopenta[13R,17]-18-norandrosta-4,8,14-
triene-7α-carboxylic acid

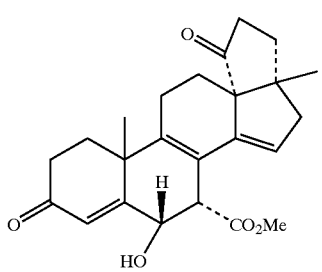

methyl 3',4',5',17-tetrahydro-6α-hydroxy-17β-methyl-
3,5'-dioxocyclopenta [13R,17]-18-norandrosta-4,8,14-
triene-7αcarboxylate

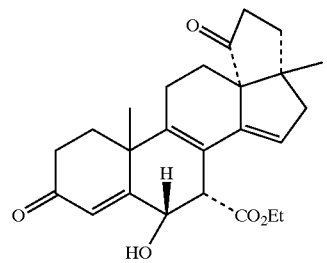

ethyl 3',4',5',17-tetrahydro-6α-hydroxy-17β-methyl-3,5'-
dioxocyclopenta [13,17]-18-norandrosta-4,8,14-
triene-7α-carboxylic acid

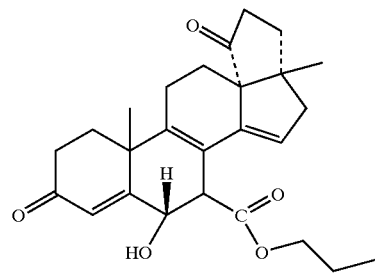

propyl 3',4',5',17-tetrahydro-6α-hydroxy-17β-methyl-3,5'-
dioxocyclopenta[13R,17]-18-norandrosta-4,8,14-triene-7α-
carboxylate

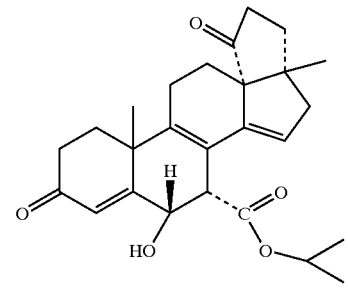

1-methylethyl 3',4',5',17-tetrahydro-6α-hydroxy-17β-methyl-
3,5'-dioxocyclopenta[13R,17]-18-norandrosta-4,8,14-
triene-7α-carboxylate

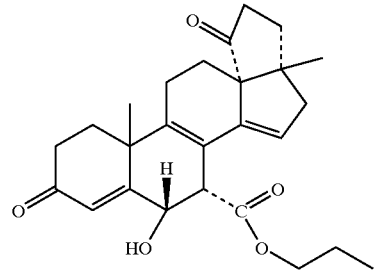

butyl 3',4',5',17-tetrahydro-6α-hydroxy-17β-methyl-3,5'-
dioxocyclopenta [13R,17]-18-norandrosta-4,8,14-triene-7α
carboxylate (C-44)

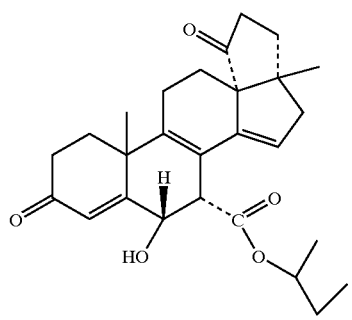

1-methylpropyl 3′,4′,5′,17-tetrahydro-6α-hydroxy-17β-methyl-3,5′-dioxocyclopenta[13R,17]-18-norandrosta-4,8,14-triene-7α-carboxylate (C-45)

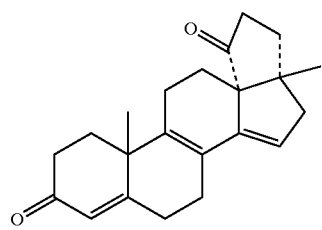

3′,4′,5′,17-tetrahydro-17β-methylcyclopenta[13R,17]-18-norandrosta-4,8,14-triene-3,5′(2′H)-dione (C-46)

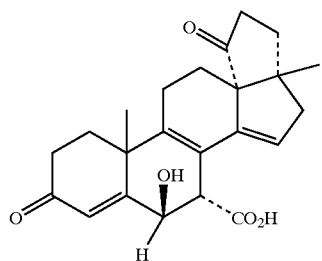

3′,4′,5′,17-tetrahydro-6β-hydroxy-17β-methyl-3,5′-dioxocyclopenta[13R,17]-18-norandrosta-4,8,14-triene-7α-carboxylic acid (C-47)

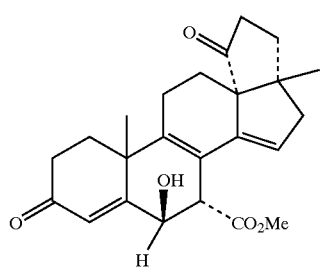

methyl 3′,4′,5′,17-tetrahydro-6β-hydroxy-17β-methyl-3,5′-dioxocyclopenta[13R,17]-18-norandrosta-4,8,14-triene-7α-carboxylate (C-48)

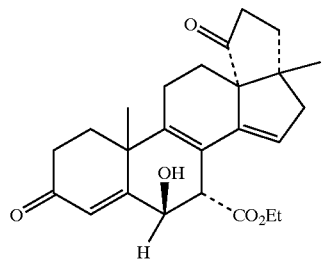

ethyl 3′,4′,5′,17-tetrahydro-6β-hydroxy-17β-methyl-3,5′-dioxocyclopenta[13R,17]-18-norandrosta-4,8,14-triene-7α-carboxylate (C-49)

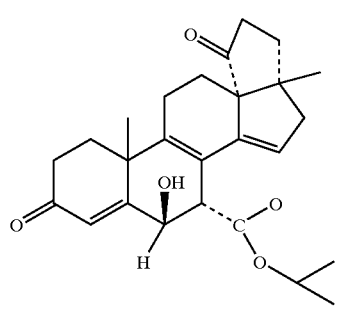

propyl 3′,4′,5′,17-tetrahydro-6β-hydroxy-17β-methyl-3,5′-dioxocyclopenta[13R,17]-18-norandrosta-4,8,14-triene-7α-carboxylate (C-50)

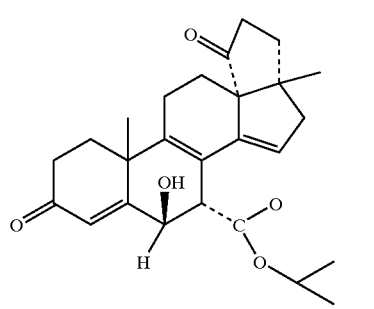

1-methylethyl 3′,4′,5′,17-tetrahydro-6β-hydroxy-17β-methyl-3,5′-dioxocyclopenta[13R,17]-18-norandrosta-4,8,14-triene-7α-carboxylate (C-51)

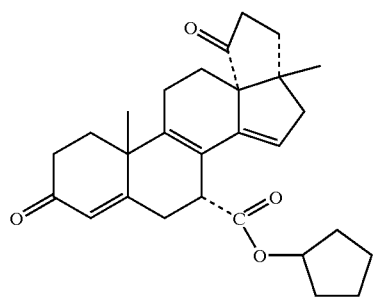

cyclopentyl 3′,4′,5′,17-tetrahydro-17β-methyl-3,5′-dioxocyclopenta[13R,17]-18-norandrosta-4,8,14-triene-7α-carboxylate -continued (C-52)

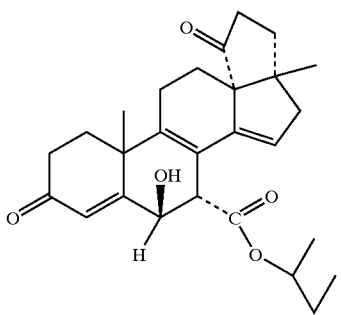

1-methylpropyl3′,4′,5′,17-tetrahydro-6β-hydroxy-17β-
methyl-3,5′-dioxocyclopenta[13R,17]-
18-norandrosta-4,8,14-triene-7α-carboxylate (C-1)

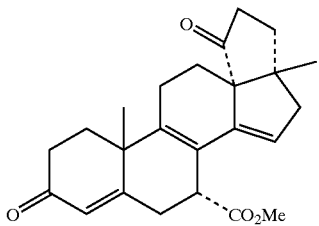

methyl2,2,3a,4,6,7,9,10,11,11a,12,13-dodecahydro-
3αβ,11αβ-dimethyl-1,9-dioxo-1H-pentaleno[1,6a-
a]phenantrene-6α-caboxylate (C-53)

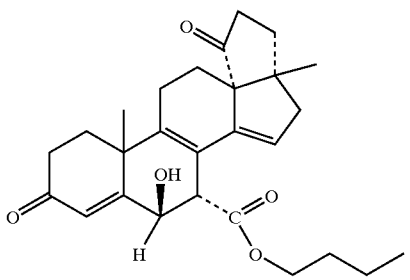

butyl3′,4′,5′,17-tetrahydro-6β-hydroxy-17β-methyl-
3,5′-dioxocyclopenta[13R,17]-18-norandrosta-4,8,14-
triene-7α-carboxylate (C-201)

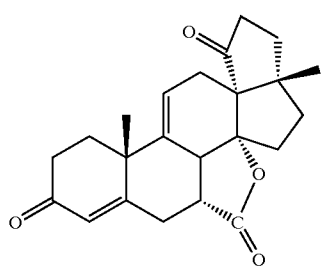

(7α,13R,17β)- 3′,4′,5′,17-tetrahydro-14-hydroxy-17-
methyl-3,5′-dioxo-γ-lactone,cyclopenta[13,17]-18-
norandrosta-4,9(11)-diene-7-carboxylic acid -continued (C-202)

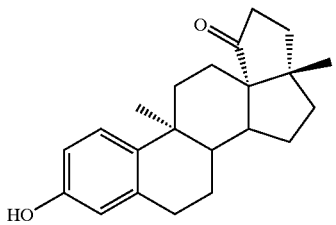

[13S,17β]-3′,4′-dihydro-3-hydroxy-9,17-
imethylcyclopenta[13,17]gona-1,3,5(10)-
triene-5′[2′H]-one (C-203)

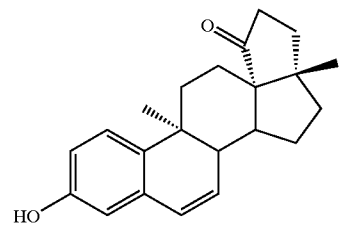

[13S,17β]- 3′,4′ -dihydro-3-hydroxy-9,17-
dimethylcyclopenta [13,17]gona-1,3,5(10),
6-tetraene-5′[2′H]-one (C-204)

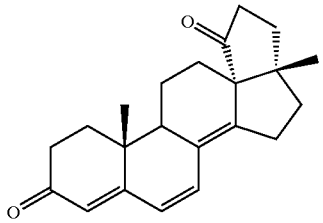

[13S,17β]- 3′,4′-dihydro-17-methyl-cyclopenta[13,17]-
18-norandrosta-4,6,8(14)-triene-3,5′ [2′H]-dione In the most preferred embodiment, the compound is
methyl 2,2,3a,4,6,7,9,10,11,11a,12,13-dodecahydro-3αβ,
11αβ-dimethyl-1,9-dioxo-1H-pentaleno[1,6a-a]
phenantrene-6α-caboxylate:

(C-1)

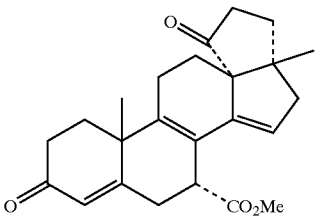

This compound of Formula C-1 is a particularly desirable
chromotographic marker in the preparation of
epoxymexrenone.

The novel compounds discussed herein may also be in the form of their salts.

Preparation of the Novel Compounds

In general, the novel compounds described immediately above may be obtained by reacting a steroid having a 20-spiroxane ring and the steroid nucleus previously described above with a trihalogenated alkanoic acid. Advantageously, the reagent for the reaction further includes an alkali metal salt of the alkanoic acid utilized. It is particularly preferred that the reagent for the reaction comprise trifluoroacetic acid and an alkali metal salt of that acid such as potassium trifluoroacetate. In addition, a drying agent such as trifluoroacetic anhydride preferably is employed in the reaction to reduce free water present in the acid.

The steroid compounds used as starting materials preferably have the following structural formula:

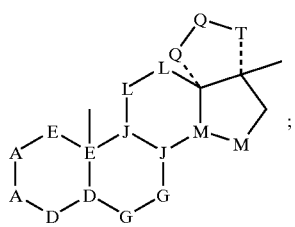

(C-3)

wherein —A—A—, —D—D—, —E—E—, —A—E—, —G—G—, —J—J—, —L—L—, —J—L—, —M—M—, —J—M—, —Q—Q—, and —Q—T— are as defined above. Such starting materials can be prepared and/or isolated by processes analogous to those disclosed in Scheme 1 of the epoxymexrenone synthesis process previously discussed herein. Alternatively, the starting materials are commercially available.

The initial concentration of the steroid compound of formula C-3 is preferably at least about 0.1% by weight of the total reaction mixture, more preferably about 2% to about 20% by weight, and even more preferably about 5% to about 15% by weight. An excess of the trihaloalkanoic acid is preferably present. Where trifluoroacetic anhydride is used, it should be present in a proportion of at least about 3% by weight of the total reaction mixture, more preferably between about 5% to about 25% by weight, most preferably between about 10% and about 15% by weight.

In addition, the reaction temperature should exceed room temperature (22° C.). Preferably, the reaction temperature is between about 40° C. and 100° C., more preferably between about 50° C. and 80° C., still more preferably between about 60° C. and 70° C., and most preferably between about 60° C. and 65° C. Increasing the reaction temperature to about 70° C. or higher increases the amount of the by-product C14 lactone produced in the reaction. The reaction time preferably should be at least about 30 minutes, more preferably between about 30 minutes and about 6 hours, still more preferably between about 45 minutes and about 4 hours, and most preferably between about one hours to two hours. In a preferred embodiment the reaction time is between about one hour to two hours and the reaction temperature is maintained at about 60° C.

Scheme S-1 below illustrates a particularly preferred embodiment of the process:

Scheme S-1

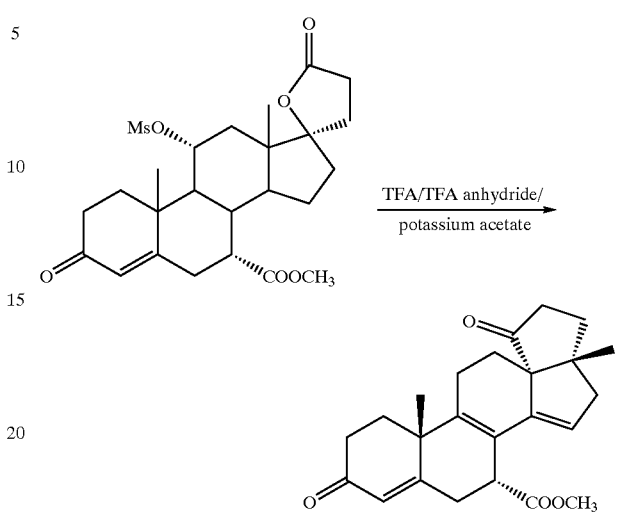

Fused ring steroids having different substituents at various positions throughout the steroid can be prepared as set forth in the reaction schemes below. Those skilled in the art are aware of additional procedures and methods not specifically disclosed herein for introducing various substituents at different positions of the steroid. The starting material may be either a fused ring steroid or a 20-spiroxane ring steroid. To simplify the description where the starting material is a fused ring steroid, the following reaction schemes employ specific steroids or groups of steroids as illustrative starting materials. It should be understood, however, that other fused ring steroid derivatives or analogs may be produced in the same series of reactions by using a different fused ring steroid as the starting material. Similarly, to simplify the description where the starting material is a 20-spiroxane ring steroid, certain specific 20-spiroxane ring steroids are used as the starting materials. It should be understood, however, that other 20-spiroxane ring steroid derivatives or analogs may be produced in the same series of reactions by using a different 20-spiroxane ring steroid as the starting material. Steroids having a C7 carboxylic acid substituent may be prepared by saponification of a steroid having a C7 alkoxycarbonyl substituent such as the compound of Formula C-1. The saponification reaction may be carried out by treatment of the starting steroid with a basic reagent such as sodium or potassium hydroxide in a suitable solvent such as methanol, ethanol, isopropanol or the like at temperatures up to the boiling point of the solvent in the presence or absence of water. As illustrated in Scheme S-2, saponification of the compound of Formula C-1 yields the carboxylic acid of Formula C-101.

Steroids having C7 carboxylic ester substituents other than methanoate can be prepared using carboxylic acids such as C-101 as the starting material. Treatment of such carboxylic acids with an alkylating agent such as an alkyl halide in the presence of a base (such as sodium bicarbonate, sodium carbonate, potassium bicarbonate, or triethylamine) in a solvent such as dimethylformamide yields the desired esters. Examples of suitable alkylating agents are ethyl iodide, ethyl bromide, isopropyl iodide, hexyl iodide, benzyl bromide, allyl iodide, and the like.

Carboxylic acid C-101 is also a suitable starting material for the synthesis of carbamyls. Treatment of the acid with a chloroformate such as isobutyl chloroformate or ethyl chloroformate in the presence of a base yields a mixed anhydride. Treatment of the mixed anhydride with an amine (such as dimethylamine, methylamine or benzylamine) yields the carbamyl wherein $R_1$ and $R_2$ are the substituents on the various amines.

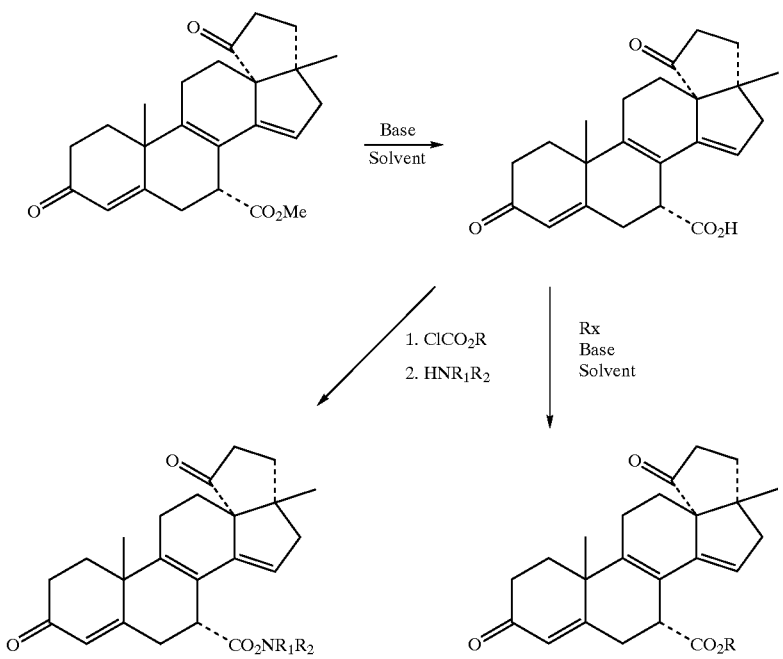

Scheme S-2

Several modifications at the C7 position are made using unsaturated ketones such as the compound of Formula C-105 (shown below in Scheme S-3) as the starting material. Sulfides are synthesized by the addition of suitable thiols under basic conditions. Examples of suitable thiols are methyl mercaptan, ethyl mercaptan and the like. Suitable bases include piperidine, triethylamine and the like.

Treatment of unsaturated ketones (such as the compound of Formula C-105) with thioalkanoic acids such as thioacetic acid provides C7 thioacyl compounds such as acetylthio.

A fused C6,C7 cyclopropyl substituent may be added is by treatment of unsaturated ketones (such as the compound of Formula C-105) with dimethylsulfoxonium methylide, which is generated by treatment of trimethylsulfoxonium halide with a suitable base (such as sodium hydride) in a suitable solvent.

These various synthesis schemes are illustrated in Scheme S-3 below:

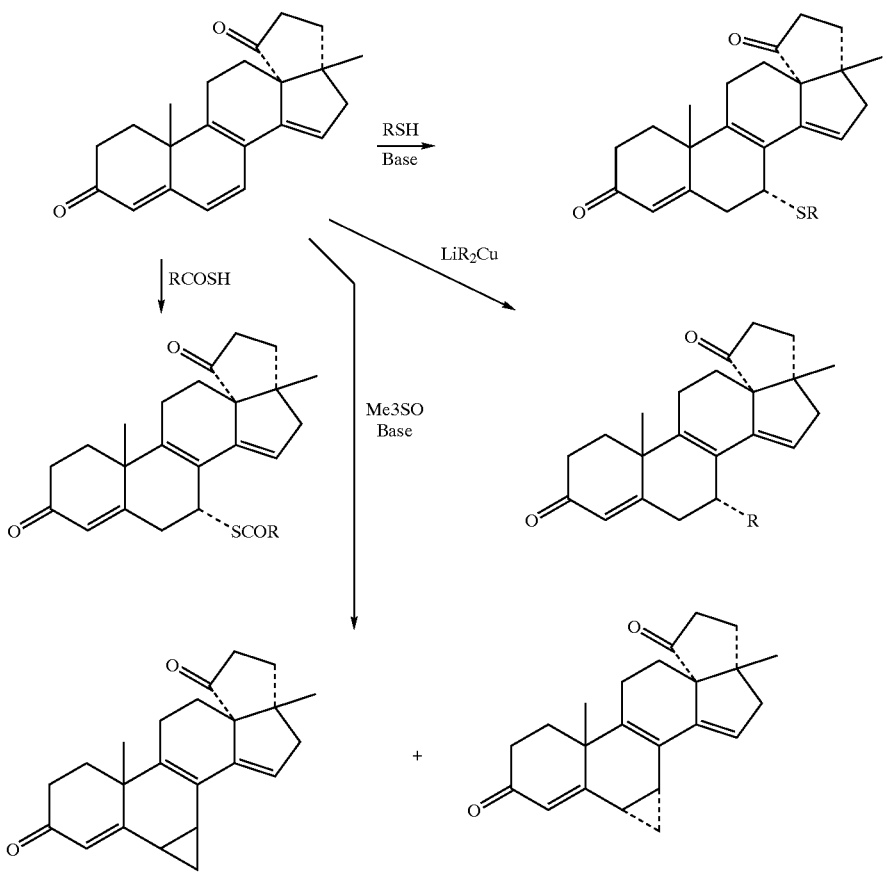

Steroids bearing a C6 spirocyclopropyl ring are synthesized according to the procedures described in Scheme S-4 below. Enones such as the compound of Formula C-110 are first protected as a C3 enol ether by treatment with an ortho ester such as triethyl orthoformate or trimethyl orthoformate in the presence of an acid such as p-toluenesulfonic acid. The resultant enol ether is treated with Vilsmeier reagent generated in situ by addition of phosphorous oxychloride to dimethylformamide to provide a formyl compound such as the compound of Formula C-112. Reduction of the formyl group is effected using a hydride reducing agent, such as lithium tri-tert-butoxyaluminum hydride, in a solvent such as tetrahydrofuran. This produces an intermediate alcohol, which upon treatment with acid, eliminates water to provide a 6-methylene compound such as the compound of Formula C-113. Suitable acids include hydrochloric acid in an aqueous medium. Treatment of the 6-methylene compound with diazomethane provides an intermediate pyrazoline, which decomposes upon heating to give a product spirocyclopropyl compound such as the compound of Formula C-114. The protected enol ether (such as the compound of Formula C-111) is a versatile intermediate and treatment with a hydride reducing agent such as sodium borohydride, followed by acid hydrolysis, provides hydroxy compounds such as the compounds of Formulae C-115 and C-116.

These various synthesis steps are illustrated in Scheme S-4 below:
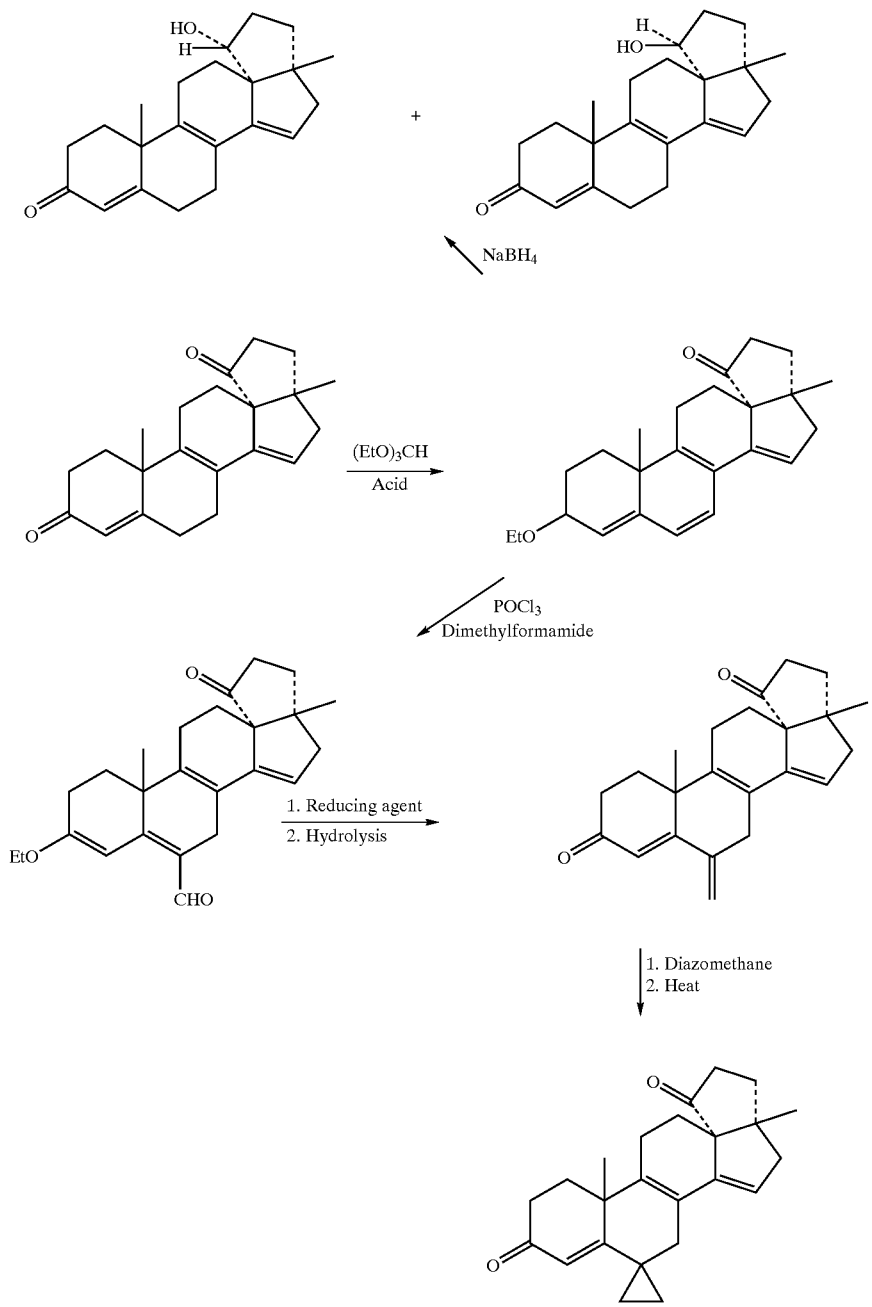

Steroids having a C6 hydroxy substituent and a C7 ester substituent may be synthesized according to the procedures illustrated below in Scheme S-5. An ester (such as the compound of Formula C-1) is protected at the C3 carbonyl by formation of the 3,5-dienol ether (such as the compound of Formula C-117) using an ortho ester such as triethyl orthoformate or trimethyl orthoformate in the presence of an acid. A suitable acid is p-toluene sulfonic acid. Treatment of the enol ether with an oxidizing agent such as meta-chloroperoxybenzoic acid results in the formation of a hydroxy compound such as the compound of Formula C-118.

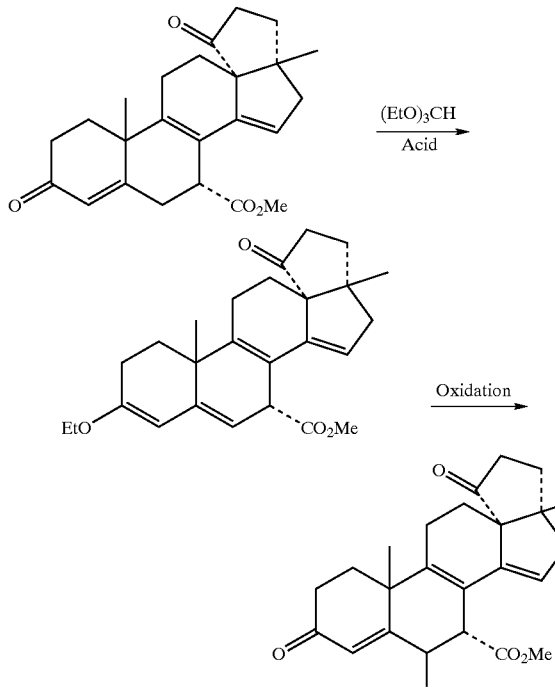

Scheme S-6 illustrates the introduction of a double bond at C1–C2 position of the steroid. This is carried out by treatment of the desired steroid (such as the compounds of Formulae C-1; C-108 and C-114), with a suitable oxidizing agent, such as dichlorodicyanobenzoquinone in a suitable solvent (such as dioxane) at temperatures ranging up to the boiling point. C1–C2 unsaturated compounds such as the compounds of Formulae C-127, C-128 and C-129 can be prepared in accordance with this procedure.

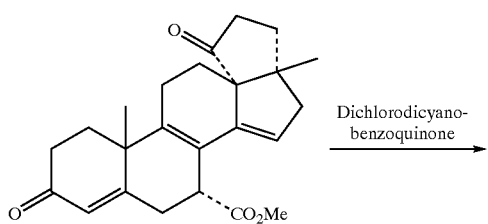

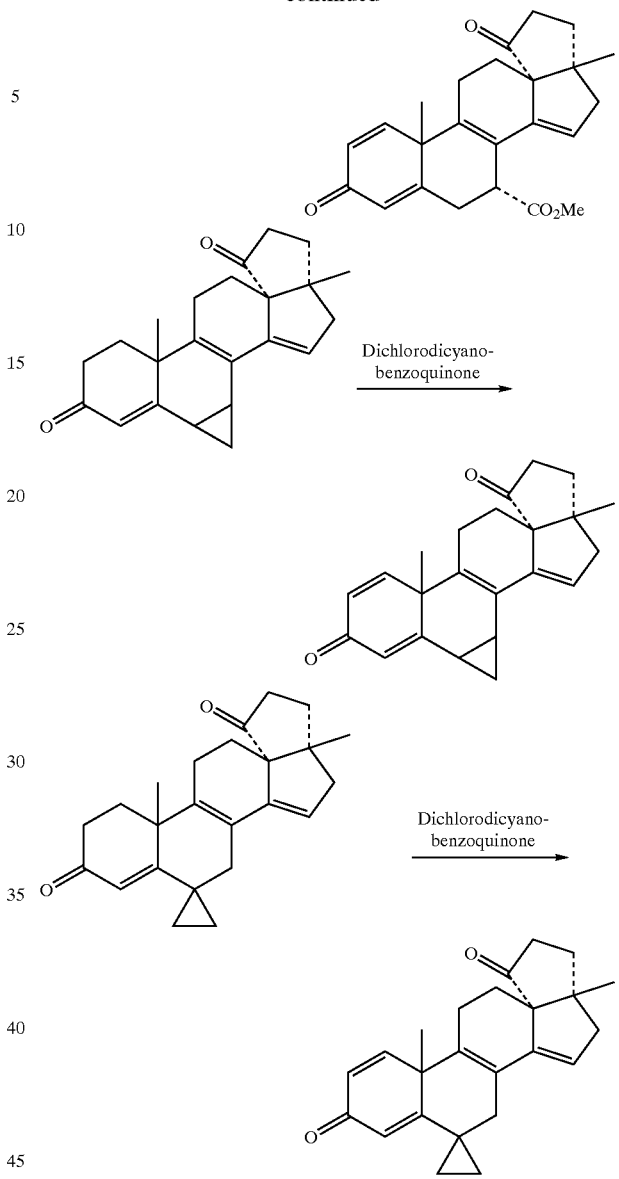

Scheme S-7 illustrates the introduction of a double bond into the fused ring. A steroid (such as the compound of Formula C-114) is treated with an ortho ester (such as triethyl orthoformate or trimethyl orthoformate) in the presence of an acid catalyst (such as p-toluensulfonic acid) to give the enol ether wherein the C3 carbonyl is protected. In the case of the compound of Formula C-114, because the C6 position is fully substituted, the enol ether formed is the C2–C3 enol ether (such as the compound of Formula C-131). Treatment of the enol ether with a strong base such as lithium diisopropylamide at low temperature (−78° C. to −30° C.), followed by treatment with a selenating agent, such as phenyl selenenyl chloride, gives the seleno derivative such as the compound of Formula C-132. Oxidation of the seleno derivative with an oxidizing agent such as hydrogen peroxide at, for example, room temperature in the presence of a base such as pyridine in a solvent such as methylene chloride, causes the elimination of the seleno group and introduction of the double bond. Hydrolysis of the enol ether gives a ketone such as the compound of Formula C-134.

Scheme S-7

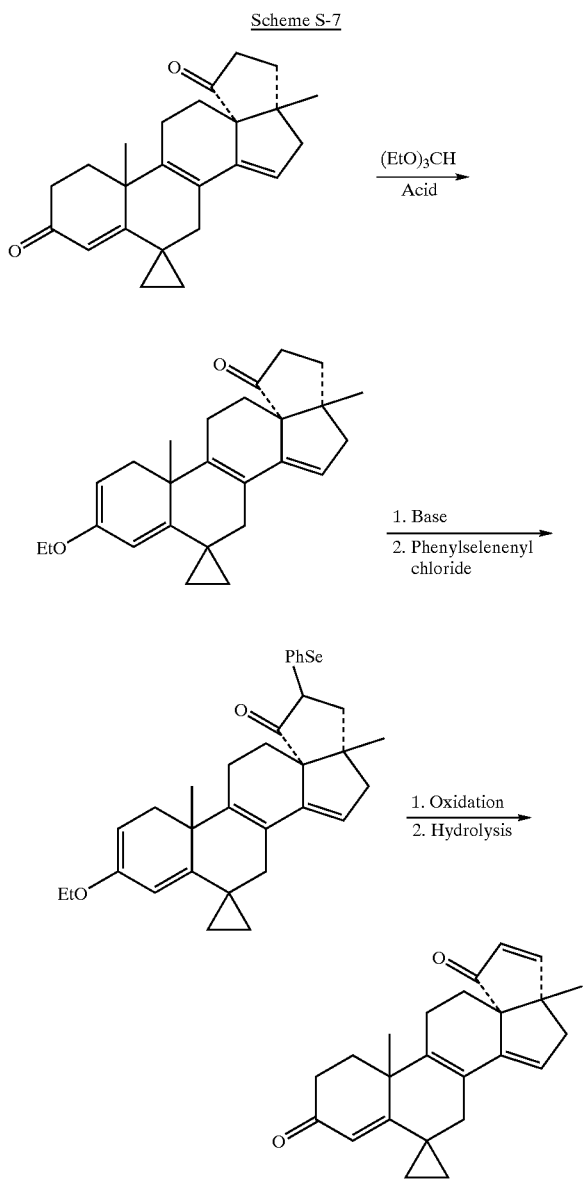

Scheme S-8 illustrates the synthesis of double bond isomers of the compound of Formula C-1. Treatment of various spiroxane compounds, such as those shown in Scheme S-8, with potassium acetate, trifluoroacetic anhydride and trifluoroacetic acid under conditions similar to those for the synthesis of the compound of Formula C-1 give the compounds of Formulae C-121 and C-123.

Scheme S-8

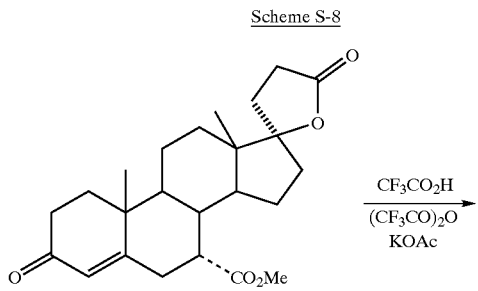

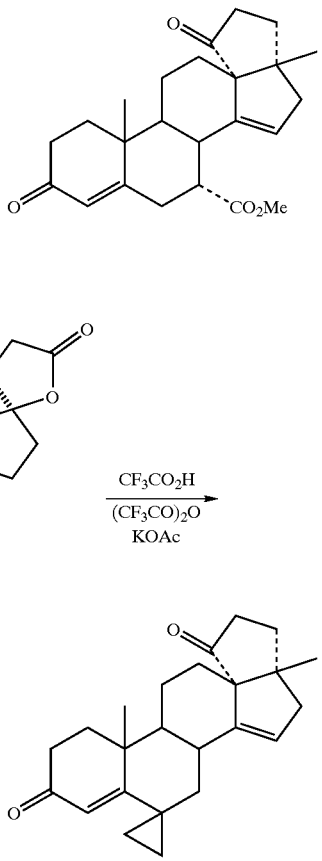

Scheme S-9 illustrates an alternative method for the synthesis of double bond isomers in this family of steroids. Starting with a preformed enone (such as the compound of Formula C-24 whose synthesis is described above) already bearing the fused ring, the C6–C7 fused cyclopropane is introduced using the chemistry described above in Scheme S-3 for the synthesis of compounds such as those of Formulae C-108 and C-109.

Scheme S-9

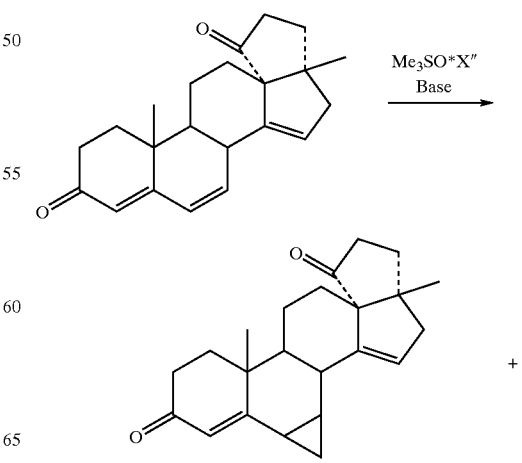

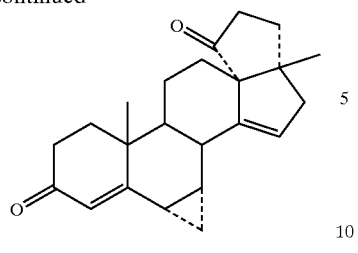

wherein X is halogen.

Fused ring steroids having an aromatic A ring can be prepared by treating steroids such as those described in P. Compain, et al., Tetrahedron, 52(31), 10405–10416 (1996) (which is incorporated by reference herein) with trifluoroacetic acid, potassium acetate and trifluoroacetic anhydride in substantially the same manner as discussed above with respect to Scheme S-1.

Those novel fused ring steroids possessing an aromatic A ring and a 3-hydroxy substituent are expected to undergo all chemical reactions which are typical of phenols. Scheme S-10 illustrates the synthesis of a 3-phenolic ether from a such a fused ring steroid. In particular, treatment of these phenolic compounds with a base and an alkyl halide or alkyl sulfonate is expected to produce the corresponding phenolic ester. See, for example, Feuer and Hooz, *In The Chemistry of the Ether Linkage*, Patai (Ed.), Interscience: New York, pp. 446–450, 460–468 (1967); and Olson, W. T., *J.Am.Chem.Soc.*, 69, 2451 (1947); which are incorporated herein by reference.

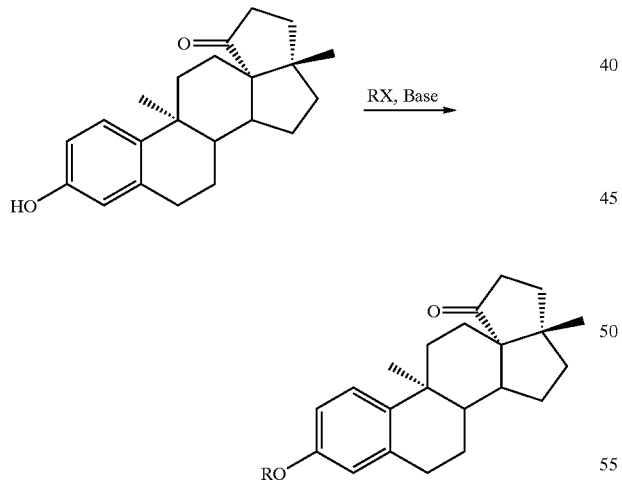

Scheme S-10

Similarly, Scheme S-11 illustrates the synthesis of a 3-phenolic ester from a fused ring steroid possessing an aromatic A ring and a 3-hydroxy substituent. In particular, treatment of these phenolic compounds with a carboxylic acid anhydride or with a carboxylic acid halide is expected to provide the corresponding phenolic ester. See, for example, March, J., *Advanced Organic Chemistry*, Wiley: New York, pp.346–347 (1985), which is incorporated herein by reference.

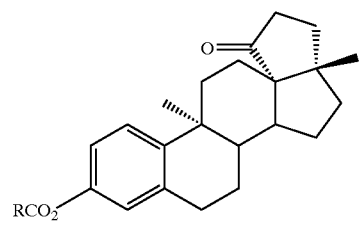

Scheme S-11

Scheme S-12 illustrates the synthesis of a 3-phenolic carbonate from a fused ring steroid possessing an aromatic A ring and a 3-hydroxy substituent. In particular, treatment of these phenolic compounds with an alkyl haloformate is expected to provide the corresponding phenolic carbonate. See, for example, March, J., *Advanced Organic Chemistry*, Wiley: New York, pp.346–347 (1985), which is incorporated herein by reference.

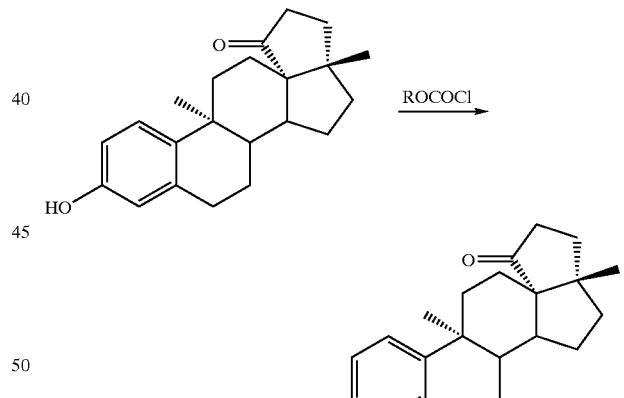

Scheme S-12

Scheme S-13 illustrates the synthesis of ortho allyl substituted phenyl derivatives from a fused ring steroid possessing an aromatic A ring and a 3-hydroxy substituent. In particular, treatment of these compounds with a base and an allyl halide is expected to provide the corresponding allyl phenyl ether. The allyl phenyl ether should give a mixture of ortho allyl substituted phenyl derivatives upon thermal rearrangement. See, for example, Shine, H., *J.Aromatic Rearrangements; Reaction Mechanisms in Organic Chemistry*, Monograph 6, American Elsevier: New York, pp. 89–120 (1967), which is incorporated herein by reference.

Scheme S-13

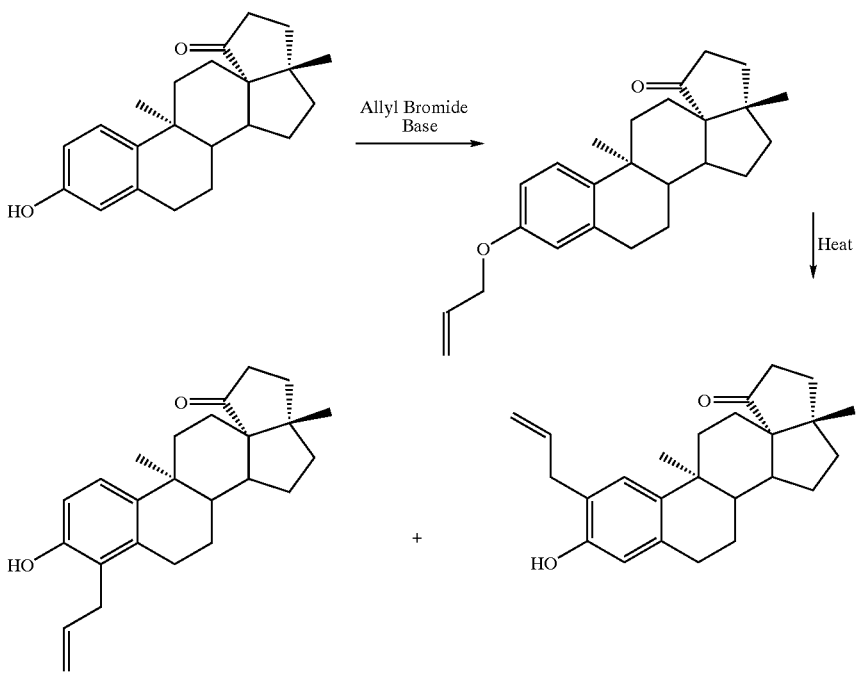

Scheme S-14 illustrates the synthesis of ortho dialkylated substituted phenyl derivatives from a fused ring steroid possessing an aromatic A ring and a 3-hydroxy substituent. In particular, treatment of these compounds with an alcohol and an acid is expected to provide the corresponding ortho dialkylated phenyl derivatives. See, for example, Calcott, W. S., *J.Am.Chem.Soc.*, 61, 1010 (1939), which is incorporated herein by reference.

Scheme S-14

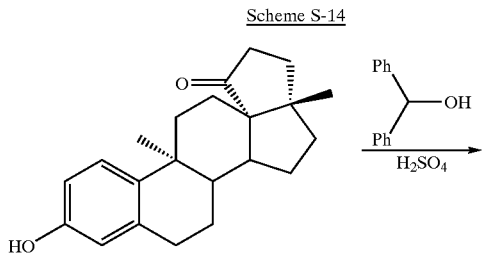

-continued

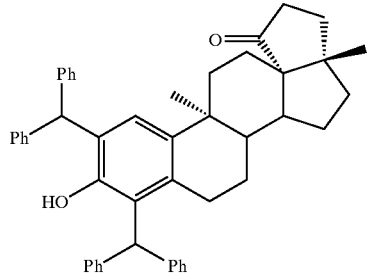

Scheme S-15 illustrates the allylic oxidation of a fused ring steroid possessing an aromatic A ring and a 3-hydroxy substituent. In particular, these compounds may be oxidized at an allylic position by reaction with selenium dioxide and t-butyl hydroperoxide to form the corresponding alcohol. Dehydration of this alcohol affords the corresponding olefin. See, for example, Schmuff, N. R., *J.Org.Chem.*, 48, 1404 (1983), which is incorporated herein by reference.

Scheme S-15

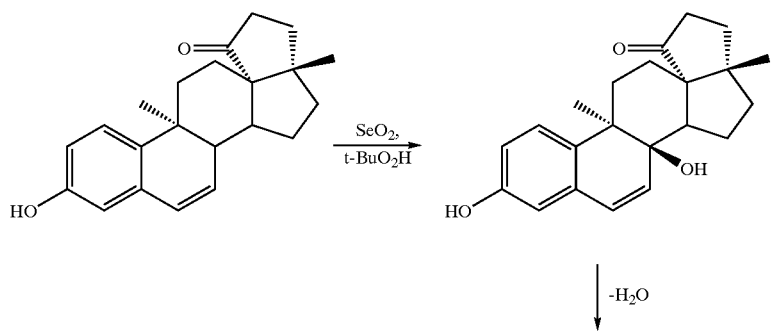

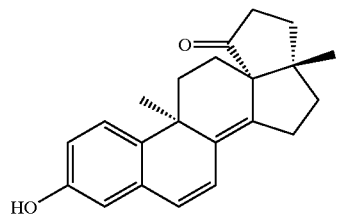

Scheme S-16 illustrates the protection of the 3-carbonyl group and the reduction of the 20-carbonyl group of the novel fused ring steroids of the present invention. In particular, these compounds may be reacted with trialkylorthoformate and an acid to form the 3-enol ether. The 3-enol ether can be reacted with sodium borohydride to reduce the C-20 carbonyl group to the corresponding C-20 alcohol. Treatment of the C-20 alcohol with an acid and water deprotects the 3-enol ether to form the 3-keto derivative.

Scheme S-16

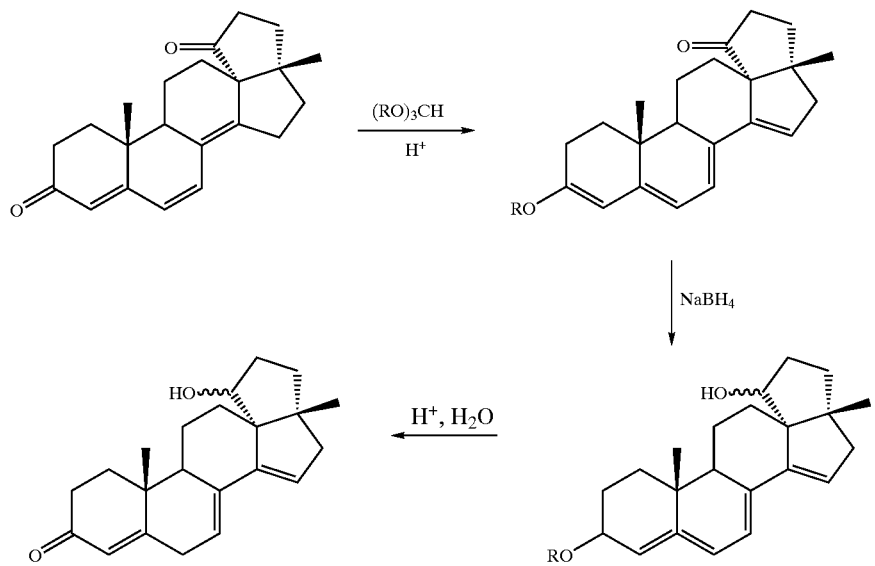

Scheme S-17 illustrates the hydrogenation of olefinic bonds in the novel fused ring steroids of the present invention. In particular, hydrogenation is expected to proceed step-wise. The C-6,C-7 double bond is first saturated followed by saturation of the C-8,C-14 double bond.

Scheme S-17

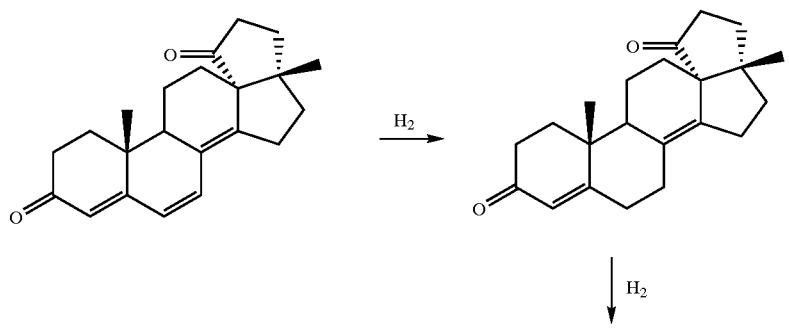

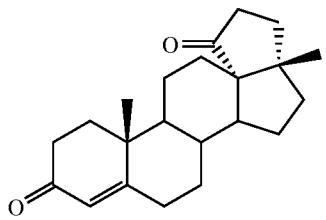

Scheme S-18 illustrates the rearrangement of protected 11α-hydroxy fused ring steroids of the present invention. In particular, the 11α-hydroxy group of the compound is first protected with a suitable protecting group such as 2-methoxyethoxymethyl ether (MEM ether). Treatment of the protected 11α-hydroxy steroid with an alkali metal salt and a trihaloalkaoic acid in the presence of an acid anhydride is expected to lead to the rearrangement of the lactone moiety in these molecules as illustrated below. Removal of the MEM ether with zinc bromide will provide the rearranged alcohols shown below.

Scheme S-18

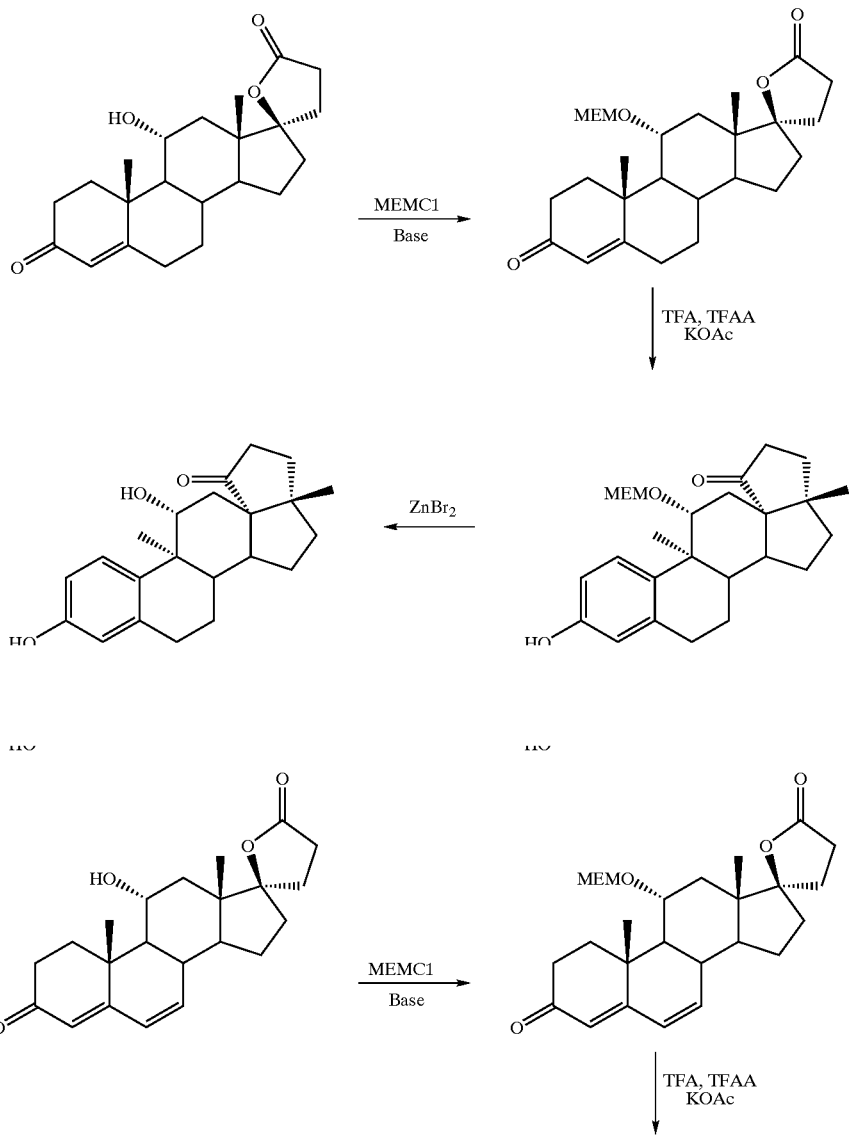

-continued

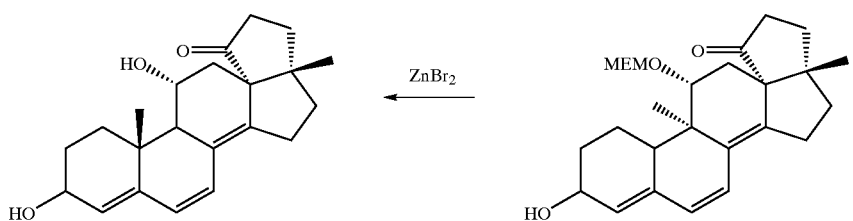

Scheme S-19 illustrates the protection of the 3-carbonyl group and the alkylation of the 19-position of the novel fused ring steroids of the present invention. In particular, the compound is first converted to the 3-alkyl enol ether as illustrated in Scheme S-16. Treatment of the 3-alkyl enol ether with lithium diisopropylamide (LDA) followed by treatment with an alkyl halide leads to the formation of the 19-alkyl derivative. Hydrolysis of the 3-alkyl enol ether protecting group gives the 3-keto derivative.

Scheme S-19

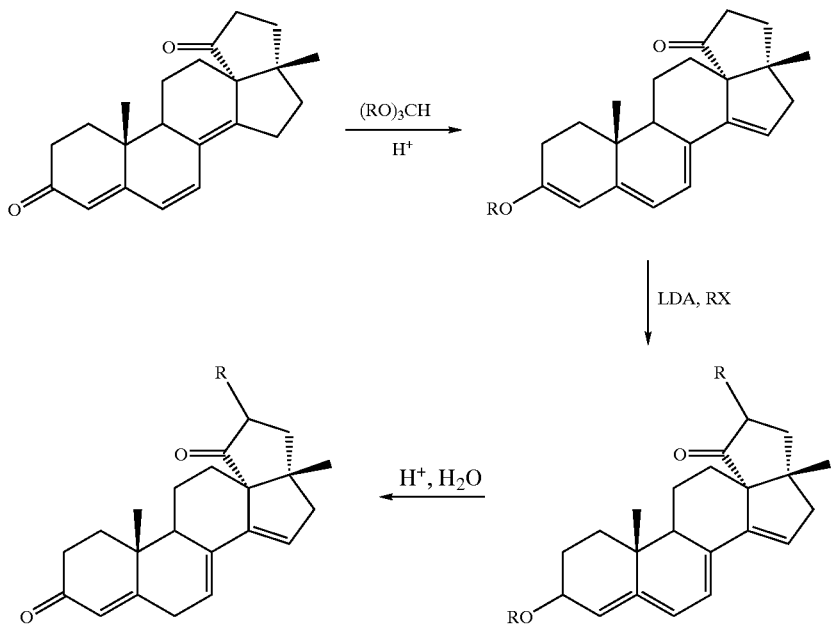

Scheme S-20 illustrates the conversion of estrone methyl ether to the corresponding spirolactone. Rearrangement of the lactone to the corresponding fused ring steroid should occur upon treatment of the lactone with a trihalogenated alkanoic acid, preferably in the presence of an alkali metal salt of the alkanoic acid utilized, under the reaction conditions previously disclosed. See, for example, Otsubo, K., *Tetrahedron Letters*, 27(47), 5763 (1986).

Scheme S-20

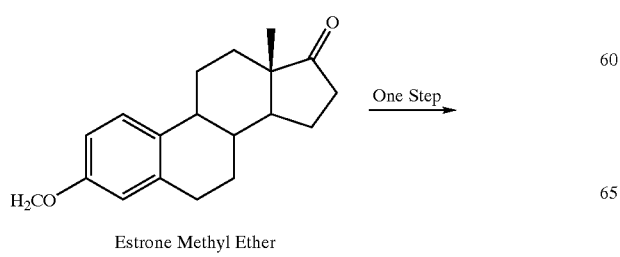

Estrone Methyl Ether

237
-continued

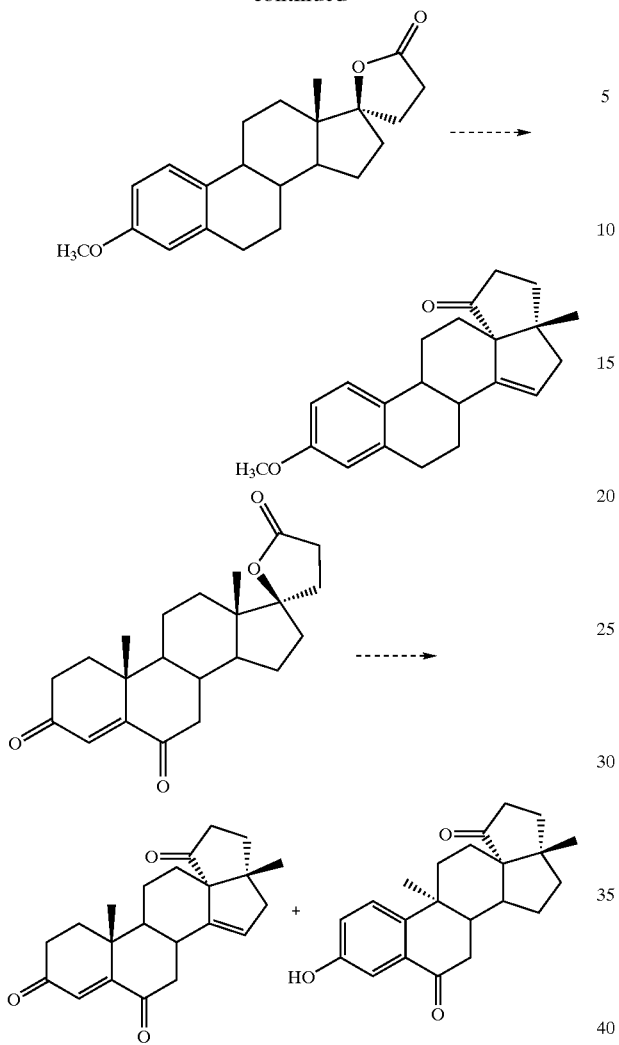

The novel compounds described herein additionally may be subjected to bioconversion processes similar to those disclosed previously to yield yet other novel fused ring steroids, such as steroids having an 9α, 9β, 11α or 11β-hydroxy substituent as well as other hydroxylated fused ring steroids. If desired, such hydroxylated steroids then can be oxidized via elimination of the hydroxy substituent to introduce an olefinic double bond such as a $\Delta^{9,11}$ olefinic double bond.

In view of the above, it will be seen that the several objects of the invention are achieved and other advantageous results attained.

As various changes could be made in the above compositions and processes without departing from the scope of the invention, it is intended that all matter contained in the above description shall be interpreted as illustrative and not in a limiting sense.

The following non-limiting examples serve to illustrate various aspects of the present invention:

238
EXAMPLE X-1A

Preparation of methyl 2,3,3a,4,6,7,9,10,11,11a,12,13-dodecahydro-3aβ,11aβ-dimethyl-1,9-dioxo-1H-pentaleno[1,6a-a]phenanthrene-6α-carboxylate (Compound C-1)

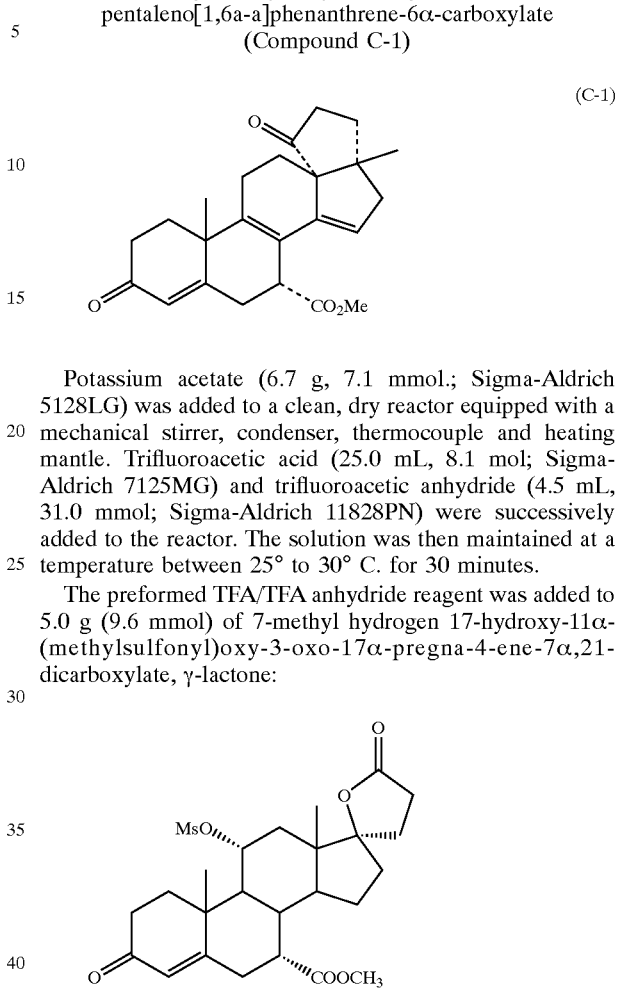

Potassium acetate (6.7 g, 7.1 mmol.; Sigma-Aldrich 5128LG) was added to a clean, dry reactor equipped with a mechanical stirrer, condenser, thermocouple and heating mantle. Trifluoroacetic acid (25.0 mL, 8.1 mol; Sigma-Aldrich 7125MG) and trifluoroacetic anhydride (4.5 mL, 31.0 mmol; Sigma-Aldrich 11828PN) were successively added to the reactor. The solution was then maintained at a temperature between 25° to 30° C. for 30 minutes.

The preformed TFA/TFA anhydride reagent was added to 5.0 g (9.6 mmol) of 7-methyl hydrogen 17-hydroxy-11α-(methylsulfonyl)oxy-3-oxo-17α-pregna-4-ene-7α,21-dicarboxylate, γ-lactone:

which was prepared in the manner described in Example 36. The resulting mixture was heated at 60° C. for 60 minutes, the degree of conversion being periodically checked by TLC and/or HPLC. When the reaction was complete (approximately 60 minutes), the mixture was transferred to 1-neck flask and concentrated under reduced pressure at 50° C. until it became a thick slurry.

The resulting slurry was diluted with 150 mL of ethyl acetate and 80 mL of a water/brine mixture. The phases were then allowed to separate and the aqueous layer was reextracted with 80 mL of ethyl acetate. Brine strength was 12% by weight. The combined ethyl acetate solution was washed once with 12% by weight brine (80 mL), then once with 1N NaOH solution (80 mL), and finally with 12% by weight brine (80 mL). The mixture was allowed to stand for separation and the separated ethyl acetate layer was concentrated to dryness under reduced pressure at 45° C. using a water aspirator to provide about 3.8 g of a crude solid product. HPLC analysis of the crude product revealed that the product contained about 40 area % of compound C-1.

The solid product then was subjected to chromatographic purification The chromatographic purification produced 210 mg of methyl 2,3,3a,4,6,7,9,10,11,11a,12,13-dodecahydro-3aβ,11aβ-dimethyl-1,9-dioxo-1H-pentaleno[1,6a-a]phenantrene-6α-carboxylate (Compound C-1).

The mass spectrometry data indicated a molecular weight of 380 and a formula of $C_{24}H_{28}O_4$ from high resolution data. The EI mass spectrum had an M+ peak at m/z 380. The APCI mass spectrum had peaks at m/z 381 (MH)+ and m/z 398 (MNH$_4$)+. Carbon and hydrogen analyses were consistent with the proposed molecular formula.

The IR spectrum had two peaks in the carbonyl absorption region: 1722 cm$^{-1}$ and 1667 cm$^{-1}$. The 1722 cm$^{-1}$ peak was assigned to two carbonyls, since the $^{13}$C NMR spectrum had signals at δ 217.7, due to a saturated ketone, and at δ 172.7, due to carbomethoxy carbonyl. Absence of the 1773 cm$^{-1}$ peak in the IR spectrum indicated loss of the lactone moiety.

The $^{13}$C APT and HETCOR NMR data indicated the presence of the following types of carbons: 3 carbonyls (δ 217.7, 198.4, 172.2); 4 fully substituted olefinic carbons (δ 166.3, 141.8, 139.3, 121.8); 2 methine olefinic carbons (δ 124.9, 122.0); 3 quaternary aliphatic carbons (δ 61.1, 50.7, 39.7); 1 methine aliphatic carbon (δ 43.3); 8 methylene carbons (δ 46.0, 37.5, 34.1, 33.3, 32.9, 31.9, 23.7, 22.2); and 3 methyl carbons (δ 51.9, 23.6, 23.1).

EXAMPLE X-1B

Preparation of (7α,13R,17β)-3',4',5',17-tetrahydro-14-hydroxy-17-methyl-3,5'-dioxo-γ-lactone, cyclopenta[13,17]-18-norandrosta-4,9(11)-diene-7-carboxylic acid (Compound C-201)

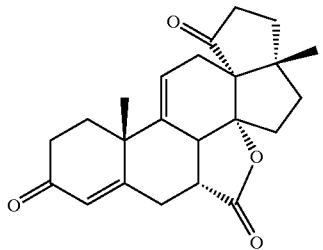

Potassium acetate (8.9 g, 90 mmol), trifluoroacetic acid (150 mL, 1.480 g/mL) and trifluoroacetic anhydride (33 mL, 1.487 g/mL) were added to the 250 mL round bottom reactor equipped with mechanical stirrer, condenser, and heating mantel. The resulting solution was stirred between about 25° C. to 30° C. for about 10 minutes.

The preformed TFA/TFA anhydride reagent was added to 15 g (30.0 mmol) of 7-methyl hydrogen 17-hydroxy-11α-(methylsulfonyl)oxy-3-oxo-17α-pregna-4-ene-7α,21-dicarboxylate, γ-lactone

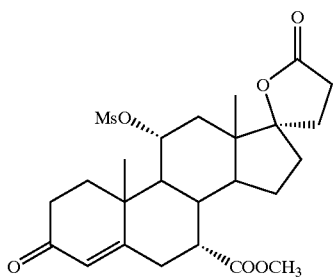

which was prepared in the manner described in Example 36. The resulting mixture was heated between about 60 to 70° C. for about 1 to 1.5 hours. This mixture was concentrated under reduced pressure at 50° C. to give a thick slurry. The slurry was dissolved in 100 mL ethyl acetate and was washed 2 times with about 20% water/brine (80 mL each time), 1 time with a 1N sodium hydroxide (80 mL) solution, followed by 1 time with about 20% water/brine (80 mL). The crude product was dried over magnesium sulfate filtered and concentrated to give about 18 g of crude wet material.

This material was purified by column chromatography twice to afford about 3 g of pure (7α,13R,17β)-3',4',5=,17-tetrahydro-14-hydroxy-17-methyl-3,5'-dioxo-γ-lactone, cyclopenta[13,17]-18-norandrosta-4,9(11)-diene-7-carboxylic acid (Compound C-201).

EXAMPLE X-1C

Preparation of [13S,17β]-3',4'-dihydro-3-hydroxy-9,17-dimethylcyclopenta[13,17]gona-1,3,5(10)-triene-5'[2'H]-one (Compound C-202)

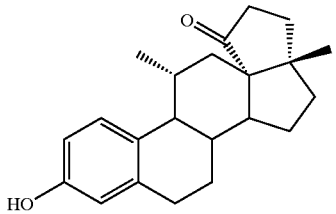

Potassium acetate (6 g, 61.1 mmol), trifluoroacetic acid (150 mL, 1.480 g/mL) and trifluoroacetic anhydride (26 mL, 1.487 g/mL) were added to a 250 mL round bottom reactor equipped with mechanical stirrer, condenser, and heating mantel. The resulting solution was stirred between about 25° C. to 30° C. for about 10 minutes.

The preformed TFA/TFA anhydride reagent was added to 15 g (43.7 mmol) of 17-hydroxy-3-oxo-17α-pregn-4-ene-21-carboxylic acid, γ-lactone (also known as aldonai; G. D. Searle & Co.):

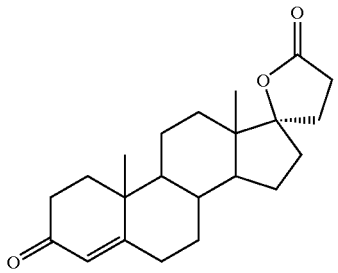

The resulting mixture was heated between 60° C. to 70° C. for about 1 to 1.5 hours. The reaction mixture was concentrated under reduced pressure at 50° C. to give thick slurry. The slurry was dissolved in 100 ml ethyl acetate and was washed 2 times with about 20% water/brine solution (80 mL each time), 1 time with 1N sodium hydroxide solution (80 mL), followed by 1 time with about 20% water/brine solution (80 mL). The crude product was dried over magnesium sulfate, filtered and concentrated to dryness under reduced pressure at 50° C. to give about 20 g of crude wet material.

This material was purified by column chromatography twice to afford about 125 g of pure [13S,17β]-3',4'-dihydro-3-hydroxy-9,17-dimethylcyclopenta[13,17]gona-1,3,5(10)-triene-5'[2'H]-one (Compound C-202).

EXAMPLE X-1D

Preparation of [13S,17β]-3',4'-dihydro-3-hydroxy-9,17-dimethylcyclopenta[13,17]gona-1,3,5(10),6-tetraene-5'[2'H]-one (Compound C-203)

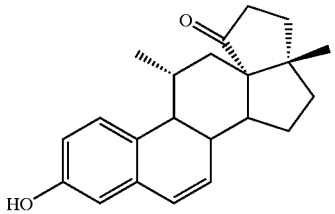

Potassium acetate (6 g, 61.1 mmol), trifluoroacetic acid (150 mL, 1.480 g/mL) and trifluoroacetic anhydride (26 mL, 1.487 g/mL) was added to a 250 mL round bottom reactor equipped with mechanical stirrer, condenser, and heating mantel. The resulting solution was stirred between about 25° C. to 30° C. for about 10 minutes.

The preformed TFA/TFA anhydride reagent was added to 15 g (45.9 mmol) of was added to 17-hydroxy-3-oxo-17α-pregn-4,9(11)-diene-21-carboxylic acid, γ-lactone (also known as Δ-9,11-aldona):

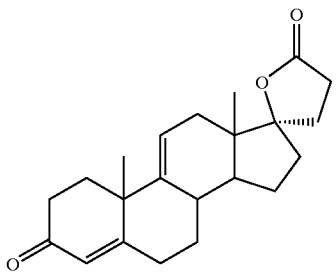

which was prepared from 3-methoxy-3,5,9(11)-androstatriene-17-one (Upjohn). The resulting mixture was heated between about 60° C. to 70° C. for about 1 to 1.5 hours. The reaction mixture was concentrated under reduced pressure at 50° C. to give thick slurry. The slurry was dissolved in 100 ml ethyl acetate and was washed 2 times with about 20% water/brine solution (80 mL each time), 1 time with 1N sodium hydroxide solution (80 mL), followed by 1 time with about 20% water/brine solution (80 mL). The crude product was dried over magnesium sulfate, filtered and concentrated to dryness under reduced pressure at 50° C. to give about 18 g of crude wet material.

This material was purified by column chromatography twice to afford about 340 g of pure [13S,17β]-3',4'-dihydro-3-hydroxy-9,17-dimethylcyclopenta[13,17]gona-1,3,5(10),6-tetraene-5'[2'H]-one (Compound C-203).

EXAMPLE X-1E

Preparation of [13S,17β]-3',4'-dihydro-17-methyl-cyclopenta[13,17]-18-norandrosta-4,6,8(14)-triene-3,5'[2'H]-dione (Compound C-204)

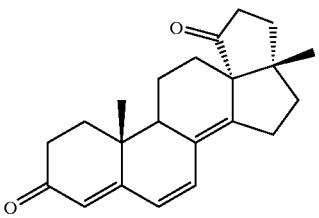

Potassium acetate (8 g, 81.5 mmol), trifluoroacetic acid (150 mL, 1.480 g/mL) and trifluoroacetic anhydride (33 mL, 1.487 g/mL) were added to a 250 mL round bottom reactor equipped with mechanical stirrer, condenser, and heating mantel. The resulting solution was stirred between about 25° C. to 30° C. for about 10 minutes.

The preformed TFA/TFA anhydride reagent was added to 15 g (44.0 mmol) of 17-hydroxy-3-oxo-17α-pregn-4,6-diene-21-carboxylic acid, γ-lactone (also known as canrenone; G. D. Searle & Co.):

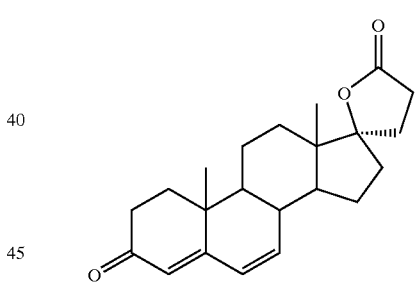

The resulting mixture was heated between about 60 to 70° C. for about 1 to 1.5 hours. The reaction mixture was concentrated under reduced pressure at 50° C. to give thick slurry. The slurry was dissolved in 100 ml ethyl acetate and was washed 2 times with about 20% water/brine solution (80 mL each time), 1 time with 1N sodium hydroxide solution (80 mL), followed by 1 time with about 20% water/brine solution (80 mL). The crude product was dried over magnesium sulfate, filtered and concentrated to dryness under reduced pressure at 50° C. to give about 18 g of crude wet material.

This material was purified by column chromatography twice to afford about 2.2 g of pure [13S,17β]-3',4'-dihydro-17-methyl-cyclopenta[13,17]-18-norandrosta-4,6,8(14)-triene-3,5'[2'H]-dione (Compound C-204).

EXAMPLE X-2

Preparation of (Compound C-105)

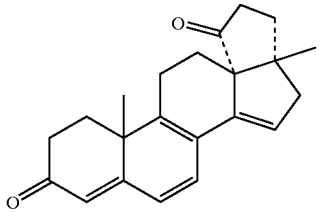

To a stirred, cold (0° C.) solution of 11α-hydroxycanrenone (3.6 g, 10 mmol) and triethylamine (1.2 g, 12 mmol) in methylene chloride (20 mL) is added methanesulfonyl chloride (1.1 g, 10 mmol). The mixture is stirred in the cold for 2 hours and allowed to warm to room temperature. Stirring is continued until thin layer chromatography indicates the reaction is complete. The mixture then is diluted with ethyl acetate and extracted with water, aqueous 5% sodium bicarbonate solution and water and dried over sodium sulfate. The drying agent is filtered and the filtrate concentrated in vacuo to give the following crude mesylate C-136 which is suitable for use in the next step:

(Compound C-136)

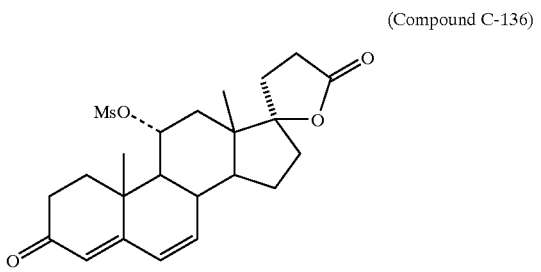

A solution of mesylate C-136 (4.3 g, 10 mmol) is reacted with trifluoracetic acid (25 mL), trifluoracetic anhydride (4.5 mL) and potassium acetate (6.7 g, 7.1 mmol) according to the procedure described for the synthesis of Compound C-1 in Example X-1. The crude product is isolated according to the same procedure as for Compound C-1 in Example X-1 and is purified by chromatography on silica gel using mixtures of ethyl acetate and toluene or ethyl acetate and hexane as eluents. The product thus obtained is further purified by recrystallization from alcohol, alcohol and water, or ethyl acetate and hexane to yield to tetraene C-105.

EXAMPLE X-3

Preparation of (Compound C-110)

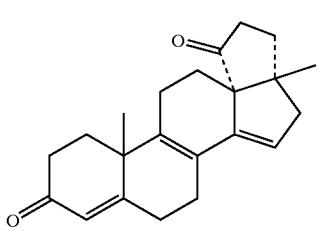

Mesylate C-138:

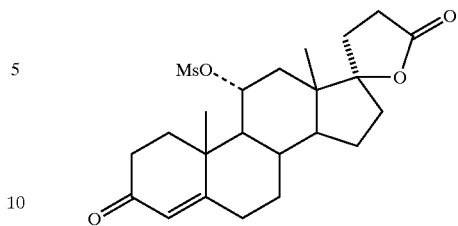

is synthesized and isolated (according to the procedure described in Example X-2 for the synthesis of mesylate C-136) using 11α,17-dihydroxy-3-oxo-17-oxo-pregn-4-ene-21-carboxylic acid, γ-lactone (3.6 g, 10 mmol), triethylamine (1.2 g, 12 mol) and methanesulfonyl chloride (1.1 g, 10 mmol) in methylene chloride (20 mL). The mesylate C-138 thus isolated is suitable for use in the following step.

A solution of mesylate C-138 (4.4 g, 10 mmol) is reacted with trifluoracetic acid (25 mL), trifluoracetic anhydride (4.5 mL) and potassium acetate (6.7 g, 7.1 mmol) according to the procedure described for the synthesis of Compound C-1 in Example X-1. The crude product C-110 is isolated according to the same procedure as for Compound C-1 in Example X-5 and is purified by chromatography on silica gel using mixtures of ethyl acetate and toluene or ethyl acetate and hexane as eluents. The product thus obtained is further purified by recrystallization from alcohol, alcohol and water, or ethyl acetate and hexane.

EXAMPLE X-4

Preparation of 3',4',5',17-tetrahydro-17β-methyl-3,5'-dioxocyclopenta[13R,17]-18-norandrosta-4,8,14-triene-7α-carboxylic acid (Compound C-101)

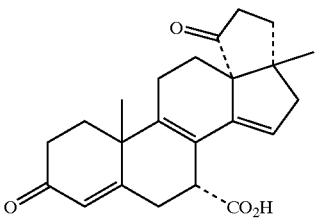

A solution of Compound C-1 (3.8 g, 10 mmol) and aqueous 1N sodium hydroxide solution (35 mL) in ethanol (60 mL) is refluxed for 8 hours. The reaction is cooled to room temperature, concentrated on the rotary evaporator in vacuo and the residual aqueous layer is extracted three times with ethyl acetate. The aqueous layer is then acidified with 1N hydrochloric acid solution and extracted three times with ethyl acetate. The combined organic layers are washed with water and dried over is sodium sulfate. The drying agent is filtered and the filtrate is concentrated on the rotary evaporator. The residual crude carboxylic acid C-101 is crystalized by treatment with ethyl acetate and is recrystallized from ethyl acetate and hexane or methanol or ethanol and water.

EXAMPLE X-5

Preparation of 1-methylethyl 3',4',5',17-tetrahydro-17β-methyl-3,5'-dioxocyclopenta[13R,17]-18-norandrosta-4,8,14-triene-7α-carboxylate (Compound C-102)

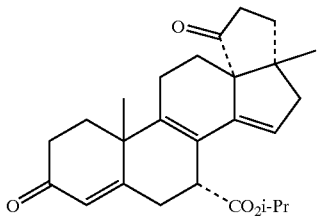

A mixture of sodium bicarbonate (3.5 g) and a solution of carboxylic acid C-101 (3.7 g, 10 mmol) and isopropyl iodide (3 mL) in dimethylformamide (35 mL) is stirred at room temperature overnight. The reaction is poured onto water and the aqueous solution is extracted three times with ethyl acetate. The combined organic layers are washed with water and dried over sodium sulfate. The drying agent is filtered and the filtrate concentrated in vacuo. The residual crude isopropyl ester C-102 is crystallized by treatment with ethyl acetate or alcohol and is purified by chromatography on silca gel and recrystallization from ethyl acetate and hexane or alcohol or alcohol and water.

EXAMPLE X-6

Preparation of ethyl 3',4',5',17-tetrahydro-17β-methyl-3,5'-dioxocyclopenta[13R,17]-1B-norandrosta-4,8,14-triene-7α-carboxylate

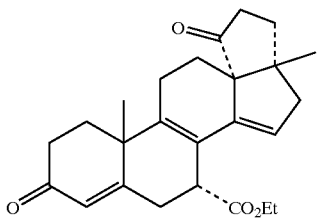

A mixture of sodium bicarbonate (3.5 g) and a solution of carboxylic acid C-101 (3.7 g, 10 mmol) and ethyl iodide (3 mL) in dimethylformamide (35 mL) is stirred at room temperature overnight. The reaction is poured onto water and the aqueous solution is extracted three times with ethyl acetate. The combined organic layers are washed with water and dried over sodium sulfate. The drying agent is filtered and the filtrate concentrated in vacuo. The residual crude ethyl ester C-103 is crystallized by treatment with ethyl acetate or alcohol and is purified by chromatography on silca gel and recrystallization from ethyl acetate and hexane or alcohol or alcohol and water.

EXAMPLE X-7

Preparation of hexyl 3',4',5',17-tetrahydro-17β-methyl-3,5'-dioxocyclopenta[13R,17]-18-norandrosta-4,8,14-triene-7α-carboxylate (Compound C-104)

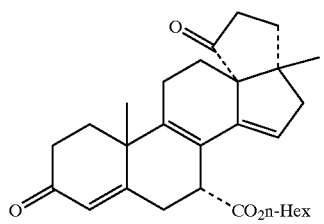

A mixture of sodium bicarbonate (3.5 g) and a solution of carboxylic acid C-101 (3.7 g, 10 mmol) and n-hexyl iodide (3 mL) in dimethylformamide (35 mL) is stirred at room temperature overnight. The reaction is poured onto water and the aqueous solution is extracted three times with ethyl acetate. The combined organic layers are washed with water and dried over sodium sulfate. The drying agent is filtered and the filtrate concentrated in vacuo. The residual crude n-hexyl ester C-104 is crystallized by treatment with ethyl acetate or alcohol and is purified by chromatography on silca gel and recrystallization from ethyl acetate and hexane or alcohol or alcohol and water.

EXAMPLE X-8

Preparation of 3',4'-dihydro-17-methyl-7α(methylthio)-cyclopenta[13,17]-18-norandrosta-4,8,14-triene-3,5'(2'H)-dione (Compound C-106)

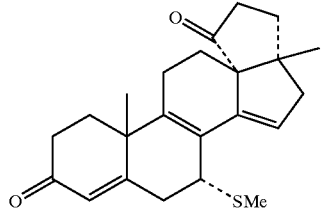

A solution of tetraene C-105 (3.2 g, 10 mmol) in methanol (40 mL) and piperidine (4 mL) is cooled to 5° C. Gaseous methyl mercaptan is passed through until a weight gain of 7 g is observed. The pressure container is sealed and held at room temperature for 20 hours. The solution is poured onto ice water and the precipitate is filtered, washed with water and air dried. The methylthio product C-106 is purified by recrystallization from methanol or ethyl acetate and hexane. See, e.g., the procedure set forth in A. Karim and E. A. Brown, Steroids, 20, 41 (1972), which is incorporated herein by reference.

EXAMPLE X-9

Preparation of 7α-(acetylthio)-3,4'-dihydro-17-methyl-cyclopenta[13,17]-18-norandrosta-4,8,14-triene-3,5'(2'H)-dione (Compound C-107)

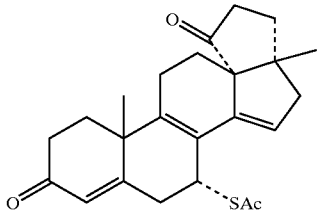

A solution of tetraene C-105 (3.2 g, 10 mmol) in thioacetic acid (10 mL) is heated t 85–95 C for 1 hour. Excess thioacetic acid is removed in vacuo and the resultant crude 7α-thioacetate C-107 is purified by recrystallization from a suitable solvent such as methanol or ethyl acetate or ethyl acetate and hexane. See e.g., the procedure set forth in U.S. Pat. No. 3,013,012, J. A. Cella and R. C. Tweit, Dec. 12, 1961 which is incorporated herein by reference.

EXAMPLE X-10

Preparation of 1,2,4bR(4bR*),5,5aS*,7,7aR*,8,9,11,12bS*-dodecahydro-7a,12b-dimethyl-10aR*-cyclopropal[1]pentaleno[1,6a-a]phenanthrene-3,10-dione

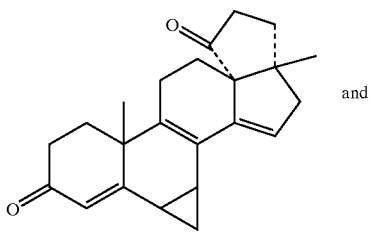

and 1,2,4bS(4bR*),5,5aS*,8,9,11,12,12bR*-dodecahydro-7a,12b-dimethyl-10aS*-cyclopropal[1]pentaleno[1,6a-a]phenanthrene-3,10-dione (Compound C-109):

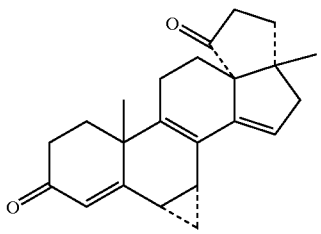

To a solution of trimethylsulfoxonium iodide (1 g, 4.6 mmol) in dry dimethylsulfoxide (20 mL) is added sodium hydride (220 mg of 50% dispersion in mineral oil, 4.6 mmol). The mixture is stirred at room temperature under nitrogen until the evolution of hydrogen ceases. A solution of tetraene C-105 (1.12 g, 3.5 mmol) in dimethylsulfoxide (4 mL) is then added and stirring is continued for 4 hours under a nitrogen atmosphere. The reaction mixture is diluted with water and the resultant precipitate is filtered and air dried. The product is a mixture of the 6α,7β (Compound C-108) and 6α,7β (Compound C-109) isomers. Separation of these isomers is effected by chromatography on silica gel and the individual isomers are further purified by recrystallization from solvents such as ethyl acetate and hexane, alcohol, or alcohol and water.

EXAMPLE X-11

Preparation of (Compound C-111)

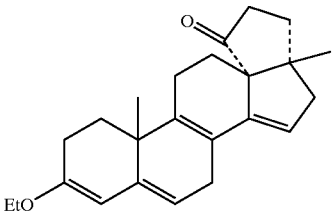

To a suspension of enone C-110 (3.2 g, 10 mmol) in ethyl orthoformate (10 mL) and anhydrous ethanol (10 mL) is added p-toluenesulfonic acid monohydrade (0.05 g). The reaction is stirred for 30 minutes at room temperature and is quenched by the addition of a few drops of pyridine. After stirring another 5 minutes at 0° C., the resultant precipitate is filtered, washed with a small amount of methanol, and recrystallized from alcohol or ethyl acetate and hexane containing traces of pyridine to provide pure enol ether C-111. Alternatively, the reaction may be worked up after addition of pyridine by removing all solvents in vacuo and crystallizing the residue by addition solvents such as ether, ethyl acetate or hexane. The crude C-111 is recrystallized as above. See, e.g., the procedure set forth in R. M. Weier and L. M. Hofmann, J. Med. Chem., 20, 1304–1308 (1977) which is incorporated herein by reference.

EXAMPLE X-12

Preparation of (Compound C-112)

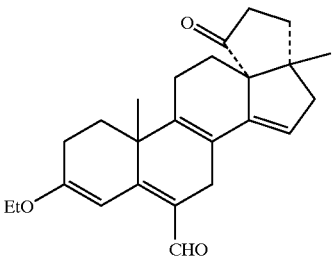

Procedure of R. M. Weier and L. M. Hofmann, J. Med. Chem, 20 1304–1308 (1977) See, e.g., which is incorporated herein by reference.

Vilsmeyer reagent is prepared by adding phosphorus oxychloride (4.59 g, 30 mmol) to dimethylformamide (30 mL) at)° C. After 5 minutes, a solution of enol ether C-111 (3.5 g, 10 mmol) in dimethylformamide (5 mL) is added and the reaction is stirred at 0° C. for 2 hours and at room temperature overnight. The reaction is poured onto aqueous sodium acetate solution and stirred for 2 hours. The precipitate is filtered and dried to give crude aldehyde C-112. Purification is effected by recrystallization from solvents such as alcohol, alcohol and water or ethyl acetate and hexane. Alternatively, the crude aldehyde C-112 is isolated from the aqueous sodium acetate solution by extraction with a solvent such as ethyl acetate. After drying over sodium sulfate and removing the solvent, the residue is purified by recrystallization or by chromatography over silica gel followed by recrystallization.

EXAMPLE X-13

Preparation of

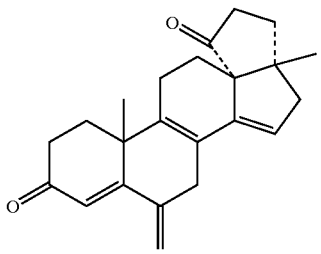
(Compound C-113)

To a stirred cold solution of lithium tri-tert-butoxyaluminum hydride (3.05 g, 12 mmol) in tetrahydrofuran is added aldehyde C-112 (3.78 g, 10 mmol). The reaction is stirred at room temperature for 5 hours and quenched by adding water and acetic acid, care being taken to keep the mixture slightly basic. The mixture is concentrated in vacuo and the resultant solid slurried in ethyl acetate. The solid is filtered and the filtrate concentrated in in vacuo. The residue is dissolved in a minimum volume of a solution of acetone and water (3:1) and added to acidified aqueous acetone (pH 1.5–2.0). The acid reaction mixture is stirred at room temperature for 1 hour and concentrated in vacuo. The resultant crude dienone C-113 is purified by recrystallization from solvents such as alcohol, alcohol and water or ethyl acetate and hexane. Alternatively, the crude dienone C-113 is purified by chromatography on silica gel and then recrystallized. See, e.g., the procedure set forth in R. M. Weier and L. M. Hofmann, J.Med. Chem., 20, 1304–1308 (1977) which is incorporated herein by reference.

EXAMPLE X-14

Preparation of 2',3',3'aα,4',6',10',11',11'aα,12',13'-decahydro-3'aR,3'a,11'a-dimethyl-13'aR*-spiro[cyclopropane-1,7'(9'H)-[1H]pentaleno[1,6a-a]phenanthrene]-1'9'-dione

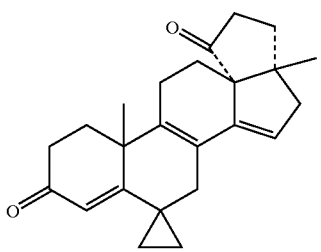
(Compound C-114)

To a solution of dienone C-113 (1.17 g, 0.05 mmol) in tetrahydrofuran (30 mL) is added a solution of diazomethane (0.2 g, 0.07 mmol) in ether (7 mL). The resultant reaction solution is stored at room temperature for several days. Acetic acid is then added to destroy excess diazomethane and the reaction is concentrated in vacuo. The residue, which is the intermediate pyrazoline, is crystallized under a solvent such as acetone, hexane, ethyl acetate or ethanol and is then recrystallized. This material is converted to the spirocyclopropane C-114. Thus, the solid C-114 is heated at 190° C. in vacuo and the resulting solid is recrystallized from alcohol, alcohol and water, acetone and water or ethyl acetate and hexane. Alternatively, a solution of the pyrazoline in acetone is treated with boron trifluoride etherate at room temperature for about 1 hour. Water is added and the resultant precipitate is filtered and air dried. Purification is effected by recrystallization. See, e.g., the procedure set forth in F. B. Colton and R. T. Nicholson, U.S. Pat. No. 3,499,891, Mar. 10, (1970) which is incorporated herein by reference.

EXAMPLE X-15

Preparation of

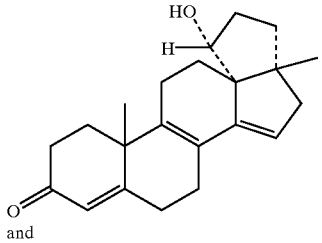
(Compound C-115)

and

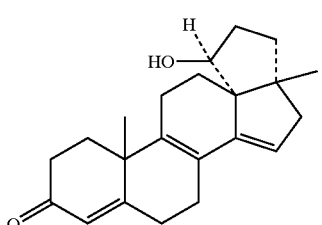
(Compound C-116)

To a solution of enol ether C-111 (3.2 g, 10 mmol) in methanol (20 mL) is added sodium borohydride (38 mg). The reaction is stirred at room temperature for 3 hours and is treated with 1N hydrochloric acid for 30 minutes. The reaction is further diluted with water and the precipitate filtered, washed with water and dried. The product, consisting of a mixture of two epimeric alcohols (Compound C-115 and Compound C-116), is chromatographed on silica gel to effect separation. The purified alcohols C-115 and C-116 are each recrystallized from solvents such alcohol, alcohol and water, ethyl acetate and hexane and acetone and hexane. Alternatively, the diluted reaction mixture is extracted with ethyl acetate, the combined organic layers dried over sodium sulfate and the crude product thus isolated is chromatographed as above to provide the separated alcohols C-115 and C-116.

EXAMPLE X-16

Preparation of

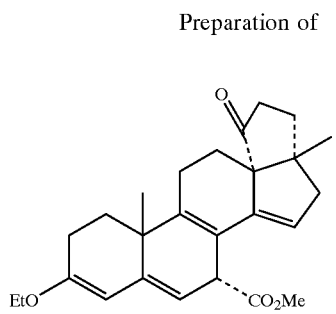

(Compound C-117)

Compound C-1 (3.8 g, 10 mmol) is converted to enol ether C-117 using ethyl orthoformate (3.2 g, 10 mmol), ethanol (10 mL) and p-toluenesulfonic acid monoydrate (0.05 g) according to the procedure described for the synthesis of Compound C-111 set forth in Example X-11.

EXAMPLE X-17

Preparation of methyl 3',4',5',17-tetrahydro-6α-hydroxy-17β-methyl-3,5'-dioxocyclopenta[13R,17]-18-norandrosta-4,8,14-triene-7α-carboxylate (Compound C-118)

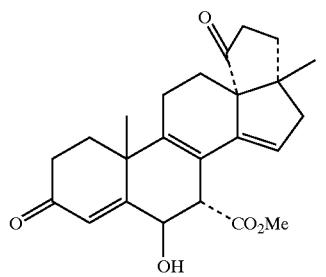

A solution of 57% m-chloroperoxybenzoic acid (3.64 g) in 10% aqueous dioxane (20 mL) is half-neutralized with 1N sodium hydroxide solution. This solution is cooled to 0° C. and added in portions to a stirred, cold (0° C.) solution of enol ether C-117 (4.1 g, 10 mmol) in 10% aqueous dioxane (20 mL). The reaction is stirred at room temperature overnight, poured onto ice water and extracted with methylene chloride or ethyl acetate. The combined organic layers are dried over sodium sulfate. Evaporation of the solvent provides the crude hydroxy ester C-118, which is purified by chromatography on silica gel. See, e.g., the procedure set forth in R. M. Weier and L. M. Hofmann, J.Med.Chem., 20, 1304–1308 (1977) which is incorporated herein by reference.

EXAMPLE X-18

Preparation of

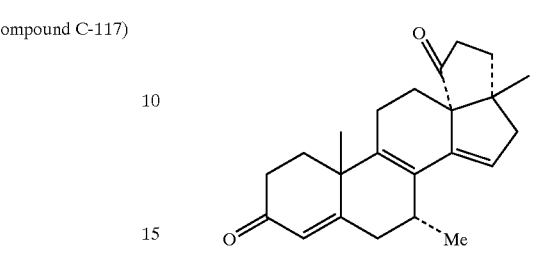

(Compound C-117)

Lithium dimethyl cuprate is prepared by adding methyllithium (19 mL of a 1.6 M solution in ether, 30 mmol) to a stirred suspension of cuprous iodide (2.86 g, 15 mmol) in ether (30 mL) at 0° C. under an inert atmosphere of argon. After stirring in the cold for 15 minutes a solution of tetraene C-105 (1.6 g, 15 mmol) in tetrahydrofuran (25 mL) is added dropwise over 25 minutes. The reaction is continued for an additional 30 minutes and poured onto saturated ammonium chloride solution with vigorous stirring. The aqueous mixture is extracted with ethyl acetate or methylene chloride. The combined organic layers are washed with aqueous ammonium chloride solution, water and dried over sodium sulfate. The solvent is removed in vacuo and the residue is dissolved in ethyl acetate or methylene chloride and treated with p-toluenesulfonic acid (100 mg) on the steam bath for 30 minutes to 1 hour. The organic solution is washed with water and dried over sodium sulfate. The solvent is removed in vacuo to give the crude enone C-119. Purification is effected by recrystallization from alcohol, alcohol and water or ethyl acetate and hexane. Alternatively, the crude enone C-119 is chromatographed on silica gel and the product then recrystallized. See, e.g., the procedure set forth in J. K. Grunwell et al., Steroids, 27, 759–771 (1976), which is incorporated herein by reference.

EXAMPLE X-19

Preparation of

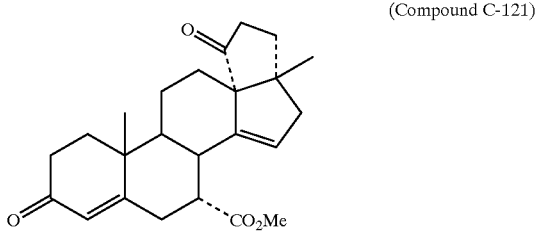

(Compound C-121)

Ester C-120 (4.00 g, 10 mmol):

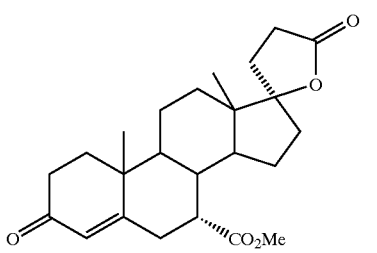
(Compound C-120)

(prepared in accordance with the procedure set forth in R. M. Weier and L. M. Hofmann, J.Med.Chem., 18, 817 (1975), which is incorporated herein by reference) is reacted with trifluoroacetic acid (25 mL), trifluoroacetic anhydride (4.5 mL) and potassium acetate (6.7 g, 7.1 mmol) according to the procedure described for the synthesis of Compound C-1 in Example X-1. The crude product C-121 is isolated according to the same procedure as for Compound C-1 in Example X-1 and is purified by chromatography on silica gel using mixtures of ethyl acetate and toluene or ethyl acetate and hexane as eluents and the product thus obtained is further purified by recrystallization from alcohol, alcohol and water, or ethyl acetate and hexane.

EXAMPLE X-20

Preparation of

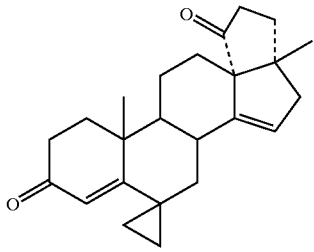
(Compound C-123)

Enone C-122 (3.68 g, 10 mmol).

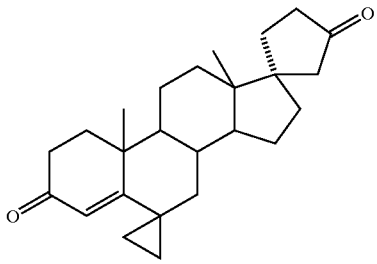
(Compound C-122)

(prepared in accordance with the procedure set forth in F. B. Colton and R. T. Nicholson, U.S. Pat. No. 3,499,891, Mar. 10, 1970, which is incorporated herein by reference) is reacted with potassium acetate (6.7 g, 7.1 mmol), trifluoracetic acid (25 mL) and trifluoroacetic acid anhydride (4.5 mL) according to the procedure described for the synthesis of Compound C-1 in Example X-1. The crude product is isolated as described in the above reference and is purified by chromatography on silica gel using mixtures of ethyl acetate and hexane or ethyl acetate and toluene as eluents.

The purified C-123 is further purified by recrystallization from alcohol, alcohol and water, or ethyl acetate and hexane.

EXAMPLE X-21

Preparation of

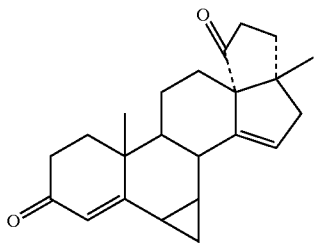
(Compound C-125)

and

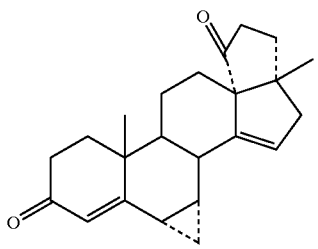
(Compound C-126)

Compounds C-125 and C-126 are synthesized according to the procedure used above for the synthesis of Compounds C-108 and C-1. Thus, to a solution of trimethylsulfoxonium iodide (1 g, 4.6 mmol) in dry dimethylsulfoxide (20 mL) is added sodium hydride (220 mg of 50% dispersion in mineral oil, 4.6 mmol). The mixture is stirred at room temperature under nitrogen until the evolution of hydrogen ceases.

A solution of trienone C-124 (1.14 g, 3.5 mmol):

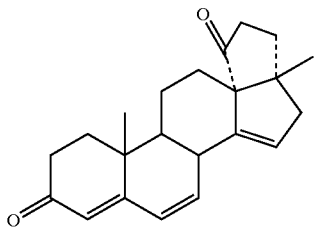
(Compound C-124)

in dimethylsulfoxide (4 mL) is then added and stirring is continued for 4 hours under a nitrogen atmosphere. Trienone C-124 is prepared in accordance with the procedure set forth in Example X-2 for the preparation of Tetraene C-105 by using canrenone as the starting material instead of 11α-hydroxy canrenone. The reaction mixture is diluted with water and the resultant precipitate is filtered and air dried. The product is a mixture of the 6α,7β (Compound C-125) and 6α,7β (Compound C-126) isomers. Separation of these isomers is effected by chromatography on silica gel and the individual isomers are further purified by recrystallization from solvents such as ethyl acetate and hexane, alcohol or alcohol and water.

EXAMPLE X-22

Preparation of methyl 3',4',5',17-tetrahydro-17β-methyl-3,5'-dioxocyclopenta[13R,17]-18-norandrosta-1,4,8,14-tetraene-7α-carboxylate (Compound C-127)

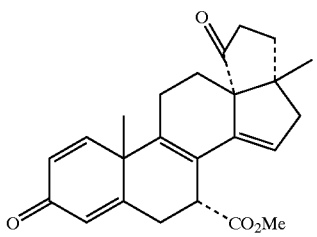

Dienone C-127 is synthesized according to the procedure described in R. M. Weier and L. M. Hofmann, J.Med. Chem. 18, 817(1975) which is incorporated by reference herein. Thus, a solution of Compound C-1 (3.8 g, 10 mmol) and dichlorodicyanobenzoquinone (2.72 g, 12 mmol) in dioxane (80 mL) is refluxed with stirring for 24 hours. The reaction mixture is concentrated in vacuo, the residue digested with methylene chloride, filtered and the filtrate washed with a 2% sodium sulfite, 5% sodium hydroxide and saturated sodium chloride solution and dried over sodium sulfate. The drying agent is filtered and the filtrate is concentrated in vacuo. The crude product dienone C-127 is purified by chromatography on silica gel using mixtures of ethyl acetate and toluene as eluents and the product 27 thus isolated is further purified by recrystallization from alcohol.

EXAMPLE X-25

Preparation of 2',3',3'aα,4',6'11'aα,12',13'-octahydro-3'aR,3'a,11'a-dimethyl-13'aR*-spiro[cyclopropane-1,7'(9'H)-[1H]pentaleno,[1,6a-a]phenanthrene]1'9'-dione (Compound C-128)

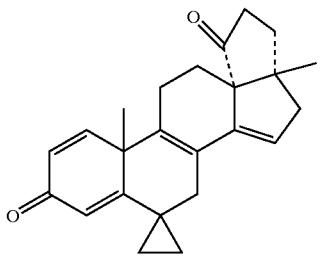

Using the procedure and workup described above in Example X-22 for the synthesis of dienone C-127, enone C-114 (3.48 g, 10 mmol) is converted to dienone C-128 using dichlorodicyanobenzoquione (2.72 g, 12 mmol) in dioxane (80 mL).

EXAMPLE X-24

Preparation of 4bR(4bR*),5,5aS*,7,7aR*,8,9,11,12,12bS*-decahydro-7A,12b-dimethyl-1OR*-cyclopropa(1)pentaleno [1,6a-a]phenanthrene-3,10-dione (Compound C-129)

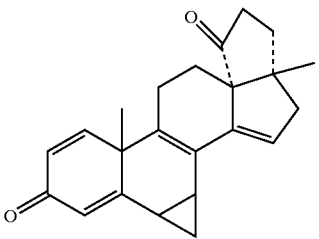

Using the procedure and workup described above in Example X-22 for the synthesis of dienone C-127, enone C-108 (3.34 g, 10 mmol) is converted to dienone C-129 using dichlorodicyanobenzoquione (2.72 g, 12 mmol) in dioxane (80 mL).

EXAMPLE X-25

Preparation of (Compound C-130)

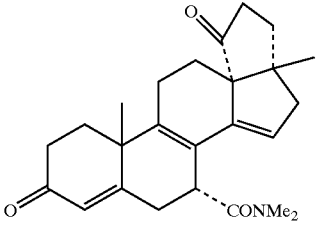

To a cold (0° C.), stirred solution of carboxylic acid C-101 (3.66 g, 10 mmol) and N-methylmorpholine (1.01 g, 10 mmol) in tetrahydrofuran (35 mL) is added isobutyl chloroformate (1.36 g, 10 mmol). The reaction is stirred at 0° C. for 20 minutes, filtered and the filtrate is concentrated in vacuo. The residue is the mixed anhydride and is suitable for use in the next step.

Gaseous dimethylamine is bubbled through a cold (0° C.) solution of mixed anhydride (4.6 g, 10 mmol) in tetrahydrofuran (40 mL) in a pressure vessel. After 15 minutes, the pressure vessel is sealed and the reaction is allowed to stand at room temperature for 24 hour. The reaction is warmed to 40 C for 30 minutes and cooled back to 0° C. After warming to room temperature, the vessel is vented to the atmosphere and excess dimethylamine is permitted to evaporate. The reaction is concentrated in vacuo, the residue dissolved in ethyl acetate and extracted with 1N sodium hydroxide solution and water. After drying over sodium sulfate, the organic layer is stripped and the residue purified by chromatography on silica gel using mixtures of ethyl acetate and toluene as the eluents. The amide C-130 thus isolated is further purified by recrystallization from alcohol, alcohol and water or ethyl acetate and hexane.

EXAMPLE X-26

Preparation of

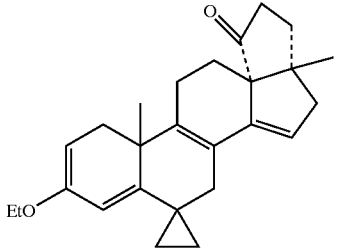

(Compound C-131)

To a suspension of enone C-114 (3.5 g, 10 mmol) in ethyl orthoformate (10 mL) and anhydrous ethanol (10 mL) is added p-toluenesulfonic acid monohydrade (0.05 g). The reaction is stirred for 30 minutes at room temperature and is quenched by the addition of a few drops of pyridine. After stirring another 5 minutes at 0° C., the resultant precipitate is filtered, washed with a small amount of methanol, and recrystallized from alcohol or ethyl acetate and hexane containing traces of pyridine to provide pure enol ether C-131. Alternatively, the reaction may be worked up after addition of pyridine by removing all solvents in vacuo and crystallizing the residue by addition solvents such as hexane, ether, ethyl acetate or hexane. The crude enol ether C-131 is recrystallized as above.

EXAMPLE X-27

Preparation of

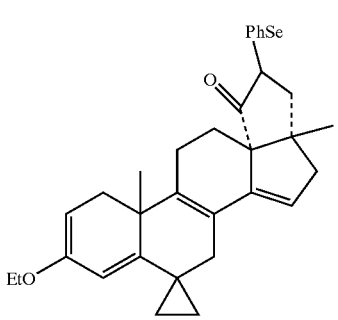

(Compound C-132)

To a cold (−78° C.) solution of lithium bis(trimethylsilyl) amide (10 mL of a 1.0 M solution in tetrahydrofuran) a solution of enol ether C-131 (3.8 g, 10 mmol) in tetrahydrofuran (20 mL) is added dropwise over 20 minutes The reaction is stirred at −78° C. for 10 minutes and a solution of phenylselenenyl chloride (1.9 g, 10 mmol) in tetrahydrofuran (5 mL) is added. The reaction is stirred 5 minutes and quenched by the addition of 1% sodium bisulfate solution. The reaction is further diluted with water and extracted with ethyl acetate. The combined organic layers are washed with 5% aqueous sodium bicarbonate solution, and water, and dried over sodium sulfate. The drying agent is filtered and the filtrate concentrated in vacuo. The residue is purified by chromatography on silica gel using mixtures of ethyl acetate and toluene or ethyl acetate and hexane as eluents to give pure selenide C-132.

EXAMPLE X-28

Preparation of

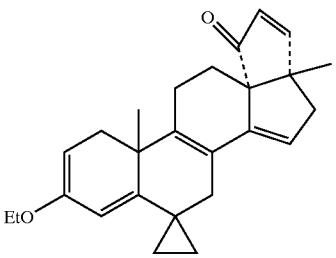

(Compound C-133)

To a cold (0° C.) solution of selenide C-132 (g, 10 mol) and pyridine (1.61 mL, 20 mmol) in methylene chloride (40 mL) is gradually added a solution of hydrogen peroxide (3.1 g of 30% solution, 27 mmol) in water (3 mL). The temperature is maintained at less than 30–35° C. After any exothermicityi subsides, the ice bath is removed and the reaction is stirred vigorously at room temperature for 15 minutes. The reaction is diluted with methylene chloride and washed with 5% sodium bicarbonate solution and water and dried over sodium sulfate. The drying agent is filtered and the filtrate is concentrated in vacuo. The residue is purified by chromatography on silica gel using mixtures of ethyl acetate and toluene or ethyl acetate and hexane as eluents to give pure unsaturated ketone C-133 which is further purified by recrystallization from ethyl acetate and hexane or alcohol.

EXAMPLE X-29

Preparation of

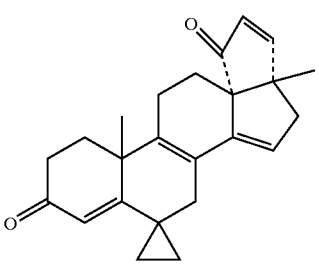

(Compound C-134)

A solution of ketone C-133 (2 g) in acetone (15 mL) is treated with 1N hydrochloric acid (4 mL) for 1 hour at room temperature. The reaction is concentrated in vacuo. The residue is diluted with water and extracted with ethyl acetate. The combined organic layers are washed with 5% sodium bicarbonate solution and water and dried over sodium sulfate. The drying agent is filtered and the filtrate concentrated in vacuo to give crude ketone C-134. The crude product is purified by chromatography on silica gel using mixtures of ethyl acetate and toluene as eluents to give pure ketone C-134 which is further purified by recrystallization from ethyl acetate and hexane or alcohol.

What is claimed is:

1. A process for the preparation of a 3-keto-7α-alkoxycarbonyl substituted Δ-4,5-steroid comprising reacting an alkylating reagent with a 4,5-dihydro-5,7-lactone steroid substrate in the presence of a base, said lactone substrate being substituted with keto or dialkoxy at the 3-carbon, and further comprising the moiety:

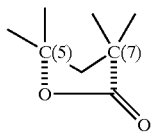

where C(5) represents the 5-carbon and C(7) represents the 7-carbon of the steroid structure of the substrate.

2. A process as set forth in claim 1 wherein said steroid substrate comprises a saturated or unsaturated nuclear structure of Formula XLI

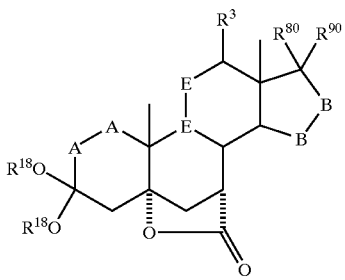

XLI

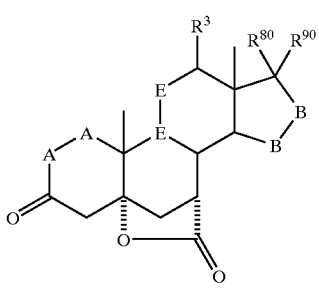

XLII or of Formula XLII wherein

—A—A— represents the group —CHR$_4$—CHR$_5$— or —CR$_4$=CR$_5$—;

R$^3$, R$^4$ and R$^5$ are independently selected from the group consisting of hydrogen, halo, hydroxy, lower alkyl, lower alkoxy, hydroxyalkyl, alkoxyalkyl, hydroxycarbonyl, cyano and aryloxy;

—B—B— represents the group —CHR$^6$—CHR$^7$— or an alpha- or beta-oriented group:

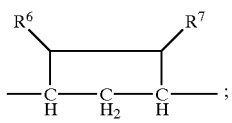

III where R$^6$ and R$^7$ are independently selected from the group consisting of hydrogen, halo, lower alkoxy, acyl, hydroxyalkyl, alkoxyalkyl, hydroxycarbonyl, alkyl, alkoxycarbonyl, acyloxyalkyl, cyano and aryloxy;

—E—E— is selected from among:

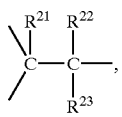

XLIII

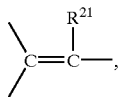

XLIV

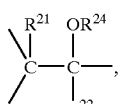

XLV

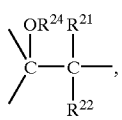

XLVI and

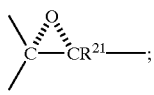

XLVII where R$^{21}$, R$^{22}$ and R$^{23}$ are independently selected from among hydrogen, alkyl, halo, nitro, and cyano; and R$^{24}$ is selected from among hydrogen and lower alkyl;

wherein R$^{18}$ is C$_1$–C$_4$ alkyl, or the R$^{18}$O— groups together form an O,O-oxyalkylene bridge; and wherein R$^{80}$ and R$^{90}$ are independently selected from R$^8$ and R$^9$, respectively, or R$^{80}$ and R$^{90}$ together form keto;

where R$^8$ and R$^9$ are independently selected from the group consisting of hydrogen, hydroxy, halo, lower alkoxy, acyl, hydroxyalkyl, alkoxyalkyl, hydroxycarbonylalkyl, alkoxycarbonylalkyl, acyloxyalkyl, cyano and aryloxy, or R$^8$ and R$^9$ together comprise a carbocyclic or heterocyclic ring structure, or R$^8$ or R$^9$ together with R$^6$ or R$^7$ comprise a carbocyclic or heterocyclic ring structure fused to the pentacyclic D ring.

3. A process as set forth in claim 2 wherein said steroid substrate and said steroid product are substituted at the 17-position with a spirolactone substituent corresponding to Formula XXXIII

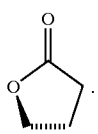

XXXIII

4. A process as set forth in claim 1 comprising a 17-keto structure.

5. A process as set forth in claim 1 wherein said lactone substrate comprises 3-dialkoxy substituents.

6. A process as set forth in claim 1 wherein said 5,7-lactone is reacted with an alkyl halide in the presence of a base.

7. A process for the preparation of a compound corresponding to Formula II:

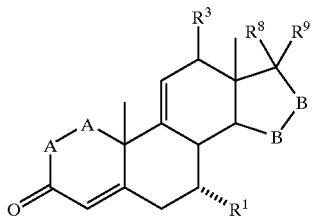

wherein
—A—A— represents the group —$CHR^4$—$CHR^5$— or —$CR^4$=$CR^5$—;
$R^1$ represents an alpha-oriented lower alkoxycarbonyl or hydroxycarbonyl radical;
$R^3$, $R^4$ and $R^5$ are independently selected from the group consisting of hydrogen, halo, hydroxy, lower alkyl, lower alkoxy, hydroxyalkyl, alkoxyalkyl, hydroxycarbonyl, cyano and aryloxy; and
—B—B— represents the group —$CHR^6$—$CHR^7$— or an alpha- or beta-oriented group:

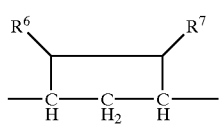

where $R^6$ and $R^7$ are independently selected from the group consisting of hydrogen, halo, lower alkoxy, acyl, hydroxyalkyl, alkoxyalkyl, hydroxycarbonyl, alkyl, alkoxycarbonyl, acyloxyalkyl, cyano and aryloxy; and
$R^8$ and $R^9$ are independently selected from the group consisting of hydrogen, hydroxy, halo, lower alkoxy, acyl, hydroxyalkyl, alkoxyalkyl, hydroxycarbonylalkyl, alkoxycarbonylalkyl, acyloxyalkyl, cyano and aryloxy, or $R^8$ and $R^9$ together comprise a carbocyclic or heterocyclic ring structure, or $R^8$ or $R^9$ together with $R^6$ or $R^7$ comprise a carbocyclic or heterocyclic ring structure fused to the pentacyclic D ring;
the process comprising:
alkylating a compound of Formula EI by hydrolysis followed by reaction with an alkylating reagent in the presence of a base, the compound of Formula EI having the structure:

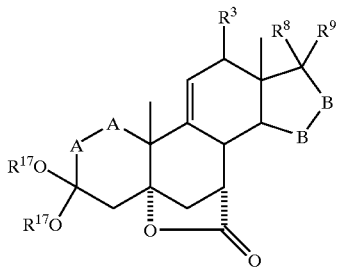

wherein —A—A—, $R^3$, $R^8$, $R^9$ and —B—B— are as defined above, and $R^{17}$ is $C_1$ to $C_4$ alkyl.

8. A process for the preparation of a compound corresponding to Formula IIC:

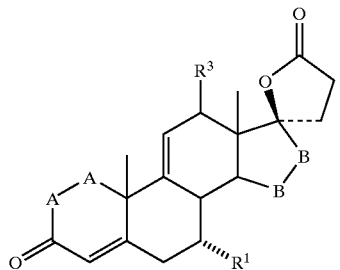

wherein
—A—A— represents the group —$CHR_4$—$CHR_5$— or —$CR_4$=$CR_5$—;
$R^1$ represents an alpha-oriented lower alkoxycarbonyl or hydroxycarbonyl radical;
$R^3$, $R^4$ and $R^5$ are independently selected from the group consisting of hydrogen, halo, hydroxy, lower alkyl, lower alkoxy, hydroxyalkyl, alkoxyalkyl, hydroxycarbonyl, cyano and aryloxy; and
—B—B— represents the group —$CHR^6$—$CHR^7$— or an alpha- or beta-oriented group:

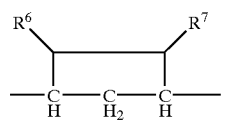

where $R^6$ and $R^7$ are independently selected from the group consisting of hydrogen, halo, lower alkoxy, acyl, hydroxyalkyl, alkoxyalkyl, hydroxycarbonyl, alkyl, alkoxycarbonyl, acyloxyalkyl, cyano and aryloxy;

the process comprising:
alkylating a compound of Formula E by hydrolysis followed by reaction with an alkylating reagent in the presence of a base, the compound of Formula E having the structure:

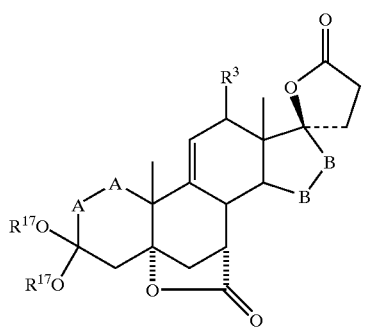

wherein —A—A—, —B—B— and $R^3$, are as defined above, and $R^{17}$ is $C_1$ to $C_4$ alkyl.

9. A process for the preparation of a compound corresponding to Formula I:

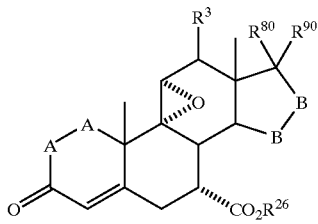

wherein
—A—A— represents the group —CHR$^4$—CHR$^5$— or —CR$^4$=CR$^5$—;
R$^3$, R$^4$ and R$^5$ are independently selected from the group consisting of hydrogen, halo, hydroxy, lower alkyl, lower alkoxy, hydroxyalkyl, alkoxyalkyl, hydroxycarbonyl, cyano and aryloxy;
R$^{26}$ is C$_1$ to C$_4$ alkyl; and
—B—B— represents the group —CHR$^6$—CHR$^7$— or an alpha- or beta-oriented group:

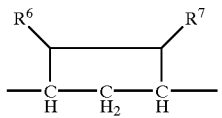

where R$^6$ and R$^7$ are independently selected from the group consisting of hydrogen, halo, lower alkoxy, acyl, hydroxyalkyl, alkoxyalkyl, hydroxycarbonyl, alkyl, alkoxycarbonyl, acyloxyalkyl, cyano and aryloxy; and
R$^{80}$ and R$^{90}$ are independently selected from R$^8$ and R$^9$, respectively, or R$^{80}$ and R$^{90}$ together form keto;
R$^8$ and R$^9$ are independently selected from the group consisting of hydrogen, hydroxy, halo, lower alkoxy, acyl, hydroxyalkyl, alkoxyalkyl, hydroxycarbonylalkyl, alkoxycarbonylalkyl, acyloxyalkyl, cyano and aryloxy, or R$^8$ and R$^9$ together comprise a carbocyclic or heterocyclic ring structure, or R$^9$ together with R$^6$ or R$^7$ comprise a carbocyclic or heterocyclic ring structure fused to the pentacyclic D ring;
the process comprising:
alkylating a compound of Formula A211 by reaction with an alkylating reagent in the presence of a base, the compound of Formula A211 having the structure:

[A211]

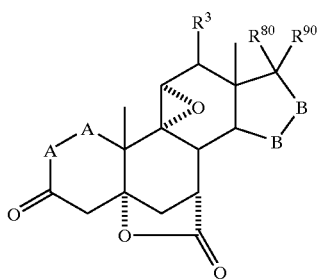

wherein —A—A—, —B—B—, R$^3$, R$^{80}$ and R$^{90}$ are as defined above.

10. A process for the preparation of a compound corresponding to Formula IE:

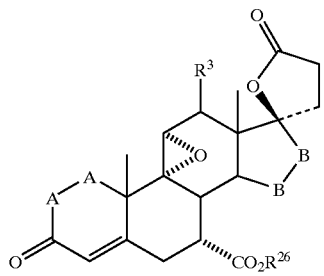

wherein
—A—A— represents the group —CHR$^4$—CHR$^5$— or —CR$^4$=CR$^5$—;
R$^3$, R$^4$ and R$^5$ are independently selected from the group consisting of hydrogen, halo, hydroxy, lower alkyl, lower alkoxy, hydroxyalkyl, alkoxyalkyl, hydroxycarbonyl, cyano and aryloxy;
R$^{26}$ is C$_1$ to C$_4$ alkyl; and
—B—B— represents the group —CHR$^6$—CHR$^7$— or an alpha- or beta-oriented group:

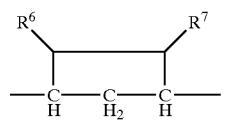

where R$^6$ and R$^7$ are independently selected from the group consisting of hydrogen, halo, lower alkoxy, acyl, hydroxyalkyl, alkoxyalkyl, hydroxycarbonyl, alkyl, alkoxycarbonyl, acyloxyalkyl, cyano and aryloxy;
the process comprising:
alkylating a compound of Formula 211 by reaction with an alkylating reagent in the presence of a base, the compound of Formula 211 having the structure:

211

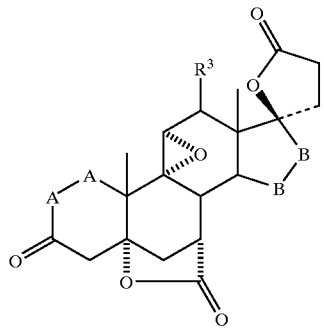

wherein —A—A—, —B—B— and R$^3$ are as defined above.

11. A process according claim 7 wherein R$^3$ is hydrogen, —A—A— represents the group —CHR$^4$—CHR$^5$—, and —B—B— represents the group —CHR$^6$—CHR$^7$—.

12. A process according to claim 8 wherein R$^3$ is hydrogen, —A—A— represents the group —CHR$^4$—CHR$^5$—, and —B—B— represents the group —CHR$^6$—CHR$^7$—.

13. A process according to claim 9 wherein R$^3$ is hydrogen, —A—A— represents the group —CHR$^4$—CHR$^5$—, and —B—B— represents the group —CHR$^6$—CHR$^7$—.

14. A process according to claim 10 wherein $R^3$ is hydrogen, —A—A— represents the group —$CHR^4$—$CHR^5$—, and —B—B— represent the group —$CHR^6$—$CHR^7$—.

15. A process according to claim 11 wherein $R^4$, $R^5$, $R^6$ and $R^7$ are each hydrogen.

16. A process according to claim 12 wherein $R^4$, $R^5$, $R^6$ and $R^7$ are each hydrogen.

17. A process according to claim 13 wherein $R^4$, $R^5$, $R^6$ and $R^7$ are each hydrogen.

18. A process according to claim 14 wherein $R^4$, $R^5$, $R^6$ and $R^7$ are each hydrogen.

* * * * *